(12) United States Patent
Francis et al.

(10) Patent No.: US 10,184,001 B2
(45) Date of Patent: *Jan. 22, 2019

(54) EFFECTOR-DEFICIENT ANTI-CD32A ANTIBODIES

(71) Applicant: Adventist Health System/Sunbelt Inc., Altamonte Springs, FL (US)

(72) Inventors: John Francis, Longwood, FL (US); Ali Amirkhosravi, Longwood, FL (US); Todd Meyer, Longwood, FL (US); Liza Robles-Carrillo, Rockledge, FL (US)

(73) Assignee: Adventist Health System/Sunbelt Inc., Altamonte Springs, FL (US)

( * ) Notice: Subject to any disclaimer, the term of this patent is extended or adjusted under 35 U.S.C. 154(b) by 283 days.

This patent is subject to a terminal disclaimer.

(21) Appl. No.: 15/171,734

(22) Filed: Jun. 2, 2016

(65) Prior Publication Data

US 2016/0347838 A1    Dec. 1, 2016

Related U.S. Application Data

(63) Continuation of application No. 14/555,556, filed on Nov. 26, 2014, now Pat. No. 9,382,321.

(51) Int. Cl.
*A61K 39/395* (2006.01)
*C07K 16/28* (2006.01)
*A61K 39/00* (2006.01)

(52) U.S. Cl.
CPC ...... *C07K 16/283* (2013.01); *A61K 2039/505* (2013.01); *C07K 2317/21* (2013.01); *C07K 2317/24* (2013.01); *C07K 2317/35* (2013.01); *C07K 2317/51* (2013.01); *C07K 2317/515* (2013.01); *C07K 2317/52* (2013.01); *C07K 2317/524* (2013.01); *C07K 2317/526* (2013.01); *C07K 2317/56* (2013.01); *C07K 2317/565* (2013.01); *C07K 2317/71* (2013.01); *C07K 2317/76* (2013.01)

(58) Field of Classification Search
None
See application file for complete search history.

(56) References Cited

U.S. PATENT DOCUMENTS

| | | | |
|---|---|---|---|
| 9,382,321 B2 * | 7/2016 | Francis | C07K 16/283 |
| 2006/0134105 A1 * | 6/2006 | Lazar | C07K 16/00 424/133.1 |
| 2006/0194290 A1 * | 8/2006 | Presta | C07K 16/00 435/69.1 |
| 2007/0253958 A1 | 11/2007 | Winkel et al. | |
| 2013/0243767 A1 | 9/2013 | Mudde et al. | |

FOREIGN PATENT DOCUMENTS

| | | |
|---|---|---|
| WO | 2006039418 A2 | 4/2006 |
| WO | 2014083379 A1 | 6/2014 |

OTHER PUBLICATIONS

An et al., "IgG2m4, an engineered antibody isotype with reduced Fc function" MAbs. Nov.-Dec.;1 (6):572-9 (2009).
Fundamental Immunology, William E. Paul, M.D. ed., 3d ed. 1993, p. 242.
Huang et al., "Human platelet FccRIIA and phagocytes in immune-complex clearance." Mol Immunol. Jan. 2011;48(4):691-6. O Dec. 17.
Janeway et al., Immunobiology, 3rd edition, 1997, Garpland Publishing Inc, pp. 3:1-3:11.
Kuwana et al., Splenic macrophages maintain the anti-platelet autoimmune response via uptake of opsonized platelets in patients with immune thrombocytopenic purpura J Thromb Hae most. Feb.;7(2):322-9 (2009).
Norgaard M., "Thrombosis in Patients with primary chronic immune thrombocytopenia" Thromb Res. Oct.;130 Suppl 1: S74-5 (2012).
Portolano et al., "Lack of Promiscuity in Autoantigen-Specific H and L Chain Combinations as Revealed by Human H and L Chain 'Roulette.'" J Immunol. Feb. 1;150(3):880-7 (1993).
Invitrogen Product insert sheet for AT-1 O antibody, Invitrogen, revision Dec. 2009, 2 pages.
Prokopec et al., "Down regulation of Fc and complement receptors on B cells in rheumatoid arthritis," Clin Immunol. 201 O Dec.;137(3):322-9. (2010).
Radstake et al., "The Functional Variant of the Inhibitory Fcc Receptor IIb (CD32B) is Associated With the Rate of Radiologic Joint Damage and Dendritic Cell Function in Rheumatoid Arthritis." Arthritis Rheum. Dec.;54(12):3828-37 (2006).
Rudikoff et al., "Single amino acid substitution altering antigen-binding specofocity." Proc Natl Acad Sci U SA. Mar. 1982;79(6):1979-83.
Vafa O et al. An engineered Fc variant of an IgG eliminates all immune effector functions via structural perturbations Methods. 65:114. Jan. 2014.
Van Royen-Kerkhof A et al. A novel human CD32 mAb blocks experimental immune haemolytic anaemia in FcgammaRIIA transgenic mice. Br J Haematol. 130:130. Jul. 2005.
Warkentin TE et al. HITlights: a career perspective on heparin-induced thrombocytopenia. Am J Hematol. 87:S92. May 2012.
Warkentin TE et al. Sera from patients with heparin-induced thrombocytopenia generate platelet-derived microparticles with procoagulant activity: an explanation for the thrombotic complications of heparin-induced thrombocytopenia. Blood. 84:3691. Dec. 1994.
Warkentin TE. Clinical presentation of heparin-induced thrombocytopenia. Semin Hematol. 35(4 Suppl 5):9-16; discussion 35-6. Oct. 1998.
Wiener E et al. Role of Fc gamma Rlla (CD32) in IgG anti-RhD-mediated red cell phagocytosis in vitro. Transfus Med. 6:235. Sep. 1996.

(Continued)

*Primary Examiner* — Michael Szperka
(74) *Attorney, Agent, or Firm* — McNeill Baur PLLC

(57) ABSTRACT

Effector-deficient anti-CD32a monoclonal antibodies are encompassed, as are method and uses for treating CD32a-mediated diseases and disorders, including, thrombocytopenia, allergy, hemostatic disorders, immune, inflammatory, and autoimmune disorders.

29 Claims, 29 Drawing Sheets

Specification includes a Sequence Listing.

(56) References Cited

OTHER PUBLICATIONS

Wines BD et al. The IgG Fc contains distinct Fc receptor (FcR) binding sites: the leukocyte receptors Fc gamma RI and Fc gamma RIIa bind to a region in the Fc distinct from that recognized by neonatal FcR and protein A. J Immunol. 164:5313. May 2000.

Wintrobe MM et al. Disorders of Platelets and Hemostasis. In: Clinical Hematology, Seventh Edition. Lea & Febiger: Philadelphia. 1974.

Woodruff RK et al. Fatal thrombotic events during treatment of autoimmune thrombocytopenia with intravenous Immunoglobulin in elderly patients. Lancet. 2:217. Jul. 1986.

Zhao X et al. Circulating immune complexes contain citrullinated fibrinogen in rheumatoid arthritis. Arthritis Res Ther. 10:R94. 2008.

Altomare I et al. Bleeding and mortality outcomes in ITP clinical trials: a review of thrombopoietin mimetics data. Am J Hematol. 87:984. Oct. 2012.

Arepally G et al. Fc gamma RIIA H/R 131 polymorphism, subclass-specific IgG anti-heparin/platelet factor 4 antibodies and clinical course in patients with heparin-induced thrombocytopenia and thrombosis. Blood. 89:370. Jan. 1997.

Arman M et al. Amplification of bacteria-induced platelet activation is triggered by Fc[gamma]RIIA, integrin [alpha]IIb [beta]3, and platelet factor 4. Blood. 123:3166. May 2014.

Ben Mkaddem S et al. Shifting Fc RIIA-ITAM from activation to inhibitory configuration ameliorates arthritis. J Clin Invest. 124:3945. Sep. 2014.

Boom DM et al. Heparin-induced thrombocytopenia and thrombosis: a potential fatal complication in a routine treatment. Neth J Med. 46:146. Mar. 1995.

Boruchov AM et al. Activating and inhibitory IgG Fc receptors on human DCs mediate opposing functions. J Clin Invest. 115:2914. Oct. 2005.

Brown MG et al. A dominant role for FcgammaRII in antibody-enhanced dengue virus infection of human mast cells and associated CCL5 release. J Leukoc Biol. 80:1242. Dec. 2006.

Bruhns P. Properties of mouse and human IgG receptors and their contribution to disease models. Blood. 119 (24):5640-9. Jun. 14, 2012.

Cines DB et al. Heparin-induced thrombocytopenia: an autoimmune disorder regulated through dynamic autoantigen assembly/disassembly. J Clin Apher. 22:31. Feb. 2007.

de Groot PG et al. The significance of autoantibodies against beta-2 glycoprotein I. Blood 120:266. Jul. 12, 2012.

Fitzgerald Jr et al. Fibronectin-binding proteins of *Staphylococcus aureus*, *Streptococcus sanguinis*, *Streptococcus gordonii*, *Streptococcus oralis*, and *Streptococcus pneumoniae* mediate activation of human platelets via fibrinogen and fibronectin bridges to integrin GPIIb/IIIa and IgG binding to the FcgammaRIIa receptor. Mol Microbiol. 59:212. Jan. 2006.

Gillis C et al. Contribution of Human FcgammaRs to Disease with Evidence from Human Polymorphisms and Transgenic Animal Studies. Front Immunol. 5:254. May 30, 2014.

Greenman J et al. Characterization of a new monoclonal anti-Fc gamma RII antibody, AT10, and its incorporation into a bispecific F(ab')2 derivative for recruitment of cytotoxic effectors. Mol Immunol. 28:1243. Nov. 1991.

Groger M et al. Dermal microvascular endothelial cells express CD32 receptors in vivo and in vitro. J Immunol. 156:1549. Feb. 15, 1996.

Haimovich B et al. The FcgammaRll receptor triggers pp125FAK phosphorylation in platelets. J Biol Chem. 271:16332. Jul. 1996.

Hasegawa S et al. Functional expression of the high affinity receptor for IgE (FcepsilonRI) in human platelets and its' [sic] intracellular expression in human megakaryocytes. Blood 93:2543. Apr. 1999.

Hogarth PM and Pietersz GA. Fc receptor-targeted therapies for the treatment of inflammation, cancer and beyond. Nat Rev Drug Discov. 11(4):311-31. Mar. 30, 2012.

Horejs-Hoeck J et al. Inhibition of immunoglobulin E synthesis through Fc gammaRII (CD32) by a mechanism independent of B-cell receptor co-cross-linking. Immunology. 115:407. Jul. 2005.

Hoylaerts MF et al. Recurrent arterial thrombosis linked to autoimmune antibodies enhancing von Willebrand factor binding to platelets and inducing Fc gamma RII receptor-mediated platelet activation. Blood. 91:2810. Apr. 1998.

Huber C et al. C3-containing serum immune complexes in patients with systemic lupus erythematosus: correlation to disease activity and comparison with other rheumatic diseases. Rheumatol Int. 9:59. 1989.

International Search Report and Written Opinion issued in PCT/US2015/062752 dated Feb. 22, 2016.

Jaffray B et al. Fatal venous thrombosis after heparin therapy. Lancet. 337:561. Mar. 19991.

Jefferis R and Lefranc MP. Human immunoglobulin allotypes: possible implications for immunogenicity. MAbs 1:332. Jul.-Aug. 2009.

Jonsonn F. et al. Human Fc-gamma-RIIa induces anaphylactic and allergic reactions. Blood. 119:2533-44. Mar. 15, 2012.

Mathsson L et al. Immune complexes from rheumatoid arthritis synovial fluid induce FcgammaRIIa dependent and rheumatoid factor correlated production of tumour necrosis factor-alpha by peripheral blood mononuclear cells. Arthritis Res Ther. 8:R64. 2006.

McKenzie et al. The role of the human Fc receptor FcgammaRIIA in the immune clearance of platelets: a transgenic mouse model. J Immunol. 162(7):4311-8. Apr. 1, 1999.

Meyer T et al. Bevacizumab immune complexes activate platelets and induce thrombosis in FCGR2A transgenic mice. J Thromb Haemost. 7:171. Jan. 2009.

Meyer, T. et al. "CD32a antobodies induce thrombocytopenia and type II hypersensitivity reactions in FCGR2A mice" Blood, 126(19):2230-2238 (2015).

Mkaddem, S.B., et al. "Shifting Fc[gamma] RIIA-ITAM from activation to inhibitory configuration ameliorates arthritis" The Journal of Clinical Investigation, 124(9): 3945-3959 (2014).

Newman PM et al. Heparin-induced thrombocytopenia: new evidence for the dynamic binding of purified anti-PF4-heparin antibodies to platelets and the resultant platelet activation. Blood. 96:182. Jul. 1, 2000.

Nielsen CT et al. Increased IgG on cell-derived plasma microparticles in systemic lupus erythematosus is associated with autoantibodies and complement activation. Arthritis Rheum. 64:1227. Apr. 2012.

Ohyama K et al. Immune complexome analysis of serum and its application in screening for immune complex antigens in rheumatoid arthritis. Clin Chem. 57:905. Jun. 2011.

Overdijk et al. Crosstalk between human IgG isotypes and murine effector cells. J Immunol. 189(7):3430-8. Oct. 1, 2012.

Page C et al. Platelets and allergic inflammation. Clin Exp Allergy. 44:901. Jul. 2014.

Paran D et al. Venous and arterial thrombosis following administration of intravenous immunoglobulins. Blood Coagul Fibrinolysis. 16:313. Jul. 2005.

Pollreisz A et al. Intravenous immunoglobulins induce CD32-mediated platelet aggregation in vitro. Br J Dermatol. 159:578. Sep. 2008.

Potaczek DP. Links between allergy and cardiovascular or hemostatic system. Int J Cardiol. 170:278. Jan. 2014.

Reilly MP et al. Heparin-induced thrombocytopenia/thrombosis in a transgenic mouse model requires human platelet factor 4 and platelet activation through FcgammaRIIA. Blood. 98(8):2442-7. Oct. 15, 2001.

Robles-Carillo L et al. Anti-CD40L immune complexes potently activate platelets in vitro and cause thrombosis in FCGR2A transgenic mice. J Immunol. 185:1577. Aug. 2010.

Ronnelid J et al. Immune complexes from SLE sera induce IL10 production from normal peripheral blood mononuclear cells by an FcgammaRII dependent mechanism: implications for a possible vicious cycle maintaining B cell hyperactivity in SLE. Ann Rheum Dis. 62:37. Jan. 2003.

(56) References Cited

OTHER PUBLICATIONS

Rosenfeld SI et al. Human platelet Fc receptor for immunoglobulin G. Identification as a 40,000-molecular-weight membrane protein shared by monocytes. J Clin Invest. 76:2317. Dec. 1985.
Rovin BH. The chemokine network in systemic lupus erythematous nephritis. Front Biosci. 13:904. Jan. 1, 2008.
Salfeld, J. G. "Isotype selection in antibody engineering" Nature Biotechnology, 25(12): 1369-1372.
Satoh T et al. Heparin-dependent and -independent anti-platelet factor 4 autoantibodies in patients with systemic lupus erythematosus. Rheumatology (Oxford). 51:1721. Sep. 2012.
Seres T et al. Correlation of Fc gamma receptor expression of monocytes with clearance function by macrophages in systemic lupus erythematosus. Scand J Immunol. 48:307. Sep. 1998.
Sikara MP et al. Beta 2 Glycoprotein I binds platelet factor 4 (PF4): implications for the pathogenesis of antiphospholipid syndrome. Blood. 115:713. Jan. 21, 2010.
Soares NM et al. An improved anti-C3/IgG ELISA for quantification of soluble immune complexes. J Immunol Methods. 249:199. Mar. 1, 2001.
Sun D et al. Bacillus anthracis peptidoglycan activates human platelets through Fc[gamma]RII and complement. Blood. 122:571. Jul. 2013.
Suzuki Y et al. Pre-existing glomerular immune complexes induce polymorphonuclear cell recruitment through an Fc receptor-dependent respiratory burst: potential role in the perpetuation of immune nephritis. J Immunol. 170:3243. Mar. 15, 2003.
Taylor SM et al. Thrombosis and shock induced by activating antiplatelet antibodies in human FcgammaRIIA ransgenic mice: the interplay among antibody, spleen, and Fc receptor. Blood. 96(13):4254-60. Dec. 15, 2000.
Béranger et al. "IMGT Scientific chart: Correspondnece between the IM GT unique numbering for C-DOM AIN, the IM GT exon numbering the Eu and Kabat numberings: Human IGHG," XP055297333 May 17, 2001 nternet:URL:http://www.imgt.org/IMGTScientificChart/Numbering/Hu_IGHGnber.html (4 pages).
Office Action issued for European Application No. 15808056.4, dated Jun. 20, 2018, 12 pages.
Strohl et al. "Antibody structure-function relationships" Elsevier Science & Technology, pp. 37-56 ProQuest Ebook Central, XP055484171 Jan. 1, 2012.

* cited by examiner

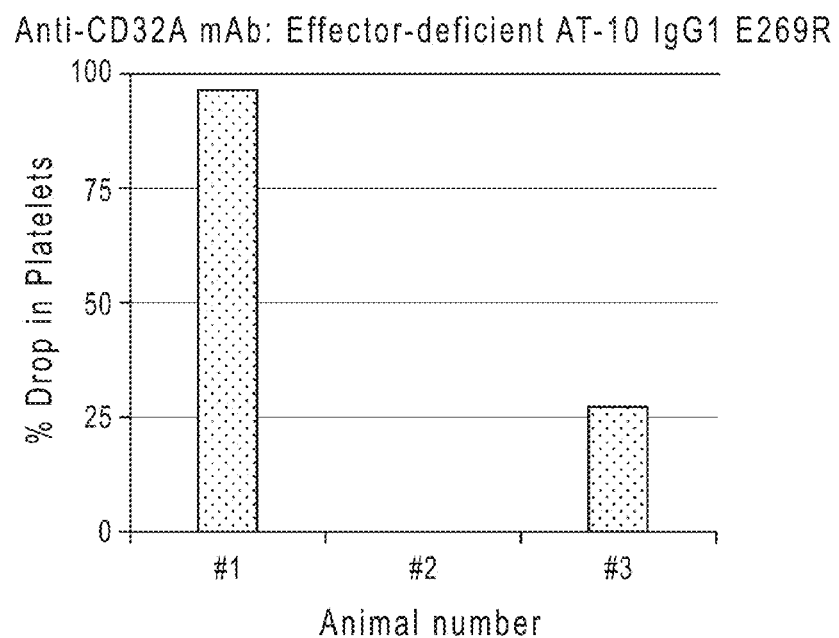
FIG. 10
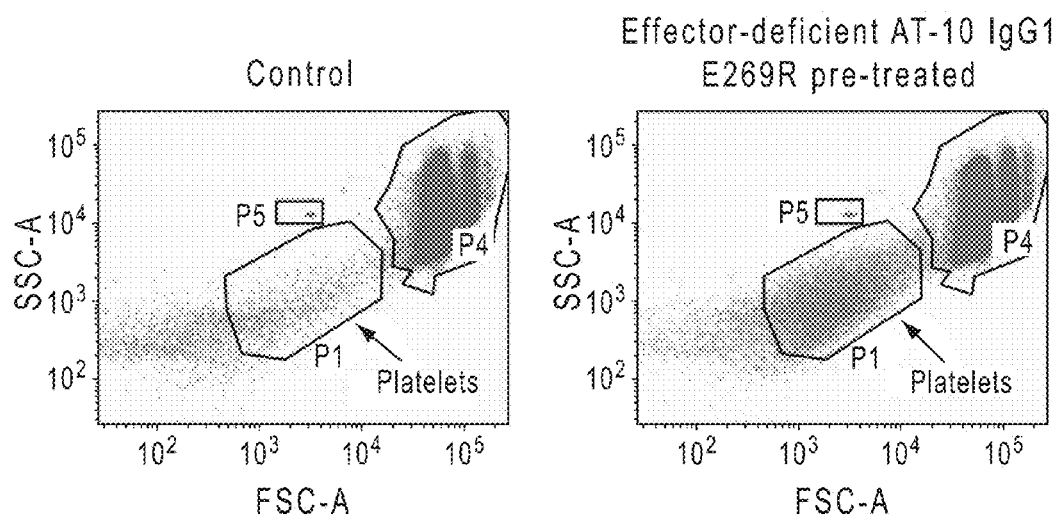
FIG. 11A
FIG. 11B

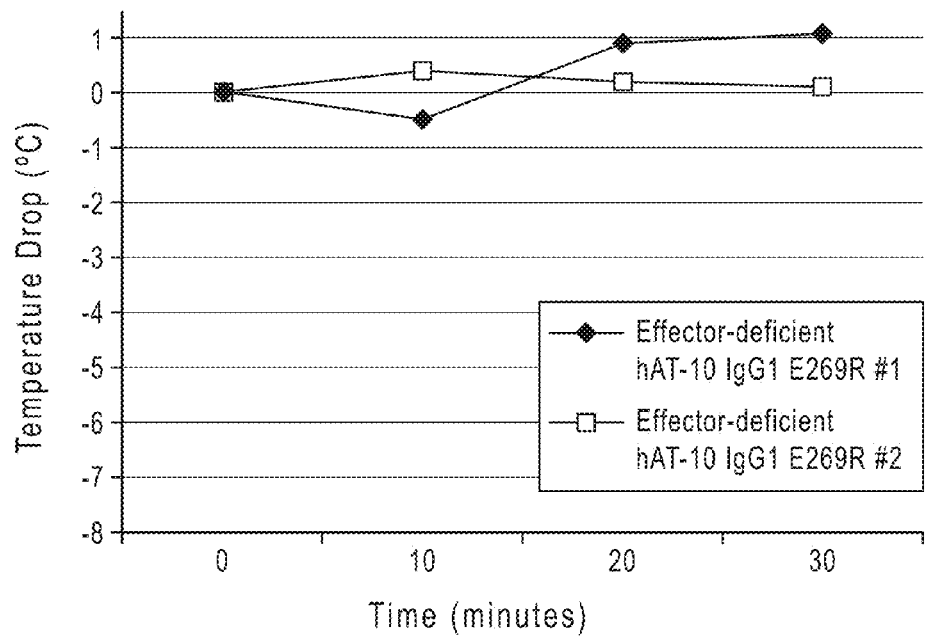
FIG. 13A
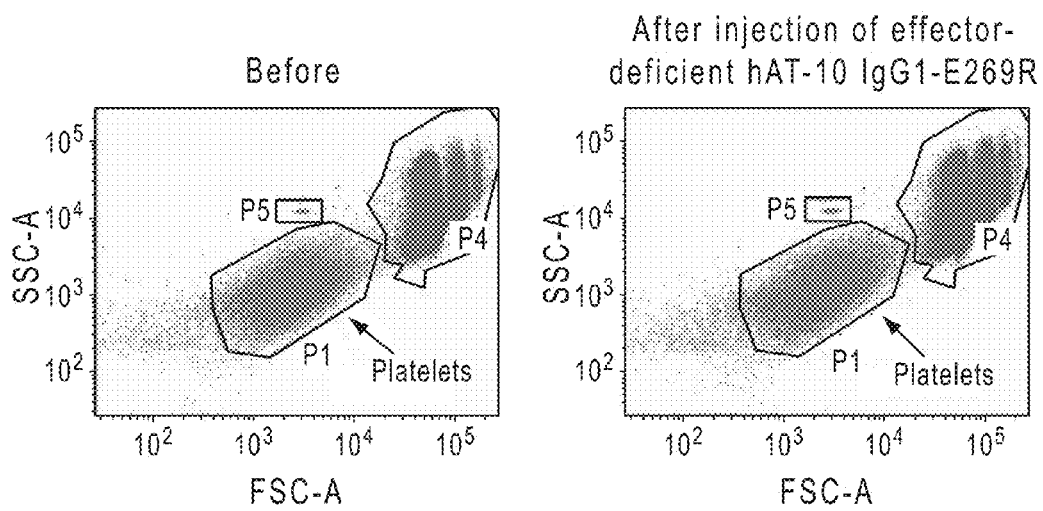
FIG. 13B
FIG. 13C

SEQUENCE LISTING

```
<160> NUMBER OF SEQ ID NOS: 102

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Tyr Tyr Trp Met Asn
1               5

<210> SEQ ID NO 2
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 2

Glu Ile Arg Leu Lys Ser Asn Asn Tyr Ala Thr His Tyr Ala Glu Ser
1               5                   10                  15

Val Lys Gly

<210> SEQ ID NO 3
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Arg Asp Glu Tyr Tyr Ala Met Asp Tyr
1               5

<210> SEQ ID NO 4
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Arg Ala Ser Glu Ser Val Asp Asn Phe Gly Ile Ser Phe Met Asn
1               5                   10                  15

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Gly Ala Ser Asn Gln Gly Ser
1               5

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Gln Gln Ser Lys Glu Val Pro Trp Thr
1               5

<210> SEQ ID NO 7
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 7
gaagtgaagc ttgaggagtc tggaggaggc ttggtgcaac tggaggatc catgaaactc      60 tcctgtgttg cctctggatt cactttcagt tactactgga tgaactgggt ccgccagtct    120
```

```
ccagagaagg ggcttgagtg ggttgctgaa attagattga aatctaataa ttatgcaaca    180
cattatgcgg agtctgtgaa agggaggttc accatctcaa gagatgattc caaaaataat    240
gtctacctgc aaatgaacaa cttaagagct gaagacactg gcatttatta ctgtaacagg    300
cgtgatgagt attacgctat ggattattgg ggtcaaggga cgtcggtatc tgtgtctagt    360
```

<210> SEQ ID NO 8
<211> LENGTH: 120
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 8

```
Glu Val Lys Leu Glu Glu Ser Gly Gly Gly Leu Val Gln Pro Gly Gly
1               5                   10                  15

Ser Met Lys Leu Ser Cys Val Ala Ser Gly Phe Thr Phe Ser Tyr Tyr
            20                  25                  30

Trp Met Asn Trp Val Arg Gln Ser Pro Glu Lys Gly Leu Glu Trp Val
        35                  40                  45

Ala Glu Ile Arg Leu Lys Ser Asn Asn Tyr Ala Thr His Tyr Ala Glu
    50                  55                  60

Ser Val Lys Gly Arg Phe Thr Ile Ser Arg Asp Asp Ser Lys Asn Asn
65                  70                  75                  80

Val Tyr Leu Gln Met Asn Asn Leu Arg Ala Glu Asp Thr Gly Ile Tyr
                85                  90                  95

Tyr Cys Asn Arg Arg Asp Glu Tyr Tyr Ala Met Asp Tyr Trp Gly Gln
            100                 105                 110

Gly Thr Ser Val Ser Val Ser Ser
        115                 120
```

<210> SEQ ID NO 9
<211> LENGTH: 333
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 9

```
gacattgtgc tgacccaatc tccaggttct ttggctgtgt ctctagggca gagggccacc     60
atctcctgca gagccagcga aagtgttgat aattttggca ttagttttat gaactggttc    120
caacagaaac caggacagcc accccgactc ctcatctatg gtgcatccaa ccaaggatcc    180
ggggtccctg ccaggtttag tggcagtggg tctgggacag acttcagcct caacatccat    240
cctgtggagg aggatgatgc tgcaatgtat ttctgtcagc aaagtaagga ggttccgtgg    300
acgttcggtg gaggcaccaa gctggaaatc aaa                                 333
```

<210> SEQ ID NO 10
<211> LENGTH: 111
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 10

Asp Ile Val Leu Thr Gln Ser Pro Gly Ser Leu Ala Val Ser Leu Gly
1               5                   10                  15

Gln Arg Ala Thr Ile Ser Cys Arg Ala Ser Glu Ser Val Asp Asn Phe
            20                  25                  30

Gly Ile Ser Phe Met Asn Trp Phe Gln Gln Lys Pro Gly Gln Pro Pro
        35                  40                  45

Arg Leu Leu Ile Tyr Gly Ala Ser Asn Gln Gly Ser Gly Val Pro Ala
    50                  55                  60

Arg Phe Ser Gly Ser Gly Ser Gly Thr Asp Phe Ser Leu Asn Ile His
65                  70                  75                  80

Pro Val Glu Glu Asp Asp Ala Ala Met Tyr Phe Cys Gln Gln Ser Lys
                85                  90                  95

Glu Val Pro Trp Thr Phe Gly Gly Gly Thr Lys Leu Glu Ile Lys
            100                 105                 110

<210> SEQ ID NO 11
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 11
gaggtgcagc tggtggagtc tgggggaggc ttggtccagc ctggagggtc cctgagactc      60
tcctgtgcag cctctggatt caccttctca tactattgga tggactgggt ccgccaggct     120
ccagggaagg gctggagtg gttggccgt atcagactga aatctaacaa ctatgccacc       180
gaatacgccg cgtctgtgaa aggcagattc accatctcaa gagatgattc aaagaactca     240
ctgtatctgc aaatgaacag cctgaaaacc gaggacacgg ccgtgtatta ctgtaacaga     300
agagatgagt attacgccat ggattattgg ggccaaggga caatggtcac cgtctcttca     360

<210> SEQ ID NO 12
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Tyr Tyr
            20                  25                  30

Trp Met Asp Trp Val Arg Gln Ala Pro Gly Lys Gly Leu Glu Trp Val
        35                  40                  45

Gly Arg Ile Arg Leu Lys Ser Asn Asn Tyr Ala Thr Glu Tyr Ala Ala
    50                  55                  60

Ser Val Lys Gly Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Asn Arg Arg Asp Glu Tyr Tyr Ala Met Asp Tyr Trp Gly Gln
             100                 105                 110

Gly Thr Met Val Thr Val Ser Ser
        115                 120

<210> SEQ ID NO 13
<211> LENGTH: 333
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 13
gaaattgtgt tgacacagtc tccagccacc ctgtctttgt ctccagggga aagagccacc      60
ctctcctgca gggccagtga atctgtggat aacttcggga tctccttctt agcctggtac     120
caacagaaac tggccaggc tcccaggctc ctcatctatg gagcctccaa cagggccact      180
ggcatcccag ccaggttcag tggcagtggg tctgggacag acttcactct caccatcagc     240
agcctagagc ctgaagattt tgcagtttat tactgtcagc aatctaaaga ggtgccatgg     300
accttcggcc aagggaccaa ggtggaaatc aaa                                  333

<210> SEQ ID NO 14
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Glu Ser Val Asp Asn Phe
            20                  25                  30

Gly Ile Ser Phe Leu Ala Trp Tyr Gln Gln Lys Pro Gly Gln Ala Pro
        35                  40                  45

Arg Leu Leu Ile Tyr Gly Ala Ser Asn Arg Ala Thr Gly Ile Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln Gln Ser Lys
                85                  90                  95

Glu Val Pro Trp Thr Phe Gly Gln Gly Thr Lys Val Glu Ile Lys
            100                 105                 110

<210> SEQ ID NO 15
<211> LENGTH: 1350
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 15
gaagtgaagc ttgaggagtc tggaggaggc ttggtgcaac ctggaggatc catgaaactc      60
tcctgtgttg cctctggatt cactttcagt tactactgga tgaactgggt ccgccagtct     120
ccagagaagg ggcttgagtg ggttgctgaa attagattga aatctaataa ttatgcaaca     180
cattatgcgg agtctgtgaa agggaggttc accatctcaa gagatgattc caaaaataat     240

```
gtctacctgc aaatgaacaa cttaagagct gaagacactg gcatttatta ctgtaacagg    300
cgtgatgagt attacgctat ggattattgg ggtcaaggga cgtcggtatc tgtgtctagt    360
gctagcacca agggcccatc ggtcttcccc ctggcaccct cctccaagag cacctctggg    420
ggcacagcgg ccctgggctg cctggtcaag gactacttcc ccgaaccggt gacggtgtcg    480
tggaactcag gcgccctgac cagcggcgtg cacaccttcc cggctgtcct acagtcctca    540
ggactctact ccctcagcag cgtggtgacc gtgccctcca gcagcttggg cacccagacc    600
tacatctgca acgtgaatca caagcccagc aacaccaagg tggacaagaa agttgagccc    660
aaatcttgtg acaaaactca cacatgccca ccgtgcccag cacctgaact cctgggggga    720
ccgtcagtct tcctcttccc cccaaaaccc aaggacaccc tcatgatctc ccggacccct    780
gaggtcacat gcgtggtggt ggacgtgagc cacagagacc ctgaggtcaa gttcaactgg    840
tacgtggacg gcgtggaggt gcataatgcc aagacaaagc cgcgggagga gcagtacaac    900
agcacgtacc gtgtggtcag cgtcctcacc gtcctgcacc aggactggct gaatggcaag    960
gagtacaagt gcaaggtctc caacaaagcc ctcccagccc ccatcgagaa aaccatctcc    1020
aaagccaaag ggcagccccg agaaccacag gtgtacaccc tgcccccatc ccgggaggag    1080
atgaccaaga accaggtcag cctgacctgc ctggtcaaag cttctatcc cagcgacatc    1140 gccgtggagt gggagagcaa tgggcagccg gagaacaact acaagaccac gcctcccgtg    1200
ctggactccg acggctcctt cttcctctac agcaagctca ccgtggacaa gagcaggtgg    1260
cagcagggga acgtcttctc atgctccgtg atgcatgagg ctctgcacaa ccactacacg    1320
cagaagagcc tctccctgtc tccgggtaaa                                    1350
```

<210> SEQ ID NO 16
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

```
Glu Val Lys Leu Glu Glu Ser Gly Gly Gly Leu Val Gln Pro Gly Gly
1               5                   10                  15

Ser Met Lys Leu Ser Cys Val Ala Ser Gly Phe Thr Phe Ser Tyr Tyr
            20                  25                  30

Trp Met Asn Trp Val Arg Gln Ser Pro Glu Lys Gly Leu Glu Trp Val
        35                  40                  45

Ala Glu Ile Arg Leu Lys Ser Asn Asn Tyr Ala Thr His Tyr Ala Glu
    50                  55                  60

Ser Val Lys Gly Arg Phe Thr Ile Ser Arg Asp Asp Ser Lys Asn Asn
65                  70                  75                  80

Val Tyr Leu Gln Met Asn Asn Leu Arg Ala Glu Asp Thr Gly Ile Tyr
                85                  90                  95

Tyr Cys Asn Arg Arg Asp Glu Tyr Tyr Ala Met Asp Tyr Trp Gly Gln
            100                 105                 110

Gly Thr Ser Val Ser Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160
```

```
Trp Asn Ser Gly Ala Leu Thr Ser Gly Val His Thr Phe Pro Ala Val
            165                 170                 175
Leu Gln Ser Ser Gly Leu Tyr Ser Leu Ser Ser Val Val Thr Val Pro
        180                 185                 190
Ser Ser Ser Leu Gly Thr Gln Thr Tyr Ile Cys Asn Val Asn His Lys
    195                 200                 205
Pro Ser Asn Thr Lys Val Asp Lys Lys Val Glu Pro Lys Ser Cys Asp
210                 215                 220
Lys Thr His Thr Cys Pro Pro Cys Pro Ala Pro Glu Leu Leu Gly Gly
225                 230                 235                 240
Pro Ser Val Phe Leu Phe Pro Pro Lys Pro Lys Asp Thr Leu Met Ile
                245                 250                 255
Ser Arg Thr Pro Glu Val Thr Cys Val Val Val Asp Val Ser His Arg
            260                 265                 270
Asp Pro Glu Val Lys Phe Asn Trp Tyr Val Asp Gly Val Glu Val His
        275                 280                 285
Asn Ala Lys Thr Lys Pro Arg Glu Glu Gln Tyr Asn Ser Thr Tyr Arg
    290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
                325                 330                 335
Lys Thr Ile Ser Lys Ala Lys Gly Gln Pro Arg Glu Pro Gln Val Tyr
            340                 345                 350
Thr Leu Pro Pro Ser Arg Glu Glu Met Thr Lys Asn Gln Val Ser Leu
        355                 360                 365
Thr Cys Leu Val Lys Gly Phe Tyr Pro Ser Asp Ile Ala Val Glu Trp
    370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                405                 410                 415
Lys Ser Arg Trp Gln Gln Gly Asn Val Phe Ser Cys Ser Val Met His
            420                 425                 430
Glu Ala Leu His Asn His Tyr Thr Gln Lys Ser Leu Ser Leu Ser Pro
        435                 440                 445
Gly Lys
    450

<210> SEQ ID NO 17
<211> LENGTH: 1338
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 17
gaagtgaagc ttgaggagtc tggaggaggc ttggtgcaac ctggaggatc catgaaactc      60
tcctgtgttg cctctggatt cactttcagt tactactgga tgaactgggt ccgccagtct     120
ccagagaagg ggcttgagtg ggttgctgaa attagattga aatctaataa ttatgcaaca     180
cattatgcgg agtctgtgaa agggaggttc accatctcaa gagatgattc caaaaataat     240
gtctacctgc aaatgaacaa cttaagagct gaagacactg gcatttatta ctgtaacagg     300
cgtgatgagt attacgctat ggattattgg ggtcaaggga cgtcggtatc ctgtgtctagt    360
```

```
gctagcacca agggcccatc ggtcttcccc ctggcgccct gctccaggag cacctccgag    420
agcacagcgg ccctgggctg cctggtcaag gactacttcc ccgaaccggt gacggtgtcg    480
tggaactcag gcgctctgac cagcggcgtg cacaccttcc cagctgtcct acagtcctca    540
ggactctact ccctcagcag cgtggtgacc gtgccctcca gcaacttcgg cacccagacc    600
tacacctgca acgtagatca caagcccagc aacaccaagg tggacaagac agttgagcgc    660
aaatgttgtg tcgagtgccc accgtgccca gcaccacctg tggcaggacc gtcagtcttc    720
ctcttccccc caaaacccaa ggacaccctc atgatctccc ggacccctga ggtcacgtgc    780
gtggtggtgg acgtgagcca cgaagacccc gaggtccagt tcaactggta cgtggacggc    840
gtggaggtgc ataatgccaa gacaaagcca cgggaggagc agttcgccag cacgttccgt    900
gtggtcagcg tcctcaccgt tgtgcaccag gactggctga acggcaagga gtacaagtgc    960
aaggtctcca acaaaggcct cccagccccc atcgagaaaa ccatctccaa aaccaaaggg   1020
cagccccgag aaccacaggt gtacaccctg cccccatccc gggaggagat gaccaagaac   1080
caggtcagcc tgacctgcct ggtcaaaggc ttctacccca gcgacatcgc cgtggagtgg   1140
gagagcaatg ggcagccgga gaacaactac aagaccacgc ctcccatgct ggactccgac   1200
ggctccttct tcctctacag caagctcacc gtggacaaga gcaggtggca gcaggggaac   1260
gtcttctcat gctccgtgat gcatgaggct ctgcacaacc actacacgca gaagagcctc   1320
tccctgtctc cgggtaaa                                                 1338

<210> SEQ ID NO 18
<211> LENGTH: 446
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Glu Val Lys Leu Glu Glu Ser Gly Gly Gly Leu Val Gln Pro Gly Gly
1               5                   10                  15

Ser Met Lys Leu Ser Cys Val Ala Ser Gly Phe Thr Phe Ser Tyr Tyr
            20                  25                  30

Trp Met Asn Trp Val Arg Gln Ser Pro Glu Lys Gly Leu Glu Trp Val
        35                  40                  45

Ala Glu Ile Arg Leu Lys Ser Asn Asn Tyr Ala Thr His Tyr Ala Glu
    50                  55                  60

Ser Val Lys Gly Arg Phe Thr Ile Ser Arg Asp Asp Ser Lys Asn Asn
65                  70                  75                  80

Val Tyr Leu Gln Met Asn Asn Leu Arg Ala Glu Asp Thr Gly Ile Tyr
                85                  90                  95

Tyr Cys Asn Arg Arg Asp Glu Tyr Tyr Ala Met Asp Tyr Trp Gly Gln
            100                 105                 110

Gly Thr Ser Val Ser Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175
```

Leu Gln Ser Ser Gly Leu Tyr Ser Leu Ser Ser Val Val Thr Val Pro
            180                 185                 190

Ser Ser Asn Phe Gly Thr Gln Thr Tyr Thr Cys Asn Val Asp His Lys
        195                 200                 205

Pro Ser Asn Thr Lys Val Asp Lys Thr Val Glu Arg Lys Cys Cys Val
    210                 215                 220

Glu Cys Pro Pro Cys Pro Ala Pro Pro Val Ala Gly Pro Ser Val Phe
225                 230                 235                 240

Leu Phe Pro Pro Lys Pro Lys Asp Thr Leu Met Ile Ser Arg Thr Pro
            245                 250                 255

Glu Val Thr Cys Val Val Val Asp Val Ser His Glu Asp Pro Glu Val
        260                 265                 270

Gln Phe Asn Trp Tyr Val Asp Gly Val Glu Val His Asn Ala Lys Thr
    275                 280                 285

Lys Pro Arg Glu Glu Gln Phe Ala Ser Thr Phe Arg Val Val Ser Val
290                 295                 300

Leu Thr Val Val His Gln Asp Trp Leu Asn Gly Lys Glu Tyr Lys Cys
305                 310                 315                 320

Lys Val Ser Asn Lys Gly Leu Pro Ala Pro Ile Glu Lys Thr Ile Ser
            325                 330                 335

Lys Thr Lys Gly Gln Pro Arg Glu Pro Gln Val Tyr Thr Leu Pro Pro
        340                 345                 350

Ser Arg Glu Glu Met Thr Lys Asn Gln Val Ser Leu Thr Cys Leu Val
    355                 360                 365

Lys Gly Phe Tyr Pro Ser Asp Ile Ala Val Glu Trp Glu Ser Asn Gly
370                 375                 380

Gln Pro Glu Asn Asn Tyr Lys Thr Thr Pro Pro Met Leu Asp Ser Asp
385                 390                 395                 400

Gly Ser Phe Phe Leu Tyr Ser Lys Leu Thr Val Asp Lys Ser Arg Trp
            405                 410                 415

Gln Gln Gly Asn Val Phe Ser Cys Ser Val Met His Glu Ala Leu His
        420                 425                 430

Asn His Tyr Thr Gln Lys Ser Leu Ser Leu Ser Pro Gly Lys
    435                 440                 445

<210> SEQ ID NO 19
<211> LENGTH: 1350
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 19
gaggtgcagc tggtggagtc tgggggaggc ttggtccagc ctggagggtc cctgagactc        60
tcctgtgcag cctctggatt caccttctca tactattgga tggactgggt ccgccaggct       120
ccagggaagg ggctggagtg ggttggccgt atcagactga atctaacaa ctatgccacc        180 gaatacgccg cgtctgtgaa aggcagattc accatctcaa gagatgattc aaagaactca       240
ctgtatctgc aaatgaacag cctgaaaacc gaggacacgg ccgtgtatta ctgtaacaga       300
agagatgagt attacgccat ggattattgg ggccaaggga caatggtcac cgtctcttca       360
gctagcacca agggcccatc ggtcttcccc ctggcaccct cctccaagag cacctctggg       420
ggcacagcgg ccctgggctg cctggtcaag gactacttcc ccgaaccggt gacggtgtcg       480
tggaactcag gcgccctgac cagcggcgtg cacaccttcc cggctgtcct acagtcctca       540

```
ggactctact ccctcagcag cgtggtgacc gtgccctcca gcagcttggg cacccagacc    600
tacatctgca acgtgaatca caagcccagc aacaccaagg tggacaagaa agttgagccc    660
aaatcttgtg acaaaactca cacatgccca ccgtgcccag cacctgaact cctgggggga    720
ccgtcagtct tcctcttccc cccaaaaccc aaggacaccc tcatgatctc ccggacccct    780
gaggtcacat gcgtggtggt ggacgtgagc cacagagacc ctgaggtcaa gttcaactgg    840
tacgtggacg gcgtggaggt gcataatgcc aagacaaagc cgcgggagga gcagtacaac    900
agcacgtacc gtgtggtcag cgtcctcacc gtcctgcacc aggactggct gaatggcaag    960
gagtacaagt gcaaggtctc caacaaagcc ctcccagccc ccatcgagaa aaccatctcc   1020
aaagccaaag ggcagccccg agaaccacag gtgtacaccc tgcccccatc ccgggaggag   1080
atgaccaaga accaggtcag cctgacctgc ctggtcaaag gcttctatcc cagcgacatc   1140
gccgtggagt gggagagcaa tgggcagccg gagaacaact acaagaccac gcctcccgtg   1200
ctggactccg acggctcctt cttcctctac agcaagctca ccgtggacaa gagcaggtgg   1260
cagcagggga acgtcttctc atgctccgtg atgcatgagg ctctgcacaa ccactacacg   1320
cagaagagcc tctccctgtc tccgggtaaa                                    1350
```

<210> SEQ ID NO 20
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Tyr Tyr
            20                  25                  30

Trp Met Asp Trp Val Arg Gln Ala Pro Gly Lys Gly Leu Glu Trp Val
        35                  40                  45

Gly Arg Ile Arg Leu Lys Ser Asn Asn Tyr Ala Thr Glu Tyr Ala Ala
    50                  55                  60

Ser Val Lys Gly Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Asn Arg Arg Asp Glu Tyr Tyr Ala Met Asp Tyr Trp Gly Gln
            100                 105                 110

Gly Thr Met Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Val Val Thr Val Pro
            180                 185                 190

Ser Ser Ser Leu Gly Thr Gln Thr Tyr Ile Cys Asn Val Asn His Lys
        195                 200                 205
```

```
Pro Ser Asn Thr Lys Val Asp Lys Lys Val Glu Pro Lys Ser Cys Asp
    210                 215                 220
Lys Thr His Thr Cys Pro Pro Cys Pro Ala Pro Glu Leu Leu Gly Gly
225                 230                 235                 240
Pro Ser Val Phe Leu Phe Pro Pro Lys Pro Lys Asp Thr Leu Met Ile
            245                 250                 255
Ser Arg Thr Pro Glu Val Thr Cys Val Val Val Asp Val Ser His Arg
        260                 265                 270
Asp Pro Glu Val Lys Phe Asn Trp Tyr Val Asp Gly Val Glu Val His
    275                 280                 285
Asn Ala Lys Thr Lys Pro Arg Glu Glu Gln Tyr Asn Ser Thr Tyr Arg
290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
            325                 330                 335
Lys Thr Ile Ser Lys Ala Lys Gly Gln Pro Arg Glu Pro Gln Val Tyr
        340                 345                 350
Thr Leu Pro Pro Ser Arg Glu Glu Met Thr Lys Asn Gln Val Ser Leu
    355                 360                 365
Thr Cys Leu Val Lys Gly Phe Tyr Pro Ser Asp Ile Ala Val Glu Trp
370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
            405                 410                 415
Lys Ser Arg Trp Gln Gln Gly Asn Val Phe Ser Cys Ser Val Met His
        420                 425                 430
Glu Ala Leu His Asn His Tyr Thr Gln Lys Ser Leu Ser Leu Ser Pro
    435                 440                 445
Gly Lys
    450

<210> SEQ ID NO 21
<211> LENGTH: 654
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 21
gacattgtgc tgacccaatc tccaggttct ttggctgtgt ctctagggca gagggccacc      60
atctcctgca gagccagcga aagtgttgat aattttggca ttagttttat gaactggttc     120
caacagaaac caggacagcc accccgactc ctcatctatg gtgcatccaa ccaaggatcc     180
ggggtccctg ccaggtttag tggcagtggg tctgggacag acttcagcct caacatccat     240
cctgtggagg aggatgatgc tgcaatgtat ttctgtcagc aaagtaagga ggttccgtgg     300
acgttcggtg gaggcaccaa gctggaaatc aaacgtacgg tggctgcacc atctgtcttc     360
atcttcccgc catctgatga gcagttgaaa tctggaactg cctctgttgt gtgcctgctg     420
aataacttct atcccagaga ggccaaagta cagtggaagg tggataacgc cctccaatcg     480
ggtaactccc aggagagtgt cacagagcag gacagcaagg acagcaccta cagcctcagc     540
```
agcaccctga cgctgagcaa agcagactac gagaaacaca aagtctacgc ctgcgaagtc    600
acccatcagg gcctgagctc gcccgtcaca aagagcttca acaggggaga gtgt          654

<210> SEQ ID NO 22
<211> LENGTH: 218
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Asp Ile Val Leu Thr Gln Ser Pro Gly Ser Leu Ala Val Ser Leu Gly
1               5                   10                  15

Gln Arg Ala Thr Ile Ser Cys Arg Ala Ser Glu Ser Val Asp Asn Phe
            20                  25                  30

Gly Ile Ser Phe Met Asn Trp Phe Gln Gln Lys Pro Gly Gln Pro Pro
        35                  40                  45

Arg Leu Leu Ile Tyr Gly Ala Ser Asn Gln Gly Ser Gly Val Pro Ala
    50                  55                  60

Arg Phe Ser Gly Ser Gly Ser Gly Thr Asp Phe Ser Leu Asn Ile His
65                  70                  75                  80

Pro Val Glu Glu Asp Asp Ala Ala Met Tyr Phe Cys Gln Gln Ser Lys
                85                  90                  95

Glu Val Pro Trp Thr Phe Gly Gly Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 23
<211> LENGTH: 654
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 23
gaaattgtgt tgacacagtc tccagccacc ctgtctttgt ctccagggga aagagccacc    60
ctctcctgca gggccagtga atctgtggat aacttcggga tctccttctt agcctggtac   120
caacagaaac ctggccaggc tcccaggctc ctcatctatg gagcctccaa cagggccact   180
ggcatcccag ccaggttcag tggcagtggg tctgggacag acttcactct caccatcagc   240
agcctagagc ctgaagattt tgcagtttat tactgtcagc aatctaaaga ggtgccatgg   300
accttcggcc aagggaccaa ggtggaaatc aaacgtacgg tggctgcacc atctgtcttc   360

```
atcttcccgc catctgatga gcagttgaaa tctggaactg cctctgttgt gtgcctgctg    420
aataacttct atcccagaga ggccaaagta cagtggaagg tggataacgc cctccaatcg    480
ggtaactccc aggagagtgt cacagagcag gacagcaagg acagcaccta cagcctcagc    540
agcaccctga cgctgagcaa agcagactac gagaaacaca agtctacgc ctgcgaagtc    600 acccatcagg gcctgagctc gcccgtcaca aagagcttca caggggaga gtgt           654
```

<210> SEQ ID NO 24
<211> LENGTH: 218
<212> TYPE: PRT
<213> ORGANISM: Artificial Sequence
<220> FEATURE:
<223> OTHER INFORMATION: Description of Artificial Sequence: Synthetic
    polypeptide <400> SEQUENCE: 24

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Glu Ser Val Asp Asn Phe
            20                  25                  30

Gly Ile Ser Phe Leu Ala Trp Tyr Gln Gln Lys Pro Gly Gln Ala Pro
        35                  40                  45

Arg Leu Leu Ile Tyr Gly Ala Ser Asn Arg Ala Thr Gly Ile Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln Gln Ser Lys
                85                  90                  95

Glu Val Pro Trp Thr Phe Gly Gln Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 25
<211> LENGTH: 5
<212> TYPE: PRT
<213> ORGANISM: Artificial Sequence
<220> FEATURE:
<223> OTHER INFORMATION: Description of Artificial Sequence: Synthetic
    peptide <400> SEQUENCE: 25

Asn Tyr Gly Met Asn
1               5

```
<210> SEQ ID NO 26
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Trp Leu Asn Thr Tyr Thr Gly Glu Ser Ile Tyr Pro Asp Asp Phe Lys
1               5                   10                  15

Gly

<210> SEQ ID NO 27
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Gly Asp Tyr Gly Tyr Asp Asp Pro Leu Asp Tyr
1               5                   10

<210> SEQ ID NO 28
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Arg Ser Ser Lys Ser Leu Leu His Thr Asn Gly Asn Thr Tyr Leu His
1               5                   10                  15

<210> SEQ ID NO 29
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Arg Met Ser Val Leu Ala Ser
1               5

<210> SEQ ID NO 30
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Met Gln His Leu Glu Tyr Pro Leu Thr
1               5

<210> SEQ ID NO 31
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide
```

<400> SEQUENCE: 31

```
cagatccagt tggtgcagtc tggacctgag ctgaagaagc ctggagagac agtcaagatc      60
tcctgcaagg cttctgggta taccttcaca aactatggaa tgaactgggt gaagcaggct     120
ccaggaaagg gtttaaagtg gatgggctgg ttaaacacct acactggaga gtcaatatat     180
cctgatgact tcaagggacg gtttgccttc tcttcggaaa cctctgccag cactgcctat     240
ttgcagatca acaacctcaa aaatgaggac atggctacat atttctgtgc aagaggggac     300
tatggttacg acgaccgttt ggactactgg ggtcaaggaa cctcagtcac cgtctcctca     360
```

<210> SEQ ID NO 32
<211> LENGTH: 120
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 32

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Tyr
            20                  25                  30

Gly Met Asn Trp Val Lys Gln Ala Pro Gly Lys Gly Leu Lys Trp Met
        35                  40                  45

Gly Trp Leu Asn Thr Tyr Thr Gly Glu Ser Ile Tyr Pro Asp Asp Phe
    50                  55                  60

Lys Gly Arg Phe Ala Phe Ser Ser Glu Thr Ser Ala Ser Thr Ala Tyr
65                  70                  75                  80

Leu Gln Ile Asn Asn Leu Lys Asn Glu Asp Met Ala Thr Tyr Phe Cys
                85                  90                  95

Ala Arg Gly Asp Tyr Gly Tyr Asp Asp Pro Leu Asp Tyr Trp Gly Gln
            100                 105                 110

Gly Thr Ser Val Thr Val Ser Ser
        115                 120

<210> SEQ ID NO 33
<211> LENGTH: 336
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 33

```
gacattgtga tgacccaggc tgcaccctct gtacctgtca ctcctggaga gtcagtatcc      60
atctcctgca ggtctagtaa gagtctcctg catactaatg caacacttta cttgcattgg     120
ttcctacaga ggccaggcca gtctcctcag ctcctgatat atcggatgtc cgtccttgcc     180
tcaggagtcc cagacaggtt cagtggcagt gggtcaggaa ctgctttcac actgagcatc     240
agtagagtgg aggctgagga tgtgggtgtt ttttactgta tgcaacatct agaatatccg     300
ctcacgttcg gtgctgggac caagctggaa ctgaaa                               336
```

<210> SEQ ID NO 34
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Asp Ile Val Met Thr Gln Ala Ala Pro Ser Val Pro Val Thr Pro Gly
1               5                   10                  15

Glu Ser Val Ser Ile Ser Cys Arg Ser Ser Lys Ser Leu Leu His Thr
            20                  25                  30

Asn Gly Asn Thr Tyr Leu His Trp Phe Leu Gln Arg Pro Gly Gln Ser
        35                  40                  45

Pro Gln Leu Leu Ile Tyr Arg Met Ser Val Leu Ala Ser Gly Val Pro
    50                  55                  60

Asp Arg Phe Ser Gly Ser Gly Ser Gly Thr Ala Phe Thr Leu Ser Ile
65                  70                  75                  80

Ser Arg Val Glu Ala Glu Asp Val Gly Val Phe Tyr Cys Met Gln His
                85                  90                  95

Leu Glu Tyr Pro Leu Thr Phe Gly Ala Gly Thr Lys Leu Glu Leu Lys
            100                 105                 110

<210> SEQ ID NO 35
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 35
caggtgcagc tggtgcaatc tgggtctgag ttgaagaagc ctggggcctc agtgaaggtt      60
tcctgcaagg cttctggata caccttcact aactatggta tgaattgggt gcgacaggcc     120
cctggacaag ggcttgagtg gatgggatgg ctcaacacct acactgggga gtcaacgtat     180
gcccagggct tcacaggacg gtttgtcttc tccttggaca cctctgtcag cacggcatat     240
ctgcagatca gcagcctaaa ggctgaggac actgccgtgt attactgtgc gagaggggac     300
tatggttacg acgacccttt ggactactgg gggcaaggga ccacggtcac cgtctcctca     360

<210> SEQ ID NO 36
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Glu Trp Met
        35                  40                  45

Gly Trp Leu Asn Thr Tyr Thr Gly Glu Ser Thr Tyr Ala Gln Gly Phe
    50                  55                  60

Thr Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

```
Ala Arg Gly Asp Tyr Gly Tyr Asp Asp Pro Leu Asp Tyr Trp Gly Gln
            100                 105                 110

Gly Thr Thr Val Thr Val Ser Ser
        115                 120

<210> SEQ ID NO 37
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 37
caggtgcagc tggtgcagtc tggccatgag gtgaagcagc ctggggcctc agtgaaggtc      60
tcctgcaagg cttctgggta taccttcaca aactatggaa tgaactgggt gaaacaggcc    120
cctggacaag ggcttaagtg gatgggctgg ttaaacacct acactggaga gtcaatatat    180
cctgatgact tcaagggacg gtttgccttc tccagtgaca cctctgccag cacagcatac    240
ctgcagatca acaacctaaa ggctgaggac atggccatgt atttctgtgc gagaggggac    300
tatggttacg acgacccttt ggactactgg gggcaaggga ccacggtcac cgtctcctca    360

<210> SEQ ID NO 38
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Gln Val Gln Leu Val Gln Ser Gly His Glu Val Lys Gln Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Lys Gln Ala Pro Gly Gln Gly Leu Lys Trp Met
        35                  40                  45

Gly Trp Leu Asn Thr Tyr Thr Gly Glu Ser Ile Tyr Pro Asp Asp Phe
    50                  55                  60

Lys Gly Arg Phe Ala Phe Ser Ser Asp Thr Ser Ala Ser Thr Ala Tyr
65                  70                  75                  80

Leu Gln Ile Asn Asn Leu Lys Ala Glu Asp Met Ala Met Tyr Phe Cys
                85                  90                  95

Ala Arg Gly Asp Tyr Gly Tyr Asp Asp Pro Leu Asp Tyr Trp Gly Gln
            100                 105                 110

Gly Thr Thr Val Thr Val Ser Ser
        115                 120

<210> SEQ ID NO 39
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 39
gatattgtga tgacccagac tccactctcc ctgcccgtca cccctggaga gccggcctcc     60
atctcctgca ggtctagtaa gtctctgctg cataccaacg gaacaccta tttggactgg    120
```

```
tacctgcaga agccagggca gtctccacag ctcctgatct ataggatgtc ctatcgggcc    180
tctggagtcc cagacaggtt cagtggcagt gggtcaggca ctgatttcac actgaaaatc    240
agcagggtgg aggctgagga tgttggagtt tattactgca tgcagcatct ggagtatcca    300
ctgaccttcg gcggagggac caaggtggag atcaaa                              336
```

<210> SEQ ID NO 40
<211> LENGTH: 336
<212> TYPE: DNA
<213> ORGANISM: Artificial Sequence
<220> FEATURE:
<223> OTHER INFORMATION: Description of Artificial Sequence: Synthetic
       polynucleotide

<400> SEQUENCE: 40

```
gatattgtga tgacccagac tccactctcc ctgcccgtca cccctggaga gccggcctcc    60
atctcctgca ggtctagtaa gagtctcctg catactaatg caacactta cttgcattgg    120 tacctgcaga agccagggca gtctccacag ctcctgatat atcggatgtc cgtccttgcc    180
tcaggagtcc cagacaggtt cagtggcagt gggtcaggca ctgatttcac actgaaaatc    240
agcagggtgg aggctgagga tgttggagtt tattactgca tgcaacatct agaatatccg    300
ctcacgttcg gcggagggac caaggtggag atcaaa                              336
```

<210> SEQ ID NO 41
<211> LENGTH: 112
<212> TYPE: PRT
<213> ORGANISM: Artificial Sequence
<220> FEATURE:
<223> OTHER INFORMATION: Description of Artificial Sequence: Synthetic
       polypeptide

<400> SEQUENCE: 41

Asp Ile Val Met Thr Gln Thr Pro Leu Ser Leu Pro Val Thr Pro Gly
1               5                   10                  15

Glu Pro Ala Ser Ile Ser Cys Arg Ser Ser Lys Ser Leu Leu His Thr
            20                  25                  30

Asn Gly Asn Thr Tyr Leu His Trp Tyr Leu Gln Lys Pro Gly Gln Ser
        35                  40                  45

Pro Gln Leu Leu Ile Tyr Arg Met Ser Val Leu Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln His
                85                  90                  95

Leu Glu Tyr Pro Leu Thr Phe Gly Gly Gly Thr Lys Val Glu Ile Lys
            100                 105                 110

<210> SEQ ID NO 42
<211> LENGTH: 1350
<212> TYPE: DNA
<213> ORGANISM: Artificial Sequence
<220> FEATURE:
<223> OTHER INFORMATION: Description of Artificial Sequence: Synthetic
       polynucleotide

<400> SEQUENCE: 42

```
cagatccagt tggtgcagtc tggacctgag ctgaagaagc ctggagagac agtcaagatc    60
tcctgcaagg cttctgggta taccttcaca aactatggaa tgaactgggt gaagcaggct    120
ccaggaaagg gtttaaagtg gatgggctgg ttaaacacct acactggaga gtcaatatat    180
```

```
cctgatgact tcaagggacg gtttgccttc tcttcggaaa cctctgccag cactgcctat    240
ttgcagatca acaacctcaa aaatgaggac atggctacat atttctgtgc aagaggggac    300
tatggttacg acgacccttt ggactactgg ggtcaaggaa cctcagtcac cgtctcctca    360
gctagcacca agggcccatc ggtcttcccc ctggcaccct cctccaagag cacctctggg    420
ggcacagcgg ccctgggctg cctggtcaag gactacttcc ccgaaccggt gacggtgtcg    480
tggaactcag gcgccctgac cagcggcgtg cacaccttcc cggctgtcct acagtcctca    540
ggactctact ccctcagcag cgtggtgacc gtgccctcca gcagcttggg cacccagacc    600
tacatctgca acgtgaatca caagcccagc aacaccaagg tggacaagaa agttgagccc    660
aaatcttgtg acaaaactca cacatgccca ccgtgcccag cacctgaact cctggggggga    720 ccgtcagtct tcctcttccc cccaaaaccc aaggacaccc tcatgatctc ccggacccct    780
gaggtcacat gcgtggtggt ggacgtgagc cacagagacc ctgaggtcaa gttcaactgg    840
tacgtggacg gcgtggaggt gcataatgcc aagacaaagc cgcggggagga gcagtacaac    900 agcacgtacc gtgtggtcag cgtcctcacc gtcctgcacc aggactggct gaatggcaag    960
gagtacaagt gcaaggtctc caacaaagcc ctcccagccc ccatcgagaa aaccatctcc    1020
aaagccaaag ggcagccccg agaaccacag gtgtacaccc tgcccccatc ccgggaggag    1080
atgaccaaga accaggtcag cctgacctgc ctggtcaaag gcttctatcc cagcgacatc    1140
gccgtggagt gggagagcaa tgggcagccg gagaacaact acaagaccac gcctcccgtg    1200
ctggactccg acggctcctt cttcctctac agcaagctca ccgtggacaa gagcaggtgg    1260
cagcagggga acgtcttctc atgctccgtg atgcatgagg ctctgcacaa ccactacacg    1320
cagaagagcc tctccctgtc tccgggtaaa                                    1350
```

<210> SEQ ID NO 43
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

```
Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Tyr
            20                  25                  30

Gly Met Asn Trp Val Lys Gln Ala Pro Gly Lys Gly Leu Lys Trp Met
        35                  40                  45

Gly Trp Leu Asn Thr Tyr Thr Gly Glu Ser Ile Tyr Pro Asp Asp Phe
    50                  55                  60

Lys Gly Arg Phe Ala Phe Ser Ser Glu Thr Ser Ala Ser Thr Ala Tyr
65                  70                  75                  80

Leu Gln Ile Asn Asn Leu Lys Asn Glu Asp Met Ala Thr Tyr Phe Cys
                85                  90                  95

Ala Arg Gly Asp Tyr Gly Tyr Asp Asp Pro Leu Asp Tyr Trp Gly Gln
            100                 105                 110

Gly Thr Ser Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140
```

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
            165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
            210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser His Arg
            260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
            325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
            355                 360                 365

Thr Cys Leu Val Lys Gly Phe Tyr Pro Ser Asp Ile Ala Val Glu Trp
            370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Lys
450

<210> SEQ ID NO 44
<211> LENGTH: 1338
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 44
cagatccagt tggtgcagtc tggacctgag ctgaagaagc ctggagagac agtcaagatc      60
tcctgcaagg cttctgggta taccttcaca aactatggaa tgaactgggt gaagcaggct     120
ccaggaaagg gtttaaagtg gatgggctgg ttaaacacct acactggaga gtcaatatat     180
cctgatgact tcaagggacg gtttgccttc tcttcggaaa cctctgccag cactgcctat     240

```
ttgcagatca acaacctcaa aaatgaggac atggctacat atttctgtgc aagaggggac     300
tatggttacg acgacccttt ggactactgg ggtcaaggaa cctcagtcac cgtctcctca     360
gctagcacca agggcccatc ggtcttcccc ctggcgccct gctccaggag cacctccgag     420
agcacagcgg ccctgggctg cctggtcaag gactacttcc ccgaaccggt gacggtgtcg     480
tggaactcag gcgctctgac cagcggcgtg cacaccttcc cagctgtcct acagtcctca     540
ggactctact ccctcagcag cgtggtgacc gtgccctcca gcaacttcgg cacccagacc     600
tacacctgca acgtagatca caagcccagc aacaccaagg tggacaagac agttgagcgc     660
aaatgttgtg tcgagtgccc accgtgccca gcaccacctg tggcaggacc gtcagtcttc     720
ctcttccccc caaaacccaa ggacaccctc atgatctccc ggacccctga ggtcacgtgc     780
gtggtggtgg acgtgagcca cgaagacccc gaggtccagt tcaactggta cgtggacggc     840
gtggaggtgc ataatgccaa gacaaagcca cgggaggagc agttcgccag cacgttccgt     900
gtggtcagcg tcctcaccgt tgtgcaccag gactggctga acggcaagga gtacaagtgc     960
aaggtctcca acaaaggcct cccagccccc atcgagaaaa ccatctccaa aaccaaaggg    1020
cagccccgag aaccacaggt gtacaccctg cccccatccc gggaggagat gaccaagaac    1080
caggtcagcc tgacctgcct ggtcaaaggc ttctacccca gcgacatcgc cgtggagtgg    1140
gagagcaatg ggcagccgga gaacaactac aagaccacgc ctcccatgct ggactccgac    1200
ggctccttct tcctctacag caagctcacc gtggacaaga gcaggtggca gcaggggaac    1260
gtcttctcat gctccgtgat gcatgaggct ctgcacaacc actacacgca gaagagcctc    1320
tccctgtctc cgggtaaa                                                  1338
```

<210> SEQ ID NO 45
<211> LENGTH: 446
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 45

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Tyr
            20                  25                  30

Gly Met Asn Trp Val Lys Gln Ala Pro Gly Lys Gly Leu Lys Trp Met
        35                  40                  45

Gly Trp Leu Asn Thr Tyr Thr Gly Glu Ser Ile Tyr Pro Asp Asp Phe
    50                  55                  60

Lys Gly Arg Phe Ala Phe Ser Ser Glu Thr Ser Ala Ser Thr Ala Tyr
65                  70                  75                  80

Leu Gln Ile Asn Asn Leu Lys Asn Glu Asp Met Ala Thr Tyr Phe Cys
                85                  90                  95

Ala Arg Gly Asp Tyr Gly Tyr Asp Asp Pro Leu Asp Tyr Trp Gly Gln
            100                 105                 110

Gly Thr Ser Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

```
Trp Asn Ser Gly Ala Leu Thr Ser Gly Val His Thr Phe Pro Ala Val
            165                 170                 175
Leu Gln Ser Ser Gly Leu Tyr Ser Leu Ser Ser Val Val Thr Val Pro
        180                 185                 190
Ser Ser Asn Phe Gly Thr Gln Thr Tyr Thr Cys Asn Val Asp His Lys
    195                 200                 205
Pro Ser Asn Thr Lys Val Asp Lys Thr Val Glu Arg Lys Cys Cys Val
210                 215                 220
Glu Cys Pro Pro Cys Pro Ala Pro Pro Val Ala Gly Pro Ser Val Phe
225                 230                 235                 240
Leu Phe Pro Pro Lys Pro Lys Asp Thr Leu Met Ile Ser Arg Thr Pro
                245                 250                 255
Glu Val Thr Cys Val Val Val Asp Val Ser His Glu Asp Pro Glu Val
            260                 265                 270
Gln Phe Asn Trp Tyr Val Asp Gly Val Glu Val His Asn Ala Lys Thr
        275                 280                 285
Lys Pro Arg Glu Glu Gln Phe Ala Ser Thr Phe Arg Val Val Ser Val
    290                 295                 300
Leu Thr Val Val His Gln Asp Trp Leu Asn Gly Lys Glu Tyr Lys Cys
305                 310                 315                 320
Lys Val Ser Asn Lys Gly Leu Pro Ala Pro Ile Glu Lys Thr Ile Ser
                325                 330                 335
Lys Thr Lys Gly Gln Pro Arg Glu Pro Gln Val Tyr Thr Leu Pro Pro
            340                 345                 350
Ser Arg Glu Glu Met Thr Lys Asn Gln Val Ser Leu Thr Cys Leu Val
        355                 360                 365
Lys Gly Phe Tyr Pro Ser Asp Ile Ala Val Glu Trp Glu Ser Asn Gly
    370                 375                 380
Gln Pro Glu Asn Asn Tyr Lys Thr Thr Pro Pro Met Leu Asp Ser Asp
385                 390                 395                 400
Gly Ser Phe Phe Leu Tyr Ser Lys Leu Thr Val Asp Lys Ser Arg Trp
                405                 410                 415
Gln Gln Gly Asn Val Phe Ser Cys Ser Val Met His Glu Ala Leu His
            420                 425                 430
Asn His Tyr Thr Gln Lys Ser Leu Ser Leu Ser Pro Gly Lys
        435                 440                 445

<210> SEQ ID NO 46
<211> LENGTH: 1350
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 46
caggtgcagc tggtgcaatc tgggtctgag ttgaagaagc ctggggcctc agtgaaggtt      60
tcctgcaagg cttctggata caccttcact aactatggta tgaattgggt gcgacaggcc    120
cctggacaag gcttgagtg gatgggatgg ctcaacacct acactgggga gtcaacgtat     180
gcccagggct tcacaggacg gtttgtcttc tccttggaca cctctgtcag cacggcatat    240
ctgcagatca gcagcctaaa ggctgaggac actgccgtgt attactgtgc gagaggggac    300
tatggttacg acgacccttt ggactactgg ggccaaggga ccacggtcac cgtctcctca    360
gctagcacca agggcccatc ggtcttcccc ctggcaccct cctccaagag cacctctggg    420
```

```
ggcacagcgg ccctgggctg cctggtcaag gactacttcc ccgaaccggt gacggtgtcg    480
tggaactcag gcgccctgac cagcggcgtg cacaccttcc cggctgtcct acagtcctca    540
ggactctact ccctcagcag cgtggtgacc gtgccctcca gcagcttggg cacccagacc    600
tacatctgca acgtgaatca caagcccagc aacaccaagg tggacaagaa agttgagccc    660
aaatcttgtg acaaaactca cacatgccca ccgtgcccag cacctgaact cctgggggga    720
ccgtcagtct tcctcttccc cccaaaaccc aaggacaccc tcatgatctc ccggacccct    780
gaggtcacat gcgtggtggt ggacgtgagc cacagagacc ctgaggtcaa gttcaactgg    840
tacgtggacg gcgtggaggt gcataatgcc aagacaaagc cgcggaggga gcagtacaac    900
agcacgtacc gtgtggtcag cgtcctcacc gtcctgcacc aggactggct gaatggcaag    960
gagtacaagt gcaaggtctc caacaaagcc ctcccagccc ccatcgagaa aaccatctcc   1020
aaagccaaag ggcagccccg agaaccacag gtgtacaccc tgcccccatc ccgggaggag   1080
atgaccaaga accaggtcag cctgacctgc ctggtcaaag gcttctatcc cagcgacatc   1140
gccgtggagt gggagagcaa tgggcagccg gagaacaact acaagaccac gcctcccgtg   1200
ctggactccg acggctcctt cttcctctac agcaagctca ccgtggacaa gagcaggtgg   1260
cagcagggga acgtcttctc atgctccgtg atgcatgagg ctctgcacaa ccactacacg   1320
cagaagagcc tctccctgtc tccgggtaaa                                     1350
```

<210> SEQ ID NO 47
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

```
Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Glu Trp Met
        35                  40                  45

Gly Trp Leu Asn Thr Tyr Thr Gly Glu Ser Thr Tyr Ala Gln Gly Phe
    50                  55                  60

Thr Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Gly Asp Tyr Gly Tyr Asp Asp Pro Leu Asp Tyr Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190
```

```
Ser Ser Ser Leu Gly Thr Gln Thr Tyr Ile Cys Asn Val Asn His Lys
            195                 200                 205
Pro Ser Asn Thr Lys Val Asp Lys Lys Val Glu Pro Lys Ser Cys Asp
210                 215                 220
Lys Thr His Thr Cys Pro Pro Cys Pro Ala Pro Glu Leu Leu Gly Gly
225                 230                 235                 240
Pro Ser Val Phe Leu Phe Pro Pro Lys Pro Lys Asp Thr Leu Met Ile
                245                 250                 255
Ser Arg Thr Pro Glu Val Thr Cys Val Val Val Asp Val Ser His Arg
                260                 265                 270
Asp Pro Glu Val Lys Phe Asn Trp Tyr Val Asp Gly Val Glu Val His
            275                 280                 285
Asn Ala Lys Thr Lys Pro Arg Glu Glu Gln Tyr Asn Ser Thr Tyr Arg
290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
                325                 330                 335
Lys Thr Ile Ser Lys Ala Lys Gly Gln Pro Arg Glu Pro Gln Val Tyr
                340                 345                 350
Thr Leu Pro Pro Ser Arg Glu Glu Met Thr Lys Asn Gln Val Ser Leu
            355                 360                 365
Thr Cys Leu Val Lys Gly Phe Tyr Pro Ser Asp Ile Ala Val Glu Trp
370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                405                 410                 415
Lys Ser Arg Trp Gln Gln Gly Asn Val Phe Ser Cys Ser Val Met His
                420                 425                 430
Glu Ala Leu His Asn His Tyr Thr Gln Lys Ser Leu Ser Leu Ser Pro
            435                 440                 445
Gly Lys
    450

<210> SEQ ID NO 48
<211> LENGTH: 1350
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 48
caggtgcagc tggtgcagtc tggccatgag gtgaagcagc tggggcctc agtgaaggtc         60 tcctgcaagg cttctgggta ccttcaca aactatggaa tgaactgggt gaaacaggcc        120
cctggacaag ggcttaagtg gatgggctgg ttaaacacct acactggaga gtcaatatat      180
cctgatgact tcaagggacg gtttgccttc tccagtgaca cctctgccag cacagcatac      240
ctgcagatca caaacctaaa ggctgaggac atggccatgt atttctgtgc gagggggac       300 tatggttacg acgaccctt ggactactgg ggcaaggga ccacggtcac cgtctcctca       360
gctagcacca aggcccatc ggtcttcccc ctggcaccct cctccaagag cacctctggg       420
ggcacagcgg ccctgggctg cctggtcaag gactacttcc ccgaaccggt gacggtgtcg     480
tggaactcag gcgccctgac cagcggcgtg cacaccttcc cggctgtcct acagtcctca     540
```

```
ggactctact ccctcagcag cgtggtgacc gtgccctcca gcagcttggg cacccagacc    600
tacatctgca acgtgaatca caagcccagc aacaccaagg tggacaagaa agttgagccc    660
aaatcttgtg acaaaactca cacatgccca ccgtgcccag cacctgaact cctgggggga    720
ccgtcagtct tcctcttccc cccaaaaccc aaggacaccc tcatgatctc ccggaccccc    780
gaggtcacat gcgtggtggt ggacgtgagc cacagagacc ctgaggtcaa gttcaactgg    840
tacgtggacg gcgtggaggt gcataatgcc aagacaaagc cgcgggagga gcagtacaac    900
agcacgtacc gtgtggtcag cgtcctcacc gtcctgcacc aggactggct gaatggcaag    960
gagtacaagt gcaaggtctc caacaaagcc ctcccagccc ccatcgagaa aaccatctcc   1020
aaagccaaag ggcagccccg agaaccacag gtgtacaccc tgcccccatc ccgggaggag   1080
atgaccaaga accaggtcag cctgacctgc ctggtcaaag gcttctatcc cagcgacatc   1140
gccgtggagt gggagagcaa tgggcagccg gagaacaact acaagaccac gcctcccgtg   1200
ctggactccg acggctcctt cttcctctac agcaagctca ccgtggacaa gagcaggtgg   1260
cagcagggga acgtcttctc atgctccgtg atgcatgagg ctctgcacaa ccactacacg   1320
cagaagagcc tctccctgtc tccgggtaaa                                    1350
```

<210> SEQ ID NO 49
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

```
Gln Val Gln Leu Val Gln Ser Gly His Glu Val Lys Gln Pro Gly Ala
1               5                   10                  15

Ser Val Lys Val Ser Cys Lys Ala Ser Gly Tyr Thr Phe Thr Asn Tyr
                20                  25                  30

Gly Met Asn Trp Val Lys Gln Ala Pro Gly Gln Gly Leu Lys Trp Met
            35                  40                  45

Gly Trp Leu Asn Thr Tyr Thr Gly Glu Ser Ile Tyr Pro Asp Asp Phe
        50                  55                  60

Lys Gly Arg Phe Ala Phe Ser Ser Asp Thr Ser Ala Ser Thr Ala Tyr
65                  70                  75                  80

Leu Gln Ile Asn Asn Leu Lys Ala Glu Asp Met Ala Met Tyr Phe Cys
                85                  90                  95

Ala Arg Gly Asp Tyr Gly Tyr Asp Asp Pro Leu Asp Tyr Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205
```

```
Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser His Arg
        260                 265                 270

Asp Pro Glu Val Lys Phe Asn Trp Tyr Val Asp Gly Val Glu Val His
    275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
            325                 330                 335

Lys Thr Ile Ser Lys Ala Lys Gly Gln Pro Arg Glu Pro Gln Val Tyr
        340                 345                 350

Thr Leu Pro Pro Ser Arg Glu Glu Met Thr Lys Asn Gln Val Ser Leu
    355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His
        420                 425                 430

Glu Ala Leu His Asn His Tyr Thr Gln Lys Ser Leu Ser Leu Ser Pro
    435                 440                 445

Gly Lys
    450

<210> SEQ ID NO 50
<211> LENGTH: 657
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 50
gacattgtga tgacccaggc tgcaccctct gtacctgtca ctcctggaga gtcagtatcc      60
atctcctgca ggtctagtaa gagtctcctg catactaatg caacacttta cttgcattgg    120
ttcctacaga ggccaggcca gtctcctcag ctcctgatat atcggatgtc cgtccttgcc    180
tcaggagtcc cagacaggtt cagtggcagt gggtcaggaa ctgctttcac actgagcatc    240
agtagagtgg aggctgagga tgtgggtgtt ttttactgta tgcaacatct agaatatccg    300
ctcacgttcg gtgctgggac caagctggaa ctgaaacgta cggtggctgc accatctgtc    360
ttcatcttcc cgccatctga tgagcagttg aaatctggaa ctgcctctgt tgtgtgcctg    420
ctgaataact tctatcccag agaggccaaa gtacagtgga aggtggataa cgccctccaa    480
tcgggtaact cccaggagag tgtcacagag caggacagca aggacagcac ctacagcctc    540
```
agcagcaccc tgacgctgag caaagcagac tacgagaaac acaaagtcta cgcctgcgaa    600
gtcacccatc agggcctgag ctcgcccgtc acaaagagct tcaacagggg agagtgt       657

<210> SEQ ID NO 51
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

Asp Ile Val Met Thr Gln Ala Ala Pro Ser Val Pro Val Thr Pro Gly
1               5                   10                  15

Glu Ser Val Ser Ile Ser Cys Arg Ser Ser Lys Ser Leu Leu His Thr
            20                  25                  30

Asn Gly Asn Thr Tyr Leu His Trp Phe Leu Gln Arg Pro Gly Gln Ser
        35                  40                  45

Pro Gln Leu Leu Ile Tyr Arg Met Ser Val Leu Ala Ser Gly Val Pro
    50                  55                  60

Asp Arg Phe Ser Gly Ser Gly Ser Gly Thr Ala Phe Thr Leu Ser Ile
65                  70                  75                  80

Ser Arg Val Glu Ala Glu Asp Val Gly Val Phe Tyr Cys Met Gln His
                85                  90                  95

Leu Glu Tyr Pro Leu Thr Phe Gly Ala Gly Thr Lys Leu Glu Leu Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 52
<211> LENGTH: 657
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 52
gatattgtga tgacccagac tccactctcc ctgcccgtca cccctggaga gccggcctcc    60
atctcctgca ggtctagtaa gagtctcctg catactaatg gcaacactta cttgcattgg    120
tacctgcaga agccagggca gtctccacag ctcctgatat atcggatgtc cgtccttgcc    180
tcaggagtcc cagacaggtt cagtggcagt gggtcaggca ctgatttcac actgaaaatc    240
agcagggtgg aggctgagga tgttggagtt tattactgca tgcaacatct agaatatccg    300
ctcacgttcg gcggagggac caaggtggag atcaaacgta cggtggctgc accatctgtc    360

```
ttcatcttcc cgccatctga tgagcagttg aaatctggaa ctgcctctgt tgtgtgcctg    420
ctgaataact tctatcccag agaggccaaa gtacagtgga aggtggataa cgccctccaa    480
tcgggtaact cccaggagag tgtcacagag caggacagca aggacagcac ctacagcctc    540
agcagcaccc tgacgctgag caaagcagac tacgagaaac acaaagtcta cgcctgcgaa    600
gtcacccatc agggcctgag ctcgcccgtc acaaagagct tcaacagggg agagtgt      657
```

<210> SEQ ID NO 53
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

Asp Ile Val Met Thr Gln Thr Pro Leu Ser Leu Pro Val Thr Pro Gly
1               5                   10                  15

Glu Pro Ala Ser Ile Ser Cys Arg Ser Ser Lys Ser Leu Leu His Thr
            20                  25                  30

Asn Gly Asn Thr Tyr Leu His Trp Tyr Leu Gln Lys Pro Gly Gln Ser
        35                  40                  45

Pro Gln Leu Leu Ile Tyr Arg Met Ser Val Leu Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln His
                85                  90                  95

Leu Glu Tyr Pro Leu Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 54
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Ser Tyr Gly Met His
1               5

```
<210> SEQ ID NO 55
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Val Ile Trp Tyr Asp Gly Ser Asn Tyr Tyr Tyr Thr Asp Ser Val Lys
1               5                   10                  15

Gly

<210> SEQ ID NO 56
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Asp Leu Gly Ala Ala Ala Ser Asp Tyr
1               5

<210> SEQ ID NO 57
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Arg Ala Ser Gln Gly Ile Asn Ser Ala Leu Ala
1               5                   10

<210> SEQ ID NO 58
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Asp Ala Ser Ser Leu Glu Ser
1               5

<210> SEQ ID NO 59
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Gln Gln Phe Asn Ser Tyr Pro His Thr
1               5

<210> SEQ ID NO 60
<211> LENGTH: 354
<212> TYPE: DNA
<213> ORGANISM: Artificial Sequence
<220> FEATURE:
<223> OTHER INFORMATION: Description of Artificial Sequence: Synthetic
      polynucleotide
```

-continued

```
<400> SEQUENCE: 60
caggtgcacc tggtggagtc tgggggaggc gtggtccagc ctgggaggtc cctgagactc    60
tcctgtgcag cgtctggatt caccttcagt agctatggca tgcactgggt ccgccaggct   120
ccaggcaagg gctggagtg gtggcagtt atatggtatg atggaagtaa ttactactat    180
acagactccg tgaagggccg attcaccatc tccagagaca attccaagaa cacgctgtat   240
ctgcaaatga acagcctgag agccgaggac acggctgtgt attactgtgc gagagatctg   300
ggggcagcag cttctgacta ctggggccag ggaaccctgg tcaccgtctc ctca         354

<210> SEQ ID NO 61
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

Gln Val His Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Tyr Tyr Thr Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Leu Gly Ala Ala Ala Ser Asp Tyr Trp Gly Gln Gly Thr
            100                 105                 110

Leu Val Thr Val Ser Ser
        115

<210> SEQ ID NO 62
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 62
gccatccagt tgacccagtc tccatcctcc ctgtctgcat ctgtaggaga cagagtcacc    60
atcacttgcc gggcaagtca gggcattaac agtgctttag cctggtatca gcagaaacca   120
gggaaagctc ctaagctcct gatctatgat gcctccagtt tggaaagtgg ggtcccatca   180
aggttcagcg gcagtggatc tgggacagat ttcactctca ccatcagcag cctgcagcct   240
gaagattttg caacttatta ctgtcaacag tttaatagtt accctcatac ttttggccag   300
gggaccaagc tggagatcaa a                                              321

<210> SEQ ID NO 63
<211> LENGTH: 107
<212> TYPE: PRT
<213> ORGANISM: Artificial Sequence
```

```
<220> FEATURE:
<223> OTHER INFORMATION: Description of Artificial Sequence: Synthetic
      polypeptide

<400> SEQUENCE: 63
```

| Ala | Ile | Gln | Leu | Thr | Gln | Ser | Pro | Ser | Leu | Ser | Ala | Ser | Val | Gly |
|---|---|---|---|---|---|---|---|---|---|---|---|---|---|---|
| 1 | | | | 5 | | | | | 10 | | | | | 15 |

| Asp | Arg | Val | Thr | Ile | Thr | Cys | Arg | Ala | Ser | Gln | Gly | Ile | Asn | Ser | Ala |
|---|---|---|---|---|---|---|---|---|---|---|---|---|---|---|---|
| | | | 20 | | | | | 25 | | | | | 30 | | |

| Leu | Ala | Trp | Tyr | Gln | Gln | Lys | Pro | Gly | Lys | Ala | Pro | Lys | Leu | Leu | Ile |
|---|---|---|---|---|---|---|---|---|---|---|---|---|---|---|---|
| | | 35 | | | | | 40 | | | | | 45 | | | |

| Tyr | Asp | Ala | Ser | Ser | Leu | Glu | Ser | Gly | Val | Pro | Ser | Arg | Phe | Ser | Gly |
|---|---|---|---|---|---|---|---|---|---|---|---|---|---|---|---|
| 50 | | | | | 55 | | | | | 60 | | | | | |

| Ser | Gly | Ser | Gly | Thr | Asp | Phe | Thr | Leu | Thr | Ile | Ser | Ser | Leu | Gln | Pro |
|---|---|---|---|---|---|---|---|---|---|---|---|---|---|---|---|
| 65 | | | | | 70 | | | | | 75 | | | | | 80 |

| Glu | Asp | Phe | Ala | Thr | Tyr | Tyr | Cys | Gln | Gln | Phe | Asn | Ser | Tyr | Pro | His |
|---|---|---|---|---|---|---|---|---|---|---|---|---|---|---|---|
| | | | | 85 | | | | | 90 | | | | | 95 | |

| Thr | Phe | Gly | Gln | Gly | Thr | Lys | Leu | Glu | Ile | Lys |
|---|---|---|---|---|---|---|---|---|---|---|
| | | | 100 | | | | | 105 | | |

```
<210> SEQ ID NO 64
<211> LENGTH: 1344
<212> TYPE: DNA
<213> ORGANISM: Artificial Sequence
<220> FEATURE:
<223> OTHER INFORMATION: Description of Artificial Sequence: Synthetic
      polynucleotide <400> SEQUENCE: 64
caggtgcacc tggtggagtc tgggggaggc gtggtccagc ctggggaggtc cctgagactc      60
tcctgtgcag cgtctggatt caccttcagt agctatggca tgcactgggt ccgccaggct     120
ccaggcaagg ggctggagtg ggtggcagtt atatggtatg atggaagtaa ttactactat     180
acagactccg tgaagggccg attcaccatc tccagagaca attccaagaa cacgctgtat     240
ctgcaaatga acagcctgag agccgaggac acggctgtgt attactgtgc gagagatctg     300
ggggcagcag cttctgacta ctggggccag ggaaccctgg tcaccgtctc ctcagctagc     360
accaagggcc catcggtctt ccccctggca ccctcctcca agagcacctc tgggggcaca     420
gcggccctgg gctgcctggt caaggactac ttccccgaac cggtgacggt gtcgtggaac     480
tcaggcgccc tgaccagcgg cgtgcacacc ttcccggctg tcctacagtc ctcaggactc     540
tactccctca gcagcgtggt gaccgtgccc tccagcagct tgggcaccca gacctacatc     600
tgcaacgtga atcacaagcc cagcaacacc aaggtggaca agaaagttga gcccaaatct     660
tgtgacaaaa ctcacacatg cccaccgtgc ccagcacctg aactcctggg gggaccgtca     720
gtcttcctct tccccccaaa acccaaggac accctcatga tctcccggac ccctgaggtc     780
acatgcgtgg tggtggacgt gagccacgaa gaccctgagg tcaagttcaa ctggtacgtg     840
gacggcgtgg aggtgcataa tgccaagaca aagccgcggg aggagcagta caacagcacg     900
taccgtgtgg tcagcgtcct caccgtcctg caccaggact ggctgaatgg caaggagtac     960
aagtgcaagg tctccaacaa agccctccca gcccccatcg agaaaaccat ctccaaagcc    1020
aaagggcagc cccgagaacc acaggtgtac accctgcccc catcccggga ggagatgacc    1080
aagaaccagg tcagcctgac ctgcctggtc aaaggcttct atcccagcga catcgccgtg    1140
gagtgggaga gcaatgggca gccggagaac aactacaaga ccacgcctcc cgtgctggac    1200
tccgacggct ccttcttcct ctacagcaag ctcaccgtgg acaagagcag gtggcagcag    1260
```

```
gggaacgtct tctcatgctc cgtgatgcat gaggctctgc acaaccacta cacgcagaag   1320
agcctctccc tgtctccggg taaa                                          1344
```

<210> SEQ ID NO 65
<211> LENGTH: 448
<212> TYPE: PRT
<213> ORGANISM: Artificial Sequence
<220> FEATURE:
<223> OTHER INFORMATION: Description of Artificial Sequence: Synthetic
       polypeptide

<400> SEQUENCE: 65

```
Gln Val His Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Val Ile Trp Tyr Asp Gly Ser Asn Tyr Tyr Tyr Thr Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Leu Gly Ala Ala Ser Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Arg Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335
```

```
Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
            355                 360                 365

Leu Val Lys Gly Phe Tyr Pro Ser Asp Ile Ala Val Glu Trp Glu Ser
        370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
            435                 440                 445

<210> SEQ ID NO 66
<211> LENGTH: 1332
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 66
caggtgcacc tggtggagtc tgggggaggc gtggtccagc ctggggaggtc cctgagactc      60 tcctgtgcag cgtctggatt caccttcagt agctatggca tgcactgggt ccgccaggct     120
ccaggcaagg gctggagtg gtggcagtt atatggtatg atggaagtaa ttactactat        180
acagactccg tgaagggccg attcaccatc tccagagaca attccaagaa cacgctgtat     240
ctgcaaatga acagcctgag agccgaggac acggctgtgt attactgtgc gagagatctg     300
ggggcagcag cttctgacta ctggggccag ggaaccctgg tcaccgtctc ctcagctagc     360
accaagggcc catcggtctt ccccctggcg ccctgctcca ggagcacctc cgagagcaca     420
gcggccctgg gctgcctggt caaggactac ttccccgaac cggtgacggt gtcgtggaac     480
tcaggcgctc tgaccagcgg cgtgcacacc ttcccagctg tcctacagtc ctcaggactc     540
tactccctca gcagcgtggt gaccgtgccc tccagcaact tcggcaccca gacctacacc     600
tgcaacgtag atcacaagcc cagcaacacc aaggtggaca agacagttga gcgcaaatgt     660
tgtgtcgagt gcccaccgtg cccagcacca cctgtggcag gaccgtcagt cttcctcttc     720
cccccaaaac ccaaggacac cctcatgatc tcccggaccc ctgaggtcac gtgcgtggtg     780
gtggacgtga gccacgaaga ccccgaggtc cagttcaact ggtacgtgga cggcgtggag     840
gtgcataatg ccaagacaaa gccacgggag gagcagttcg ccagcacgtt ccgtgtggtc     900
agcgtcctca ccgttgtgca ccaggactgg ctgaacggca aggagtacaa gtgcaaggtc     960
tccaacaaag gcctcccagc ccccatcgag aaaaccatct ccaaaaccaa agggcagccc    1020
cgagaaccac aggtgtacac cctgcccca tcccgggagg agatgaccaa gaaccaggtc     1080
agcctgacct gcctggtcaa aggcttctac cccagcgaca tcgccgtgga gtgggagagc    1140
aatgggcagc cggagaacaa ctacaagacc acgcctccca tgctggactc cgacggctcc    1200
ttcttcctct acagcaagct caccgtggac aagagcaggt ggcagcaggg gaacgtcttc    1260
tcatgctccg tgatgcatga ggctctgcac aaccactaca cgcagaagag cctctccctg    1320
tctccgggta aa                                                        1332
```

<210> SEQ ID NO 67
<211> LENGTH: 444
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 67

```
Gln Val His Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Tyr Tyr Thr Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Leu Gly Ala Ala Ser Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Asn Phe Gly Thr Gln Thr Tyr Thr Cys Asn Val Asp His Lys Pro Ser
        195                 200                 205

Asn Thr Lys Val Asp Lys Thr Val Glu Arg Lys Cys Cys Val Glu Cys
    210                 215                 220

Pro Pro Cys Pro Ala Pro Pro Val Ala Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser His Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Ala Ser Thr Phe Arg Val Val Ser Val Leu Thr
    290                 295                 300

Val Val His Gln Asp Trp Leu Asn Gly Lys Glu Tyr Lys Cys Lys Val
305                 310                 315                 320

Ser Asn Lys Gly Leu Pro Ala Pro Ile Glu Lys Thr Ile Ser Lys Thr
                325                 330                 335

Lys Gly Gln Pro Arg Glu Pro Gln Val Tyr Thr Leu Pro Pro Ser Arg
            340                 345                 350

Glu Glu Met Thr Lys Asn Gln Val Ser Leu Thr Cys Leu Val Lys Gly
        355                 360                 365
```

Phe Tyr Pro Ser Asp Ile Ala Val Glu Trp Glu Ser Asn Gly Gln Pro
370                 375                 380

Glu Asn Asn Tyr Lys Thr Thr Pro Pro Met Leu Asp Ser Asp Gly Ser
385                 390                 395                 400

Phe Phe Leu Tyr Ser Lys Leu Thr Val Asp Lys Ser Arg Trp Gln Gln
            405                 410                 415

Gly Asn Val Phe Ser Cys Ser Val Met His Glu Ala Leu His Asn His
        420                 425                 430

Tyr Thr Gln Lys Ser Leu Ser Leu Ser Pro Gly Lys
        435                 440

<210> SEQ ID NO 68
<211> LENGTH: 642
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 68

```
gccatccagt tgacccagtc tccatcctcc ctgtctgcat ctgtaggaga cagagtcacc    60
atcacttgcc gggcaagtca gggcattaac agtgctttag cctggtatca gcagaaacca   120
gggaaagctc ctaagctcct gatctatgat gcctccagtt tggaaagtgg ggtcccatca   180
aggttcagcg gcagtggatc tgggacagat ttcactctca ccatcagcag cctgcagcct   240
gaagattttg caacttatta ctgtcaacag tttaatagtt accctcatac ttttggccag   300
gggaccaagc tggagatcaa acgtacggtg gctgcaccat ctgtcttcat cttcccgcca   360
tctgatgagc agttgaaatc tggaactgcc tctgttgtgt gcctgctgaa taacttctat   420
cccagagagg ccaaagtaca gtggaaggtg gataacgccc tccaatcggg taactcccag   480
gagagtgtca cagagcagga cagcaaggac agcacctaca gcctcagcag caccctgacg   540
ctgagcaaag cagactacga gaaacacaaa gtctacgcct gcgaagtcac ccatcagggc   600
ctgagctcgc ccgtcacaaa gagcttcaac aggggagagt gt                      642
```

<210> SEQ ID NO 69
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 69

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Asn Ser Ala
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro His
            85                  90                  95

Thr Phe Gly Gln Gly Thr Lys Leu Glu Ile Lys Arg Thr Val Ala Ala
        100                 105                 110

```
Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 70
<211> LENGTH: 317
<212> TYPE: PRT
<213> ORGANISM: Homo sapiens

<400> SEQUENCE: 70

Met Thr Met Glu Thr Gln Met Ser Gln Asn Val Cys Pro Arg Asn Leu
1               5                   10                  15

Trp Leu Leu Gln Pro Leu Thr Val Leu Leu Leu Leu Ala Ser Ala Asp
                20                  25                  30

Ser Gln Ala Ala Ala Pro Pro Lys Ala Val Leu Lys Leu Glu Pro Pro
            35                  40                  45

Trp Ile Asn Val Leu Gln Glu Asp Ser Val Thr Leu Thr Cys Gln Gly
    50                  55                  60

Ala Arg Ser Pro Glu Ser Asp Ser Ile Gln Trp Phe His Asn Gly Asn
65                  70                  75                  80

Leu Ile Pro Thr His Thr Gln Pro Ser Tyr Arg Phe Lys Ala Asn Asn
                85                  90                  95

Asn Asp Ser Gly Glu Tyr Thr Cys Gln Thr Gly Gln Thr Ser Leu Ser
            100                 105                 110

Asp Pro Val His Leu Thr Val Leu Ser Glu Trp Leu Val Leu Gln Thr
        115                 120                 125

Pro His Leu Glu Phe Gln Glu Gly Glu Thr Ile Met Leu Arg Cys His
        130                 135                 140

Ser Trp Lys Asp Lys Pro Leu Val Lys Val Thr Phe Phe Gln Asn Gly
145                 150                 155                 160

Lys Ser Gln Lys Phe Ser His Leu Asp Pro Thr Phe Ser Ile Pro Gln
                165                 170                 175

Ala Asn His Ser His Ser Gly Asp Tyr His Cys Thr Gly Asn Ile Gly
                180                 185                 190

Tyr Thr Leu Phe Ser Ser Lys Pro Val Thr Ile Thr Val Gln Val Pro
            195                 200                 205

Ser Met Gly Ser Ser Ser Pro Met Gly Ile Ile Val Ala Val Val Ile
        210                 215                 220

Ala Thr Ala Val Ala Ala Ile Val Ala Ala Val Val Ala Leu Ile Tyr
225                 230                 235                 240

Cys Arg Lys Lys Arg Ile Ser Ala Asn Ser Thr Asp Pro Val Lys Ala
                245                 250                 255

Ala Gln Phe Glu Pro Pro Gly Arg Gln Met Ile Ala Ile Arg Lys Arg
            260                 265                 270
```

```
Gln Leu Glu Glu Thr Asn Asn Asp Tyr Glu Thr Ala Asp Gly Gly Tyr
            275                 280                 285

Met Thr Leu Asn Pro Arg Ala Pro Thr Asp Asp Lys Asn Ile Tyr
290                 295                 300

Leu Thr Leu Pro Pro Asn Asp His Val Asn Ser Asn Asn
305                 310                 315

<210> SEQ ID NO 71
<211> LENGTH: 317
<212> TYPE: PRT
<213> ORGANISM: Homo sapiens

<400> SEQUENCE: 71

Met Thr Met Glu Thr Gln Met Ser Gln Asn Val Cys Pro Arg Asn Leu
1               5                   10                  15

Trp Leu Leu Gln Pro Leu Thr Val Leu Leu Leu Leu Ala Ser Ala Asp
                20                  25                  30

Ser Gln Ala Ala Ala Pro Pro Lys Ala Val Leu Lys Leu Glu Pro Pro
            35                  40                  45

Trp Ile Asn Val Leu Gln Glu Asp Ser Val Thr Leu Thr Cys Gln Gly
        50                  55                  60

Ala Arg Ser Pro Glu Ser Asp Ser Ile Gln Trp Phe His Asn Gly Asn
65                  70                  75                  80

Leu Ile Pro Thr His Thr Gln Pro Ser Tyr Arg Phe Lys Ala Asn Asn
                85                  90                  95

Asn Asp Ser Gly Glu Tyr Thr Cys Gln Thr Gly Gln Thr Ser Leu Ser
            100                 105                 110

Asp Pro Val His Leu Thr Val Leu Ser Glu Trp Leu Val Leu Gln Thr
        115                 120                 125

Pro His Leu Glu Phe Gln Glu Gly Glu Thr Ile Met Leu Arg Cys His
    130                 135                 140

Ser Trp Lys Asp Lys Pro Leu Val Lys Val Thr Phe Phe Gln Asn Gly
145                 150                 155                 160

Lys Ser Gln Lys Phe Ser Arg Leu Asp Pro Thr Phe Ser Ile Pro Gln
                165                 170                 175

Ala Asn His Ser His Ser Gly Asp Tyr His Cys Thr Gly Asn Ile Gly
            180                 185                 190

Tyr Thr Leu Phe Ser Ser Lys Pro Val Thr Ile Thr Val Gln Val Pro
        195                 200                 205

Ser Met Gly Ser Ser Ser Pro Met Gly Ile Ile Val Ala Val Val Ile
    210                 215                 220

Ala Thr Ala Val Ala Ala Ile Val Ala Ala Val Val Ala Leu Ile Tyr
225                 230                 235                 240

Cys Arg Lys Lys Arg Ile Ser Ala Asn Ser Thr Asp Pro Val Lys Ala
                245                 250                 255

Ala Gln Phe Glu Pro Pro Gly Arg Gln Met Ile Ala Ile Arg Lys Arg
            260                 265                 270

Gln Leu Glu Glu Thr Asn Asn Asp Tyr Glu Thr Ala Asp Gly Gly Tyr
        275                 280                 285

Met Thr Leu Asn Pro Arg Ala Pro Thr Asp Asp Lys Asn Ile Tyr
    290                 295                 300

Leu Thr Leu Pro Pro Asn Asp His Val Asn Ser Asn Asn
305                 310                 315
```

-continued

```
<210> SEQ ID NO 72
<211> LENGTH: 310
<212> TYPE: PRT
<213> ORGANISM: Homo sapiens

<400> SEQUENCE: 72
```

| Met | Gly | Ile | Leu | Ser | Phe | Leu | Pro | Val | Leu | Ala | Thr | Glu | Ser | Asp | Trp |
|---|---|---|---|---|---|---|---|---|---|---|---|---|---|---|---|
| 1 | | | | 5 | | | | | 10 | | | | | 15 | |

| Ala | Asp | Cys | Lys | Ser | Pro | Gln | Pro | Trp | Gly | His | Met | Leu | Leu | Trp | Thr |
|---|---|---|---|---|---|---|---|---|---|---|---|---|---|---|---|
| | | | 20 | | | | | 25 | | | | | 30 | | |

| Ala | Val | Leu | Phe | Leu | Ala | Pro | Val | Ala | Gly | Thr | Pro | Ala | Ala | Pro | Pro |
|---|---|---|---|---|---|---|---|---|---|---|---|---|---|---|---|
| | | 35 | | | | | 40 | | | | | 45 | | | |

| Lys | Ala | Val | Leu | Lys | Leu | Glu | Pro | Gln | Trp | Ile | Asn | Val | Leu | Gln | Glu |
|---|---|---|---|---|---|---|---|---|---|---|---|---|---|---|---|
| | 50 | | | | | 55 | | | | | 60 | | | | |

| Asp | Ser | Val | Thr | Leu | Thr | Cys | Arg | Gly | Thr | His | Ser | Pro | Glu | Ser | Asp |
|---|---|---|---|---|---|---|---|---|---|---|---|---|---|---|---|
| 65 | | | | | 70 | | | | | 75 | | | | | 80 |

| Ser | Ile | Gln | Trp | Phe | His | Asn | Gly | Asn | Leu | Ile | Pro | Thr | His | Thr | Gln |
|---|---|---|---|---|---|---|---|---|---|---|---|---|---|---|---|
| | | | | 85 | | | | | 90 | | | | | 95 | |

| Pro | Ser | Tyr | Arg | Phe | Lys | Ala | Asn | Asn | Asn | Asp | Ser | Gly | Glu | Tyr | Thr |
|---|---|---|---|---|---|---|---|---|---|---|---|---|---|---|---|
| | | | 100 | | | | | 105 | | | | | 110 | | |

| Cys | Gln | Thr | Gly | Gln | Thr | Ser | Leu | Ser | Asp | Pro | Val | His | Leu | Thr | Val |
|---|---|---|---|---|---|---|---|---|---|---|---|---|---|---|---|
| | | 115 | | | | | 120 | | | | | 125 | | | |

| Leu | Ser | Glu | Trp | Leu | Val | Leu | Gln | Thr | Pro | His | Leu | Glu | Phe | Gln | Glu |
|---|---|---|---|---|---|---|---|---|---|---|---|---|---|---|---|
| | 130 | | | | | 135 | | | | | 140 | | | | |

| Gly | Glu | Thr | Ile | Val | Leu | Arg | Cys | His | Ser | Trp | Lys | Asp | Lys | Pro | Leu |
|---|---|---|---|---|---|---|---|---|---|---|---|---|---|---|---|
| 145 | | | | | 150 | | | | | 155 | | | | | 160 |

| Val | Lys | Val | Thr | Phe | Phe | Gln | Asn | Gly | Lys | Ser | Lys | Lys | Phe | Ser | Arg |
|---|---|---|---|---|---|---|---|---|---|---|---|---|---|---|---|
| | | | | 165 | | | | | 170 | | | | | 175 | |

| Ser | Asp | Pro | Asn | Phe | Ser | Ile | Pro | Gln | Ala | Asn | His | Ser | His | Ser | Gly |
|---|---|---|---|---|---|---|---|---|---|---|---|---|---|---|---|
| | | | 180 | | | | | 185 | | | | | 190 | | |

| Asp | Tyr | His | Cys | Thr | Gly | Asn | Ile | Gly | Tyr | Thr | Leu | Tyr | Ser | Ser | Lys |
|---|---|---|---|---|---|---|---|---|---|---|---|---|---|---|---|
| | | 195 | | | | | 200 | | | | | 205 | | | |

| Pro | Val | Thr | Ile | Thr | Val | Gln | Ala | Pro | Ser | Ser | Ser | Pro | Met | Gly | Ile |
|---|---|---|---|---|---|---|---|---|---|---|---|---|---|---|---|
| | 210 | | | | | 215 | | | | | 220 | | | | |

| Ile | Val | Ala | Val | Val | Thr | Gly | Ile | Ala | Val | Ala | Ala | Ile | Val | Ala | Ala |
|---|---|---|---|---|---|---|---|---|---|---|---|---|---|---|---|
| 225 | | | | | 230 | | | | | 235 | | | | | 240 |

| Val | Val | Ala | Leu | Ile | Tyr | Cys | Arg | Lys | Lys | Arg | Ile | Ser | Ala | Leu | Pro |
|---|---|---|---|---|---|---|---|---|---|---|---|---|---|---|---|
| | | | | 245 | | | | | 250 | | | | | 255 | |

| Gly | Tyr | Pro | Glu | Cys | Arg | Glu | Met | Gly | Glu | Thr | Leu | Pro | Glu | Lys | Pro |
|---|---|---|---|---|---|---|---|---|---|---|---|---|---|---|---|
| | | | 260 | | | | | 265 | | | | | 270 | | |

| Ala | Asn | Pro | Thr | Asn | Pro | Asp | Glu | Ala | Asp | Lys | Val | Gly | Ala | Glu | Asn |
|---|---|---|---|---|---|---|---|---|---|---|---|---|---|---|---|
| | | 275 | | | | | 280 | | | | | 285 | | | |

| Thr | Ile | Thr | Tyr | Ser | Leu | Leu | Met | His | Pro | Asp | Ala | Leu | Glu | Glu | Pro |
|---|---|---|---|---|---|---|---|---|---|---|---|---|---|---|---|
| | 290 | | | | | 295 | | | | | 300 | | | | |

| Asp | Asp | Gln | Asn | Arg | Ile |
|---|---|---|---|---|---|
| 305 | | | | | 310 |

```
<210> SEQ ID NO 73
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 73

Gly Phe Thr Phe Ser Tyr Tyr Trp
1               5

<210> SEQ ID NO 74
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Ile Arg Leu Lys Ser Asn Asn Tyr Ala Thr
1               5                   10

<210> SEQ ID NO 75
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Asn Arg Arg Asp Glu Tyr Tyr Ala Met Asp Tyr
1               5                   10

<210> SEQ ID NO 76
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Glu Ser Val Asp Asn Phe Gly Ile Ser Phe
1               5                   10

<210> SEQ ID NO 77
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Gly Ala Ser
1

<210> SEQ ID NO 78
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Gln Gln Ser Lys Glu Val Pro Trp Thr
1               5
```

```
<210> SEQ ID NO 79
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Gly Tyr Thr Phe Thr Asn Tyr Gly
1               5

<210> SEQ ID NO 80
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Leu Asn Thr Tyr Thr Gly Glu Ser
1               5

<210> SEQ ID NO 81
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Ala Arg Gly Asp Tyr Gly Tyr Asp Asp Pro Leu Asp Tyr
1               5                   10

<210> SEQ ID NO 82
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Lys Ser Leu Leu His Thr Asn Gly Asn Thr Tyr
1               5                   10

<210> SEQ ID NO 83
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Arg Met Ser
1

<210> SEQ ID NO 84
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 84

Met Gln His Leu Glu Tyr Pro Leu Thr
1               5

<210> SEQ ID NO 85
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 85

Asp Ile Val Met Thr Gln Thr Pro Leu Ser Leu Pro Val Thr Pro Gly
1               5                   10                  15

Glu Pro Ala Ser Ile Ser Cys Arg Ser Ser Lys Ser Leu Leu His Thr
            20                  25                  30

Asn Gly Asn Thr Tyr Leu Asp Trp Tyr Leu Gln Lys Pro Gly Gln Ser
        35                  40                  45

Pro Gln Leu Leu Ile Tyr Arg Met Ser Tyr Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln His
                85                  90                  95

Leu Glu Tyr Pro Leu Thr Phe Gly Gly Gly Thr Lys Val Glu Ile Lys
            100                 105                 110

<210> SEQ ID NO 86
<211> LENGTH: 657
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 86
gatattgtga tgacccagac tccactctcc ctgcccgtca cccctggaga gccggcctcc      60
atctcctgca ggtctagtaa gtctctgctg cataccaacg ggaacaccta tttggactgg     120
tacctgcaga agccagggca gtctccacag ctcctgatct ataggatgtc ctatcgggcc     180
tctggagtcc cagacaggtt cagtggcagt gggtcaggca ctgatttcac actgaaaatc     240
agcagggtgg aggctgagga tgttggagtt tattactgca tgcagcatct ggagtatcca     300
ctgaccttcg gcggagggac caaggtggag atcaaacgta cggtggctgc accatctgtc     360
ttcatcttcc cgccatctga tgagcagttg aaatctggaa ctgcctctgt tgtgtgcctg     420
ctgaataact tctatcccag agaggccaaa gtacagtgga aggtggataa cgccctccaa     480
tcgggtaact cccaggagag tgtcacagag caggacagca aggacagcac ctacagcctc     540
agcagcaccc tgacgctgag caaagcagac tacgagaaac acaaagtcta cgcctgcgaa     600
gtcacccatc agggcctgag ctcgcccgtc acaaagagct tcaacagggg agagtgt       657

<210> SEQ ID NO 87
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 87

```
Asp Ile Val Met Thr Gln Thr Pro Leu Ser Leu Pro Val Thr Pro Gly
1               5                   10                  15

Glu Pro Ala Ser Ile Ser Cys Arg Ser Ser Lys Ser Leu Leu His Thr
            20                  25                  30

Asn Gly Asn Thr Tyr Leu Asp Trp Tyr Leu Gln Lys Pro Gly Gln Ser
        35                  40                  45

Pro Gln Leu Leu Ile Tyr Arg Met Ser Tyr Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln His
                85                  90                  95

Leu Glu Tyr Pro Leu Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 88
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 88

```
Gly Phe Thr Phe Ser Tyr Tyr Trp
1               5
```

<210> SEQ ID NO 89
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 89

```
Ile Arg Leu Lys Ser Asn Asn Tyr Ala Thr
1               5                   10
```

<210> SEQ ID NO 90
<211> LENGTH: 11
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 90

Asn Arg Arg Asp Glu Tyr Tyr Ala Met Asp Tyr
1               5                   10

<210> SEQ ID NO 91
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Glu Ser Val Asp Asn Phe Gly Ile Ser Phe
1               5                   10

<210> SEQ ID NO 92
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Gly Ala Ser
1

<210> SEQ ID NO 93
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Gln Gln Ser Lys Glu Val Pro Trp Thr
1               5

<210> SEQ ID NO 94
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Gly Phe Thr Phe Ser Ser Tyr Gly
1               5

<210> SEQ ID NO 95
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Ile Trp Tyr Asp Gly Ser Asn Tyr
1               5
```

```
<210> SEQ ID NO 96
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Ala Arg Asp Leu Gly Ala Ala Ala Ser Asp Tyr
1               5                   10

<210> SEQ ID NO 97
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Gln Gly Ile Asn Ser Ala
1               5

<210> SEQ ID NO 98
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Asp Ala Ser
1

<210> SEQ ID NO 99
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Gln Gln Phe Asn Ser Tyr Pro His Thr
1               5

<210> SEQ ID NO 100
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Lys Ser Leu Leu His Thr Asn Gly Asn Thr Tyr
1               5                   10

<210> SEQ ID NO 101
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 101

Arg Met Ser
1

<210> SEQ ID NO 102
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Met Gln His Leu Glu Tyr Pro Leu Thr
1               5
```

EFFECTOR-DEFICIENT ANTI-CD32A ANTIBODIES

This application is a continuation of U.S. Ser. No. 14/555,556, filed Nov. 26, 2014, now U.S. Pat. No. 9,382,321.

SEQUENCE LISTING

The instant application contains a Sequence Listing, which has been submitted electronically in ASCII format and is hereby incorporated by reference in its entirety. Said ASCII copy, created on Nov. 20, 2014, is named 01119-0008-00US_SL.txt and is 111,245 bytes in size.

FIELD

Methods and compositions for treating and preventing diseases and disorders mediated by CD32a are provided.

BACKGROUND

The effector, or Fc, regions of antibodies bind to various receptors on many different cell types. One such receptor is the CD32a IgG receptor (also known as FcgammaRIIa). It has been reported that human platelets and other human cells, such as basophils, eosinophils, monocytes, neutrophils, dendritic cells, macrophages, and mast cells, display cell surface CD32a receptors (Hogarth P M et al. Fc receptor-targeted therapies for the treatment of inflammation, cancer and beyond (March 2012) Nat Rev Drug Discov 11:311; PubMed ID: 22460124; Bruhns P. Properties of mouse and human IgG receptors and their contribution to disease models (June 2012) Blood 119:5640; PubMed ID: 22535666). Activation of CD32a by Fc regions of IgG antibodies (regardless of antigen specificity) results in a number of in vivo reactions, many of which have negative consequences for the human host. For example, IgG activation of CD32a can contribute to fatality in heparin-induced thrombocytopenia (HIT; see Boon D M et al. Heparin-induced thrombocytopenia and thrombosis: a potential fatal complication in a routine treatment (March 1995) Neth J Med 46:146; PubMed ID: 7731489; and Warkentin T E et al. Sera from patients with heparin-induced thrombocytopenia generate platelet-derived microparticles with procoagulant activity: an explanation for the thrombotic complications of heparin-induced thrombocytopenia (December 1994) Blood 84:3691; PubMed ID: 7949124). It has also been reported that IgG-mediated activation of CD32a on neutrophils, monocytes, and macrophages promotes airway inflammation, allergic reactions, and anaphylaxis. See, e.g. Jönsson F. et al. Human Fc-gamma-RIIA induces anaphylactic and allergic reactions (2012 March 15) Blood 119:2533-44, PubMed ID: 22138510. Activation of CD32a by IgG-Fc can also contribute to thrombosis in HIT (see, e.g. Arepally G et al. Fc gamma RIIA H/R 131 polymorphism, subclass-specific IgG anti-heparin/platelet factor 4 antibodies and clinical course in patients with heparin-induced thrombocytopenia and thrombosis (January 1997) Blood 89:370; PubMed ID: 9002937; Newman P M et al. Heparin-induced thrombocytopenia: new evidence for the dynamic binding of purified anti-PF4-heparin antibodies to platelets and the resultant platelet activation (July 2000) Blood 96:182; PubMed ID: 10891449; Jaffray B et al. Fatal venous thrombosis after heparin therapy (March 1991) Lancet 337:561; PubMed ID: 1671929).

In a 2012 report by Jönsson et al., the authors reported that blocking the CD32a receptor protected mice from local and systemic anaphylaxis, and concluded that "[t]argeting Fc[gamma]RIIA with specific blocking molecules in inflammation and autoimmune/allergic reactions in humans might lead to similar inhibition as we reported recently for mouse Fc[gamma]RIIIA in a murine model of rheumatoid arthritis." Id. at 2542. Jönsson continued that "[b]locking Fc[gamma]RIIA using divalent ligands (eg, mAb IV.3) to prevent allergic and autoimmune disease in humans, however, should not be envisioned, as we report here that high-doses of mAb IV.3 induced rather than prevented anaphylaxis." Id. at 2542 (emphasis added). Thus, while blockade of CD32a was a desired goal for treating inflammatory, autoimmune and allergic disorders, those of skill in the art did not envision blockade with CD32a antibodies due to their known negative side effects upon in vivo administration. The inventors have now solved this problem by providing novel CD32a antibodies that do not elicit negative side effects such as anaphylaxis.

In addition to diseases and disorders mediated by activation of CD32a, a number of diseases and disorders are mediated by CD32a interactions with the Fc regions of immobilized IgG, which do not directly activate CD32a. "Immobilized IgG" refers to antibody molecules that are bound to, or precipitated on, a surface and thus have restricted mobility (i.e., are "immobilized"). Cells having immobilized IgG may alternatively be described as "IgG-coated" cells. CD32a is known to interact only weakly with the Fc region of single IgG molecules, whether soluble (Hogarth P M et al. Fc receptor-targeted therapies for the treatment of inflammation, cancer and beyond (March 2012) Nat Rev Drug Discov 11:311; PubMed ID: 22460124) or immobilized (Wines B D et al. The IgG Fc contains distinct Fc receptor (FcR) binding sites: the leukocyte receptors Fc gamma RI and Fc gamma RIIa bind to a region in the Fc distinct from that recognized by neonatal FcR and protein A (May 2000) J Immunol 164:5313; PubMed ID: 10799893). Thus, antibodies incapable of directly activating CD32a nevertheless caused CD32a-mediated diseases and disorders such as thrombocytopenia when such antibodies were immobilized on the platelet surface (McKenzie et al. The role of the human Fc receptor FcgammaRIIA in the immune clearance of platelets: a transgenic mouse model (April 1999) J Immunol 162:4311; PubMed ID: 10201963).

IgG-coated platelets (or other cells) are actively cleared from the circulating blood. For example, it is well known that in immune thrombocytopenic purpura (ITP), human patients with circulating anti-platelet antibodies (typically IgG) experience platelet clearance mediated in large part by the spleen and the liver, where Fc-receptors (including CD32a) on phagocytes bind and retain the IgG-coated platelets. Removal of the spleen (splenectomy) can alleviate this condition. Unlike with HIT, however, thrombosis is not typically associated with the clearance of IgG-coated platelets in ITP; rather, the clinical problem of bleeding is the more prominent concern, and improved therapeutic strategies for this problem are needed (Altomare I et al. Bleeding and mortality outcomes in ITP clinical trials: a review of thrombopoietin mimetics data (October 2012) Am J Hematol 87:984; PubMed ID: 22729832).

CD32a is also known to mediate clearance of IgG-coated red blood cells (erythrocytes) in CD32a mediated diseases and disorders such as autoimmune hemolytic anemia (AIHA). Targeting CD32a with blocking mAbs would thus seem to be of great utility in treating AIHA; indeed, this was reported with the anti-CD32 mAb, MDE-8, which was shown to ameliorate IgG antibody-induced anemia in mice having a human CD32a transgene but otherwise lacking classical mouse IgG receptor function—that is, the animals used to test MDE-8 lacked functional mouse IgG receptors of type I (CD64) and type III (CD16), leaving open the question as to how these might affect MDE-8 activity in vivo (van Royen-Kerkhof A et al. A novel human CD32 mAb blocks experimental immune haemolytic anaemia in FcgammaRIIA transgenic mice (July 2005) Br J Haematol 130: 130; PubMed ID: 15982355). MDE-8 has not been developed as a therapeutic antibody. Reasons for the lack of preclinical development of MDE-8 have not been publicly disclosed. However, the inventors have now identified and solved a previously undescribed problem with MDE-8 and other anti-CD32a antibodies, namely by modifying them to reduce binding to IgG Fc-receptors, and so that they no longer mediate clearance via CD32a when immobilized on cells, thereby making clinical development possible.

Compositions that can prevent CD32a-mediated clearance of IgG-coated cells without causing negative side effects are therefore desired. The inventors herein describe such compositions and detail their successful use to treat and prevent CD32a-mediated diseases and disorders.

SUMMARY

In accordance with the description, the inventors have discovered that administration of native anti-CD32a antibodies in vivo causes adverse reactions that include thrombocytopenia, drop in body temperature, and symptoms of shock. The inventors have found that administering effector-deficient anti-CD32a antibodies alleviates these adverse reactions.

Therefore, in one embodiment, the present invention provides a method for preventing adverse reactions caused by administration of anti-CD32a antibodies by administering effector-deficient anti-CD32a antibodies. Similarly, methods for treating CD32a-mediated diseases or disorders comprising administering effector-deficient CD32a antibodies are provided.

In some instances, the CD32a-mediated disease or disorder is thrombocytopenia.

In other embodiments, the CD32a-mediated disease or disorder is a symptom of shock, including anaphylactic shock.

In still further embodiments, the CD32a-mediated disease or disorder is an inflammatory, immune, or autoimmune disease or disorder, including rheumatoid arthritis (RA), psoriasis, psoriatic arthritis, inflammatory bowel disease, osteoarthritis, and systemic lupus erythematous (SLE).

In still further embodiments, the CD32a-mediated disease or disorder is heparin-induced thrombocytopenia (HIT), immune thrombocytopenic purpura (ITP), antiphospholipid syndrome (APS), thrombosis or thrombocytopenia associated with autoimmunity or with certain drugs (e.g., heparin) and antibody therapies (e.g., anti-VEGF, anti-TNFalpha, anti-IgE, or anti-CD40L immunotherapies), transfusion or organ transplantation reactions, viral infection, bacterial infection, allergic asthma, allergic rhinitis, lupus nephritis, antibody-mediated anemia, anaphylaxis, chronic idiopathic urticaria (CIU), or airway inflammation.

The inventors have further discovered that administering effector-competent non-anti-CD32a IgG antibodies can cause adverse reactions, including thrombocytopenia, a drop in body temperature, or symptoms of shock. Administering effector-deficient anti-CD32a antibodies prevents these adverse reactions. Therefore, in one embodiment, the present invention provides a method of administering effector-deficient anti-CD32a antibodies to treat adverse reactions caused by IgG antibodies, including non-CD32a antibodies.

Compounds for use in these methods are provided, including effector-deficient chimeric and humanized AT-10 and IV.3 and effector-deficient human MDE-8 monoclonal IgG antibodies. The effector-deficient antibodies comprise at least a portion of the Fc region, and may be full length or may be truncated.

BRIEF DESCRIPTION OF THE DRAWINGS

FIG. 1 shows core body temperatures as a representative measure of infusion reaction in CD32A mice injected with either native human MDE-8 antibodies (IgG1, IgG2), or two different effector-deficient versions of the same MDE-8 antibodies. These effector-deficient antibodies do not cause infusion reactions.

FIG. 2 shows severe thrombocytopenia following intravenous injection of native human MDE-8 mAbs into CD32A mice and no thrombocytopenia following intravenous injection of two representative effector-deficient human MDE-8 antibodies.

FIG. 3A shows flow cytometric analysis of whole blood from CD32A mice prior to injection of native MDE-8 IgG1 mAbs.

FIG. 3B shows flow cytometric analysis of whole blood from CD32A mice after intravenous injection of native MDE-8 IgG1 mAbs.

FIG. 3C shows flow cytometric analysis of whole blood from CD32A mice prior to injection of effector-deficient MDE-8 IgG1 mAbs.

FIG. 3D shows flow cytometric analysis of whole blood from CD32A mice after intravenous injection of effector-deficient MDE-8 IgG1 mAbs.

FIG. 3E shows flow cytometric analysis of whole blood from CD32A mice prior to injection of native MDE-8 IgG2 mAbs.

FIG. 3F shows flow cytometric analysis of whole blood from CD32A mice after intravenous injection of native MDE-8 IgG2 mAbs.

FIG. 3G shows flow cytometric analysis of whole blood from CD32A mice prior to injection of effector-deficient MDE-8 IgG2 mAbs.

FIG. 3H shows flow cytometric analysis of whole blood from CD32A mice after intravenous injection of effector-deficient MDE-8 IgG2 mAbs.

FIG. 4A shows flow cytometric analysis of whole blood from CD32A mice after intravenous injection of IgG immune complexes.

FIG. 4B shows flow cytometric analysis of whole blood from effector-deficient MDE-8 IgG1 E269R anti-CD32a mAb pre-treated CD32A mice after intravenous injection of IgG immune complexes.

FIG. 4C shows flow cytometric analysis of whole blood from CD32A mice after intravenous injection of IgG immune complexes.

FIG. 4D shows flow cytometric analysis of whole blood from effector-deficient MDE-8 IgG2 N297A anti-CD32a mAb pre-treated CD32A mice after intravenous injection of IgG immune complexes.

FIG. 5A shows severe thrombocytopenia following intravenous injection of IgG immune complexes into CD32A mice (#1) but not following immune complex injection into CD32A mice pretreated with effector-deficient MDE-8 IgG1 E269R anti-CD32a mAb (#'s 2-4).

FIG. 5B shows severe thrombocytopenia following intravenous injection of IgG immune complexes into CD32A mice (#1) but not following immune complex injection into CD32A mice pretreated with effector-deficient MDE-8 IgG2 N297A anti-CD32a mAb (#'s 2-3).

FIG. 6A shows the presence of thrombi in the pulmonary blood vessels of CD32A mice after injection of IgG immune complexes.

FIG. 6B shows no thrombosis in the pulmonary blood vessels following IgG immune complex injection into CD32A mice pretreated with effector-deficient MDE-8 IgG1 E269R anti-CD32a mAbs.

FIG. 7A shows the presence of thrombi in the pulmonary blood vessels of CD32A mice after injection of IgG immune complexes.

FIG. 7B shows no thrombosis in the pulmonary blood vessels following IgG immune complex injection into CD32A mice pretreated with effector-deficient MDE-8 IgG2 N297A anti-CD32a mAbs.

FIG. 10 shows severe thrombocytopenia following intravenous injection of IgG immune complexes into CD32A mice (#1) but not following immune complex injection into CD32A mice pretreated with effector-deficient chimeric AT-10 human IgG1 E269R anti-CD32a mAb (#'s 2-3).

FIG. 11A shows flow cytometric analysis of whole blood from CD32A mice after intravenous injection of IgG immune complexes.

FIG. 11B shows flow cytometric analysis of whole blood from effector-deficient chimeric AT-10 human IgG1 E269R anti-CD32a mAb pre-treated CD32A mice after intravenous injection of IgG immune complexes.

FIG. 12A shows the presence of thrombi in the pulmonary blood vessels of CD32A mice after injection of IgG immune complexes.

FIG. 12B shows no thrombosis in the pulmonary blood vessels following IgG immune complex injection into CD32A mice pretreated with effector-deficient chimeric AT-10 human IgG1 E269R anti-CD32a mAb.

FIG. 13A shows no drop in body temperature of CD32A mice injected with effector-deficient humanized AT-10 IgG1 E269R (here and below, this is "hAT-10" mAb).

FIG. 13B shows flow cytometric analysis of whole blood from CD32A mice before intravenous injection of effector-deficient humanized AT-10 IgG1 E269R FIG. 13C shows flow cytometric analysis of whole blood from CD32A mice after intravenous injection of effector-deficient humanized AT-10 IgG1 E269R.

FIG. 13G shows the presence of occlusive thrombi in the pulmonary blood vessels of CD32A mice after injection of IgG immune complexes.

FIG. 13H shows no thrombosis in the pulmonary blood vessels following IgG immune complex injection into CD32A mice pretreated with effector-deficient humanized AT-10 IgG1 E269R anti-CD32a mAb.

FIG. 18A shows the presence of occlusive thrombi in the pulmonary blood vessels of CD32A mice after injection of IgG immune complexes.

FIG. 18B shows no thrombosis in the pulmonary blood vessels following IgG immune complex injection into CD32A mice pretreated with effector-deficient chimeric IV.3 human IgG2 N297A anti-CD32a mAbs.

Figure 32:
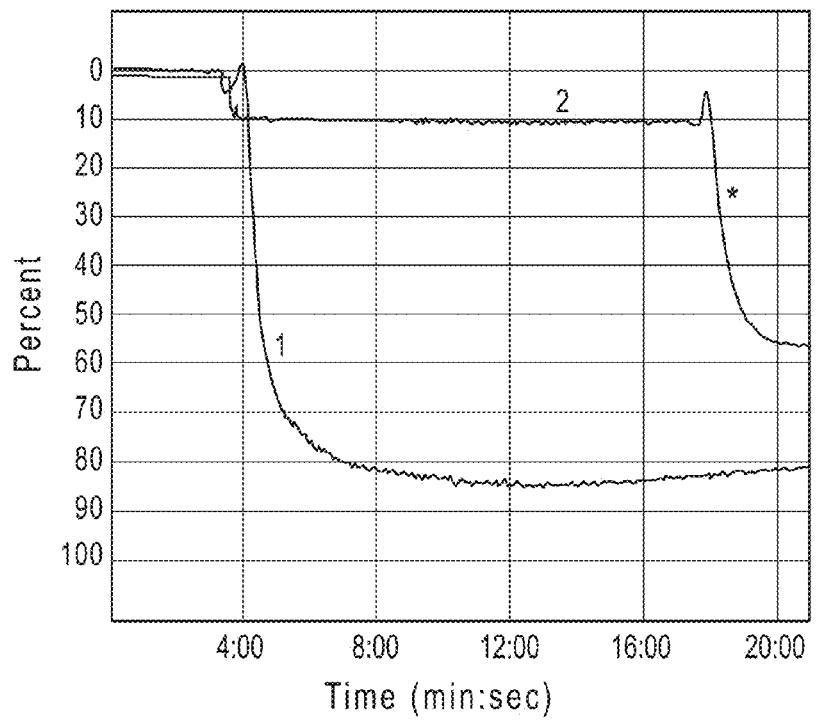

FIG. 32 shows platelet aggregation response to IgG immune complexes in the presence of vehicle (#1) or a combination of effector-deficient humanized IV.3.1 IgG1 E269R, effector-deficient humanized AT-10 IgG1 E269R, and effector-deficient human MDE-8 IgG1 E269R anti-CD32a mAbs (#2). The standard platelet agonist collagen (*) was added to #2 as a positive control in order demonstrate aggregation competence of the platelets.

Figure 33:
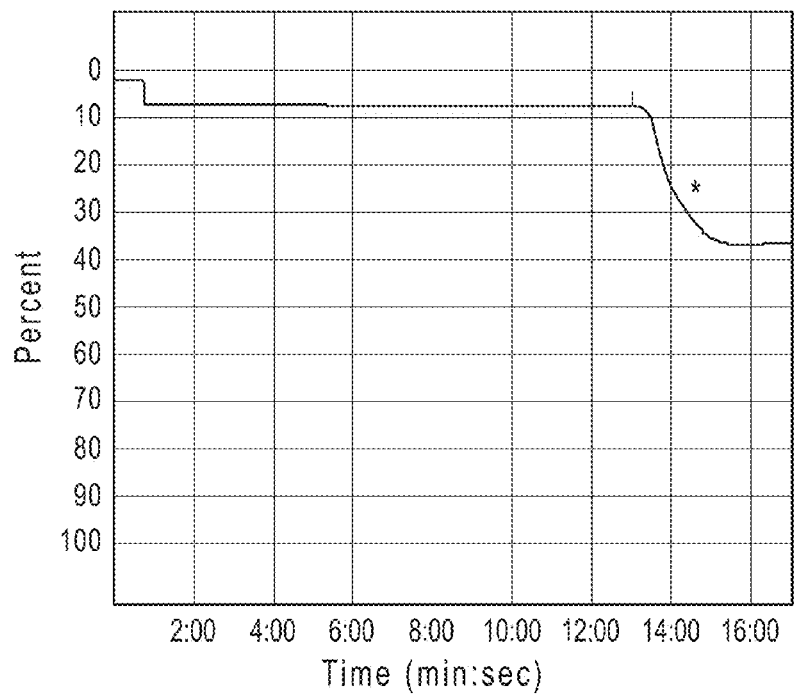

FIG. 33 shows a lack of platelet aggregation response to a combination of effector-deficient chimeric AT-10 human IgG1 E269R, effector-deficient chimeric IV.3 human IgG2 N297A, and effector-deficient human MDE-8 IgG1 E269R anti-CD32a mAbs.

Figure 34:
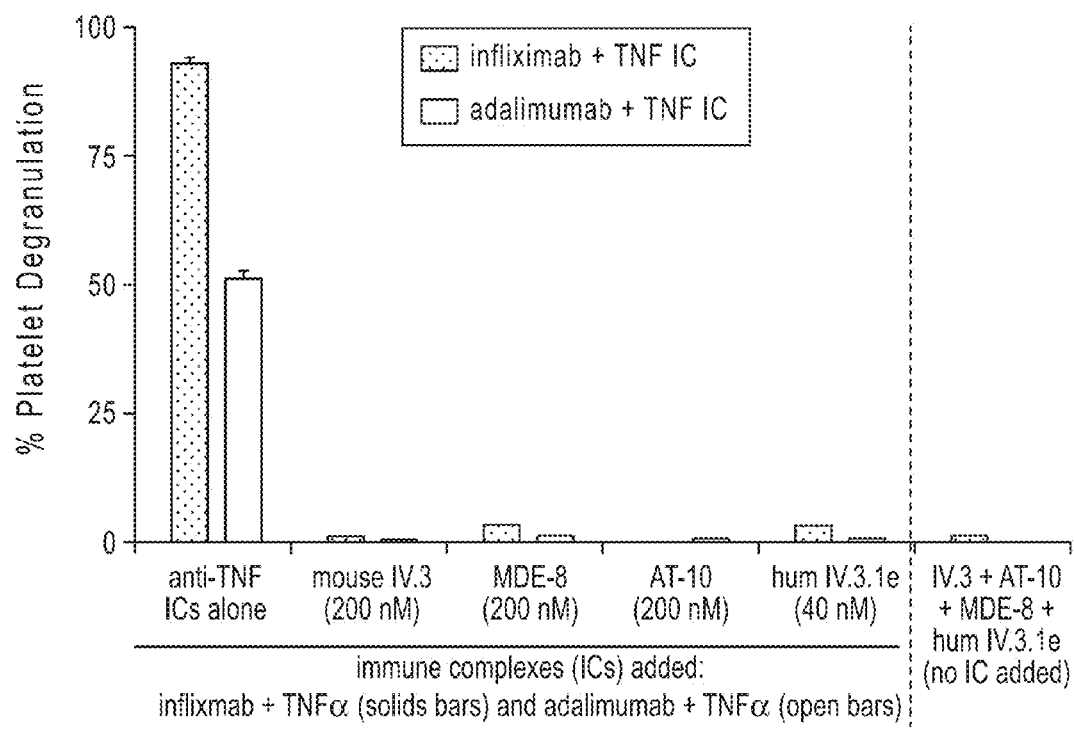

FIG. 34 shows platelet degranulation in response to IgG antibodies.

Figure 35:
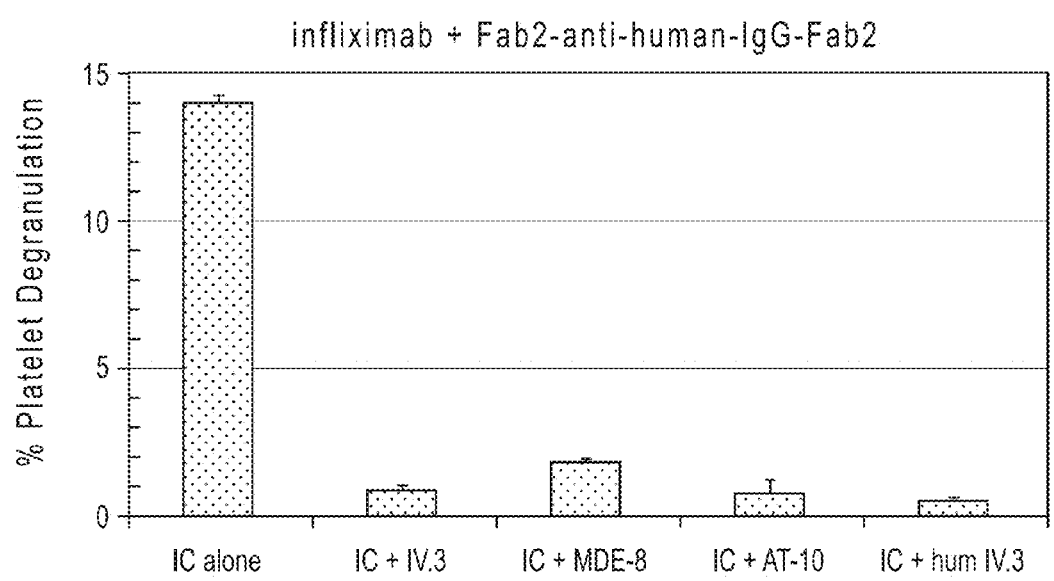

FIG. 35 shows platelet degranulation in response to infliximab immune complexes (bar 1) and the protective effect of the effector-deficient antibodies described herein (bars 2-4).

Figure 36A:
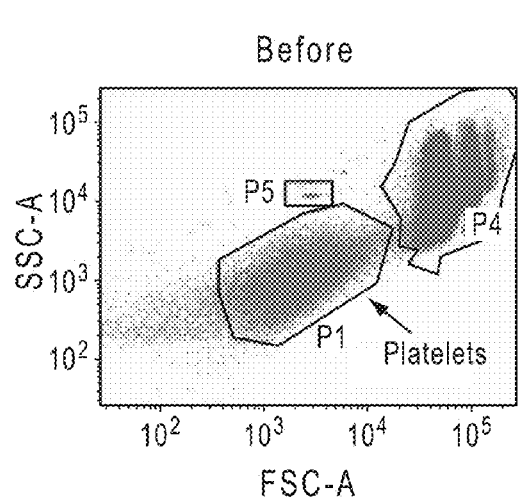

FIG. 36A shows flow cytometric analysis of whole blood from CD32A mice prior to injection of a combination of three effector-deficient anti-CD32a mAbs.

Figure 36B:
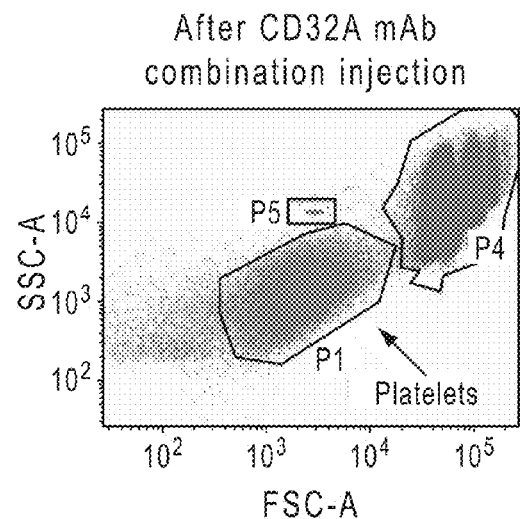

FIG. 36B shows flow cytometric analysis of whole blood from CD32A mice after the injection of a combination of three effector-deficient anti-CD32a mAbs (chimeric AT-10 human IgG1 E269R, chimeric IV.3 human IgG2 N297A, and human MDE-8 IgG1 E269R; 50 μg of each mAb injected).

Figure 36C:
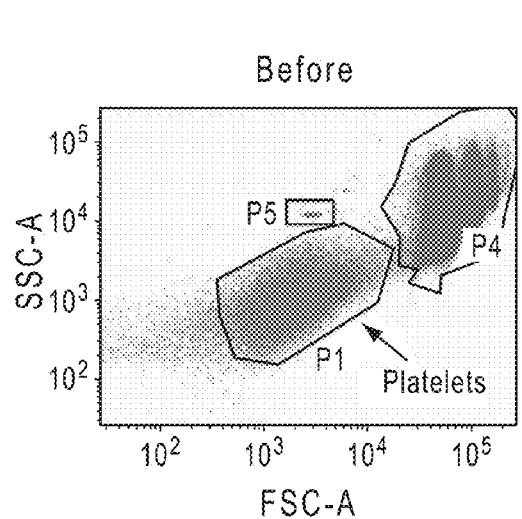

FIG. 36C shows flow cytometric analysis of whole blood from CD32A mice prior to injection of a combination of three effector-deficient anti-CD32a mAbs.

Figure 36D:
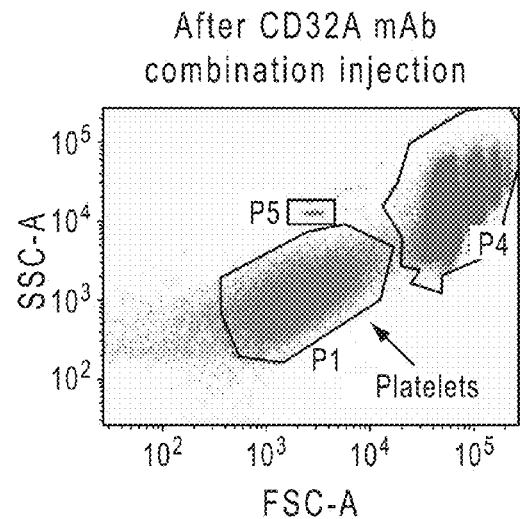

FIG. 36D shows flow cytometric analysis of whole blood from CD32A mice after the injection of a combination of three effector-deficient anti-CD32a mAbs (chimeric AT-10 human IgG1 E269R, chimeric IV.3 human IgG2 N297A, and human MDE-8 IgG1 E269R; 100 μg of each mAb injected).

Figure 36E:
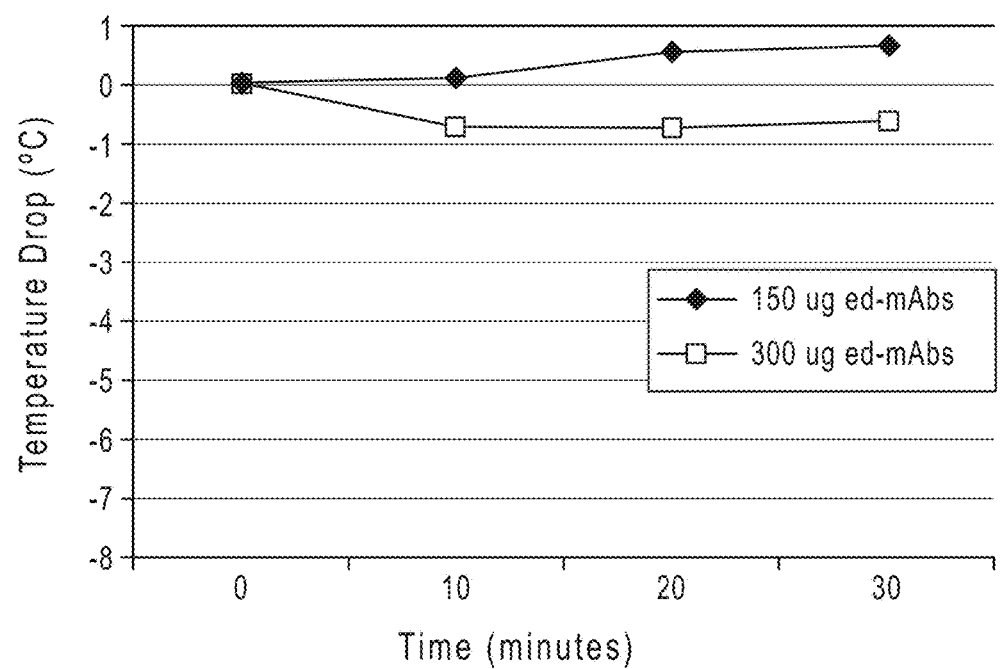

FIG. 36E shows no drop in core body temperature of CD32A mice after the injection of a combination of three effector-deficient anti-CD32a mAbs (chimeric AT-10 human IgG1 E269R, chimeric IV.3 human IgG2 N297A, and human MDE-8 IgG1 E269R (denoted "ed-mAbs" in this Figure).

DESCRIPTION OF THE SEQUENCES

Tables 1-5 provide listings of certain sequences referenced herein.

TABLE 1

| SEQ ID NO. | Description | Sequence |
|---|---|---|
| 1 | AT-10 VH Kabat CDR1 AA | YYWMN |
| 2 | AT-10 VH Kabat CDR2 AA | EIRLKSNNYATHYAESVKG |
| 3 | AT-10 VH Kabat CDR3 AA | RDEYYAMDY |
| 4 | AT-10 VL Kabat CDR1 AA | RASESVDNFGISFMN |
| 5 | AT-10 VL Kabat CDR2 AA | GASNQGS |
| 6 | AT-10 VL Kabat CDR3 AA | QQSKEVPWT |
| 25 | IV.3 VH Kabat CDR1 AA | NYGMN |
| 26 | IV.3 VH Kabat CDR2 AA | WLNTYTGESIYPDDFKG |
| 27 | IV.3 VH Kabat CDR3 AA | GDYGYDDPLDY |
| 28 | IV.3 VL Kabat CDR1 AA | RSSKSLLHTNGNTYLH |
| 29 | IV.3 VL Kabat CDR2 AA | RMSVLAS |

TABLE 1-continued

CDR sequences

| SEQ ID NO. | Description | Sequence |
|---|---|---|
| 30 | IV.3 VL Kabat CDR3 AA | MQHLEYPLT |
| 54 | MDE-8 VH Kabat CDR1 AA | SYGMH |
| 55 | MDE-8 VH Kabat CDR2 AA | VIWYDGSNYYYTDSVKG |
| 56 | MDE-8 VH Kabat CDR3 AA | DLGAAASDY |
| 57 | MDE-8 VL Kabat CDR1 AA | RASQGINSALA |
| 58 | MDE-8 VL Kabat CDR2 AA | DASSLES |
| 59 | MDE-8 VL Kabat CDR3 AA | QQFNSYPHT |
| 73 | hAT-10 VH IMGT CDR1 AA | GFTFSYYW |
| 74 | hAT-10 VH IMGT CDR2 AA | IRLKSNNYAT |
| 75 | hAT-10 VH IMGT CDR3 AA | NRRDEYYAMDY |
| 76 | hAT-10 VL IMGT CDR1 AA | ESVDNFGISF |
| 77 | hAT-10 VL IMGT CDR2 AA | GAS |
| 78 | hAT-10 VL IMGT CDR3 AA | QQSKEVPWT |
| 79 | hIV.3.1e VH IMGT CDR1 AA | GYTFTNYG |
| 80 | hIV.3.1e VH IMGT CDR2 AA | LNTYTGES |
| 81 | hIV.3.1e VH IMGT CDR3 AA | ARGDYGYDDPLDY |
| 82 | hIV.3.2b VL IMGT CDR1 AA | KSLLHTNGNTY |
| 83 | hIV.3.2b VL IMGT CDR2 AA | RMS |
| 84 | hIV.3.2b VL IMGT CDR3 AA | MQHLEYPLT |
| 88 | AT-10 VH IMGT CDR1 AA | GFTFSYYW |
| 89 | AT-10 VH IMGT CDR2 AA | IRLKSNNYAT |
| 90 | AT-10 VH IMGT CDR3 AA | NRRDEYYAMDY |
| 91 | AT-10 VL IMGT CDR1 AA | ESVDNFGISF |
| 92 | AT-10 VL IMGT CDR2 AA | GAS |
| 93 | AT-10 VL IMGT CDR3 AA | QQSKEVPWT |
| 94 | ATDE-8 VH IMGT CDR1 AA | GFTFSSYG |
| 95 | ATDE-8 VH IMGT CDR2 AA | IWYDGSNY |
| 96 | ATDE-8 VH IMGT CDR3 AA | ARDLGAAASDY |
| 97 | ATDE-8 VL IMGT CDR1 AA | QGINSA |
| 98 | ATDE-8 VL IMGT CDR2 AA | DAS |
| 99 | ATDE-8 VL IMGT CDR3 AA | QQFNSYPHT |
| 100 | hIV.3.1c VL IMGT CDR1 AA | KSLLHTNGNTY |
| 101 | hIV.3.1c VL IMGT CDR2 AA | RMS |
| 102 | hIV.3.1c VL IMGT CDR3 AA | MQHLEYPLT |

TABLE 2

AT-10 antibody sequences

| SEQ ID NO. | Description | Sequence |
|---|---|---|
| 7 | AT-10 VH DNA | gaagtgaagcttgaggagtctggaggaggc ttggtgcaacctggaggatccatgaaactc tcctgtgttgcctctggattcactttcagt tactactggatgaactgggtccgccagtct ccagagaaggggcttgagtggttgctgaa attagattgaaatctaataattatgcaaca cattatgcggagtctgtgaaagggaggttc accatctcaagagatgattccaaaaataat gtctacctgcaaatgaacaacttaagagct gaagacactggcatttattactgtaacagg cgtgatgagtattacgctatggattattgg ggtcaagggacgtcggtatctgtgtctagt |
| 8 | AT-10 VH AA | EVKLEESGGGLVQPGGSMKISCVASGFTFS YYWMNWVRQSPEKGLEWVAEIRLKSNNYAT HYAESVKGRFTISRDDSKNNVYLQMNNLRA EDTGIYYCNRRDEYYAMDYWGQGTSVSVSS |
| 9 | AT-10 VL DNA | gacattgtgctgacccaatctccaggttct ttggctgtgtctctagggcagagggccacc atctcctgcagagccagcgaaagtgttgat aattttggcattagttttatgaactggttc aacagaaaccaggacagccaccccgactc ctcatctatggtgcatccaaccaaggatcc ggggtccctgccaggtttagtggcagtggg tctgggacagacttcagcctcaacatccat cctgtggaggaggatgatgctgcaatgtat ttctgtcagcaaagtaaggaggttccgtgg acgttcggtggaggcaccaagctggaaatc aaa |

TABLE 2-continued

AT-10 antibody sequences

| SEQ ID NO. | Description | Sequence |
|---|---|---|
| 10 | AT-10 VL AA | DIVLTQSPGSLAVSLGQRATISCRASESVD NFGISFMNWFQQKPGQPPRLLIYGASNQGSGVPARFSGSGSGTDFSLNIHPVEEDDAAMYFCQQSKEVPWTFGGGTKLEIK |
| 11 | hAT-10 VH DNA Variable heavy CDR graft based on HV3-72*01 HJ3-01 acceptor framework | gaggtgcagctggtggagtctgggggaggcttggtccagcctggagggtccctgagactctcctgtgcagcctctggattcaccttctcatactattggatggactgggtccgccaggctccagggaaggggctggagtgggttggccgtatcagactgaaatctaacaactatgccaccgaatacgccgcgtctgtgaaaggcagattcaccatctcaagagatgattcaaagaactcactgtatctgcaaatgaacagcctgaaaaccgaggacacggccgtgtattactgtaacagaagagatgagtattacgccatggattattggggccaagggacaatggtcaccgtctcttca |
| 12 | hAT-10 VH AA Variable heavy CDR graft based on HV3-72*01 HJ3-01 acceptor framework | EVQLVESGGGLVQPGGSLRLSCAASGFTFS YYWMDWVRQAPGKGLEWVGRIRLKSNNYATEYAASVKGRFTISRDDSKNSLYLQMNSLKTEDTAVYYCNRRDEYYAMDYWGQGTMVTVSS |
| 13 | hAT-10 VL DNA Variable light CDR graft based on KV3-11*01 KJ1*01 acceptor framework | gaaattgtgttgacacagtctccagccaccctgtctttgtctccaggggaaagagccaccctctcctgcagggccagtgaatctgtggataacttcgggatctccttcttagcctggtaccaacagaaacctggccaggctcccaggctctcatctatggagcctccaacagggccactggcatcccagccaggttcagtggcagtgggtctgggacagacttcactctcaccatcagcagcctagagcctgaagattttgcagtttattactgtcagcaatctaaagaggtgccatggaccttcggccaagggaccaaggtggaaatcaaa |
| 14 | hAT-10 VL AA Variable light CDR graft based on KV3-11*01 KJ1*01 acceptor framework | EIVLTQSPATLSLSPGERATLSCRASESVD NFGISFLAWYQQKPGQAPRLLIYGASNRATGIPARFSGSGSGTDFTLTISSLEPEDFAVYYCQQSKEVPWTFGQGTKVEIK |
| 15 | AT-10 HC IgG1 E269R DNA (including constant region) | gaagtgaagcttgaggagtctgaggaggcttggtgcaacctggaggatccatgaaactctcctgtgttgcctctggattcactttcagttactactggatgaactgggtccgccagtctccagagaaggggcttgagtggttgctgaaattagattgaaatctaataattatgcaacacattatgcggagtctgtgaaagggaggttcaccatctcaagagatgattccaaaaataatgtctacctgcaaatgaacaacttaagagctgaagacactggcatttattactgtaacaggcgtgatgagtattacgctatggattattggggtcaagggacgtcggtatctgtgtctagtgctagcaccaagggcccatcggtcttccccctggcaccctcctccaagagcacctctgggggcacagcggccctgggctgcctggtcaaggactacttccccgaaccggtgacggtgtcgtggaactcaggcgccctgaccagcggcgtgcacaccttcccggctgtcctacagtcctcaggactctactccctcagcagcgtggtgaccgtgccctccagcagcttgggcacccagacctacatctgcaacgtaatcacaagcccagcaacaccaaggtggacaagaaagttgagcccaaatcttgtgacaaaactcacacatgcccaccgtgcccagcacctgaactcctggggggaccgtcagtcttcctcttccccccaaaacccaaggacaccctcatgatctcccggacccctgaggtcacatgcgtggtggtggacgtgagccacagagaccctgaggtcaagttcaactggtacgtggacggcgtggaggtgcataatgccaagacaaagccgcgggaggagcagtacaacagcacgtaccgtgtggtcagcgtcctcaccgtcctgcaccaggactggctgaatggcaaggagtacaagtgcaaggtctccaacaaagcc |

TABLE 2-continued

AT-10 antibody sequences

| SEQ ID NO. | Description | Sequence |
|---|---|---|
| | | ctcccagcccccatcgagaaaaccatctcc aaagccaaagggcagccccgagaaccacag gtgtacaccctgcccccatcccgggaggag atgaccaagaaccaggtcagcctgacctgc ctggtcaaaggcttctatcccagcgacatc gccgtggagtgggagagcaatgggcagccg gagaacaactacaagaccacgcctcccgtg ctggactccgacggctccttcttcctctac agcaagctcaccgtggacaagagcaggtgg cagcaggggaacgtcttctcatgctccgtg atgcatgaggctctgcacaaccactacacg cagaagagcctctccctgtctccgggtaaa |
| 16 | AT-10 HC IgG1 E269R AA (including constant region) | EVKLEESGGGLVQPGGSMKISCVASGFTFS YYWMNWVRQSPEKGLEWVAEIRLKSNNYAT HYAESVKGRFTISRDDSKNNVYLQMNNLRA EDTGIYYCNRRDEYYAMDYWGQGTSVSVSS ASTKGPSVFPLAPSSKSTSGGTAALGCLVK DYFPEPVTVSWNSGALTSGVHTFPAVLQSS GLYSLSSVVTVPSSSLGTQTYICNVNHKPS NTKVDKKVEPKSCDKTHTCPPCPAPELLGG PSVFLFPPKPKDTLMISRTPEVTCVVVDVS HRDPEVKFNWYVDGVEVHNAKTKPREEQYN STYRVVSVLTVLHQDWLNGKEYKCKVSNKA LPAPIEKTISKAKGQPREPQVYTLPPSREE MTKNQVSLTCLVKGFYPSDIAVEWESNGQP ENNYKTTPPVLDSDGSFFLYSKLTVDKSRW QQGNVFSCSVMHEALHNHYTQKSLSLSPGK |
| 17 | AT-10 HC IgG2 N297A DNA (including constant region) | gaagtgaagcttgaggagtctggaggaggc ttggtgcaacctggaggatccatgaaactc tcctgtgttgcctctggattcactttcagt tactactggatgaactgggtccgccagtct ccagagaaggggcttgagtggttgctgaa attagattgaaatctaataattatgcaaca cattatgcggagtctgtgaaagggaggttc accatctcaagagatgattccaaaaataat gtctacctgcaaatgaacaacttaagagct gaagacactggcatttattactgtaacagg cgtgatgagtattacgctatggattattgg ggtcaagggacgtcggtatctgtgtctagt gctagcaccaagggcccatcggtcttcccc ctggcgccctgctccaggagcacctccgag agcacagcggccctgggctgcctggtcaag gactacttccccgaaccggtgacggtgtcg tggaactcaggcgctctgaccagcggcgtg cacaccttcccagctgtcctacagtcctca ggactctactccctcagcagcgtggtgacc gtgccctccagcaacttcggcacccagacc tacacctgcaacgtagatcacaagcccagc aacaccaaggtggacaagacagttgagcgc aaatgttgtgtcgagtgcccaccgtgccca gcaccacctgtggcaggaccgtcagtcttc ctcttccccccaaaacccaaggacaccctc atgatctcccggacccctgaggtcacgtgc gtggtggtggacgtgagccacgaagacccc gaggtccagttcaactggtacgtggacggc gtggaggtgcataatgccaagacaaagcca cgggaggagcagttcgccagcacgttccgt gtggtcagcgtcctcaccgttgtgcaccag gactggctgaacggcaaggagtacaagtgc aaggtctccaacaaaggcctcccagccccc atcgagaaaaccatctccaaaaccaaaggg cagccccgagaaccacaggtgtacaccctg cccccatcccgggaggagatgaccaagaac caggtcagcctgacctgcctggtcaaaggc ttctaccccagcgacatcgccgtggagtgg gagagcaatgggcagccggagaacaactac aagaccacgcctcccatgctggactccgac ggctccttcttcctctacagcaagctcacc gtggacaagagcaggtggcagcaggggaac gtcttctcatgctccgtgatgcatgaggct ctgcacaaccactacacgcagaagagcctc tccctgtctccgggtaaa |

TABLE 2-continued

AT-10 antibody sequences

| SEQ ID NO. | Description | Sequence |
|---|---|---|
| 18 | AT-10 HC IgG2 N297A AA (including constant region) | EVKLEESGGGLVQPGGSMKLSCVASGFTFS YYWMNWVRQSPEKGLEWVAEIRLKSNNYAT HYAESVKGRFTISRDDSKNNVYLQMNNLRA EDTGIYYCNRRDEYYAMDYWGQGTSVSVSS ASTKGPSVFPLAPCSRSTSESTAALGCLVK DYFPEPVTVSWNSGALTSGVHTFPAVLQSS GLYSLSSVVTVPSSNFGTQTYTCNVDHKPS NTKVDKTVERKCCVECPPCPAPPVAGPSVF LFPPKPKDTLMISRTPEVTCVVVDVSHEDP EVQFNWYVDGVEVHNAKTKPREEQFASTFR VVSVLTVVHQDWLNGKEYKCKVSNKGLPAP IEKTISKTKGQPREPQVYTLPPSREEMTKN QVSLTCLVKGFYPSDIAVEWESNGQPENNY KTTPPMLDSDGSFFLYSKLTVDKSRWQQGN VFSCSVMHEALHNHYTQKSLSLSPGK |
| 19 | hAT-10 HC IgG1 E269R DNA (including constant region) | gaggtgcagctggtggagtctgggggaggc ttggtccagcctggagggtccctgagactc tcctgtgcagcctctggattcaccttctca tactattggatggactgggtccgccaggct ccagggaaggggctggagtgggttggccgt atcagactgaaatctaacaactatgccacc gaatacgccgcgtctgtgaaaggcagattc accatctcaagagatgattcaaagaactca ctgtatctgcaaatgaacagcctgaaaacc gaggacacggccgtgtattactgtaacaga agagatgagtattacgccatggattattgg ggccaagggacaatggtcaccgtctcttca gctagcaccaagggcccatcggtcttcccc ctggcaccctcctccaagagcacctctggg ggcacagcggccctgggctgcctggtcaag gactacttccccgaaccggtgacggtgtcg tggaactcaggcgccctgaccagcggcgtg cacaccttcccggctgtcctacagtcctca ggactctactccctcagcagcgtggtgacc gtgccctccagcagcttgggcacccagacc tacatctgcaacgtgaatcacaagcccagc aacaccaaggtggacaagaaagttgagccc aaatcttgtgacaaaactcacacatgccca ccgtgcccagcacctgaactcctggggga ccgtcagtcttcctcttccccccaaaaccc aaggacaccctcatgatctcccggacccct gaggtcacatgcgtggtggtggacgtgagc cacagagaccctgaggtcaagttcaactgg tacgtggacggcgtggaggtgcataatgcc aagacaaagccgcgggaggagcagtacaac agcacgtaccgtgtggtcagcgtcctcacc gtcctgcaccaggactggctgaatggcaag gagtacaagtgcaaggtctccaacaaagcc ctcccagcccccatcgagaaaaccatctcc aaagccaaagggcagccccgagaaccacag gtgtacaccctgcccccatcccgggaggag atgaccaagaaccaggtcagcctgacctgc ctggtcaaaggcttctatcccagcgacatc gccgtggagtgggagagcaatgggcagccg gagaacaactacaagaccacgcctcccgtg ctggactccgacggctccttcttcctctac agcaagctcaccgtggacaagagcaggtgg cagcaggggaacgtcttctcatgctccgtg atgcatgaggctctgcacaaccactacacg cagaagagcctctccctgtccgggtaaa |
| 20 | hAT-10 HC IgG1 E269R AA (including constant region) | EVQLVESGGGLVQPGGSLRLSCAASGFTFS YYWMDWVRQAPGKGLEWVGRIRLKSNNYAT EYAASVKGRFTISRDDSKNSLYLQMNSLKT EDTAVYYCNRRDEYYAMDYWGQGTMVTVSS ASTKGPSVFPLAPSSKSTSGGTAALGCLVK DYFPEPVTVSWNSGALTSGVHTFPAVLQSS GLYSLSSVVTVPSSSLGTQTYICNVNHKPS NTKVDKKVEPKSCDKTHTCPPCPAPELLGG PSVFLFPPKPKDTLMISRTPEVTCVVVDVS HRDPEVKFNWYVDGVEVHNAKTKPREEQYN STYRVVSVLTVLHQDWLNGKEYKCKVSNKA LPAPIEKTISKAKGQPREPQVYTLPPSREE MTKNQVSLTCLVKGFYPSDIAVEWESNGQP |

TABLE 2-continued

AT-10 antibody sequences

| SEQ ID NO. | Description | Sequence |
|---|---|---|
| | | ENNYKTTPPVLDSDGSFFLYSKLTVDKSRW QQGNVFSCSVMHEALHNHYTQKSLSLSPGK |
| 21 | AT-10 LC kappa DNA (including constant region) | gacattgtgctgacccaatctccaggttct ttggctgtgtctctagggcagagggccacc atctcctgcagagccagcgaaagtgttgat aattttggcattagttttatgaactggttc caacagaaaccaggacagccaccccgactc ctcatctatggtgcatccaaccaaggatcc ggggtccctgccaggtttagtggcagtggg tctgggacagacttcagcctcaacatccat cctgtggaggaggatgatgctgcaatgtat ttctgtcagcaaagtaaggaggttccgtgg acgttcggtggaggcaccaagctggaaatc aaacgtacggtggctgcaccatctgtcttc atcttcccgccatctgatgagcagttgaaa tctggaactgcctctgttgtgtgcctgctg aataacttctatcccagagaggccaaagta cagtggaaggtggataacgccctccaatcg ggtaactcccaggagagtgtcacagagcag gacagcaaggacagcacctacagcctcagc agcaccctgacgctgagcaaagcagactac gagaaacacaaagtctacgcctgcgaagtc acccatcagggcctgagctcgcccgtcaca aagagcttcaacaggggagagtgt |
| 22 | AT-10 LC kappa AA (including constant region) | DIVLTQSPGSLAVSLGQRATISCRASESVD NFGISFMNWFQQKPGQPPRLLIYGASNQGS GVPARFSGSGSGTDFSLNIHPVEEDDAAMY FCQQSKEVPWTFGGGTKLEIKRTVAAPSVF IFPPSDEQLKSGTASVVCLLNNFYPREAKV QWKVDNALQSGNSQESVTEQDSKDSTYSLS STLTLSKADYEKHKVYACEVTHQGLSSPVT KSFNRGEC |
| 23 | hAT-10 LC kappa DNA (including constant region) | gaaattgtgttgacacagtctccagccacc ctgtctttgtctccaggggaaagagccacc ctctcctgcagggccagtgaatctgtggat aacttcgggatctccttcttagcctggtac caacagaaacctggccaggctcccaggctc ctcatctatggagcctccaacagggccact ggcatcccagccaggttcagtggcagtggg tctgggacagacttcactctcaccatcagc agcctagagcctgaagattttgcagtttat tactgtcagcaatctaaagaggtgccatgg accttcggccaagggaccaaggtggaaatc aaacgtacggtggctgcaccatctgtcttc atcttcccgccatctgatgagcagttgaaa tctggaactgcctctgttgtgtgcctgctg aataacttctatcccagagaggccaaagta cagtggaaggtggataacgccctccaatcg ggtaactcccaggagagtgtcacagagcag gacagcaaggacagcacctacagcctcagc agcaccctgacgctgagcaaagcagactac gagaaacacaaagtctacgcctgcgaagtc acccatcagggcctgagctcgcccgtcaca aagagcttcaacaggggagagtgt |
| 24 | hAT-10 LC kappa AA (including constant region) | EIVLTQSPATLSLSPGERATLSCRASESVD NFGISFLAWYQQKPGQAPRLLIYGASNRAT GIPARFSGSGSGTDFTLTISSLEPEDFAVY YCQQSKEVPWTFGQGTKVEIKRTVAAPSVF IFPPSDEQLKSGTASVVCLLNNFYPREAKV QWKVDNALQSGNSQESVTEQDSKDSTYSLS STLTLSKADYEKHKVYACEVTHQGLSSPVT KSFNRGEC |

TABLE 3

IV.3 antibody sequences

| SEQ ID NO. | Description | Sequence |
|---|---|---|
| 31 | IV.3 VH DNA | cagatccagttggtgcagtctggacctgag ctgaagaagcctggagagacagtcaagatc tcctgcaaggcttctgggtataccttcaca aactatggaatgaactgggtgaagcaggct ccaggaaagggttttaaagtggatgggctgg ttaaacacctacactggagagtcaatatat cctgatgacttcaagggacggttttgccttc tcttcggaaacctctgccagcactgcctat ttgcagatcaacaacctcaaaaatgaggac atggctacatatttctgtgcaagaggggac tatggttacgacgaccctttggactactgg ggtcaaggaacctcagtcaccgtctcctca |
| 32 | IV.3 VH AA | QIQLVQSGPELKKPGETVKISCKASGYTFTNYGMNWVKQAPGKGLKWMGWLNTYTGESIYPDDFKGRFAFSSETSASTAYLQINNLKNEDMATYFCARGDYGYDDPLDYWGQGTSVTVSS |
| 33 | IV.3 VL DNA | gacattgtgatgacccaggctgcaccctct gtacctgtcactcctggagagtcagtatcc atctcctgcaggtctagtaagagtctcctg catactaatggcaacacttacttgcattgg ttcctacagaggccaggccagtctcctcag ctcctgatatatcggatgtccgtccttgcc tcaggagtcccagacaggttcagtggcagt gggtcaggaactgctttcacactgagcatc agtagagtggaggctgaggatgtgggtgat tttactgtatgcaacatctagaatatccgc tcacgttcggtgctgggaccaagctggaac tgaaa |
| 34 | IV.3 VL AA | DIVMTQAAPSVPVTPGESVSISCRSSKSLLHTNGNTYLHWFLQRPGQSPQLLIYRMSVLASGVPDRFSGSGSGTAFTLSISRVEAEDVGVFYCMQHLEYPLTFGAGTKLELK |
| 35 | hIV.3.1e VH DNA Variable heavy CDR graft based on HV7-4-1*2 HJ6*01 acceptor framework | caggtgcagctggtgcaatctgggtctgag ttgaagaagcctggggcctcagtgaaggtt tcctgcaaggcttctggatacaccttcact aactatggtatgaattgggtgcgacaggcc cctggacaagggcttgagtggatgggatgg ctcaacacctacactggggagtcaacgtat gcccagggcttcacaggacggttgtcttc tccttggacacctctgtcagcacggcatat ctgcagatcagcagcctaaaggctgaggac actgccgtgtattactgtgcgagaggggac tatggttacgacgaccctttggactactgg gggcaagggaccacggtcaccgtctcctca |
| 36 | hIV.3.1e VH AA Variable heavy CDR graft based on HV7-4-1*2 HJ6*01 acceptor framework | QVQLVQSGSELKKPGASVKVSCKASGYTFTNYGMNWVRQAPGQGLEWMGWLNTYTGESTYAQGFTGRFVFSLDTSVSTAYLQISSLKAEDTAVYYCARGDYGYDDPLDYWGQGTTVTVSS |
| 37 | hIV.3.2d VH DNA Variable heavy CDR graft based on HV7-81*01 HJ6*01 acceptor framework | caggtgcagctggtgcagtctggccatgag gtgaagcagcctggggcctcagtgaaggtc tcctgcaaggcttctgggtataccttcaca aactatggaatgaactgggtgaaacaggcc cctggacaagggcttaagtggatgggctgg ttaaacacctacactggagagtcaatatat cctgatgacttcaagggacggttttgccttc tccagtgacacctctgccagcacagcatac ctgcagatcaacaacctaaaggctgaggac atggccatgtatttctgtgcgagaggggac tatggttacgacgaccctttggactactgg gggcaagggaccacggtcaccgtctcctca |
| 38 | hIV.3.2d VH AA Variable heavy CDR graft based on HV7-81*01 HJ6*01 acceptor framework | QVQLVQSGHEVKQPGASVKVSCKASGYTFTNYGMNWVKQAPGQGLKWMGWLNTYTGESIYPDDFKGRFAFSSDTSASTAYLQINNLKAEDMAMYFCARGDYGYDDPLDYWGQGTTVTVSS |

TABLE 3-continued

IV.3 antibody sequences

| SEQ ID NO. | Description | Sequence |
|---|---|---|
| 39 | hIV.3.1c VL DNA Variable light CDR graft based on KV2-40*01 KJ4*02 acceptor framework | gatattgtgatgacccagactccactctcc ctgcccgtcacccctggagagccggcctcc atctcctgcaggtctagtaagtctctgctg catactaacgggaacacctatttggactgg tacctgcagaagccagggcagtctccacag ctcctgatctataggatgtcctatcgggcc tctggagtcccagacaggttcagtggcagt gggtcaggcactgatttcacactgaaaatc agcagggtggaggctgaggatgttggagtt tattactgcatgcagcatctggagtatcca ctgaccttcggcggagggaccaaggtggag atcaaa |
| 85 | hIV.3.1c VL AA Variable light CDR graft based on KV2-40*01 KJ4*02 acceptor framework | DIVMTQTPLSLPVTPGEPASISCRSSKSLL HTNGNTYLDWYLQKPGQSPQLLIYRMSYRA SGVPDRFSGSGSGTDFTLKISRVEAEDVGV YYCMQHLEYPLTFGGGTKVEIK |
| 40 | hIV.3.2b VL DNA Variable light CDR graft based on KV2-40*01 KJ4*02 acceptor framework | gatattgtgatgacccagactccactctcc ctgcccgtcacccctggagagccggcctcc atctcctgcaggtctagtaagagtctcctg catactaatggcaacacttacttgcattgg tacctgcagaagccagggcagtctccacag ctcctgatatatcggatgtccgtccttgcc tcaggagtcccagacaggttcagtggcagt gggtcaggcactgatttcacactgaaaatc agcagggtggaggctgaggatgttggagtt tattactgcatgcaacatctagaatatccg ctcacgttcggcggagggaccaaggtggag atcaaa |
| 41 | hIV.3.2b VL AA Variable light CDR graft based on KV2-40*01 KJ4*02 acceptor framework | DIVMTQTPLSLPVTPGEPASISCRSSKSLL HTNGNTYLHWYLQKPGQSPQLLIYRMSVLA SGVPDRFSGSGSGTDFTLKISRVEAEDVGV YYCMQHLEYPLTFGGGTKVEIK |
| 42 | IV.3 HC IgG1 E269R DNA (including constant region) | cagatccagttggtgcagtctggacctgag ctgaagaagcctggagagacagtcaagatc tcctgcaaggcttctgggtataccttcaca aactatggaatgaactgggtgaagcaggct ccaggaaagggtttaaagtggatgggctgg ttaaacacctacactggagagtcaatatat cctgatgacttcaagggacggtttgccttc tcttcggaaacctctgccagcactgcctat ttgcagatcaacaacctcaaaaatgaggac atggctacatatttctgtgcaagaggggac tatggttacgacgaccattggactactggg gtcaaggaacctcagtcaccgtctcctcag ctagcaccaagggcccatcggtcttcccc tggcaccctcctccaagagcacctctgggg gcacagcggccctgggctgcctggtcaagg actacttccccgaaccggtgacggtgtcgt ggaactcaggcgccctgaccagcggcgtgc acaccttcccggctgtcctacagtcctcag gactctactccctcagcagcgtggtgaccg tgccctccagcagcttgggcacccagacct acatctgcaacgtgaatcacaagcccagca acaccaaggtggacaagaaagttgagccca aatcttgtgacaaaactcacacatgcccac cgtgcccagcacctgaactcctggggggac cgtcagtcttcctcttccccccaaaaccca aggacaccctcatgatctcccggacccctg aggtcacatgcgtggtggtggacgtgagcc acagagaccctgaggtcaagttcaactggt acgtggacggcgtggaggtgcataatgcca agacaaagccgcgggaggagcagtacaaca gcacgtaccgtgtggtcagcgtcctcaccg tcctgcaccaggactggctgaatggcaagg agtacaagtgcaaggtctccaacaaagccc tcccagcccccatcgagaaaaccatctcca aagccaaagggcagccccgagaaccacagg tgtacaccctgcccccatcccgggaggaga tgaccaagaaccaggtcagcctgacctgcc |

TABLE 3-continued

IV.3 antibody sequences

| SEQ ID NO. | Description | Sequence |
|---|---|---|
| | | tggtcaaaggcttctatcccagcgacatcg ccgtggagtgggagagcaatgggcagccgg agaacaactacaagaccacgcctcccgtgc tggactccgacggctccttcttcctctaca gcaagctcaccgtggacaagagcaggtggc agcaggggaacgtcttctcatgctccgtga tgcatgaggctctgcacaaccactacacgc agaagagcctctccctgtctccgggtaaa |
| 43 | IV.3 HC IgG1 E269R AA (including constant region) | QIQLVQSGPELKKPGETVKISCKASGYTFT NYGMNWVKQAPGKGLKWMGWLNTYTGESIY PDDFKGRFAFSSETSASTAYLQINNLKNED MATYFCARGDYGYDDPLDYWGQGTSVTVSS ASTKGPSVFPLAPSSKSTSGGTAALGCLVK DYFPEPVTVSWNSGALTSGVHTFPAVLQSS GLYSLSSVVTVPSSSLGTQTYICNVNHKPS NTKVDKKVEPKSCDKTHTCPPCPAPELLGG PSVFLFPPKPKDTLMISRTPEVTCVVVDVS HRDPEVKFNWYVDGVEVHNAKTKPREEQYN STYRVVSVLTVLHQDWLNGKEYKCKVSNKA LPAPIEKTISKAKGQPREPQVYTLPPSREE MTKNQVSLTCLVKGFYPSDIAVEWESNGQP ENNYKTTPPVLDSDGSFFLYSKLTVDKSRW QQGNVFSCSVMHEALHNHYTQKSLSLSPGK |
| 44 | IV.3 HC IgG2 N297A DNA (including constant region) | cagatccagttggtgcagtctggacctgag ctgaagaagcctggagagacagtcaagatc tcctgcaaggcttctgggtataccttcaca aactatggaatgaactgggtgaagcaggct ccaggaaaggggtttaaagtggatgggctgg ttaaacacctacactggagagtcaatatat cctgatgacttcaagggacggtttgccttc tcttcggaaacctctgccagcactgcctat ttgcagatcaacaacctcaaaaatgaggac atggctacatatttctgtgcaagaggggac tatggttacgacgacccctttggactactgg ggtcaaggaacctcagtcaccgtctcctca gctagcaccaagggcccatcggtcttcccc ctggcgccctgctccaggagcacctccgag agcacagcggccctgggctgcctggtcaag gactacttccccgaaccggtgacggtgtcg tggaactcaggcgctctgaccagcggcgtg cacaccttcccagctgtcctacagtcctca ggactctactccctcagcagcgtggtgacc gtgccctccagcaacttcggcacccagacc tacacctgcaacgtagatcacaagcccagc aacaccaaggtggacaagacagttgagcgc aaatgttgtgtcgagtgcccaccgtgccca gcaccacctgtggcaggaccgtcagtcttc ctcttccccccaaaacccaaggacaccctc atgatctcccggacccctgaggtcacgtgc gtggtggtggacgtgagccacgaagacccc gaggtccagttcaactggtacgtggacggc gtggaggtgcataatgccaagacaaagcca cgggaggagcagttcgccagcacgttccgt gtggtcagcgtcctcaccgttgtgcaccag gactggctgaacggcaaggagtacaagtgc aaggtctccaacaaaggcctcccagccccc atcgagaaaaccatctccaaaaccaaaggg cagccccgagaaccacaggtgtacaccctg cccccatcccgggaggagatgaccaagaac caggtcagcctgacctgcctggtcaaaggc ttctaccccagcgacatcgccgtggagtgg gagagcaatgggcagccggagaacaactac aagaccacgcctcccatgctggactccgac ggctccttcttcctctacagcaagctcacc gtggacaagagcaggtggcagcaggggaac gtcttctcatgctccgtgatgcatgaggct ctgcacaaccactacacgcagaagagcctc tccctgtctccgggtaaa |
| 45 | IV.3 HC IgG2 N297A AA (including constant region) | QIQLVQSGPELKKPGETVKISCKASGYTFT NYGMNWVKQAPGKGLKWMGWLNTYTGESIY PDDFKGRFAFSSETSASTAYLQINNLKNED MATYFCARGDYGYDDPLDYWGQGTSVTVSS |

TABLE 3-continued

IV.3 antibody sequences

| SEQ ID NO. | Description | Sequence |
|---|---|---|
| | | ASTKGPSVFPLAPCSRSTSESTAALGCLVK DYFPEPVTVSWNSGALTSGVHTFPAVLQSS GLYSLSSVVTVPSSNFGTQTYTCNVDHKPS NTKVDKTVERKCCVECPPCPAPPVAGPSVF LFPPKPKDTLMISRTPEVTCVVVDVSHEDP EVQFNWYVDGVEVHNAKTKPREEQFASTFR VVSVLTVVHQDWLNGKEYKCKVSNKGLPAP IEKTISKTKGQPREPQVYTLPPSREEMTKN QVSLTCLVKGFYPSDIAVEWESNGQPENNY KTTPPMLDSDGSFFLYSKLTVDKSRWQQGN VFSCSVMHEALHNHYTQKSLSLSPGK |
| 46 | hIV.3.1e HC IgG1 E269R DNA (including constant region) | caggtgcagctggtgcaatctgggtctgag ttgaagaagcctggggcctcagtgaaggtt tcctgcaaggcttctggatacaccttcact aactatggtatgaattgggtgcgacaggcc cctggacaagggcttgagtggatgggatgg ctcaacacctacactggggagtcaacgtat gcccagggcttcacaggacggtttgtcttc tccttggacacctctgtcagcacggcatat ctgcagatcagcagcctaaaggctgaggac actgccgtgtattactgtgcgagaggggac tatggttacgacgacccctttggactactgg gggcaagggaccacggtcaccgtctcctca gctagcaccaagggcccatcggtcttcccc ctggcaccctcctccaagagcacctctggg ggcacagcggccctgggctgcctggtcaag gactacttccccgaaccggtgacggtgtcg tggaactcaggcgccctgaccagcggcgtg cacaccttcccggctgtcctacagtcctca ggactctactccctcagcagcgtggtgacc gtgccctccagcagcttgggcacccagacc tacatctgcaacgtgaatcacaagcccagc aacaccaaggtggacaagaaagttgagccc aaatcttgtgacaaaactcacacatgccca ccgtgcccagcacctgaactcctggggga ccgtcagtcttcctcttccccccaaaaccc aaggacaccctcatgatctcccggacccct gaggtcacatgcgtggtggtggacgtgagc cacagagaccctgaggtcaagttcaactgg tacgtggacggcgtggaggtgcataatgcc aagacaaagccgcgggaggagcagtacaac agcacgtaccgtgtggtcagcgtcctcacc gtcctgcaccaggactggctgaatggcaag gagtacaagtgcaaggtctccaacaaagcc ctcccagcccccatcgagaaaaccatctcc aaagccaaagggcagccccgagaaccacag gtgtacaccctgcccccatcccgggaggag atgaccaagaaccaggtcagcctgacctgc ctggtcaaaggcttctatcccagcgacatc gccgtggagtgggagagcaatgggcagccg gagaacaactacaagaccacgcctcccgtg ctggactccgacggctccttcttcctctac agcaagctcaccgtggacaagagcaggtgg cagcaggggaacgtcttctcatgctccgtg atgcatgaggctctgcacaaccactacacg cagaagagcctctccctgtctccgggtaaa |
| 47 | hIV.3.1e HC IgG1 E269R AA (including constant region) | QVQLVQSGSELKKPGASVKVSCKASGYTFT NYGMNWVRQAPGQGLEWMGWLNTYTGESTY AQGFTGRFVFSLDTSVSTAYLQISSLKAED TAVYYCARGDYGYDDPLDYWGQGTTVTVSS ASTKGPSVFPLAPSSKSTSGGTAALGCLVK DYFPEPVTVSWNSGALTSGVHTFPAVLQSS GLYSLSSVVTVPSSSLGTQTYICNVNHKPS NTKVDKKVEPKSCDKTHTCPPCPAPELLGG PSVFLFPPKPKDTLMISRTPEVTCVVVDVS HRDPEVKFNWYVDGVEVHNAKTKPREEQYN STYRVVSVLTVLHQDWLNGKEYKCKVSNKA LPAPIEKTISKAKGQPREPQVYTLPPSREE MTKNQVSLTCLVKGFYPSDIAVEWESNGQP ENNYKTTPPVLDSDGSFFLYSKLTVDKSRW QQGNVFSCSVMHEALHNHYTQKSLSLSPGK |

TABLE 3-continued

IV.3 antibody sequences

| SEQ ID NO. | Description | Sequence |
|---|---|---|
| 48 | hIV.3.2d HC IgG1 E269R DNA (including constant region) | caggtgcagctggtgcagtctggccatgag gtgaagcagcctggggcctcagtgaaggtc tcctgcaaggcttctgggtataccttcaca aactatggaatgaactgggtgaaacaggcc cctggacaagggcttaagtggatgggctgg ttaaacacctacactggagagtcaatatat cctgatgacttcaagggacggtttgccttc tccagtgacacctctgccagcacagcatac ctgcagatcaacaacctaaaggctgaggac atggccatgtatttctgtgcgagaggggac tatggttacgacgacccttggactactgg gggcaagggaccacggtcaccgtctcctca gctagcaccaagggcccatcggtcttcccc ctggcaccctcctccaagagcacctctggg ggcacagcggccctgggctgcctggtcaag gactacttccccgaaccggtgacggtgtcg tggaactcaggcgccctgaccagcggcgtg cacaccttcccggctgtcctacagtcctca ggactctactccctcagcagcgtggtgacc gtgccctccagcagcttgggcacccagacc tacatctgcaacgtgaatcacaagcccagc aacaccaaggtggacaagaaagttgagccc aaatcttgtgacaaaactcacacatgccca ccgtgcccagcacctgaactcctggggga ccgtcagtcttcctcttccccccaaaaccc aaggacaccctcatgatctcccggacccct gaggtcacatgcgtggtggtggacgtgagc cacagagaccctgaggtcaagttcaactgg tacgtggacggcgtggaggtgcataatgcc aagacaaagccgcgggaggagcagtacaac agcacgtaccgtgtggtcagcgtcctcacc gtcctgcaccaggactggctgaatggcaag gagtacaagtgcaaggtctccaacaaagcc ctcccagcccccatcgagaaaaccatctcc aaagccaaagggcagccccgagaaccacag gtgtacaccctgcccccatcccgggaggag atgaccaagaaccaggtcagcctgacctgc ctggtcaaaggcttctatcccagcgacatc gccgtggagtgggagagcaatgggcagccg gagaacaactacaagaccacgcctcccgtg ctggactccgacggctccttcttcctctac agcaagctcaccgtggacaagagcaggtgg cagcaggggaacgtcttctcatgctccgtg atgcatgaggctctgcacaaccactacacg cagaagagcctctccctgtctccgggtaaa |
| 49 | hIV.3.2d HC IgG1 E269R AA (including constant region) | QVQLVQSGHEVKQPGASVKVSCKASGYTFT NYGMNWVKQAPGQGLKWMGWLNTYTGESIY PDDFKGRFAFSSDTSASTAYLQINNLKAED MAMYFCARGDYGYDDPLDYWGQGTTVTVSS ASTKGPSVFPLAPSSKSTSGGTAALGCLVK DYFPEPVTVSWNSGALTSGVHTFPAVLQSS GLYSLSSVVTVPSSSLGTQTYICNVNHKPS NTKVDKKVEPKSCDKTHTCPPCPAPELLGG PSVFLFPPKPKDTLMISRTPEVTCVVVDVS HRDPEVKFNWYVDGVEVHNAKTKPREEQYN STYRVVSVLTVLHQDWLNGKEYKCKVSNKA LPAPIEKTISKAKGQPREPQVYTLPPSREE MTKNQVSLTCLVKGFYPSDIAVEWESNGQP ENNYKTTPPVLDSDGSFFLYSKLTVDKSRW QQGNVFSCSVMHEALHNHYTQKSLSLSPGK |
| 50 | IV.3 LC kappa DNA (including constant region) | gacattgtgatgacccaggctgcaccctct gtacctgtcactcctggagagtcagtatcc atctcctgcaggtctagtaagagtctcctg catactaatggcaacacttacttgcattgg ttcctacagaggccaggccagtctcctcag ctcctgatatatcggatgtccgtcctttgcc tcaggagtcccagacaggttcagtggcagt gggtcaggaactgctttcacactgagcatc agtagagtggaggctgaggatgtgggtgat tttactgtatgcaacatctagaatatccgc tcacgttcggtgctgggaccaagctggaac tgaaacgtacggtggctgcaccatctgtct tcatcttcccgccatctgatgagcagttga |

TABLE 3-continued

IV.3 antibody sequences

| SEQ ID NO. | Description | Sequence |
|---|---|---|
| | | aatctggaactgcctctgttgtgtgcctgc tgaataacttctatcccagagaggccaaag tacagtggaaggtggataacgccctccaat cgggtaactcccaggagagtgtcacagagc aggacagcaaggacagcacctacagcctca gcagcaccctgacgctgagcaaagcagact acgagaaacacaaagtctacgcctgcgaag tcacccatcagggcctgagctcgcccgtca caaagagcttcaacaggggagagtgt |
| 51 | IV.3 LC kappa AA (including constant region) | DIVMTQAAPSVPVTPGESVSISCRSSKSLL HTNGNTYLHWFLQRPGQSPQLLIYRMSVLA SGVPDRFSGSGSGTAFTLSISRVEAEDVGV FYCMQHLEYPLTFGAGTKLELKRTVAAPSV FIFPPPSDEQLKSGTASVVCLLNNFYPREAK VQWKVDNALQSGNSQESVTEQDSKDSTYSL SSTLTLSKADYEKHKVYACEVTHQGLSSPV TKSFNRGEC |
| 86 | hIV.3.1c LC kappa DNA (including constant region | gatattgtgatgacccagactccactctcc ctgcccgtcacccctggagagccggcctcc atctcctgcaggtctagtaagtctctgctg cataccaacgggaacacctatttggactgg tacctgcagaagccagggcagtctccacag ctcctgatctataggatgtcctatcgggcc tctggagtcccagacaggttcagtggcagt gggtcaggcactgatttcacactgaaaatc agcagggtggaggctgaggatgttggagtt tattactgcatgcagcatctggagtatcca ctgaccttcggcggagggaccaaggtggag atcaaacgtacggtggctgcaccatctgtc ttcatcttcccgccatctgatgagcagttg aaatctggaactgcctctgttgtgtgcctg ctgaataacttctatcccagagaggccaaa gtacagtggaaggtggataacgccctccaa tcgggtaactcccaggagagtgtcacagag caggacagcaaggacagcacctacagcctc agcagcaccctgacgctgagcaaagcagac tacgagaaacacaaagtctacgcctgcgaa gtcacccatcagggcctgagctcgcccgtc acaaagagcttcaacaggggagagtgt |
| 87 | hIV.3.1c LC kappa AA (including constant region | DIVMTQTPLSLPVTPGEPASISCRSSKSLL HTNGNTYLDWYLQKPGQSPQLLIYRMSYRA SGVPDRFSGSGSGTDFTLKISRVEAEDVGV YYCMQHLEYPLTFGGGTKVEIKRTVAAPSV FIFPPPSDEQLKSGTASVVCLLNNFYPREAK VQWKVDNALQSGNSQESVTEQDSKDSTYSL SSTLTLSKADYEKHKVYACEVTHQGLSSPV TKSFNRGEC |
| 52 | hIV.3.2b LC kappa DNA (including constant region) | gatattgtgatgacccagactccactctcc ctgcccgtcacccctggagagccggcctcc atctcctgcaggtctagtaagagtctcctg catactaatggcaacacttacttgcattgg tacctgcagaagccagggcagtctccacag ctcctgatatatcggatgtccgtccttgcc tcaggagtcccagacaggttcagtggcagt gggtcaggcactgatttcacactgaaaatc agcagggtggaggctgaggatgttggagtt tattactgcatgcaacatctagaatatccg ctcacgttcggcggagggaccaaggtggag atcaaacgtacggtggctgcaccatctgtc ttcatcttcccgccatctgatgagcagttg aaatctggaactgcctctgttgtgtgcctg ctgaataacttctatcccagagaggccaaa gtacagtggaaggtggataacgccctccaa tcgggtaactcccaggagagtgtcacagag caggacagcaaggacagcacctacagcctc agcagcaccctgacgctgagcaaagcagac tacgagaaacacaaagtctacgcctgcgaa gtcacccatcagggcctgagctcgcccgtc acaaagagcttcaacaggggagagtgt |

TABLE 3-continued

IV.3 antibody sequences

| SEQ ID NO. | Description | Sequence |
|---|---|---|
| 53 | hIV.3.2b LC kappa AA (including constant region) | DIVMTQTPLSLPVTPGEPASISCRSSKSLL HTNGNTYLHWYLQKPGQSPQLLIYRMSVLA SGVPDRFSGSGSGTDFTLKISRVEAEDVGV YYCMQHLEYPLTFGGGTKVEIKRTVAAPSV FIFPPSDEQLKSGTASVVCLLNNFYPREAK VQWKVDNALQSGNSQESVTEQDSKDSTYSL SSTLTLSKADYEKHKVYACEVTHQGLSSPV TKSFNRGEC |

TABLE 4

MDE-8 antibody sequences

| SEQ ID NO. | Description | Sequence |
|---|---|---|
| 60 | MDE-8 VH DNA | caggtgcacctggtggagtctggggggaggc gtggtccagcctgggaggtccctgagactc tcctgtgcagcgtctggattcaccttcagt agctatggcatgcactgggtccgccaggct ccaggcaaggggctggagtgggtggcagtt atatggtatgatggaagtaattactactat acagactccgtaagggccgattcaccatc tccagagacaattccaagaacacgctgtat ctgcaaatgaacagcctgagagccgaggac acggctgtgtattactgtgcgagagatctg ggggcagcagcttctgactactggggccag ggaaccctggtcaccgtctcctca |
| 61 | MDE-8 VH AA | QVHLVESGGGVVQPGRSLRLSCAASGFTFSSYGMHWVRQAPGKGLEWVAVIWYDGSNYYY TDSVKGRFTISRDNSKNTLYLQMNSLRAED TAVYYCARDLGAAASDYWGQGTLVTVSS |
| 62 | MDE-8 VL DNA | gccatccagttgacccagtctccatcctcc ctgtctgcatctgtaggagacagagtcacc atcacttgccgggcaagtcagggcattaac agtgctttagcctggtatcagcagaaacca gggaaagctcctaagctcctgatctatgat gcctccagtttggaaagtggggtcccatca aggttcagcggcagtggatctgggacagat ttcactctcaccatcagcagcctgcagcct gaagattttgcaacttattactgtcaacag tttaatagttaccctcatacttttggccag gggaccaagctggagatcaaa |
| 63 | MDE-8 VL AA | AIQLTQSPSSLSASVGDRVTITCRASQGIN SALAWYQQKPGKAPKLLIYDASSLESGVPS RFSGSGSGTDFTLTISSLQPEDFATYYCQQ FNSYPHTFGQGTKLEIK |
| 64 | MDE-8 HC IgG1 E269R DNA (including constant region) | caggtgcacctggtggagtctggggggaggc gtggtccagcctgggaggtccctgagactc tcctgtgcagcgtctggattcaccttcagt agctatggcatgcactgggtccgccaggct ccaggcaaggggctggagtgggtggcagtt atatggtatgatggaagtaattactactat acagactccgtaagggccgattcaccatc tccagagacaattccaagaacacgctgtat ctgcaaatgaacagcctgagagccgaggac acggctgtgtattactgtgcgagagatctg ggggcagcagcttctgactactggggccag ggaaccctggtcaccgtctcctcagctagc accaagggcccatcggtcttccccctggca ccctcctccaagagcacctctgggggcaca gcggccctgggctgcctggtcaaggactac ttccccgaaccggtgacggtgtcgtggaac tcaggcgccctgaccagcggcgtgcacacc ttcccggctgtcctacagtcctcaggactc tactccctcagcagcgtggtgaccgtgccc tccagcagcttgggcacccagacctacatc tgcaacgtgaatcacaagcccagcaacacc |

TABLE 4-continued

MDE-8 antibody sequences

| SEQ ID NO. | Description | Sequence |
|---|---|---|
| | | aaggtggacaagaaagttgagcccaaatct tgtgacaaaactcacacatgcccaccgtgc ccagcacctgaactcctgggggaccgtca gtcttcctcttccccccaaaacccaaggac accctcatgatctcccggacccctgaggtc acatgcgtggtggtggacgtgagccacaga gaccctgaggtcaagttcaactggtacgtg gacggcgtggaggtgcataatgccaagaca aagccgcgggaggagcagtacaacagcacg taccgtgtggtcagcgtcctcaccgtcctg caccaggactggctgaatggcaaggagtac aagtgcaaggtctccaacaaagcccccca gcccccatcgagaaaaccatctccaaagcc aaagggcagccccgagaaccacaggtgtac accctgcccccatcccgggaggagatgacc aagaaccaggtcagcctgacctgcctggtc aaaggcttctatcccagcgacatcgccgtg gagtgggagagcaatgggcagccggagaac aactacaagaccacgcctcccgtgctggac tccgacggctccttcttcctctacagcaag ctcaccgtggacaagagcaggtggcagcag gggaacgtcttctcatgctccgtgatgcat gaggctctgcacaaccactacacgcagaag agcctctccctgtctccgggtaaa |
| 65 | MDE-8 HC IgG1 E269R AA (including constant region) | QVHLVESGGGVVQPGRSLRLSCAASGFTFS SYGMHWVRQAPGKGLEWVAVIWYDGSNYYY TDSVKGRFTISRDNSKNTLYLQMNSLRAED TAVYYCARDLGAAASDYWGQGTLVTVSSAS TKGPSVFPLAPSSKSTSGGTAALGCLVKDY FPEPVTVSWNSGALTSGVHTFPAVLQSSGL YSLSSVVTVPSSSLGTQTYICNVNHKPSNT KVDKKVEPKSCDKTHTCPPCPAPELLGGPS VFLFPPKPKDTLMISRTPEVTCVVVDVSHR DPEVKFNWYVDGVEVHNAKTKPREEQYNST YRVVSVLTVLHQDWLNGKEYKCKVSNKALP APIEKTISKAKGQPREPQVYTLPPSREEMT KNQVSLTCLVKGFYPSDIAVEWESNGQPEN NYKTTPPVLDSDGSFFLYSKLTVDKSRWQQ GNVFSCSVMITEALHNHYTQKSLSLSPGK |
| 66 | MDE-8 HC IgG2 N297A DNA (including constant region) | caggtgcacctggtggagtctgggggaggc gtggtccagcctggggaggtccctgagactc tcctgtgcagcgtctggattcaccttcagt agctatggcatgcactgggtccgccaggct ccaggcaaggggctggagtgggtggcagtt atatggtatgatggaagtaattactactat acagactccgtgaagggccgattcaccatc tccagagacaattccaagaacacgctgtat ctgcaaatgaacagcctgagagccgaggac acggctgtgtattactgtgcgagagatctg ggggcagcagcttctgactactggggccag ggaaccctggtcaccgtctcctcagctagc accaagggcccatcggtcttccccctggcg ccctgctccaggagcacctccgagagcaca gcggccctgggctgcctggtcaaggactac ttccccgaaccggtgacggtgtcgtggaac tcaggcgctctgaccagcggcgtgcacacc ttcccagctgtcctacagtcctcaggactc tactccctcagcagcgtggtgaccgtgccc tccagcaacttcggcacccagacctacacc tgcaacgtagatcacaagcccagcaacacc aaggtggacaagacagttgagcgcaaatgt tgtgtcgagtgcccaccgtgcccagcacca cctgtggcaggaccgtcagtcttcctcttc ccccaaaacccaaggacaccctcatgatc tcccggacccctgaggtcacgtgcgtggtg gtggacgtgagccacgaagaccccgaggtc cagttcaactggtacgtggacggcgtggag gtgcataatgccaagacaaagccacgggag gagcagttcgccagcacgttccgtgtggtc agcgtcctcaccgttgtgcaccaggactgg ctgaacggcaaggagtacaagtgcaaggtc tccaacaaaggcctcccagcccccatcgag aaaaccatctccaaaaccaaagggcagccc |

TABLE 4-continued

MDE-8 antibody sequences

| SEQ ID NO. | Description | Sequence |
|---|---|---|
| | | cgagaaccacaggtgtacaccctgccccca tcccgggaggagatgaccaagaaccaggtc agcctgacctgcctggtcaaaggcttctac cccagcgacatcgccgtggagtgggagagc aatgggcagccggagaacaactacaagacc acgcctcccatgctggactccgacggctcc ttcttcctctacagcaagctcaccgtggac aagagcaggtggcagcaggggaacgtcttc tcatgctccgtgatgcatgaggctctgcac aaccactacacgcagaagagcctctccctg tctccgggtaaa |
| 67 | MDE-8 HC IgG2 N297A AA (including constant region) | QVHLVESGGGVVQPGRSLRLSCAASGFTFS SYGMHWVRQAPGKGLEWVAVIWYDGSNYYY TDSVKGRFTISRDNSKNTLYLQMNSLRAED TAVYYCARDLGAAASDYWGQGTLVTVSSAS TKGPSVFPLAPCSRSTSESTAALGCLVKDY FPEPVTVSWNSGALTSGVHTFPAVLQSSGL YSLSSVVTVPSSNFGTQTYTCNVDHKPSNT KVDKTVERKCCVECPPCPAPPVAGPSVFLF PPKPKDTLMISRTPEVTCVVVDVSHEDPEV QFNWYVDGVEVHNAKTKPREEQFASTFRVV SVLTVVHQDWLNGKEYKCKVSNKGLPAPIE KTISKTKGQPREPQVYTLPPSREEMTKNQV SLTCLVKGFYPSDIAVEWESNGQPENNYKT TPPMLDSDGSFFLYSKLTVDKSRWQQGNVF SCSVMHEALHNHYTQKSLSLSPGK |
| 68 | MDE-8 LC kappa DNA (including constant region) | gccatccagttgacccagtctccatcctcc ctgtctgcatctgtaggagacagagtcacc atcacttgccgggcaagtcagggcattaac agtgctttagcctggtatcagcagaaacca gggaaagctcctaagctcctgatctatgat gcctccagtttggaaagtggggtcccatca aggttcagcggcagtggatctgggacagat ttcactctcaccatcagcagcctgcagcct gaagattttgcaacttattactgtcaacag tttaatagttaccctcatacttttggccag gggaccaagctggagatcaaacgtacggtg gctgcaccatctgtcttcatcttcccgcca tctgatgagcagttgaaatctggaactgcc tctgttgtgtgcctgctgaataacttctat cccagagaggccaaagtacagtggaaggtg gataacgccctccaatcgggtaactcccag gagagtgtcacagagcaggacagcaaggac agcacctacagcctcagcagcaccctgacg ctgagcaaagcagactacgagaaacacaaa gtctacgcctgcgaagtcacccatcagggc ctgagctcgcccgtcacaaagagcttcaac aggggagagtgt |
| 69 | MDE-8 LC kappa AA (including constant region) | AIQLTQSPSSLSASVGDRVTITCRASQGIN SALAWYQQKPGKAPKLLIYDASSLESGVPS RFSGSGSGTDFTLTISSLQPEDFATYYCQQ FNSYPHTFGQGTKLEIKRTVAAPSVFIFPP SDEQLKSGTASVVCLLNNFYPREAKVQWKV DNALQSGNSQESVTEQDSKDSTYSLSSTLT LSKADYEKHKVYACEVTHQGLSSPVTKSFN RGEC |

TABLE 5 other sequences

| SEQ ID NO. | Description | Sequence |
|---|---|---|
| 70 | NP_001129691.1 CD32a-H131 [Homo sapiens] | MTMETQMSQNVCPRNLWLLQPLTV LLLLASADSQAAAPPKAVLKLEPP WINVLQEDSVTLTCQGARSPESDS IQWFHNGNLIPTHTQPSYRFKANN NDSGEYTCQTGQTSLSDPVHLTVL SEWLVLQTPHLEFQEGETIMLRCH SWKDKPLVKVTFFQNGKSQKFSHL DPTFSIPQANHSHSGDYHCTGNIG YTLFSSKPVTITVQVPSMGSSSPM GIIVAVVIATAVAAIVAAVVALIY |

TABLE 5-continued other sequences

| SEQ ID NO. | Description | Sequence |
|---|---|---|
| | | CRKKRISANSTDPVKAAQFEPPGR QMIAIRKRQLEETNNDYETADGGY MTLNPRAPTDDDKNIYLTLPPNDH VNSNN |
| 71 | NP_001129691.1: p.His167 Arg CD32a-R131 [Homo sapiens] | MTMETQMSQNVCPRNLWLLQPLTV LLLLASADSQAAAPPKAVLKLEPP WINVLQEDSVTLTCQGARSPESDS IQWFHNGNLIPTHTQPSYRFKANN NDSGEYTCQTGQTSLSDPVHLTVL SEWLVLQTPHLEFQEGETIMLRCH SWKDKPLVKVTFFQNGKSQKFSRL DPTFSIPQANHSHSGDYHCTGNIG YTLFSSKPVTITVQVPSMGSSSPM GIIVAVVIATAVAAIVAAVVALIY CRKKRISANSTDPVKAAQFEPPGR QMIAIRKRQLEETNNDYETADGGY MTLNPRAPTDDDKNIYLTLPPNDH VNSNN |
| 72 | NP_003992.3 CD32b isoform 1 [Homo sapiens] | MGILSFLPVLATESDWADCKSPQP WGHMLLWTAVLFLAPVAGTPAAPP KAVLKLEPQWINVLQEDSVTLTCR GTHSPESDSIQWFHNGNLIPTHTQ PSYRFKANNNDSGEYTCQTGQTSL SDPVHLTVLSEWLVLQTPHLEFQE GETIVLRCHSWKDKPLVKVTFFQN GKSKKFSRSDPNFSIPQANHSHSG DYHCTGNIGYTLYSSKPVTITVQA PSSSPMGIIVAVVTGIAVAAIVAA VVALIVCRKKRISALPGYPECREM GETLPEKPANPTNPDEADKVGAEN TITYSLLMHPDALEEPDDQNRI |

DESCRIPTION OF THE EMBODIMENTS

In one embodiment, a method for treating a CD32a-mediated disease or disorder in a human subject is encompassed, wherein a therapeutically effective amount of one or more effector-deficient anti-CD32a monoclonal antibodies as described herein, is administered to a human subject, thereby treating the CD32a-mediated disease or disorder.

In one embodiment, the anti-CD32a monoclonal antibody is capable of 1) preventing activation of CD32a by IgG immune complexes; and 2) has an Fc region that has been altered so as to reduce or eliminate Fc-binding to CD16, CD32, or CD64 type IgG receptors.

In one embodiment, the anti-CD32a monoclonal antibody is capable of 1) preventing activation of CD32a by IgG immune complexes; and 2) has an Fc region that has been altered so as to reduce or eliminate Fc-binding to CD16, CD32, and CD64 type IgG receptors.

In one embodiment, the reduction in Fc-binding to CD16, CD32, and/or CD64 is a complete reduction as compared to an effector-competent antibody control. In other aspects, the reduction in about 50%, about 60%, about 70%, about 80%, about 90%, or about 95%, or more, as compared to an effector-competent antibody control.

Antibodies

Any effector-deficient anti-CD32a antibody may be used in the method embodiments. The antibodies of the composition and method embodiments comprise at least a portion of the Fc region.

In one embodiment, the effector-deficient antibody is an AT-10, IV.3, or MDE-8 antibody comprising one or more of the CDRs described for each antibody, respectively, as in Tables 1-5, and is effector-deficient. In other embodiments, the effector-deficient antibody is an AT-10, IV.3, or MDE-8 antibody comprising the variable heavy and light chains described for each antibody, respectively, as in Tables 1-5, and is effector-deficient. In other embodiments, the effector-deficient antibody is an AT-10, IV.3, or MDE-8 antibody comprising the full-length heavy and full-length light chains described for each antibody, respectively, as in Tables 1-5, and is effector-deficient.

In one embodiment, the effector-deficient antibody is an AT-10, IV.3, or MDE-8 antibody comprising one or more of the CDRs of that antibody, wherein the CDRs are identical to the CDR sequences described for each antibody, respectively, in Tables 1-5, or wherein one, two, or three of the CDRs have 1 or 2 mutations as compared to the sequences described for each antibody, as in Table 1, and is effector-deficient.

In other embodiments, the effector-deficient antibody is an AT-10, IV.3, or MDE-8 antibody comprising the variable heavy and light chains described in Tables 1-5 for each antibody, respectively, wherein the variable heavy and light chains are 75%, 80%, 85%, 90%, 95%, 96%, 97%, 98%, or 99% identical to the variable heavy and variable light chains described in Tables 1-5 for each antibody, respectively, and wherein the antibody is effector-deficient.

In other embodiments, the effector-deficient antibody is an AT-10, IV.3, or MDE-8 antibody comprising a full length heavy and light chain described in Tables 1-5 for each antibody, respectively, or a variable heavy and light chain that is 75%, 80%, 85%, 90%, 95%, 96%, 97%, 98%, or 99% identical to a heavy and light chain described in Tables 1-5 for each antibody, respectively, and is effector-deficient.

The antibody compositions of the invention, as well as the antibodies used in the methods and uses described herein, are capable of preventing activation of CD32a by IgG immune complexes. Whether an antibody is capable of preventing activation of CD32a by IgG immune complexes can be tested by methods well known in the art, namely, by testing washed platelets for aggregation or degranulation responses to IgG immune complexes, as per the "IgG Immune Complex Test" described below. See, e.g., Meyer T et al. Bevacizumab immune complexes activate platelets and induce thrombosis in FCGR2A transgenic mice (January 2009) J Thromb Haemost 7:171; PubMed ID: 18983497.

"IgG Immune Complex Test": The following steps can determine whether an antibody can prevent activation of CD32a by IgG immune complexes. First, for example, human platelets can be isolated from other blood cells by "washing" methods (see, e.g., Meyer T et al. (January 2009) J Thromb Haemost 7:171; PubMed ID: 18983497). Alternatively, platelets from FCGR2A transgenic mice can be isolated using similar methods (see, e.g., Robles-Carrillo L et al. Anti-CD40L immune complexes potently activate platelets in vitro and cause thrombosis in FCGR2A transgenic mice (August 2010) J Immunol 185:1577; PubMed ID: 20585032). Second, such washed platelets can then be used to test for CD32a-mediated activation by IgG antibodies known to activate human CD32a, for example anti-CD9 mAb (e.g., as in PubMed ID: 18983497, op cit), or anti-CD40L mAb, M90 (e.g., as in PubMed ID: 20585032, op cit). In order to activate CD32a on washed platelets, some antibodies may need to be clustered by antigen so as to form an immune complex (IC), as is the case for M90, which is combined with CD40L prior to exposure to washed platelets. CD32a-activating antibodies can be identified using a platelet aggregometer, such as a Chrono-Log model 490 series aggregometer. If the antibody causes platelet aggregation after introduction into the aggregometer cuvette, and such aggregation is prevented by an anti-CD32a blocking antibody (e.g., such as IV.3, AT-10, or MDE-8; many others are commercially available and are known to those skilled in the art), then the antibody specifically activates platelet CD32a and is therefore sufficient for use as a required reagent in the "IgG Immune Complex Test". An alternative to the washed platelet aggregation test is the serotonin release assay (or "SRA"), which measures platelet degranulation (see, e.g., PubMed IDs 18983497 and 20585032 op cit). CD32a is the only IgG receptor on human platelets; therefore, these tests are capable of specifically identifying CD32a-activating antibodies. The third step in the "IgG Immune Complex Test" requires exposure of washed platelets to candidate anti-CD32a antibodies prior to introduction of the CD32a-activating IgG antibody. For example, washed human platelets suspended in assay buffer (typically, 250/nanoliter) are placed in an aggregometer cuvette. The instrument settings are adjusted so as to establish an assay signal range and baseline. Next, the candidate anti-CD32a blocking antibody (e.g., IV.3, AT-10, or MDE-8) is introduced into the cuvette (typically at or near 10 micrograms per milliliter). Next, the platelet activating IgG antibody or IgG immune complex (e.g., M90+CD40L, typically at 50-500 nM final assay concentration) is added to the platelet suspension in the cuvette. Finally, platelet aggregation is monitored for at least one minute (or, typically, more than five minutes) to assess whether the anti-CD32a mAb prevents IgG antibody/immune complex-induced platelet aggregation. If an anti-CD32a antibody, using these steps, can prevent the activation of CD32a by IgG antibodies or IgG immune complexes, as evidenced by inhibition of aggregation (or degranulation if the SRA is used), then the anti-CD32a antibody satisfies the "IgG Immune Complex Test". Similarly, if an anti-CD32a antibody lacks the capacity to prevent platelet aggregation and degranulation, said anti-CD32a antibody fails to satisfy the "IgG Immune Complex Test".

In the Examples included herein, FIGS. 19-33 demonstrate by washed platelet aggregation (i.e., using the "IgG Immune Complex Test") that mouse IV.3, chimeric IV.3, and humanized IV.3, that chimeric AT-10 and humanized AT-10, and that human MDE-8 IgG anti-CD32a mAbs all satisfy the "IgG Immune Complex Test", regardless of whether such anti-CD32a antibodies are of the IgG1 or IgG2 isotype subclass, and regardless of whether such anti-CD32a mAbs have native or effector-deficient Fc regions. As an alternative to the use of platelet aggregation as an "IgG Immune Complex Test", FIGS. 34 and 35 demonstrate similar results for IV.3, AT-10, and MDE-8 antibody variants using the SRA instead of platelet aggregation; here also, all tested antibodies prevent IC-induced platelet activation and therefore satisfy the "IgG Immune Complex Test".

a. Effector-Deficiency

The antibody compositions of the invention, as well as the antibodies used in the methods and uses described herein, are "effector-deficient." As used herein, an "effector-deficient" antibody is defined as an antibody having an Fc region that has been altered so as to reduce or eliminate Fc-binding to CD16, CD32, and/or CD64 type IgG receptors.

In one embodiment, the reduction in Fc-binding to CD16, CD32, and/or CD64 is a complete reduction as compared to an effector-competent control. In other aspects, the reduction in about 50%, about 60%, about 70%, about 80%, about 90%, or about 95%, or more, as compared to an effector-competent antibody control. Methods for determining whether an antibody has a reduced Fc-binding to CD16, CD32, and/or CD64 are well known in the art. See, e.g., US20110212087 A1, WO 2013165690, and Vafa O. et al. An engineered Fc variant of an IgG eliminates all immune effector functions via structural perturbations (January 2014) Methods 65:114; PubMed ID: 23872058.

In further embodiments, an effector-deficient anti-CD32a antibody is an antibody that is capable of 1) preventing activation of CD32a by IgG immune complexes; 2) has an Fc region that has been altered so as to reduce or eliminate Fc-binding to CD16, CD32, and/or CD64 type IgG receptors; and 3) does not induce Fc-mediated adverse host reactions following administration.

Whether the anti-CD32a effector-deficient antibodies of the present invention are capable of inducing an adverse host reaction following administration can be tested by the "Immobilized IgG Test" described below.

"Immobilized IgG Test": The following steps can determine whether an anti-CD32a antibody is capable of inducing an IgG-mediated adverse reaction following intravenous administration into a host animal. The host animal must be a mammal and must display CD32 IgG receptors having at least one epitope to which the anti-CD32a antibody to be tested is known to bind as an antigen. For example, IV.3 is an IgG mAb known to bind CD32a antigen (e.g., as in SEQ ID NO: 70, and as in SEQ ID NO: 71; see, e.g., Rosenfeld S I et al. Human platelet Fc receptor for immunoglobulin G. Identification as a 40,000-molecular-weight membrane protein shared by monocytes (December 1985) J Clin Invest 76:2317; PubMed ID: 2934409); AT-10 is an IgG mAb known to bind CD32 antigen (e.g., as in SEQ ID NOs: 70-72; see e.g., Greenman J et al. Characterization of a new monoclonal anti-Fc gamma MI antibody, AT10, and its incorporation into a bispecific F(ab')2 derivative for recruitment of cytotoxic effectors (November 1991) Mol Immunol 28:1243; PubMed ID: 1835758); and MDE-8 is an IgG mAb known to bind CD32 antigen (e.g., as in SEQ ID NOs: 70-72; see e.g., van Royen-Kerkhof A et al. A novel human CD32 mAb blocks experimental immune haemolytic anaemia in FcgammaRIIA transgenic mice (July 2005) Br J Haematol 130:130; PubMed ID: 15982355). One suitable host animal for use in the "Immobilized IgG Test" for anti-CD32a mAbs is the FCGR2A mouse ("B6; SJL-Tg (FCGR2A)11Mkz/J" mice, #003542, The Jackson Laboratory, Bar Harbor, Me., USA). Other suitable CD32-positive host animals are known to those skilled in the art. The "Immobilized IgG Test" is then conducted by, for example, injecting the purified anti-CD32a test antibody (preferably in physiologic saline, phosphate buffered saline, or another suitably inert vehicle) into the tail vein of (in this case) the FCGR2A (i.e., CD32A) mouse. Typically, 50-100 micrograms is injected; however, lack of reaction may suggest greater quantities of antibody should be injected: for example, 120 micrograms or 140 micrograms may be required to elicit a reaction. Quantities greater than 150 micrograms are typically not required for FCGR2A mice. Immediately following injection of the test antibody (in this example, the anti-CD32a mAb), the animal in monitored for core body temperature (typically, using a rectal thermometer) every 10 minutes for at least 20 minutes post injection (baseline temperature is established prior to test mAb injection). A temperature drop of more than two degrees celcius (i.e., hypothermia) that is sustained for more than five minutes, represents an adverse reaction indicating that the anti-CD32a test mAb failed to satisfy the "Immobilized IgG Test". Additionally, at least twenty minutes after injection of the anti-CD32a test mAb, and preferably thirty minutes after injection of the anti-CD32a test mAb, whole blood is collected from the host animal (retro-orbitally, or by venipuncture) and analyzed to assess changes in the number of circulating target cells. Cell counts can be obtained by flow cytometry, by automated cell counter, or by use of a hemocytometer. In the case of testing anti-CD32a mAbs in FCGR2A mice, baseline platelet counts are obtained on the day prior to testing, or at least one to three hours prior to injection of the anti-CD32a test mAb. Note that the process of blood draw, and in particular serial blood draws, can reduce apparent cell counts. Typically, baseline platelet counts in FCGR2A mice will exceed 700 per nanoliter, and are more typically greater than 800 per nanoliter, and may be as high as 1200, 1500, 1800, or 2000 per nanoliter. In the case of testing anti-CD32a mAbs in FCGR2A (CD32A) mice, a drop in circulating platelet counts of greater than 50% represents an adverse reaction indicating that the anti-CD32a test mAb failed to satisfy the "Immobilized IgG Test". In contrast, if 50 or more micrograms of an anti-CD32a mAb is intravenously injected into CD32A mice and core body temperature does not drop more than two degrees celcius for more than five minutes and circulating platelet counts are not reduced by more than 50% within thirty minutes, the anti-CD32a antibody satisfies the "Immobilized IgG Test".

In the Examples included herein, FIGS. 1-17 and FIG. 36 demonstrate (i.e., using the "Immobilized IgG Test") that effector-deficient but not native formats of chimeric IV.3, chimeric AT-10, humanized AT-10, and human MDE-8 IgG anti-CD32a mAbs satisfy the "Immobilized IgG Test", regardless of whether such anti-CD32a antibodies are of the IgG1 or IgG2 isotype subclass. Notably, all native anti-CD32a IgG mAbs tested by the "Immobilized IgG Test" failed to satisfy the "Immobilized IgG Test" in these examples, while all effector-deficient anti-CD32a IgG mAbs tested by the "Immobilized IgG Test" satisfied the "Immobilized IgG Test".

Methods for engineering effector-deficient antibodies with reduced capacity for Fc-dependent binding to CD16, CD32, and/or CD64 are well known in the art. For example, in order to achieve this result, an effector-deficient antibody may have one or more of the following mutations: E233P, G237M, D265A, D265N, E269R, D270A, D270N, N297A, N297Q, N297D, N297R, S298N, T299A (numbering is EU index of Kabat).

In certain embodiments, the Fc region mutation is selected from M252Y+S254T+T256E, G385D+Q386P+N389S, and H433K+N434F+Y436H, which are mutations known to extend circulating half-life of the therapeutic antibody (see, e.g., U.S. Pat. No. 8,323,962).

In certain embodiments, the anti-CD32a mAbs of the invention are modified to remove T-cell epitopes, which are known in the art to promote immunogenicity.

1. Effector-Deficient AT-10 Monoclonal Antibodies

In one embodiment, the effector-deficient anti-CD32a antibody is an effector-deficient AT-10 antibody. In one aspect, the AT-10 antibody comprises:
a. a heavy chain variable region CDR1 sequence comprising a sequence that is identical to the sequence YYWMN (SEQ ID NO: 1) or GFTFSYYW (SEQ ID NO: 73 and SEQ ID NO: 88), or is a sequence having 1 amino acid difference as compared to YYWMN (SEQ ID NO: 1) or GFTFSYYW (SEQ ID NO: 73 and SEQ ID NO: 88);
b. a heavy chain variable region CDR2 sequence comprising a sequence that is identical to the sequence EIRLKSNNYATHYAESVKG (SEQ ID NO: 2) or IRLKSNNYAT (SEQ ID NO: 74 and SEQ ID NO: 89), or is a sequence having 1 or 2 amino acid differences as compared to EIRLKSNNYATHYAESVKG (SEQ ID NO: 2) or IRLKSNNYAT (SEQ ID NO: 74 and SEQ ID NO: 89);
c. a heavy chain variable region CDR3 sequence comprising a sequence that is at identical to the sequence RDEYYAMDY (SEQ ID NO: 3) or NRRDEYYAMDY (SEQ ID NO: 75 and SEQ ID NO: 90), or is a sequence having 1 or 2 amino acid differences as compared to RDEYYAMDY (SEQ ID NO: 3) or NRRDEYYAMDY (SEQ ID NO: 75 and SEQ ID NO: 90);
d. a light chain variable region CDR1 sequence comprising a sequence that is at identical to the sequence RASESVDNFGISFMN (SEQ ID NO: 4) or ESVDNFGISF (SEQ ID NO: 76 and SEQ ID NO: 91), or is a sequence having 1 or 2 amino acid differences as compared to RASESVDNFGISFMN (SEQ ID NO: 4) or ESVDNFGISF (SEQ ID NO: 76 and SEQ ID NO: 91);
e. a light chain variable region CDR2 sequence comprising a sequence that is at identical to the sequence GASNQGS (SEQ ID NO: 5) or GAS (SEQ ID NO: 77 and SEQ ID NO: 92), or is a sequence having 1 or 2 amino acid differences as compared to GASNQGS (SEQ ID NO: 5) or GAS (SEQ ID NO: 77 and SEQ ID NO: 92); and
f. a light chain variable region CDR3 sequence comprising a sequence that is identical to the sequence QQSKEVPWT (SEQ ID NO: 6) or QQSKEVPWT (SEQ ID NO:78 and SEQ ID NO: 93), or is a sequence having 1 or 2 amino acid differences as compared to QQSKEVPWT (SEQ ID NO: 6) or QQSKEVPWT (SEQ ID NO:78 and SEQ ID NO: 93).

In other aspects, the effector-deficient AT-10 antibody comprises a variable heavy chain sequence comprising a sequence that is at least 75%, 80%, 85%, 90%, 95%, 96%, 97%, 98%, or 99% identical to the sequence shown in SEQ ID NO: 8, and a variable light chain sequence comprising a sequence that is at least 75%, 80%, 85%, 90%, 95%, 96%, 97%, 98%, or 99% identical to the sequence shown in SEQ ID NO: 10.

In other aspects, the effector-deficient AT-10 antibody comprises:
a. a heavy chain sequence that is at least 75%, 80%, 85%, 90%, 95%, 96%, 97%, 98%, or 99% identical to the sequence shown in SEQ ID NO: 16 or SEQ ID NO: 18; and
b. a light chain sequence that is at least 75%, 80%, 85%, 90%, 95%, 96%, 97%, 98%, or 99% identical to the sequence shown in SEQ ID NO: 22.

In another embodiment, the effector-deficient humanized AT-10 antibody comprises a variable heavy chain sequence comprising a sequence that is at least 75%, 80%, 85%, 90%, 95%, 96%, 97%, 98%, or 99% identical to the sequence shown in SEQ ID NO: 12; and a variable light chain sequence comprising a sequence that is at least 75%, 80%, 85%, 90%, 95%, 96%, 97%, 98%, or 99% identical to the sequence shown in SEQ ID NO: 14.

In another aspect, the effector-deficient humanized AT-10 antibody comprises:
a heavy chain sequence that is at least 75%, 80%, 85%, 90%, 95%, 96%, 97%, 98%, or 99% identical to the sequence shown in SEQ ID NO: 20; and
a light chain sequence that is at least 75%, 80%, 85%, 90%, 95%, 96%, 97%, 98%, or 99% identical to the sequence shown in SEQ ID NO: 24.

2. Effector-Deficient IV.3 Monoclonal Antibodies

In one embodiment, the effector-deficient anti-CD32a antibody is an effector-deficient IV.3 antibody. In one aspect, the IV.3 antibody comprises:
 a. a heavy chain variable region CDR1 sequence comprising a sequence that is at identical to the sequence NYGMN (SEQ ID NO: 25) or GYTFTNYG (SEQ ID NO: 79), or is a sequence having 1 or 2 amino acid differences as compared to the sequence NYGMN (SEQ ID NO: 25) or GYTFTNYG (SEQ ID NO: 79);
 b. a heavy chain variable region CDR2 sequence comprising a sequence that is identical to the sequence WLNTYTGESIYPDDFKG (SEQ ID NO: 26) or LNTYTGES (SEQ ID NO: 80), or is a sequence having 1 or 2 amino acid differences as compared to the sequence WLNTYTGESIYPDDFKG (SEQ ID NO: 26) or LNTYTGES (SEQ ID NO: 80);
 c. a heavy chain variable region CDR3 sequence comprising a sequence that is identical to the sequence GDYGYDDPLDY (SEQ ID NO: 27) or ARGDYGYDDPLDY (SEQ ID NO: 81), or is a sequence having 1 or 2 amino acid differences as compared to the sequence GDYGYDDPLDY (SEQ ID NO: 27) or ARGDYGYDDPLDY (SEQ ID NO: 81);
 d. a light chain variable region CDR1 sequence comprising a sequence that is identical to the sequence RSSKSLLHTNGNTYLH (SEQ ID NO: 28) or KSLLHTNGNTY (SEQ ID NO: 82 and SEQ ID NO: 100), or is a sequence having 1 or 2 amino acid differences as compared to the sequence RSSKSLLHTNGNTYLH (SEQ ID NO: 28) or KSLLHTNGNTY (SEQ ID NO: 82 and SEQ ID NO: 100);
 e. a light chain variable region CDR2 sequence comprising a sequence that is identical to the sequence RMSVLAS (SEQ ID NO: 29) or RMS (SEQ ID NO: 83 and SEQ ID NO: 101), or is a sequence having 1 or 2 amino acid differences as compared to the sequence RMSVLAS (SEQ ID NO: 29) or RMS (SEQ ID NO: 83 and SEQ ID NO: 101); and
 f. a light chain variable region CDR3 sequence comprising a sequence that is identical to the sequence MQHLEYPLT (SEQ ID NO: 30) or MQHLEYPLT (SEQ ID NO: 84 and SEQ ID NO: 102), or is a sequence having 1 or 2 amino acid differences as compared to the sequence MQHLEYPLT (SEQ ID NO: 30) or MQHLEYPLT (SEQ ID NO: 84 and SEQ ID NO: 102).

In other aspects, the effector-deficient IV.3 antibody comprises a variable heavy chain sequence comprising a sequence that is at least 75%, 80%, 85%, 90%, 95%, 96%, 97%, 98%, or 99% identical to the sequence shown in SEQ ID NO: 32; and a variable light chain sequence comprising a sequence that is at least 75%, 80%, 85%, 90%, 95%, 96%, 97%, 98%, or 99% identical to the sequence shown in SEQ ID NO: 34.

In other aspects, the effector-deficient IV.3 antibody comprises:
 a. a heavy chain sequence comprising a sequence that is at least 75%, 80%, 85%, 90%, 95%, 96%, 97%, 98%, or 99% identical to the sequence shown in SEQ ID NO: 43 or SEQ ID NO: 45, and
 b. a light chain sequence comprising a sequence that is at least 75%, 80%, 85%, 90%, 95%, 96%, 97%, 98%, or 99% identical to the sequence shown in SEQ ID NO: 51.

In one embodiment, the effector-deficient IV.3 antibody is a humanized antibody comprising a variable heavy chain sequence comprising a sequence that is at least 75%, 80%, 85%, 90%, 95%, 96%, 97%, 98%, or 99% identical to the sequence shown in SEQ ID NO:36 or SEQ ID NO: 38; and a variable light chain sequence comprising a sequence that is at least 75%, 80%, 85%, 90%, 95%, 96%, 97%, 98%, or 99% identical to the sequence shown in SEQ ID NO: 41 or SEQ ID NO: 85.

In certain embodiments, the effector-deficient humanized IV.3 antibody comprises:
 a. a heavy chain sequence that is at least 75%, 80%, 85%, 90%, 95%, 96%, 97%, 98%, or 99% identical to the sequence shown in SEQ ID NO: 47 or SEQ ID NO: 49; and
 b. a light chain sequence that is at least 75%, 80%, 85%, 90%, 95%, 96%, 97%, 98%, or 99% identical to the sequence shown in SEQ ID NO: 53 or SEQ ID NO: 87.

3. Effector-Deficient MDE-8 Monoclonal Antibodies

In some aspects, the effector-deficient anti-CD32a antibody is an effector-deficient MDE-8 antibody. In some aspects the effector-deficient MDE-8 antibody comprises:
 a. a heavy chain variable region CDR1 sequence comprising a sequence that is identical to the sequence SYGMH (SEQ ID NO: 54) or GFTFSSY (residues 1-7 of SEQ ID NO: 94), or is a sequence having 1 or 2 amino acid differences as compared to the sequence SYGMH (SEQ ID NO: 54) or GFTFSSY (residues 1-7 of SEQ ID NO: 94);
 b. a heavy chain variable region CDR2 sequence comprising a sequence that is identical to the sequence VIWYDGSNYYYTDSVKG (SEQ ID NO: 55) or IWYDGSNY (SEQ ID NO: 95), or is a sequence having 1 or 2 amino acid differences as compared to the sequence VIWYDGSNYYYTDSVKG (SEQ ID NO: 55) or IWYDGSNY (SEQ ID NO: 95);
 c. a heavy chain variable region CDR3 sequence comprising a sequence that is identical to the sequence DLGAAASDY (SEQ ID NO: 56) or ARDLGAAASDY (SEQ ID NO: 96), or is a sequence having 1 or 2 amino acid differences as compared to the sequence DLGAAASDY (SEQ ID NO: 56) or ARDLGAAASDY (SEQ ID NO: 96);
 d. a light chain variable region CDR1 sequence comprising a sequence that is identical to the sequence RASQGINSALA (SEQ ID NO: 57) or QGINSA (SEQ ID NO: 97), or is a sequence having 1 or 2 amino acid differences as compared to the sequence RASQGINSALA (SEQ ID NO: 57) or QGINSA (SEQ ID NO: 97);
 e. a light chain variable region CDR2 sequence comprising a sequence that is identical to the sequence DASSLES (SEQ ID NO: 58) or DAS (SEQ ID NO: 98), or is a sequence having 1 amino acid differences as compared to the sequence DASSLES (SEQ ID NO: 58) or DAS (SEQ ID NO: 98); and
 f. a light chain variable region CDR3 sequence comprising a sequence that is identical to the sequence QQFNSYPHT (SEQ ID NO: 59) or QQFNSYPHT (SEQ ID NO: 99), or is a sequence having 1 or 2 amino acid differences as compared to the sequence QQFNSYPHT (SEQ ID NO: 59) or QQFNSYPHT (SEQ ID NO: 99).

In other aspects, the effector-deficient MDE-8 antibody comprises a variable heavy chain sequence comprising a sequence that is at least 75%, 80%, 85%, 90%, 95%, 96%, 97%, 98%, or 99% identical to the sequence shown in SEQ ID NO: 61; and a variable light chain sequence comprising a sequence that is at least 75%, 80%, 85%, 90%, 95%, 96%, 97%, 98%, or 99% identical to the sequence shown in SEQ ID NO: 63.

In one embodiment, the effector-deficient anti-CD32a antibody is an effector-deficient anti-MDE8 antibody comprising:
 a. a heavy chain sequence that is at least 75%, 80%, 85%, 90%, 95%, 96%, 97%, 98%, or 99% identical to the sequence shown in SEQ ID NO: 65 or SEQ ID NO: 67; and
 b. a light chain sequence that is at least 75%, 80%, 85%, 90%, 95%, 96%, 97%, 98%, or 99% identical to the sequence shown in SEQ ID NO: 69.

The antibodies of the composition and method embodiments may be fully human, humanized, chimeric, recombinant, or synthetic.

In some aspects, the invention comprises an isolated antibody that competes for binding to CD32a with an effector-deficient antibody disclosed herein.

In some aspects, the invention comprises a pharmaceutical composition comprising an effector-deficient anti-CD32a antibody as described herein.

In one embodiment, the effector-deficient anti-CD32a antibody is an effector-deficient MDE-8, IV.3, or AT-10 monoclonal antibody. In one embodiment, the effector-deficient MDE-8, IV.3, or AT-10 monoclonal antibody is humanized.

An effector deficient anti-CD32a monoclonal antibody that specifically binds CD32a comprising at least a portion of an Fc domain that is mutated at one or more amino acids, wherein the mutation prevents Fc-mediated binding to CD16, CD32, or CD64 IgG receptors is encompassed.

b. Further Antibody Embodiments

The antibodies in the composition and method embodiments may exhibit any or all of the following functional features:
 a. the antigen-binding portions of the antibodies bind human CD32a with an equilibrium affinity constant value ("$K_D$") stronger (less than) than $10^{-8}$ M when in aqueous solution;
 b. the antigen-binding portions of the antibodies bind human CD32 where such binding inhibits stable interactions between such bound-CD32 and the Fc-region of any human or therapeutic IgG molecule where such human or therapeutic IgG molecule is either: (1) bound in a Fab-dependent manner to at least one antigen molecule, or (2) clustered into an assembly of at least two such human or therapeutic IgG molecules, or (3) localized to a surface in such a manner so as to restrict aqueous diffusion of the human or therapeutic IgG molecule;
 c. the antibodies include at least a portion of an Fc-region, and either lack the capacity, or have reduced capacity, for Fc-region binding to human IgG receptors (FcgammaRs) of classical types I (CD64), II (CD32), or III (CD16), where such reduced or absent binding is comparatively more than 20%, 30%, 40%, 45%, or 50% weaker, than that of corresponding naturally occurring classical IgG-Fc-regions (i.e., either of IgG1, IgG2, IgG3, or IgG4), where any such classical IgG-Fc-region exhibits binding to CD16, CD32, or CD64.

The antibodies in the composition and method embodiments may exhibit any or all of the following structural features:
 a. The antibodies comprise, consist, or consist essentially of (in terms of amino acid composition) the following arrangement of a total of four polypeptides per single IgG molecule:
  i. two heavy chain polypeptides covalently bound together by at least two cysteine-to-cysteine disulfide bonds, wherein such interchain disulfide bonds are located in or near the hinge region, and wherein such heavy chain polypeptides are of the IgG isotype (class 1, 2, 3, or 4, or any hybrid version comprising segments of the same) of heavy chain immunoglobulin molecule, and where each such heavy chain polypeptide is comprised of at least a portion of one variable domain (VH) and one, two, or three constant domains (CH1, CH2, and CH3) or portions thereof. An example of a hybrid constant region IgG heavy chain molecule would be one having an IgG1 CH1 domain with a hinge region derived from IgG1 and the remaining carboxy-terminal portion of the polypeptide derived from that of the CH2 and CH3 domains of the IgG2 heavy chain;
  ii. two light chain polypeptides covalently bound each (individually) to a single heavy chain polypeptide (of item [i] immediately above), wherein such covalent bond consists of at least one cysteine-to-cysteine interchain disulfide bond between a single said light chain and a single said heavy chain polypeptide, and wherein such light chain polypeptides are of the kappa or the lambda type of light chain immunoglobulin molecules, each of which comprising, consisting, or consisting essentially of at least one variable domain (VL) and at least one light chain constant domain;
 b. The antibodies may have an apparent molecular mass (as determined by SDS-PAGE analysis using 8%-12% polyacrylamide gels under non-reducing conditions) greater than about 100,000 daltons and less than about 250,000 daltons, greater than about 120,000 and less than about 180,000 daltons, or about 140,000 to 165,000 daltons, in apparent molecular mass;
 c. The antibodies may have heavy chain constant regions with amino acid compositions that are at least 85%, 90%, 95%, 96%, 97%, 98%, or 99% identical to the heavy chain constant regions of naturally occurring human IgG isotype molecules of class 1 (IgG1), 2 (IgG2), 3 (IgG3), or 4 (IgG4), wherein such identity is determined for each amino acid of the antibodies compared to each corresponding position naturally occurring in human IgG heavy chains of any isotype, as found by genetic sequencing or as reported in the relevant literature or as found in any therapeutic IgG antibody used to treat human patients, wherein such identity comparison allows sufficient sequence gap-lengths and a sufficient quantity of gaps so as to maximize identity between compared polypeptides. The composition of said naturally occurring human antibody molecules includes any and all allotypic variants (see, e.g., Jefferis R, Lefranc M P. Human immunoglobulin allotypes: possible implications for immunogenicity (2009 July-August) MAbs 1:332; PubMed ID: 20073133);
 d. The antibodies may have light chain constant regions with amino acid compositions that at least 85%, 90%, 95%, 96%, 97%, 98%, or 99% identical to the light chain constant regions of naturally occurring human kappa or lambda type molecules, wherein such identity is determined for each amino acid of the antibodies compared to each corresponding position naturally occurring in human light chains as found by genetic sequencing or as reported in the relevant literature or as found in any therapeutic antibody used to treat human patients, wherein such identity comparison allows sufficient sequence gap-lengths and a sufficient quantity of gaps so as to maximize identity between compared polypeptides. The composition of said naturally occurring human antibody molecules includes any and all possible allotypic variants (see, e.g., Jefferis R, Lefranc M P. Human immunoglobulin allotypes: possible implications for immunogenicity (2009 July-August) MAbs 1:332; PubMed ID: 20073133);

e. The antibodies may comprise, consist, or consist essentially of heavy chain variable (VH) and light chain variable (VL) domains derived from a mammalian source (e.g., human, primate, rabbit, ruminant, mouse or other rodent). In cases where the VH or the VL coding source is not human, the antibody may be either chimeric (due to the presence of human constant regions) or humanized (due to the grafting of non-human amino acid sequences onto a human framework variable region);

f. In one embodiment, the antibodies are not conjugated to any of the following: (1) a cytotoxin (e.g., vincristine), (2) a radioactive substance (e.g., $^{111}$indium), (3) an imaging agent (e.g., fluorescein), (4) a small molecule therapeutic drug (e.g., bleomycin), (5) a therapeutic non-antibody polypeptide (e.g., interferon-gamma), (6) an enzyme (e.g., a peroxidase), (7) a vaccine-substance (e.g., a viral polypeptide), or (8) a polyethylene glycol molecule (e.g., PEG).

g. In one embodiment, the antibodies are conjugated to any of the following: (1) a cytotoxin (e.g., vincristine), (2) a radioactive substance (e.g., $^{111}$indium), (3) an imaging agent (e.g., fluorescein), (4) a small molecule therapeutic drug (e.g., bleomycin), (5) a therapeutic non-antibody polypeptide (e.g., interferon-gamma), (6) an enzyme (e.g., a peroxidase), (7) a vaccine-substance (e.g., a viral polypeptide), or (8) a polyethylene glycol molecule (e.g., PEG).

The antibodies in the composition and method embodiments may exhibit any or all of the following structure-function correlates:

a. The antibodies may comprise, consist, or consist essentially of two CD32 binding domains that derive from the variable (Fab) regions formed by each of the two heavy-light chain pairs, and because of this divalent structure have the capacity to bind either one or two antigen epitopes;

b. The Fc region of the antibodies is either reduced in its ability, or completely lacking the ability, to bind human CD16, CD32, or CD64 IgG receptors, wherein such reduced IgG receptor binding activity is the result of either (1) fusion (e.g., hybridization) of two or more IgG-Fc-region polypeptide sequences, (2) enzymatic modification of Fc-region carbohydrate molecules (e.g., modification or removal of a carbohydrate molecule from the asparagine residue located at position 297 in the EU index of Kabat), or (3) engineered amino acid mutations at one or more positions in the constant region of the IgG heavy chain, wherein such engineered mutation reduces or eliminates Fc-dependent binding to the following types of classical human IgG receptors: CD16, CD32, and CD64;

c. The antibodies, when bound to human CD32, form stable immune complexes that inhibit the capacity of the Fc region of other IgG antibodies to cause said CD32 molecules to directly induce inflammatory cellular reactions, wherein such other IgG antibodies are either: (1) bound in a Fab-dependent manner to at least one antigen molecule, or (2) clustered into an assembly of at least two such IgG molecules, or (3) localized to a surface in such a manner so as to restrict aqueous diffusion of said IgG molecule.

Nucleic Acids, Vectors, and Host Cells

The invention also provides a synthetic or recombinant nucleic acid sequence encoding any of the antibodies described herein. Such nucleic acid is, for instance, isolated from a B-cell that is capable of producing an antibody described herein. Such nucleic acids encode the heavy and light chain sequences set forth herein. Alternatively, such nucleic acids encode heavy and light chain sequences comprising the heavy and light chain CDRs, respectively, set forth herein. In some embodiments, the nucleic acids will encode functional parts of the antibodies described herein. Due to the degeneracy of the nucleic acid code, multiple nucleic acids will encode the same amino acid and all are encompassed herein. Certain encompassed nucleic acids are described in Tables 1-5.

In some aspects, the invention comprises a vector comprising a nucleic acid molecule as described herein. In some embodiments, the invention comprises a host cell comprising a nucleic acid molecule as described herein.

In some aspects, the invention comprises a nucleic acid molecule encoding at least one antibody disclosed herein.

Methods of Making Antibodies

In one embodiment, a method of making an effector-deficient anti-CD32a antibody is provided. In one aspect the method comprises culturing a host cell comprising a nucleic acid encoding an effector-deficient anti-CD32a antibody and isolating a secreted antibody. The nucleic acid encoding the effector-deficient anti-CD32a antibody may be any nucleic acid described in Tables 1-5 or fragments or variants thereof.

In one embodiment, a host cell expressing an effector-deficient anti-CD32a antibody is encompassed. The host cell may be a mammalian cell. Non-limiting examples include host cells derived from a human individual, rodent, rabbit, llama, pig, cow, goat, horse, ape, or gorilla. In one embodiment, said host cell comprises a human cell, a murine cell, a rabbit cell and/or a llama cell.

In one embodiment, a host cell may comprise Chinese hamster ovary (CHO) cell line, 293(T) cells, COS cells, NS0 cells and other cell lines known in the art and comprise nucleic acid sequences encoding the antibody described herein. Host cells may be adapted to commercial antibody production ("producer cell"). Proliferation of said producer cell results in a producer cell line capable of producing effector-deficient anti-CD32a antibodies. A producer cell line may be suitable for producing compounds for use in humans. Hence, said producer cell line may be free of pathogenic agents such as pathogenic micro-organisms.

Further provided is a method for producing antibodies which are capable of specifically binding CD32a, wherein the antibody prevents the activation of CD32a by immobilized IgG or prevents activation of CD32 by IgG immune complexes, the method comprising: producing an antibody-producing cell capable of producing said effector-deficient antibodies and obtaining antibodies produced by said antibody producing cell.

An isolated or recombinant antibody, as well as an isolated or recombinant host cell, obtainable by one of the methods provided herein, or a functional equivalent thereof, is also provided.

In one embodiment, the antibodies were produced by obtaining nucleic acid molecules coding for the variable region of light chain and heavy chains of anti-CD32a antibodies (IV.3, AT-10, and MDE-8). For example, the antibodies may be obtained: 1) from hybridoma cell lines by Reverse Transcription-Polymerase Chain Reaction (RT-PCR) using ribonucleic acid (RNA) isolated from these cell lines and oligo primers directed to the 5' leader coding sequence and 5' constant chain coding sequence, or 2) by producing synthetic molecules (by commercially available means) containing the known nucleic acid sequences of variable regions of light chain and heavy chains of anti-CD32a antibodies.

In one embodiment, nucleic acid molecules coding for humanized variable regions of light chain and heavy chains of anti-CD32a antibodies were obtained by producing synthetic molecules (by commercially available means) containing the known nucleic acid sequences with the modification described herein.

In one embodiment, nucleic acid molecules coding for the variable region of light chain and heavy chains of anti-CD32a antibodies (IV.3, AT-10, and MDE-8) were cloned into commercially available plasmid vectors, pFUSE, that contain the respective nucleic acid sequences coding for the light chain constant region (immunoglobulin kappa), and the heavy chain constant regions (human IgG1 or human IgG2).

In one embodiment, effector-deficient anti-CD32a antibodies were produced by creating nucleic acid mutations by site-directed mutagenesis on the heavy chain constant regions coding sequences of pFUSE plasmids.

In one embodiment, anti-CD32a antibodies were produced by transfecting human embryonic kidney cells (e.g. Expi293 cells) with pFUSE plasmid vectors containing nucleic acid molecules coding for variable regions as well as constant regions of light and heavy antibody chains. In some aspects, the nucleic acid molecules coded for chimeric, humanized, or human anti-CD32a mAbs, in IgG1 or IgG2 isotype, in native (effector-competent) or mutated (effector-deficient) format.

In one embodiment, anti-CD32a antibodies secreted by transfected cells were purified from culture media by Protein G column purification and dialized in buffered saline prior to use.

Pharmaceutical Compositions

The invention comprises a pharmaceutical composition comprising at least one effector-deficient anti-CD32a antibody as described herein and a pharmaceutically acceptable excipient. In some embodiments, the pharmaceutical composition further comprises an additional active agent.

In certain embodiments, the pharmaceutical composition will be determined by one skilled in the art depending upon, for example, the intended route of administration, delivery format and desired dosage. See, for example, Remington's Pharmaceutical Sciences, 18$^{th}$ Edition, A. R. Gennaro, ed., Mack Publishing Company (1995). In certain embodiments, such compositions may influence the physical state, stability, rate of in vivo release and rate of in vivo clearance of the antibodies of the invention.

In certain embodiments, the excipient in the pharmaceutical composition can be either aqueous or non-aqueous in nature. For example, in certain embodiments, a suitable excipient can be water for injection, physiological saline solution or artificial cerebrospinal fluid, possibly supplemented with other materials common in compositions for parenteral administration. In some embodiments, the saline comprises isotonic phosphate-buffered saline. In certain embodiments, neutral buffered saline or saline mixed with serum albumin are further exemplary excipients. In certain embodiments, pharmaceutical compositions comprise Tris buffer of about pH 7.0-8.5, or acetate buffer of about pH 4.0-5.5, which can further include sorbitol or a suitable substitute therefore. In certain embodiments, a composition comprising an effector-deficient antibody as described herein, with or without at least one additional therapeutic agents, can be prepared for storage by mixing the selected composition having the desired degree of purity with optional formulation agents (Remington's Pharmaceutical Sciences, supra) in the form of a lyophilized cake or an aqueous solution. Further, in certain embodiments, a composition comprising an effector-deficient antibody as described herein, with or without at least one additional therapeutic agents, can be formulated as a lyophilizate using appropriate excipients such as sucrose.

The antibodies/compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques.

CD32a-Mediated Mediated Diseases and Disorders

CD32a-mediated diseases and disorders include heparin-induced thrombocytopenia (HIT), immune thrombocytopenic purpura (ITP), antiphospholipid syndrome (APS), thrombosis associated with autoimmunity or with certain drugs (e.g., heparin) and antibody therapies (e.g., anti-VEGF or anti-CD40L immunotherapies), transfusion or organ transplantation reactions, certain viral infections, rheumatoid arthritis (RA), psoriasis, psoriatic arthritis, inflammatory bowel disease, osteoarthritis, systemic lupus erythematous (SLE), asthma, allergic rhinitis, lupus nephritis, antibody-mediated anemias, anaphylaxis and airway inflammation. See, e.g., Gillis C et al. Contribution of Human FcgammaRs to Disease with Evidence from Human Polymorphisms and Transgenic Animal Studies (2014 May 30) Front Immunol 5:254; PubMed ID: 24910634; Bruhns P. Properties of mouse and human IgG receptors and their contribution to disease models (2012 Jun. 14) Blood, 119 (24):5640-9, PubMed ID: 22535666; and Hogarth P M and Pietersz G A, Fc receptor-targeted therapies for the treatment of inflammation, cancer and beyond (2012 Mar. 30) Nat Rev Drug Discov 11(4):311-31, PubMed ID: 22460124.

In one embodiment, the CD32a-mediated disease or disorder is thrombocytopenia. Thrombocytopenia is characterized by a drop in circulating platelets. In one embodiment, thrombocytopenia is defined as a platelet count less than the lower limit of normal (usually taken as $150 \times 10^9$/L). In other embodiments, thrombocytopenia is defined as a fall in the number of circulating platelets. For example, a fall in the platelet count of 30-50% or more, following administration of heparin, may be a symptom of heparin-induced thrombocytopenia, even if the platelet count does not fall below $150 \times 10^9$/L. (Warkentin T E. Clinical presentation of heparin-induced thrombocytopenia (October 1998) Semin Hematol 35(4 Suppl 5):9-16; discussion 35-6; PubMed ID:

9855179). The platelet count is typically measured by electronic counting methods, and usually as part of a Complete Blood Count (CBC). Methods for treating thrombocytopenia with any one of, or a combination of, the effector-deficient antibodies described herein, alone or in combination with other therapies, are encompassed.

In another embodiment, the CD32a-mediated disease or disorder is IgG-mediated thrombosis. In one embodiment, IgG-mediated thrombosis is thrombosis caused by IgG immune complexes or by immobilized IgG (see, e.g., Reilly M P et al. Heparin-induced thrombocytopenia/thrombosis in a transgenic mouse model requires human platelet factor 4 and platelet activation through FcgammaRIIA. Blood. 2001 Oct. 15; 98(8):2442-7. PubMed ID: 11588041; and also Taylor S M et al. Thrombosis and shock induced by activating antiplatelet antibodies in human FcgammaRIIA transgenic mice: the interplay among antibody, spleen, and Fc receptor. Blood. 2000 Dec. 15; 96(13):4254-60. PubMed ID: 11110699, respectively). Methods for treating IgG-mediated thrombosis with any one of, or a combination of, the effector-deficient antibodies described herein are encompassed. A method for treating IgG-mediated thrombosis comprising administering one or a combination of an effector-deficient antibody as described herein, alone or in combination with other therapies, wherein IgG-thrombosis is any thrombosis caused by IgG immune complexes or by immobilized IgG In some aspects, the CD32a-mediated disease or disorder is caused, at least in part, by activation of CD32a on or in cells (Hogarth P M et al. Fc receptor-targeted therapies for the treatment of inflammation, cancer and beyond (30 Mar. 2012) Nat Rev Drug Discov 11:311; PubMed ID: 22460124), including platelets, monocytes, neutrophils, basophils, eosinophils, macrophages, dendritic cells (Boruchov A M et al. Activating and inhibitory IgG Fc receptors on human DCs mediate opposing functions (October 2005) J Clin Invest 115:2914; PubMed ID: 16167082), mast cells, and dermal microvascular endothelial cells (Groger M et al. Dermal microvascular endothelial cells express CD32 receptors in vivo and in vitro (15 Feb. 1996) J Immunol 156:1549; PubMed ID: 8568259). In some other aspects, the CD32a-mediated disease or disorder is caused, at least in part, by activation of CD32a on malignant cells, e.g., Hodgkin's disease, non-Hodgkin's lymphoma, Burkitt's lymphoma, anaplastic large cell lymphoma, cutaneous T-cell lymphomas, nodular small cleaved-cell lymphomas, lymphocytic lymphomas, peripheral T-cell lymphomas, Lennert's lymphomas, immunoblastic lymphomas, T-cell leukemias/lymphomas, adult T-cell leukemia, follicular lymphomas, diffuse large cell lymphomas of B lineage, angioimmunoblastic lymphadenopathy (AILD)-like T-cell lymphoma, HIV-associated body cavity based lymphomas, Embryonal carcinomas, undifferentiated carcinomas of the rhino-pharynx, Castleman's disease, Kaposi sarcoma and other B-cell lymphomas. Methods for treating a disease or disorder characterized by activation of CD32a with any one of or a combination of, the effector-deficient antibodies described herein, alone or in combination with other therapies, are encompassed.

In one embodiment, the CD32a-mediated disease or disorder is an immune, autoimmune, allergic, or inflammatory disease or disorder. The immune, autoimmune, allergic, or inflammatory disorder may be rheumatoid arthritis (RA), psoriasis, psoriatic arthritis, inflammatory bowel disease, including Crohn's disease and ulcerative colitis, antiphospholipid syndrome (APS), atopic dermatitis, chronic inflammatory pulmonary disease, osteoarthritis, systemic lupus erythematous (SLE), lupus nephritis, systemic scelrosis, Graves' disease, Hashimoto's thyroiditis, Wegner's granulomatosis, Omen's syndrome, chronic renal failure, idiopathic thrombocytopenic purpura, insulin-dependent diabetes mellitus, acute infectious mononucleosis, HIV, herpes virus-associated diseases, multiple sclerosis, hemolytic anemia, thyroiditis, stiff man syndrome, pemphigus vulgaris, and myasthenia gravis, antibody-mediated arthritis, or antibody-induced anemias or cytopenias Methods for treating an immune, autoimmune, allergic, or inflammatory disease or disorder with any one of, or a combination of, the effector-deficient antibodies described herein are encompassed. Methods for treating rheumatoid arthritis (RA), psoriasis, psoriatic arthritis, inflammatory bowel disease, including Crohn's disease and ulcerative colitis, antiphospholipid syndrome (APS), atopic dermatitis, chronic inflammatory pulmonary disease, osteoarthritis, systemic lupus erythematous (SLE), lupus nephritis, antibody-mediated arthritis, or antibody-induced anemias or cytopenias with any one of, or a combination of, the effector-deficient antibodies described herein, alone or in combination with other therapies, are encompassed.

The CD32a-mediated disease or disorder may be an immune complex-mediated disease or disorder. Immune complex-mediated diseases or disorders are characterized by localized or systemic inflammatory processes that damage cells and tissues, as in the cases, for example, of inflammation caused by IgG-induced release of Tumor Necrosis Factor alpha (TNF-alpha, an inflammatory cytokine) from monocytes in RA (Mathsson L et al. Immune complexes from rheumatoid arthritis synovial fluid induce FcgammaRIIa dependent and rheumatoid factor correlated production of tumour necrosis factor-alpha by peripheral blood mononuclear cells (2006) Arthritis Res Ther 8:R64; PubMed ID: 16569263), or of kidney damage caused by polymorphonuclear cells (neutrophils, basophils, eosinophils) in SLE and glomerulonephritis (Suzuki Y et al. Pre-existing glomerular immune complexes induce polymorphonuclear cell recruitment through an Fc receptor-dependent respiratory burst: potential role in the perpetuation of immune nephritis (2003 Mar. 15) J Immunol 170:3243; PubMed ID: 12626583; Rovin B H. The chemokine network in systemic lupus erythematous nephritis (2008 January 1) Front Biosci 13:904; PubMed ID: 17981599). Immune complex-mediated diseases or disorders include numerous other acute and chronic conditions (Gillis C et al. Contribution of Human FcgammaRs to Disease with Evidence from Human Polymorphisms and Transgenic Animal Studies (2014 May 30) Front Immunol 5:254; PubMed ID: 24910634). Methods for treating an immune complex-mediated disease or disorder with any one of, or any combination of the effector-deficient antibodies described herein, alone or in combination with other therapies, are encompassed.

Diseases or disorders known to be associated with immune complex formation include rheumatoid arthritis (RA), systemic lupus erythematosus (SLE), heparin-induced thrombocytopenia (HIT), lupus nephritis, and APS. Methods for treating rheumatoid arthritis (RA), systemic lupus erythematosus (SLE), heparin-induced thrombocytopenia (HIT), lupus nephritis, and APS with any one of or any combination of the effector-deficient antibodies described herein, alone or in combination with other therapies, are encompassed.

The types of immune complexes associated with such diseases or disorders include circulating IgG immune complexes, deposited IgG immune complexes, and immobilized IgG immune complexes. Methods for treating any disease or disorder characterized by circulating IgG immune complexes, deposited IgG immune complexes, or immobilized IgG immune complexes with any one of, or any combination of the effector-deficient antibodies described herein, alone or in combination with other therapies, are encompassed.

In one embodiment, a disease or disorder characterized by circulating IgG immune complexes, deposited IgG immune complexes, or immobilized IgG immune complexes includes RA and SLE characterized by circulating IgG immune complexes. See, e.g., Zhao X et al. Circulating immune complexes contain citrullinated fibrinogen in rheumatoid arthritis (2008) Arthritis Res Ther 10:R94; PubMed ID: 18710572; Ohyama K et al. Immune complexome analysis of serum and its application in screening for immune complex antigens in rheumatoid arthritis (2011 June) Clin Chem 57:905; PubMed ID: 21482748; Soares N M et al. An improved anti-C3/IgG ELISA for quantification of soluble immune complexes (1 Mar. 2001) J Immunol Methods 249:199; PubMed ID: 11226477; and Huber C et al. C3-containing serum immune complexes in patients with systemic lupus erythematosus: correlation to disease activity and comparison with other rheumatic diseases (1989) Rheumatol Int 9:59; PubMed ID: 2814209). Methods for treating RA and SLE, wherein the RA or SLE is characterized by circulating IgG immune complexes with any one of, or any combination of, the effector-deficient antibodies described herein, alone or in combination with other therapies, are encompassed.

In one embodiment, a disease or disorder characterized by circulating IgG immune complexes, deposited IgG immune complexes, or immobilized IgG immune complexes includes RA, SLE, and APS characterized by IgG immune complexes deposited on circulating cells or particles or in tissues. See, e.g., Zhao X et al. Circulating immune complexes contain citrullinated fibrinogen in rheumatoid arthritis (2008) Arthritis Res Ther 10:R94; PubMed ID: 18710572; Nielsen C T et al. Increased IgG on cell-derived plasma microparticles in systemic lupus erythematosus is associated with autoantibodies and complement activation (April 2012) Arthritis Rheum 64:1227; PubMed ID: 22238051; and de Groot P G et al. The significance of autoantibodies against beta-2 glycoprotein I (Jul. 12, 2012) Blood 120:266; PubMed ID: 22553312). Methods for treating RA, SLE, and APS, wherein the RA, SLE, or APS is characterized by IgG immune complexes deposited on or circulating cells or particles or in tissues with any one of, or any combination of, the effector-deficient antibodies described herein, alone or in combination with other therapies, are encompassed.

In one embodiment, a disease or disorder characterized by circulating IgG immune complexes, deposited IgG immune complexes, or immobilized IgG immune complexes includes RA, SLE, HIT, and APS, wherein the RA, SLE, HIT, or APS is characterized by soluble or immobilized immune complexes. See, e.g., Ohyama K et al. Immune complexome analysis of serum and its application in screening for immune complex antigens in rheumatoid arthritis (2011 June) Clin Chem 57:905; PubMed ID: 21482748; Rönnelid J et al. Immune complexes from SLE sera induce IL10 production from normal peripheral blood mononuclear cells by an FcgammaRII dependent mechanism: implications for a possible vicious cycle maintaining B cell hyperactivity in SLE (January 2003) Ann Rheum Dis 62:37; PubMed ID: 12480667; Cines D B et al. Heparin-induced thrombocytopenia: an autoimmune disorder regulated through dynamic autoantigen assembly/disassembly (February 2007) J Clin Apher 22:31; PubMed ID: 17285619; and de Groot P G et al. The significance of autoantibodies against beta-2 glycoprotein I (Jul. 12, 2012) Blood 120:266; PubMed ID: 22553312. Methods for treating RA, SLE, HIT, or APS, wherein the RA, SLE, HIT, or APS is characterized by soluble or immobilized immune complexes with any one of or any combination of the effector-deficient antibodies described herein, alone or in combination with other therapies, are encompassed.

Importantly, more than one type of the above-mentioned immune complexes may be present simultaneously or at differing times in these and other immune complex diseases and disorders. Even in this scenario, the effector-deficient antibodies described herein may be administered to treat one or all of the diseases and disorders.

In one embodiment, methods of treating diseases or disorders characterized by antibodies that bind PF4 comprising administering any one of, or any combination of, the effector-deficient anti-CD32a monoclonal antibodies is encompassed. Antibodies to human platelet factor 4 (PF4) have been identified in RA, APS, SLE, and HIT. See, e.g., Ohyama K et al. Immune complexome analysis of serum and its application in screening for immune complex antigens in rheumatoid arthritis (2011 June) Clin Chem 57:905; PubMed ID: 21482748; Sikara M P et al. Beta 2 Glycoprotein I binds platelet factor 4 (PF4): implications for the pathogenesis of antiphospholipid syndrome (Jan. 21, 2010) Blood 115:713; PubMed ID: 19805618; Satoh T et al. Heparin-dependent and -independent anti-platelet factor 4 autoantibodies in patients with systemic lupus erythematosus (2012 September) Rheumatology (Oxford) 51:1721 PubMed ID: 22718864; and Warkentin T E et al. HITlights: a career perspective on heparin-induced thrombocytopenia (2012 May) Am J Hematol 87:S92; PubMed ID: 22367928. Thus, in one embodiment, methods of treating RA, APS, SLE, and HIT, wherein the RA, APS, SLE, or HIT is characterized by antibodies that bind PF4, comprising administering any one of, or any combination of, the effector-deficient anti-CD32a monoclonal antibodies, either alone or in combination with existing therapies, are encompassed.

In HIT, anti-PF4 IgG antibodies are known to mediate thrombocytopenia and thrombosis via platelet CD32a, where therapeutic amounts of heparin (where heparin is bound to PF4 antigen) play a key role in localizing HIT immune complexes to the platelet surface. See, e.g., Newman P M et al. Heparin-induced thrombocytopenia: new evidence for the dynamic binding of purified anti-PF4-heparin antibodies to platelets and the resultant platelet activation (1 Jul. 2000) Blood 96:182; PubMed ID: 10891449.

In one embodiment, the immune complex-mediated disease is an anti-therapeutic-antibody (ATA) response caused by administration of a non-anti-CD32a antibody or antigen-binding fragment thereof. The non-anti-CD32a antibody may be infliximab, adalimumab, the IgG-Fc-fusion therapeutic, etanercept, certolizumab pegol, golimumab, etanercept, ustekinumab, bevacizumab, omalizumab, belimumab, or tabalumab. In these method embodiments, the effector deficient anti-CD32a antibody may be administered prior to, concurrently with, or following the non-anti-CD32a monoclonal antibody.

In one embodiment, the immune complex-mediated disease or disorder occurs in a patient being treated with a non-anti-CD32a monoclonal antibody for the treatment of RA, SLE, HIT, lupus nephritis, or antiphospholipid syndrome (APS). Methods for treating RA, SLE, HIT, lupus nephritis, or antiphospholipid syndrome (APS), wherein the patient is or has received a non-anti-CD32a monoclonal antibody, with any one of, or any combination of, the effector-deficient antibodies described herein, alone or in combination with other therapies, are encompassed.

In other embodiments, the disease or disorder is a hemostatic disorder. The hemostatic disorder may be selected from the group consisting of antibody-mediated-thrombocytopenia, immune-mediated-thrombocytopenia (ITP), heparin-induced thrombocytopenia (HIT), and heparin-induced thrombocytopenia with thrombosis Methods for treating a hemostatic disorder comprising administering any one of, or any combination of, the effector-deficient antibodies described herein is encompassed. Also encompassed are methods for treating antibody-mediated-thrombocytopenia, immune-mediated-thrombocytopenia (ITP), heparin-induced thrombocytopenia (HIT), and heparin-induced thrombocytopenia with thrombosis (HITT) comprising administering any one of or any combination of, the effector-deficient antibodies described herein, alone or in combination with other therapies (e.g., anticoagulants), is encompassed.

Also encompassed are methods for treating hemostatic disorders caused by treatment of patients with IV-Ig comprising administering any one of, or any combination of, the effector-deficient antibodies described herein, where such effector-deficient antibodies are administered prior to IV-Ig, concurrently with IV-Ig, or subsequently to IV-Ig treatment. IV-Ig is useful for treating autoimmune and transplant patients, but is associated with side effects such as thrombocytopenia and acute arterial and venous thrombosis, anaphylactic shock, transitory renal failure, increased risk of infection, and leucopenia. Thrombosis has been increasing recognized in treatment with IV-Ig (Paran D et al. Venous and arterial thrombosis following administration of intravenous immunoglobulins (July (2005) Blood Coagul Fibrinolysis 16:313; PubMed ID: 15970713; Woodruff R K et al. Fatal thrombotic events during treatment of autoimmune thrombocytopenia with intravenous immunoglobulin in elderly patients (July 1986) Lancet 2:217; PubMed ID: 2873457). Serious thromboembolic events observed with IV-Ig use include deep venous thrombosis (DVT), myocardial infarction (MI), pulmonary embolism (PE), central retinal vein occlusion, and cerebrovascular accidents (CVA). Pollreisz and colleagues showed that IVIg can induce activation, aggregation, degranulation, and inflammatory cytokine release from platelets in a CD32-dependent manner, and this IVIg-induced CD32-dependent platelet activation was completely blocked by AT-10, demonstrating that platelet CD32 was both necessary and sufficient for IVIg-induced prothrombotic activity (Pollreisz A et al. Intravenous immunoglobulins induce CD32-mediated platelet aggregation in vitro (September 2008) Br J Dermatol 159: 578; PubMed PMID: 18565176).

In still other embodiments, the CD32a-mediated disease or disorder is an allergic disorder. The allergic disorder may be selected from the group consisting of asthma, contact dermatitis, allergic rhinitis, anaphylaxis, and allergic reactions. Methods for treating allergic disorder comprising administering any one of, or any combination of, the effector-deficient antibodies described herein is encompassed. Likewise, methods for treating asthma, contact dermatitis, allergic rhinitis, anaphylaxis, and allergic reactions comprising administering any one of, or any combination of, the effector-deficient antibodies described herein, alone or in combination with other therapies, are encompassed.

The presence of both the CD32 IgG receptor and the CD23 IgE receptor (Hasegawa S et al. Functional expression of the high affinity receptor for IgE (FcepsilonRI) in human platelets and its' [sic] intracellular expression in human megakaryocytes (April 1999) Blood 93:2543; PubMed ID: 10194433) on the surface of human platelets indicates a vital link between platelets and allergy, which is particularly evident in pulmonary inflammation, as occurs in asthma and chronic lung disease (Page C et al. Platelets and allergic inflammation (July 2014) Clin Exp Allergy 44:901; PubMed ID: 24708345). The link between CD32 and CD23 has similarly been recognized for immature B-lymphocytes, where IV.3 or AT-10 blockade of CD32 on human tonsillar B-cells was shown to suppress both inducible IgG and inducible IgE synthesis (Horejs-Hoeck J et al. Inhibition of immunoglobulin E synthesis through Fc gammaRII (CD32) by a mechanism independent of B-cell receptor co-cross-linking (July 2005) Immunology 115:407; PubMed ID: 15946258). A mechanistic explanation for CD32/CD23 synergy may have recently been identified in the capacity of IV.3 and AT-10 to induce an anti-inflammatory state in CD32a-bearing cells (Ben Mkaddem S et al. Shifting Fc[gamma]RIIA-ITAM from activation to inhibitory configuration ameliorates arthritis (September 2014) J Clin Invest 124:3945; PubMed PMID: 25061875). The role of CD32a in allergy may also be linked to disorders of hemostasis (Potaczek D P. Links between allergy and cardiovascular or hemostatic system (January 2014) Int J Cardiol 170:278; PubMed ID: 24315352).

In one embodiment, effector-deficient anti-CD32a monoclonal antibodies are used to suppress inflammation driven by reactions in cells displaying CD32a, where such CD32a binds IgG molecules that are immobilized on a surface, such as that of platelets or red blood cells. For example, immobilized IgG binds and activates platelet CD32a, leading to adhesion and granule secretion, and this process has been shown to be blocked by IV.3 (Haimovich B et al. The FcgammaRII receptor triggers pp125FAK phosphorylation in platelets (July 1996) J Biol Chem 271:16332; PubMed ID: 8663117). Additionally, IgG-coated red blood cells are phagocytosed via CD32a, and this activity is inhibited by IV.3 (Wiener E et al. Role of Fc gamma RIIa (CD32) in IgG anti-RhD-mediated red cell phagocytosis in vitro (September 1996) Transfus Med 6:235; PubMed ID: 8885153). Additionally, IgG-coated cells are cleared in a CD32a-dependent manner in patients with SLE, where such clearance is known to be inhibited by IV.3 (Seres T et al. Correlation of Fc gamma receptor expression of monocytes with clearance function by macrophages in systemic lupus erythematosus (September 1998) Scand J Immunol 48:307; PubMed ID: 9743218).

In one embodiment, effector-deficient anti-CD32a monoclonal antibodies are used to suppress inflammation driven by reactions in cells displaying CD32a, where such CD32a interacts with IgG molecules bound to self antigens, such as von Willebrand Factor (vWF), and localize to the CD32a-positive cell, leading to inflammatory activation that is known to be inhibited by IV.3 (for example, see Hoylaerts M F et al. Recurrent arterial thrombosis linked to autoimmune antibodies enhancing von Willebrand factor binding to platelets and inducing Fc gamma RII receptor-mediated platelet activation (April 1998) Blood 91:2810; PubMed ID: 9531591). Thus, methods for suppressing inflammation comprising administering one or more effector-deficient anti-CD32a monoclonal antibodies, thereby suppressing inflammation, are encompassed.

In one embodiment, effector-deficient anti-CD32a monoclonal antibodies are used to suppress inflammation driven by infectious viruses. For example, IV.3 is known to inhibit dengue virus infection of human mast cells (Brown M G et al. A dominant role for FcgammaRII in antibody-enhanced dengue virus infection of human mast cells and associated CCL5 release (December 2006) J Leukoc Biol 80:1242; PubMed ID: 16940332). Thus, methods for suppressing inflammation comprising administering one or more effector-deficient anti-CD32a monoclonal antibodies, wherein the inflammation is mediated by infectious viruses, thereby suppressing inflammation, are encompassed.

In one embodiment, effector-deficient anti-CD32a monoclonal antibodies are used to suppress inflammation driven by infectious microbes. For example, *staphylococcus aureus* can cause infective endocarditis, inducing platelet-driven CD32a inflammatory reactivity, which is inhibited by IV.3 (Fitzgerald J R et al. Fibronectin-binding proteins of *Staphylococcus aureus, Streptococcus sanguinis, Streptococcus gordonii, Streptococcus oralis*, and *Streptococcus pneumoniae* mediate activation of human platelets via fibrinogen and fibronectin bridges to integrin GPIIb/IIIa and IgG binding to the FcgammaRIIa receptor (January 2006) Mol Microbiol 59:212; PubMed ID: 16359330; Arman M et al. Amplification of bacteria-induced platelet activation is triggered by Fc[gamma]RIIA, integrin [alpha]IIb [beta]3, and platelet factor 4 (May 2014) Blood 123:3166; PubMed ID: 24642751). Similarly, systemic inflammation, sepsis-associated vascular leakage, platelet activation, and coagulation dysfunction in gram-positive sepsis can be CD32a-mediated, and these inflammatory processes are blocked by IV.3 (Sun D et al. *Bacillus anthracis* peptidoglycan activates human platelets through Fc[gamma]RII and complement (July 2013) Blood 122:571; PubMed ID: 23733338). Thus, methods for suppressing inflammation comprising administering one or more effector-deficient anti-CD32a monoclonal antibodies, wherein the inflammation is mediated by infectious microbes, thereby suppressing inflammation, are encompassed.

In one embodiment, effector-deficient anti-CD32a monoclonal antibodies are administered as treatment to patients along with or as a replacement for IV-Ig. Intravenous immunoglobulin (IgG), or "IV-Ig", is approved by the FDA for treatment of various autoimmune or inflammatory diseases, including Primary Humoral Immunodeficiency, Multifocal Motor Neuropathy, B-cell Chronic Lymphocytic Leukemia, Immune Thrombocytopenic Purpura, Kawasaki syndrome, Chronic Inflammatory Demyelinating Polyneuropathy. IVIg is also used to treat neonatal alloimmune thrombocytopenia, HIV-associated thrombocytopenia, autoimmune neutropenia, autoimmune hemolytic anemia, interstitial pneumonia or cytomegalovirus infection in bone marrow transplant patients, bullous pemphigoid, epidermolysis bullosa acquisita, mucous-membrane pemphigoid, necrotizing fasciitis, *pemphigus foliaceus, pemphigus vulgaris*, toxic epidermal necrolysis or Stevens-Johnson syndrome, birdshot retinopathy, Guillain-Barré syndrome, Lambert-Eaton myasthenic syndrome, myasthenia gravis, opsoclonus-myoclonus, polyradiculoneuropathy, refractory dermatomyositis, refractory polymyositis, relapsing-remitting multiple sclerosis. Effector-deficient anti-CD32a monoclonal antibodies may be used to treat these conditions.

In each of the method embodiments, the CD32a-mediated disease or disorder may be characterized by symptoms of shock. As used herein, the term "shock" includes, but is not limited to, hypersensitivity reactions of type I (i.e., mediated by IgE), type II (i.e., mediated by immobilized IgG), or type III (i.e., mediated by IgG complexes), IgG-mediated thrombotic reactions, and IgG-mediated neurologic reactions. Methods for alleviating the symptoms of shock comprising administering any one of or any combination of, the effector-deficient antibodies described herein, alone or in combination with other therapies, is encompassed.

Exemplary Embodiments

In one embodiment, a method for treating a CD32a-mediated disease or disorder in a human subject comprising administering a therapeutically effective amount of an effector-deficient anti-CD32a monoclonal antibody to a human subject, wherein the antibody comprises at least a portion of an Fc region and is effector-deficient, thereby treating the CD32a-mediated disease or disorder is provided.

In one embodiment, the effector-deficient antibody satisfies both the IgG Immune Complex Test and the Immobilized IgG Test, and has an FC region that has been altered so as to reduce or eliminate Fc-binding to CD16, CD32, and/or CD64 type IgG receptors.

In any of the method embodiments described herein, the CD32a-mediated disease or disorder may be an IgG-mediated hemostatic disorder. The hemostatic disorder may be thrombosis with or without thrombocytopenia. The hemostatic disorder may be selected from the group consisting of IgG-mediated-thrombocytopenia, immune-mediated-thrombocytopenia (ITP), antiphospholipid syndrome (APS), anti-platelet-antibody disorders, heparin-induced thrombocytopenia (HIT), heparin-induced thrombocytopenia with thrombosis (HITT), cancer-induced platelet activation, cancer-induced hypercoagulability, platelet-mediated tumor cell metastasis, and platelet-mediated cancer metastasis.

In any of the method embodiments described herein, the CD32a-mediated disease or disorder may be characterized by IgG-Fc-mediated activation of CD32a on platelets, monocytes, neutrophils, basophils, eosinophils, macrophages, dendritic cells, synovial cells, mast cells, or dermal microvascular endothelial cells.

In any of the method embodiments described herein, the CD32a-mediated disease or disorder may be an IgG-mediated immune, autoimmune, or inflammatory disease or disorder. The IgG-mediated immune, autoimmune or inflammatory disorder may be selected from the group consisting of rheumatoid arthritis (RA), psoriasis, psoriatic arthritis, ankylosing spondylitis, inflammatory bowel disease, ulcerative colitis, Crohn's disease, antiphospholipid syndrome (APS), osteoarthritis, systemic lupus erythematous (SLE), lupus nephritis, IgG antibody-induced anemia, and IgG-mediated cytopenia.

In any of the method embodiments described herein, the CD32a-mediated disease or disorder may be an IgG immune complex-mediated disease or disorder. The IgG immune complex-mediated disease may be an anti-therapeutic-antibody (ATA) response caused by administration of a non-anti-CD32a monoclonal antibody or fragment thereof. In any of the method embodiments described herein, the non-anti-CD32a antibody may be infliximab, adalimumab, certolizumab pegol (antibody-like), golimumab, etanercept (antibody-like), ustekinumab, omalizumab, or bevacizumab. In any of the method embodiments described herein, the effector deficient anti-CD32a antibody may be administered prior to, concurrently with, or following the non-anti-CD32a monoclonal antibody. In any of the method embodiments, alone or in combination with other methods, the IgG immune complex-mediated disease or disorder may occur in a patient being treated with a non-anti-CD32a monoclonal antibody for the treatment of rheumatoid arthritis, systemic lupus erythematosus (SLE), lupus nephritis, or inflammatory bowel disease (IBD), including ulcerative colitis and Crohn's disease.

In any of the method embodiments, the CD32a-mediated disease or disorder may be characterized by IgG localized on the surface of cells circulating in the blood of the human subject. The circulating cell type may be one or more of the following: platelets, erythrocytes, monocytes, neutrophils, basophils, eosinophils, B-lymphocytes, macrophages, mast cells, leukemia cells, or microbes such as viruses, bacteria, fungal, or parasitic organisms. In any of the method embodiments, the disease or disorder that is characterized by IgG localized on the surface of cells may be one or more of the following: thrombocytopenia, leukopenia, neutropenia, lymphopenia, monocytopenia, anemia, hemolytic anemia, or sepsis.

In some embodiments, a method for treating antibody-mediated allergic or hypersensitivity reactions of type I, type II, or type III in a human subject comprising: administering a therapeutically effective amount of an effector-deficient anti-CD32a monoclonal antibody to a human subject, wherein the antibody comprises at least a portion of an Fc region and is effector-deficient, thereby treating the antibody-mediated allergic or hypersensitivity reactions of type I, type II, or type III, is provided. In this and any of the method embodiments, or in any combination of method embodiments, the effector-deficient antibody satisfies both the IgG Immune Complex Test and the Immobilized IgG Test, and has an FC region that has been altered so as to reduce or eliminate Fc-binding to CD16, CD32, and/or CD64 type IgG receptors. In any of the method embodiments, the allergic disorder may be selected from the group consisting of atopy, contact dermatitis, allergic rhinitis, systemic anaphylaxis, localized anaphylaxis as exhibited in hay fever, asthma, hives, food allergies, and eczema, allergic reactions to vaccines, allergic reactions to foods, allergic reactions to, allergic reactions to insect products, allergic reactions to drugs, allergic reactions to mold spores, allergic reactions to animal hair and dander, allergic reactions to latex, blood transfusion reactions, platelet transfusion reactions, erythrocyte transfusion reactions, erythroblastosis fetalis, hemolytic anemia, serum sickness, infusion reactions, necrotizing vasculitis, glomerulonephritis, rheumatoid arthritis, systemic lupus erythematosus, and allergic reactions to microorganisms.

In each of the method embodiments described herein, including any combination of the various embodiments, the effector-deficient anti-CD32a antibody may be an effector-deficient MDE-8, IV.3, or AT-10 monoclonal antibody, and the monoclonal antibody may be human or humanized.

In each of the method embodiments described herein, including any combinations of the various method embodiments, the MDE-8, IV.3, and AT-10 monoclonal antibodies may comprise the six CDRs for each antibody, as described herein and in the sequence listing, or may comprise a sequence having 1 or 2 amino acid differences between the CDRs as recited herein and in the sequence listing.

An effector deficient anti-CD32a monoclonal antibody that specifically binds human CD32a, wherein the antibody comprises at least a portion of an Fc region that is effector deficient, wherein the effector-deficient antibody comprises an altered Fc region that reduces or eliminates Fc-binding to CD16, CD32, and/or CD64 type IgG receptors, as compared to a non-altered control is provided.

Definitions

As used herein, the term "Human CD32A mice," "CD32A mice," "transgenic CD32A mice," and "transgenic human CD32A mice" are used interchangeably. CD32A mice have been previously described (McKenzie et al., The role of the human Fc receptor FcgammaRIIA in the immune clearance of platelets: a transgenic mouse model. J Immunol. 1999 Apr. 1; 162(7):4311-8. PubMed ID: 10201963).

Fc receptors (FcR) are leukocyte surface glycoproteins that specifically bind the Fc portion of antibodies. The receptors for IgG, that is FcgammaR, are the most widespread and diverse, the major types being FcgammaRI (CD64), FcgammaRII (CD32) and FcgammaRIII (CD16). As used herein, the term "CD32a" is synonymous with the activating type of FcgammaRII and iterations thereof such as iterations using the Greek gamma symbol in lieu of "gamma".

The term "antibody" refers to an intact immunoglobulin of any isotype, or a fragment thereof that can compete with the intact antibody for specific binding to the target antigen, and includes, for instance, chimeric, humanized, fully human, and bispecific antibodies. An intact antibody may comprise at least two full-length heavy chains and two full-length light chains, but in some instances can include fewer chains such as antibodies naturally occurring in camelids, which can comprise only heavy chains Antibodies can be derived solely from a single source, or can be "chimeric," that is, different portions of the antibody can be derived from two different antibodies. The antigen binding proteins, antibodies, or binding fragments can be produced in hybridomas, by recombinant DNA techniques, or by enzymatic or chemical cleavage of intact antibodies. Unless otherwise indicated, the term "antibody" includes, in addition to antibodies comprising two full-length heavy chains and two full-length light chains, derivatives, variants, fragments, and muteins thereof. Furthermore, unless explicitly excluded, antibodies include monoclonal antibodies, bispecific antibodies, minibodies, domain antibodies, synthetic antibodies (sometimes referred to herein as "antibody mime tics"), chimeric antibodies, humanized antibodies, human antibodies, antibody fusions (sometimes referred to herein as "antibody conjugates"), and fragments thereof.

As used herein, "specific binding" refers to antibody binding to a predetermined antigen. Typically, the antibody binds with a dissociation constant ($K_D$) of 10E7 M or less, and binds to the predetermined antigen with a $K_D$ that is at least two-fold less than its $K_D$ for binding to a non-specific antigen (e.g., albumin, casein) other than the predetermined antigen or a closely-related antigen.

The term "$K_{assoc}$" or "$K_a$", as used herein, is intended to refer to the association rate of a particular antibody-antigen interaction, whereas the term "$K_{dis}$" or "$K_d$," as used herein, is intended to refer to the dissociation rate of a particular antibody-antigen interaction. The term "$K_D$", as used herein, is intended to refer to the dissociation constant, which is obtained from the ratio of $K_d$ to $K_a$ (i.e., $K_d/K_a$) and is expressed as a molar concentration (M).

As used herein, "isotype" refers to the antibody class (e.g., IgM or IgG1) that is encoded by heavy chain constant region genes.

As used herein, the terms "inhibits binding" and "blocks binding" (e.g., referring to inhibition/blocking of binding of CD32 ligand, e.g., IgG, to CD32) are used interchangeably and encompass both partial and complete inhibition/blocking. The inhibition/blocking of IgG to CD32 preferably reduces or alters the normal level or type of effector cell functions that occurs when IgG binds to CD32 without inhibition or blocking. Inhibition and blocking are also intended to include any measurable decrease in the binding affinity of IgG to CD32 when in contact with an anti-CD32 antibody as compared to the ligand not in contact with an anti-CD32 antibody, e.g., the blocking of CD32 ligands to CD32 by at least about 10%, 20%, 30%, 40%, 50%, 60%, 70%, 80%, 90%, 99%, or 100%.

An "Fc" region comprises two heavy chain fragments comprising some or all of the constant "CH" domains of an antibody. The two heavy chain fragments are held together by two or more disulfide bonds. The Fc region may comprise all or part of the hinge region, either with or without additional amino acids from the heavy chain constant region. In other words, the Fc region may optionally comprise one or both of CH2 and CH3.

A "Fab' fragment" comprises one light chain and a portion of one heavy chain that contains the VH domain and the C—H1 domain and also the region between the CH1 and CH2 domains, such that an interchain disulfide bond can be formed between the two heavy chains of two Fab' fragments to form an F(ab')2 molecule.

The term "vector" means any molecule or entity (e.g., nucleic acid, plasmid, bacteriophage or virus) used to transfer protein-coding information into a host cell.

As used herein, the term "thrombocytopenia" refers to a subnormal number of platelets in the circulating blood (Wintrobe M M et al. Disorders of Platelets and Hemostasis. In: Clinical Hematology, Seventh Edition, Lea & Febiger, Philadelphia, 1974). This is typically defined as a platelet count less than the lower limit of normal (usually taken as 150×109/L). It may also be characterized as a fall in the number of circulating platelets. For example, a fall in the platelet count of 30-50% or more, following administration of heparin, may be a symptom of heparin-induced thrombocytopenia, even if the platelet count does not fall below 150×109/L. (Warkentin T E. Clinical presentation of heparin-induced thrombocytopenia (October 1998) Semin Hematol 35(4 Suppl 5):9-16; discussion 35-6; PubMed ID: 9855179). The platelet count is measured by electronic counting methods, usually as part of a Complete Blood Count (CBC).

As used herein, the term "thrombosis" refers to the formation of a blood clot inside a blood vessel (venous or arterial). Typically the blood clot, or thrombus, would consist of fibrin and blood cells, including activated platelets in various proportions.

As used herein, the phrase "IgG-mediated thrombosis" refers to thrombosis where IgG antibody molecules contribute to the formation of the thrombus.

The term "patient" and "subject" are used interchangeably herein to refer to a mammal in need of administration of a therapy.

The terms "disease" and "disorder" as used herein are intended also to include medical conditions and syndromes regarded as abnormal or indicative of impaired function, as distinguished from normal health by signs, symptoms, or laboratory-based diagnostics suggesting the presence of medical diseases or disorders.

"Treating" includes both treating and preventing.

The term "identity" refers to a relationship between the sequences of two or more polypeptide molecules or two or more nucleic acid molecules, as determined by aligning and comparing the sequences. "Percent identity" means the percent of identical residues between the amino acids or nucleotides in the compared molecules and is calculated based on the size of the smallest of the molecules being compared. For these calculations, gaps in alignments (if any) are preferably addressed by a particular mathematical model or computer program (i.e., an "algorithm") Methods that can be used to calculate the identity of the aligned nucleic acids or polypeptides include those described in Computational Molecular Biology, (Lesk, A. M., ed.), 1988, New York: Oxford University Press; Biocomputing Informatics and Genome Projects, (Smith, D. W., ed.), 1993, New York: Academic Press; Computer Analysis of Sequence Data, Part I, (Griffin, A. M., and Griffin, H. G., eds.), 1994, New Jersey: Humana Press; von Heinje, G., 1987, Sequence Analysis in Molecular Biology, New York: Academic Press; Sequence Analysis Primer, (Gribskov, M. and Devereux, J., eds.), 1991, New York: M. Stockton Press; and Carillo et al., 1988, SIAM J. Applied Math. 48:1073.

The term "chimeric antibody" is intended to refer to antibodies in which the variable region sequences are derived from one species and the constant region sequences from another. For example, an antibody in which the heavy and light chain variable region sequences are derived from a mouse antibody and the constant region sequences are derived from a human antibody, might be described as a mouse-human chimeric antibody.

The term "humanized antibody" is intended to refer to antibodies in which CDR sequences derived from antibodies from various mammalian species, such as a mouse, have been grafted onto human germline variable framework sequences. Additional framework region amino acid modifications may be introduced.

The term "effector function" refers to the functional ability of the Fc or constant region of the antibody to bind proteins and/or cells of the immune system and platelets. Typical effector functions of IgG antibodies include the ability to bind complement protein (e.g., C1q), the neonatal receptor (FcRn), or an IgG Fc receptor (FcgammaR) (e.g., Fcgamma RI, Fcgamma RII, Fcgamma RIII). The effects of being able to bind one or more of the foregoing molecules include, but are not limited to antigen-dependent cellular cytotoxicity (ADCC), complement-dependent cytotoxicity (CDC), phagocytosis, opsonization, and effector cell modulation. Abrogation or decrease of effector function may refer to abrogation or decrease in one or more of the biochemical or cellular activities induced at least in part by binding of Fc to its receptors or to a complement protein or an effector cell, while maintaining the antigen-binding activity of the variable region of the antibody.

As used herein, an "effector-deficient" antibody is defined as an antibody having an Fc region that has been altered so as to reduce or eliminate Fc-binding to CD16, CD32, and/or CD64 type IgG receptors.

The term "antigen" refers to any natural or synthetic substance that could bind specifically to an antibody.

The term "specific binding" refers to antibody binding to a predetermined antigen. Typically, the antibody binds with an affinity equilibrium constant stronger than $10^{-7}$ M, and binds to the predetermined antigen with at least two-fold stronger binding to a non-specific antigen.

As used herein, the term "immune complex" refers to the molecular structures consisting of one or more antibody molecules specifically bound to one or more antigen molecules.

The term "epitope" refers to a protein determinant capable of specific binding to, or specific binding by, an antibody.

EXAMPLES

Example 1

Effector-Deficient Monoclonal Antibody MDE-8

The inventors have demonstrated that native human MDE-8 mAbs cause infusion reactions in mice transgenic for its human antigen (i.e., CD32A). These mice are referred to herein as "CD32A mice." Observable signs of IgG-mediated infusion reactions in CD32A mice include hypothermia, rapid or shallow breathing, hunched posture, and locomotor dysfunction; observable signs of severe infusion reactions also include immobilization, convulsion, apparent loss of consciousness, and (infrequently) fatality.

Altering the effector domain (i.e., Fc domain) of the MDE-8 mAb to an effector-deficient IgG format eliminated infusion reactions when administered to CD32A mice.

Moreover, when effector-deficient MDE-8 mAbs were provided prior to challenge with immune complexes, the effector-deficient MDE-8 mAbs prevented immune complex-induced infusion reactions, as well as thrombocytopenia, thrombosis, and shock.

Thus, effector-deficient monoclonal MDE-8 antibodies may be used in place of native MDE-8 antibodies to treat any CD32a mediated disease or disorder. The reasons include that the effector-deficient MDE-8 antibodies will not elicit infusion reactions as observed with native MDE-8. Moreover, when administered prophylactically or therapeutically, effector-deficient MDE-8 antibodies may be used to treat and/or prevent any disease or disorder caused by IgG immune complexes.

Materials and Methods

Effector-competent and effector-deficient variants of MDE-8 mAbs (in both IgG1 and IgG2 formats) were injected intravenously (tail vein) into CD32A mice. Two effector-deficient variants of MDE-8 were assessed in this study; E269R and N297A. CD32A mice have been previously described in McKenzie et al., 1999 Apr. 1, J Immunol, 162(7):4311-8, PubMed ID: 10201963. After MDE-8 mAb injection (100 microgram), animals were monitored for 30 minutes for assessment of infusion reactions. Blood was collected retro-orbitally before and 30 minutes after MDE-8 mAb injection. Platelets were counted by flow cytometry from this collected blood. After 3 hours, some animals were injected intravenously with a 200 micro-liter bolus of immune complexes (ICs) consisting of 150 micro-grams mouse monoclonal anti-human CD40L antibody (clone M90, a murine IgG1 mAb purified by Protein G chromatography from ATCC HB-12055 hybridoma-conditioned media) in balanced stoichiometry with its antigen, CD40L trimer (50 micro-grams) (Peprotech #310-02). Thirty minutes after IC injection, platelets were again counted. Animals were then immediately sacrificed (i.e., 30 minutes after M90+CD40L IC injection), and lungs were harvested, processed for H&E staining, and examined microscopically for the presence of thrombi.

Results

Figure 1:
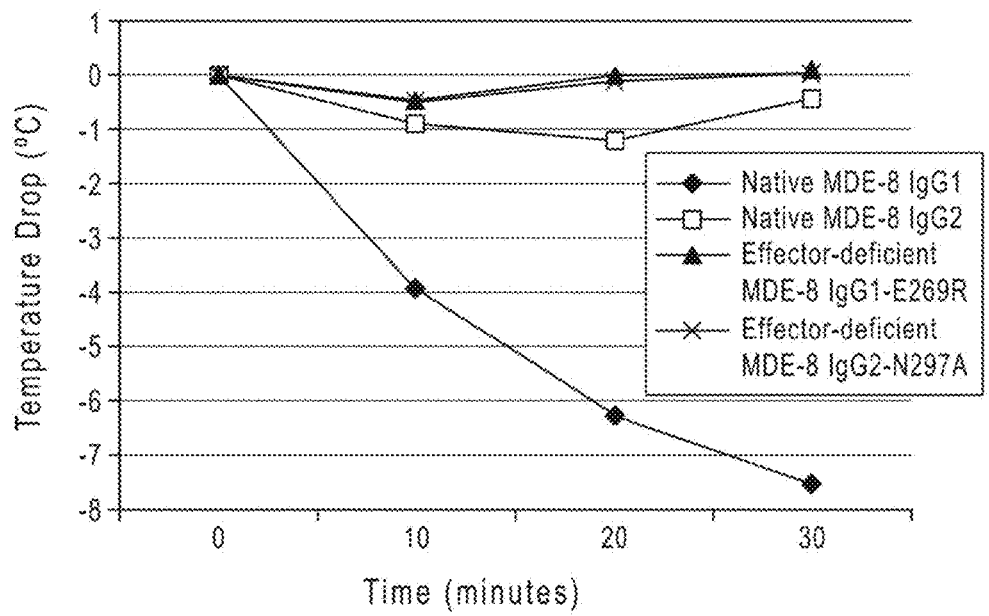

Effector-Deficient MDE-8 mAbs do not Cause Infusion Reactions that are Seen with Effector Competent MDE-8 Antibodies When injected intravenously into CD32A mice, native human MDE-8 IgG1 antibodies cause infusion reactions characterized by hypothermia, as measured by core body temperature (FIG. 1; diamonds). Mice injected with native human MDE-8 IgG1 antibodies also showed signs of severe infusion reactions, including apparent loss of consciousness (data not shown). Mouse IgG receptors have reduced binding to human IgG2 (See, e.g., Overdijk et al., Crosstalk between human IgG isotypes and murine effector cells, 2012 Oct. 1, J Immunol, 189(7): 3430-8, PubMed ID: 22956577), which is consistent with the failure of native anti-human MDE-8 antibodies in IgG2 format to cause hypothermia (FIG. 1; squares). Importantly, two representative effector-deficient human MDE-8 mAbs (in both IgG1 and IgG2 formats) (antibodies comprising the amino acids of SEQ ID NO: 69 together with SEQ ID NO: 65 or SEQ ID NO: 67) did not cause infusion reactions as observed with native human MDE-8 IgG1 antibodies (FIG. 1; triangles and X's). The failure of the IgG2 effector-competent mAb to cause hypothermia (as may be expected), even though it did cause thrombocytopenia, may be surprising to one skilled in the art. This surprising finding also makes clear that lack of hyperthermia does not indicate that the mAb is safe. The effector-deficient results provided in this experiment demonstrate that the effector-deficient antibodies described herein solves the previously unrecognized safety problem of thrombocytopenia.

Figure 2:
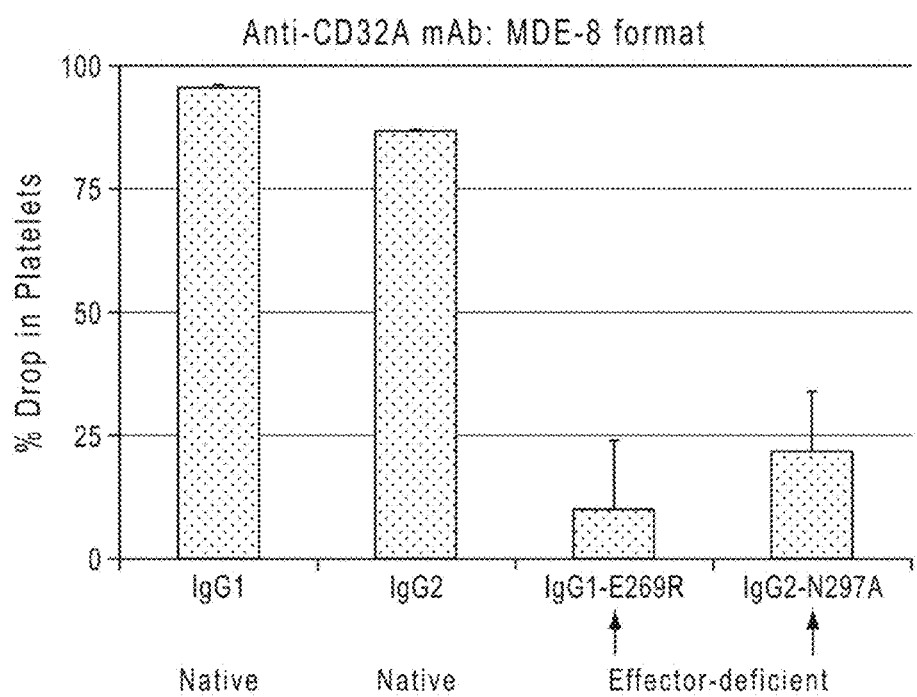

It was next observed that severe thrombocytopenia followed intravenous injection of native human MDE-8 mAbs into CD32A transgenic mice in both IgG1 and IgG2 formats (FIG. 2, columns 1 and 2). In contrast, two representative effector-deficient human MDE-8 mAbs (antibodies comprising the amino acids of SEQ ID NO: 69 together with SEQ ID NO: 65 or SEQ ID NO: 67) did not induce thrombocytopenia when injected into CD32A mice (FIG. 2, columns 3 and 4). The small reduction in circulating platelet numbers seen in FIG. 2 columns 3 and 4 is typical and caused from repeated blood draws.

These experiments demonstrate that thrombocytopenia is independent of hypothermia, and that a drop in platelet count is a more sensitive indicator of infusion reaction than temperature drop, since MDE-8 in IgG2 format failed to cause hypothermia (see FIG. 1) yet largely depleted circulating platelets (FIG. 2).

Figure 3A:
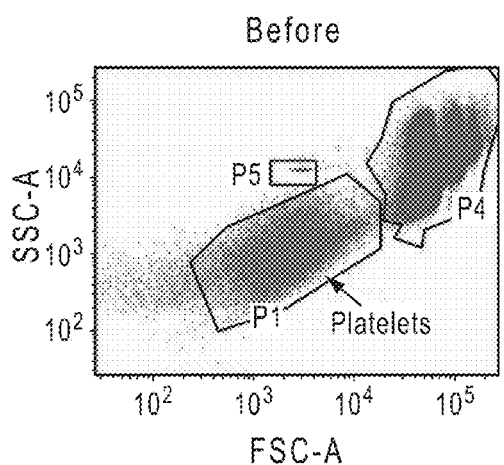
Figure 3B:
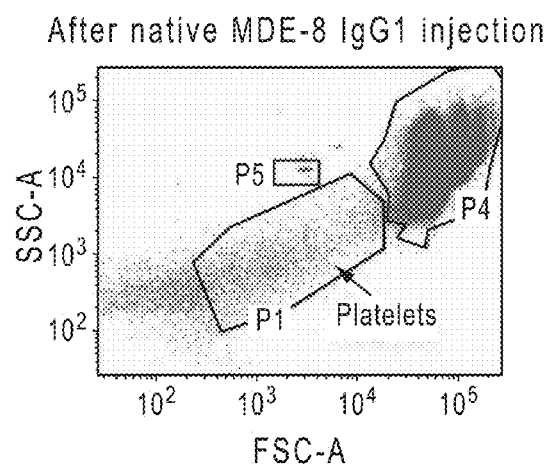

Flow cytometric analysis of whole blood from CD32A transgenic mice before (FIG. 3A) and after (FIG. 3B) intravenous injection of native human MDE-8 mAbs in human IgG1 format showed severe platelet depletion (FIG. 3B). (Fluorescent beads [1 micro-meter] were included to control for blood volume [gate P5]; the upper right quadrant includes red blood cells and white blood cells [gate P4].)

Figure 3C:
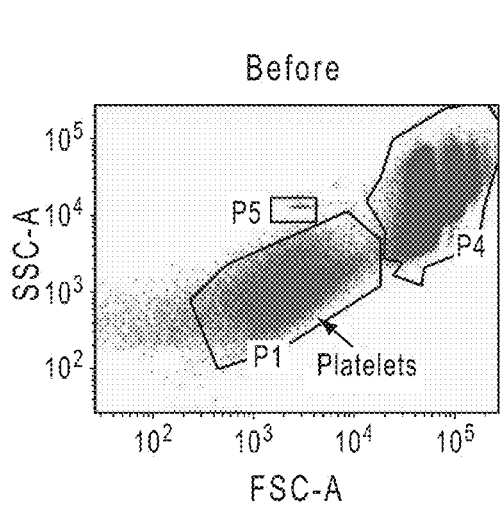
Figure 3D:
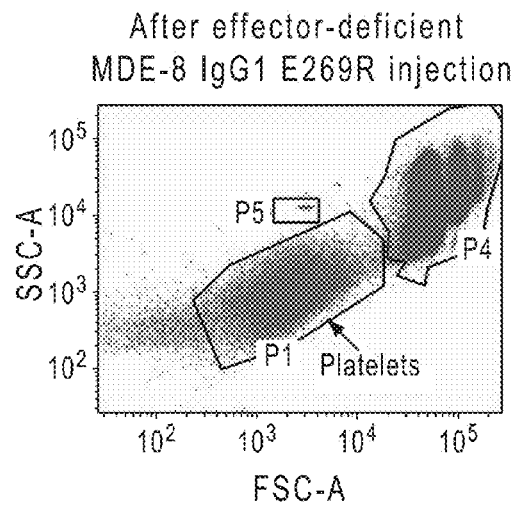
Figure 3E:
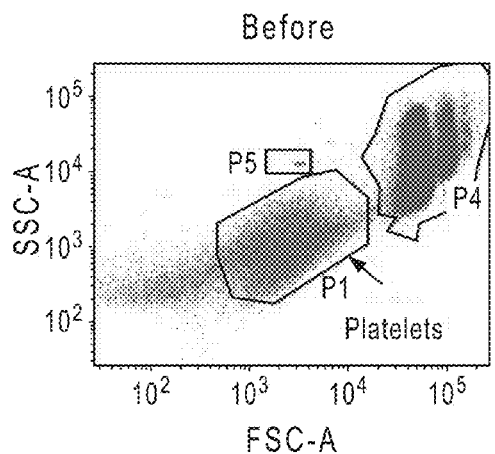

Importantly, when native human MDE-8 IgG1 mAbs were made effector-deficient (antibodies comprising the amino acids of SEQ ID NO: 69 together with SEQ ID NO: 65), they failed to clear circulating platelets (compare FIG. 3C [before injection] and FIG. 3D [after injection of effector-deficient human MDE-8 mAbs] with FIG. 3A and FIG. 3B). Thus, effector-deficient human MDE-8 mAbs did not deplete platelets (FIG. 3D). Further, mice injected with effector-deficient human MDE-8 mAbs (IgG1 E269R and IgG2 N297A) showed no observable signs of infusion reactions (data not shown).

Figure 3F:
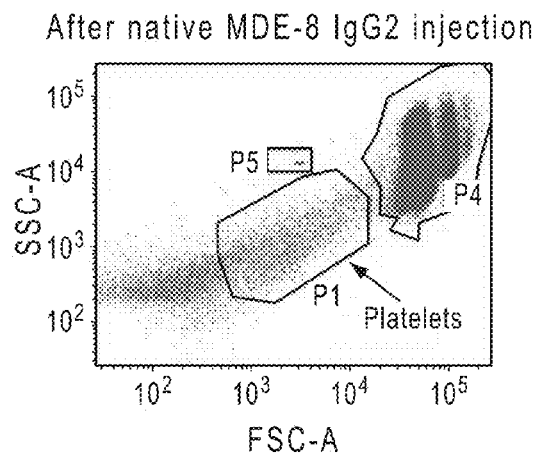
Figure 3G:
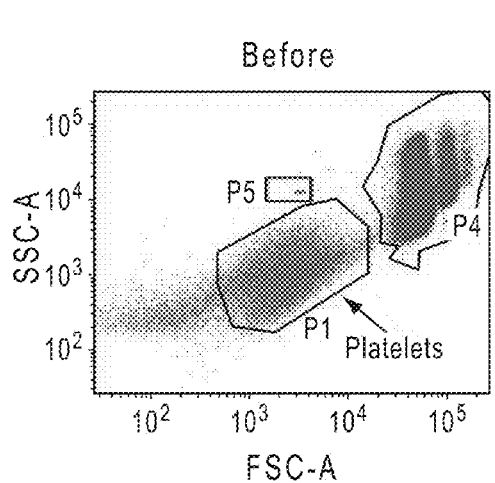

Similar results were obtained when using a different IgG subclass of effector-deficient human MDE-8 mAbs: MDE-8 (antibodies comprising the amino acids of SEQ ID NO: 69 together with SEQ ID NO: 67). Flow cytometric analysis of whole blood from CD32A transgenic mice before (FIG. 3E) and after (FIG. 3F) intravenous injection of native MDE-8 mAb IgG2 showed severe platelet depletion (FIG. 3F). Importantly, when the native MDE-8 mAb IgG2 was made effector-deficient, it no longer cleared circulating platelets (compare FIG. 3G [before injection] and FIG. 3H [after injection of effector-deficient human MDE-8 mAb] with FIG. 3E and FIG. 3F).

Figure 3H:
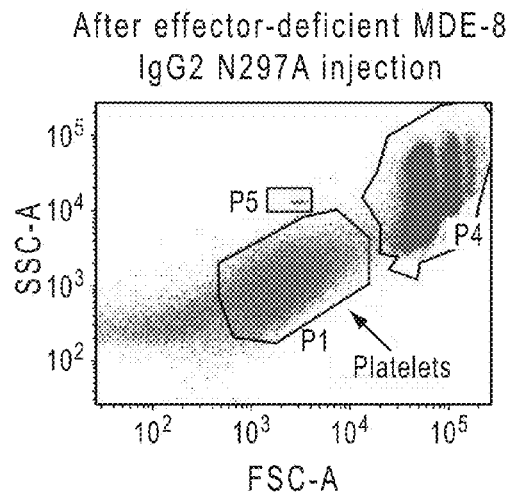

These results show that two representative IgG subclass types of effector-deficient human MDE-8 mAbs did not deplete circulating platelets (FIGS. 3D and 3H).

The results shown in FIG. 3 demonstrate that the effector domain of native MDE-8 IgG mAbs cause infusion reactions in CD32A mice, and such infusion reactions are eliminated by altering the IgG-Fc domain. Thus, ablating an anti-CD32a antibody's capacity to efficiently bind IgG Fc-receptors is beneficial in eliminating infusion reactions. Rendering MDE-8 mAbs effector-deficient also abrogates the antibodies' capacity to clear platelets from circulating blood, indicating such clearance is also mediated by the IgG-Fc domain, which, in the case of MDE-8, is immobilized on the surface of CD32A transgenic mouse platelets.

Figure 4A:
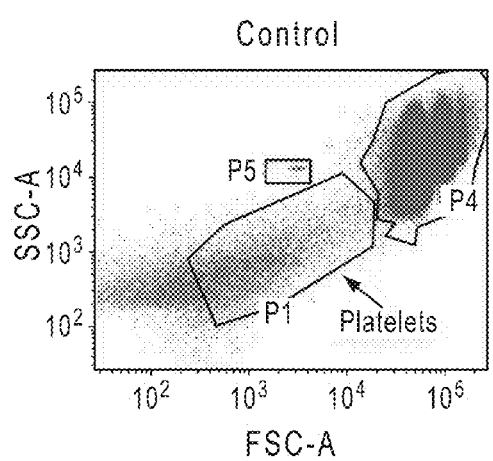
Figure 4B:
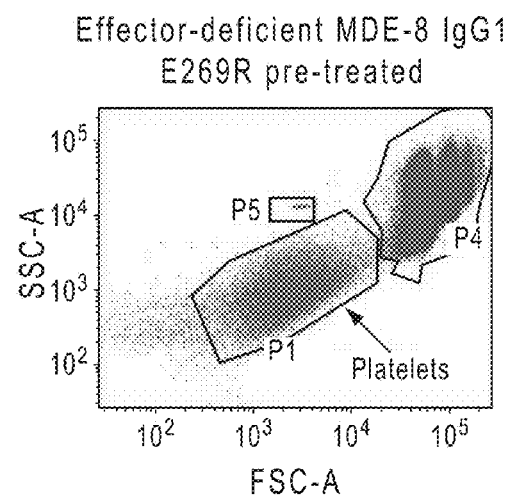

Effector-Deficient MDE-8 mAbs Protect CD32A Transgenic Mice from Immune Complex-Induced Thrombocytopenia It was next determined that effector-deficient MDE-8 mAbs protect CD32A transgenic mice against immune complex-induced thrombocytopenia (drop in circulating platelet count). Three hours prior to immune complex challenge, CD32A mice were treated with vehicle phosphate buffered saline (PBS) or one of two representative effector-deficient human MDE-8 mAbs (100 micro-grams): 1) effector-deficient MDE-8 IgG1 E269R (SEQ ID NO: 69 together with SEQ ID NO: 65); or 2) effector-deficient MDE-8 IgG2 N297A (SEQ ID NO: 69 together with SEQ ID NO: 67). Mice were challenged with immune complex (M90+CD40L, total of 200 micro-grams), and whole blood was collected 30 minutes after challenge. FIG. 4 shows the results. In mice pre-treated with vehicle control, IC injection resulted in the mice having signs of severe shock (data not shown) and severe platelet depletion Animals pre-treated with effector-deficient MDE-8 IgG1 E269R did not exhibit signs of IC-dependent infusion reactions or shock (data not shown). Moreover, as shown in FIG. 4B, mice pre-treated with effector-deficient MDE-8 IgG1 E269R did not experience IC-induced thrombocytopenia (i.e., platelets were not cleared by ICs; FIG. 4B). Due to infusion reactions, it was not possible to similarly test effector competent MDE-8 mAbs in native IgG1 format.

Figure 4C:
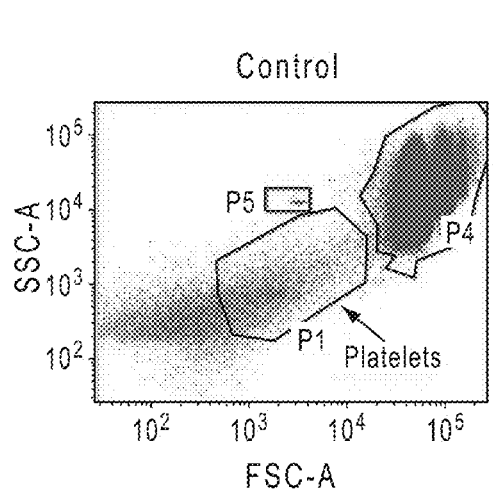
Figure 4D:
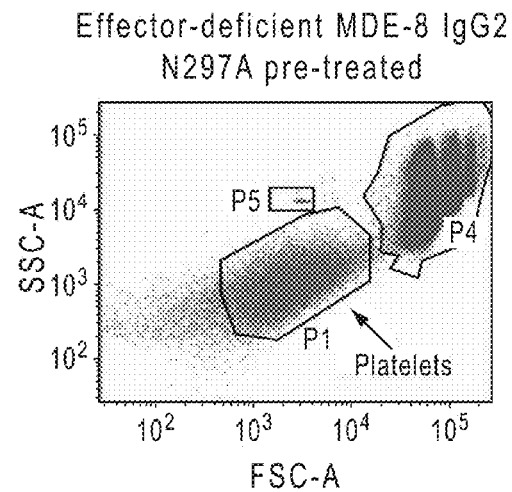

Similar results were obtained with effector-deficient MDE-8 IgG2 N297A. FIG. 4C shows the platelet count from a CD32A mouse pre-treated with vehicle control and following IC injection. FIG. 4D shows the post-IC injection platelet count of a CD32A mouse pre-treated with effector-deficient MDE-8 IgG2 N297. The data in FIG. 4 are representative of all animals tested.

Figure 5A:
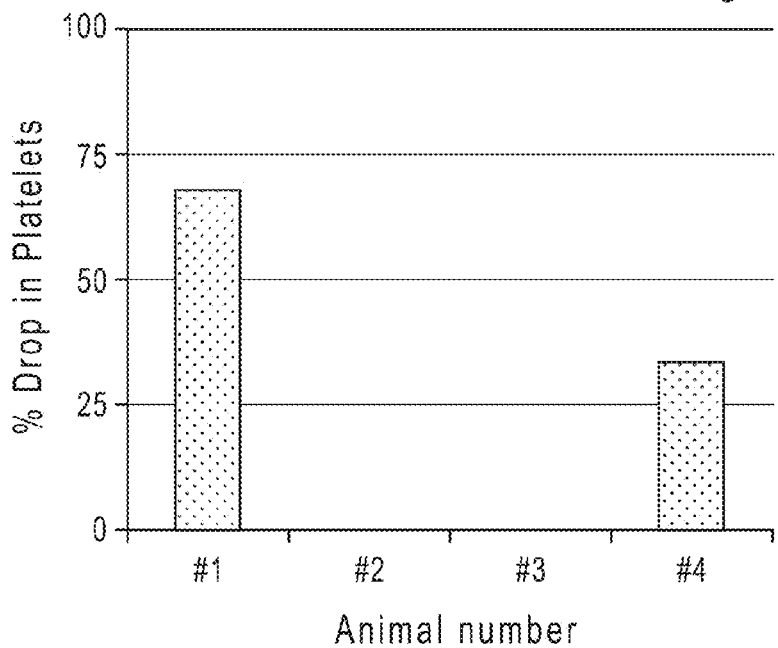
Figure 5B:
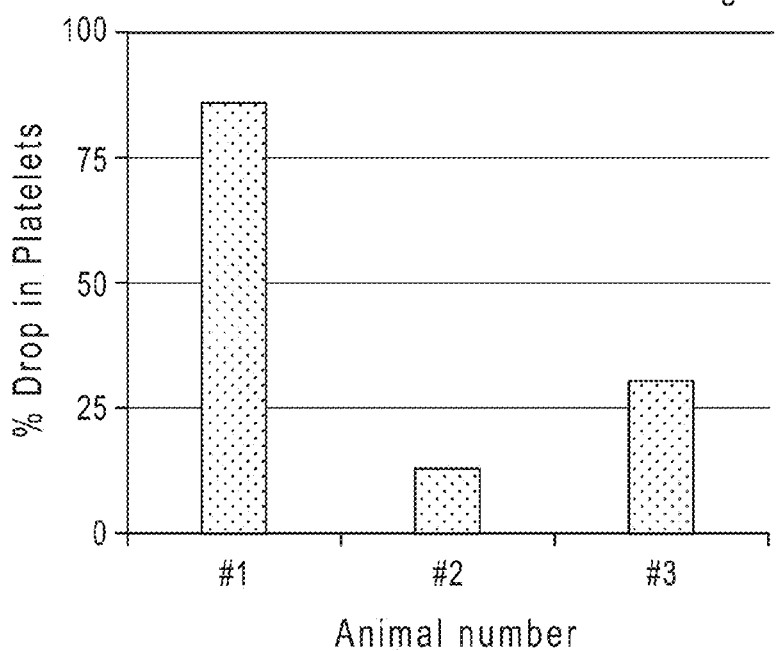

FIG. 5 shows a bar graph depicting the % drop in circulating platelets following IC injection into CD32A mice pre-treated with either vehicle or effector-deficient MDE-8 antibodies (pre-treatment at three hours prior to IC challenge). CD32A mice pre-treated with vehicle (PBS) became severely thrombocytopenic (FIGS. 5A and 5B, bars #1), whereas mice pre-treated with effector-deficient MDE-8 IgG1 E269R (FIG. 5A) or effector-deficient MDE-8 IgG2 N297A (FIG. 5B) were largely protected from loss of circulating platelets. Animal #1 in FIG. 5A and FIG. 5B was pre-treated with vehicle (PBS). M90+CD40L immune complexes were injected intravenously into all animals Thirty minutes later, blood was drawn and platelets were counted. FIG. 5A shows that effector-deficient MDE-8 IgG1 E269R protects mice from immune complex-mediated thrombocytopenia (See FIG. 5A, columns 2, 3, and 4). FIG. 5B shows that effector-deficient MDE-8 IgG2 N297A protects mice from immune complex-mediated thrombocytopenia (See FIG. 5B, columns 2 and 3). Thus, two representative IgG subclasses (IgG1, IgG2) of effector-deficient MDE-8 mAbs protected CD32A transgenic mice from immune complex-induced thrombocytopenia.

Effector-Deficient MDE-8 Antibodies Protect CD32A Transgenic Mice from Pulmonary Thrombosis Caused by Immune Complexes (ICs)

CD32A transgenic mice were pre-treated with vehicle (PBS) or with 100 micro-grams of representative effector-deficient MDE-8 mAbs (SEQ ID NO: 69 together with SEQ ID NO: 65 or SEQ ID NO: 67). Three hours later, mice were challenged with M90+CD40L ICs (200 micro-grams). After thirty minutes, mice were sacrificed and their lungs harvested for analysis. FIG. 6A shows an H&E stained lung section from a mouse pre-treated with vehicle three hours prior to IC challenge. Pervasive occlusive pulmonary thrombi (*) were observed in mice pre-treated with vehicle. Surprisingly, mice pre-treated with effector-deficient MDE-8 IgG1 E269R exhibited normal lung anatomy without evidence of thrombosis (FIG. 6B). Effector-deficient MDE-8 IgG1 E269R pre-treated mice also showed normal blood vessels having abundant red blood cells in normal (healthy) alveolar tissue (FIG. 6B), as compared to vehicle treated mice (FIG. 6A), whose blood vessels were abnormal, with fewer numbers of red blood cells observed in blood vessels, as well as evidence of inflamed alveolar tissue.

Pulmonary thrombi per field were counted by H&E microscopy of mouse lungs following IC challenge. Four mice were injected with M90+CD40L IC Animal #1 (FIG. 6C, bar 1; vehicle control) showed pervasive pulmonary thrombosis (mean of 20 per field), whereas animals #2-4 (FIG. 6C, bars 2-4) that were pre-treated with effector-deficient MDE-8 IgG1 E269R prior to IC challenge exhibited normal lung anatomy without evidence of thrombosis. The findings depicted in FIG. 6C also demonstrate that effector-deficient MDE-8 IgG1 E269R did not cause pulmonary thrombosis.

Figure 6C:
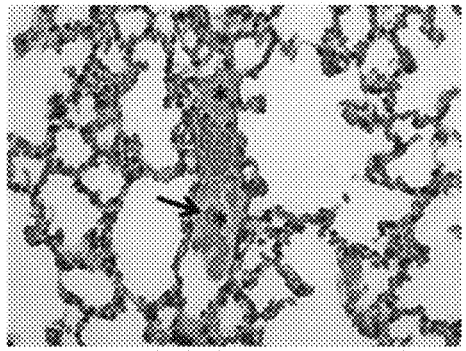
FIG. 6C shows the number of pulmonary thrombi in CD32A mice either treated with vehicle (#1) or with effector-deficient MDE-8 IgG1 E269R anti-CD32a mAbs (#'s 2-4).
Figure 6C:
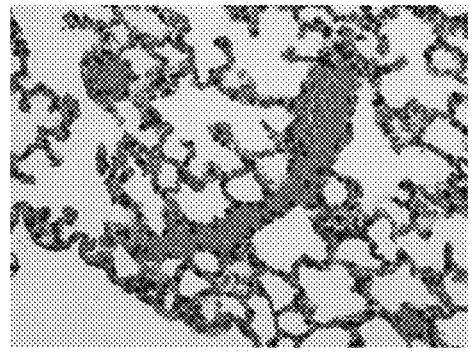
Figure 6C:
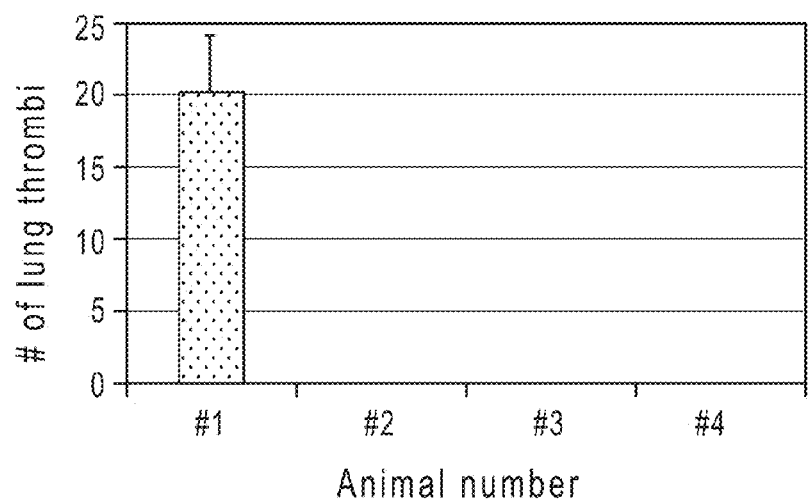

Similar results were obtained with effector-deficient MDE-8 IgG2 N297A. FIG. 7A shows an H&E stained lung section from a mouse which had been pre-treated with vehicle three hours prior to IC challenge. In FIG. 7A, pervasive occlusive pulmonary thrombi (*) were observed. In contrast, mice pre-treated with effector-deficient MDE-8 IgG2 N297A exhibited normal lung anatomy without evidence of thrombosis (FIG. 7B). Effector-deficient MDE-8 IgG2 N297A pre-treated mice also showed normal blood vessels having abundant red blood cells amidst healthy alveolar tissue (FIG. 7B), in contrast to the abnormal (with fewer numbers of red blood cells observed in blood vessels, as well as evidence of inflamed) alveolar tissue of the vehicle (PBS) pre-treated mice (FIG. 7A). The data in FIGS. 6 and 7 is representative of all animals tested.

Figure 7C:
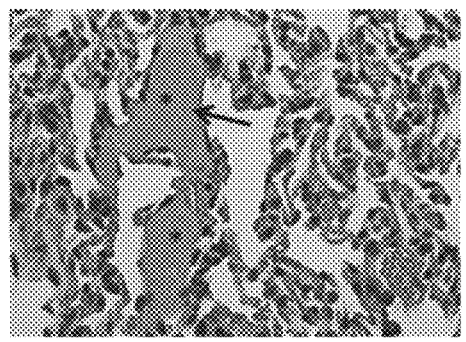
FIG. 7C shows the number of pulmonary thrombi in CD32A mice either treated with vehicle (#1) or with effector-deficient MDE-8 IgG2 N297A anti-CD32a mAbs (#'s 2-3).
Figure 7C:
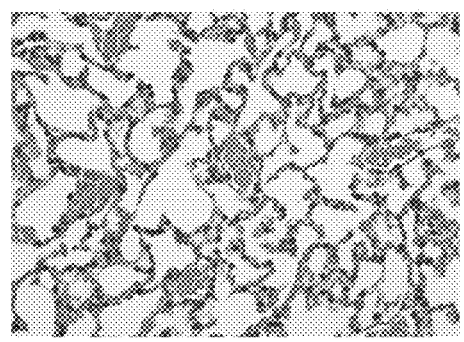
Figure 7C:
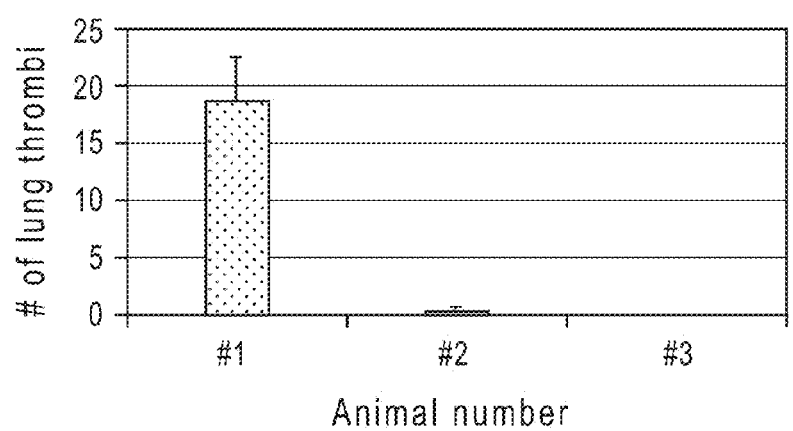

FIG. 7C shows H&E microscopy of mouse lungs after IC challenge in mice pre-treated with vehicle or effector-deficient MDE-8 antibodies. Pulmonary thrombi per field were counted. Four mice were injected with M90+CD40L IC Animal #1 (FIG. 7C, bar 1; control) showed pervasive pulmonary thrombosis (mean of 18.6 per field), whereas animals #2 and #3 (FIG. 7C, bars 2 and 3), which were pre-treated with effector-deficient MDE-8 IgG2 N297A, exhibited normal lung anatomy without evidence of thrombosis. These findings also demonstrate that MDE-8 IgG2 N297A mAb by itself did not cause pulmonary thrombosis.

Taken together, the data presented in Example 1 demonstrate: (1) that native (effector competent) anti-CD32a IgG mAbs cause infusions reactions and induce thrombocytopenia; (2) that altering MDE-8 mAbs to an effector-deficient format renders the IgG of choice infusion-safe and hemostatically safe (in that it does not induce thrombocytopenia); (3) that native MDE-8 mAb mediated infusion reactions and thrombocytopenia are dependent on the function of the IgG-Fc (effector) domain; (4) that effector-deficient MDE-8 IgG1 and IgG2 mAbs protect CD32A transgenic mice from immune complex-mediated infusion reactions, shock, thrombocytopenia, and thrombosis; and (5) that the CD32A IgG receptor largely controls infusion reactions, thrombocytopenia, thrombosis, and shock as mediated by ICs in these immunologically intact (e.g., having the full array of murine IgG receptors) CD32A transgenic mice. The dominant effect of the human CD32A transgene product over all other mouse IgG-Fc receptors (murine FcgammaRI, FcgammaRIIb, and FcgammaRIII), in response to thrombotic ICs, is an unexpected finding.

Example 2

Effector-Deficient Chimeric Monoclonal Antibody AT-10

The inventors have further demonstrated that native chimeric (mouse-human) AT-10 IgG mAbs cause infusion reactions in mice transgenic for CD32a (e.g., in CD32A mice). Observable signs of IgG-mediated infusion reactions in CD32A mice include hypothermia, rapid or shallow breathing, hunched posture, and locomotor dysfunction. Observable signs of severe infusion reactions include immobilization, convulsion, and (infrequently) fatality.

We show herein that altering the effector domain (i.e., the Fc domain) of the native AT-10 mAbs to an effector-deficient IgG format eliminated infusion reactions when administered to CD32A mice.

Moreover, when effector-deficient AT-10 mAbs were administered prior to challenge with immune complexes, the effector-deficient AT-10 mAbs prevented immune complex-induced infusion reactions, as well as thrombocytopenia and thrombotic shock.

Thus, effector-deficient monoclonal AT-10 antibodies may be used in place of native AT-10 antibodies to treat any CD32a mediated disease or disorder. The reasons include that the effector-deficient AT-10 antibodies will not elicit infusion reactions as observed with native AT-10 mAbs. Moreover, effector-deficient AT-10 mAbs may be used to treat and/or prevent any disease or disorder caused by immune complexes when given prophylactically or therapeutically.

Materials and Methods

Effector-competent and effector-deficient variants of AT-10 mAbs (IgG1 and IgG1 E269R, respectively) were injected intravenously (tail vein) into CD32A mice (as in Example 1). After injection (100 micro-grams), mice were monitored for 30 minutes for assessment of infusion reactions. Blood was collected (retro-orbitally) before, and 30 minutes after AT-10 mAb injection. Platelets were counted by flow cytometry from this collected blood. After 3 hours, some animals were injected with immune complexes (ICs, as in Example 1, 200 micro-grams), and blood was collected 30 minutes after injection. Platelets were again counted from this collected blood. Lungs were harvested 30 minutes after injection of ICs, processed for H&E staining, and examined microscopically for the presence of thrombi.

Results

Figure 8:
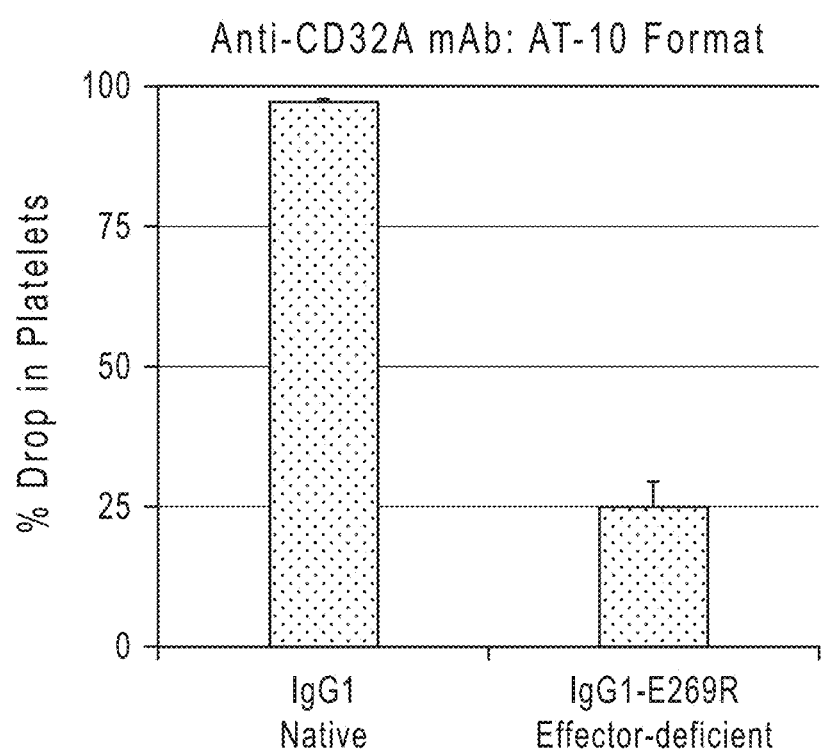
FIG. 8 shows severe thrombocytopenia following intravenous injection of native chimeric AT-10 human IgG1 mAb into CD32A mice but not following intravenous injection of effector-deficient chimeric AT-10 human IgG1 E269R.
Figure 9A:
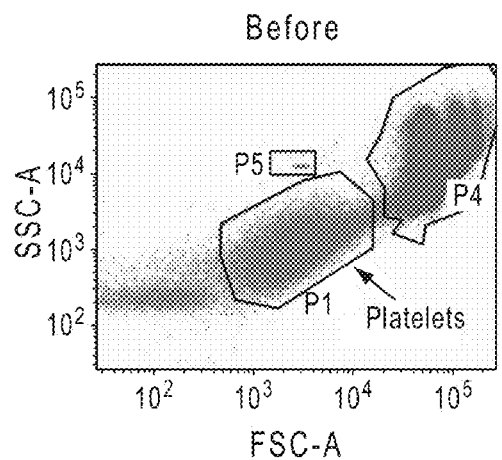
FIG. 9A shows flow cytometric analysis of whole blood from CD32A mice prior to injection of native chimeric AT-10 human IgG1 mAbs.
Figure 9B:
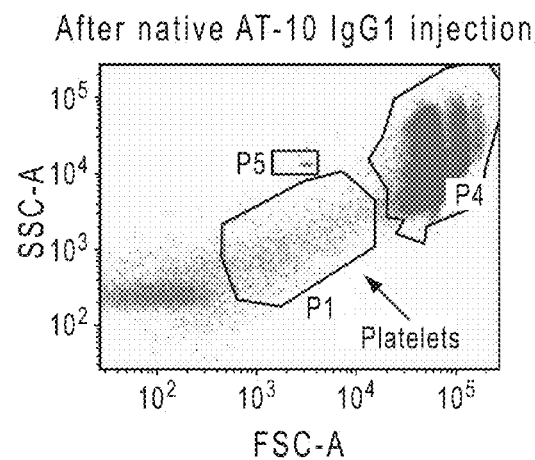
FIG. 9B shows flow cytometric analysis of whole blood from CD32A mice after intravenous injection of native chimeric AT-10 human IgG1 mAbs.
Figure 9C:
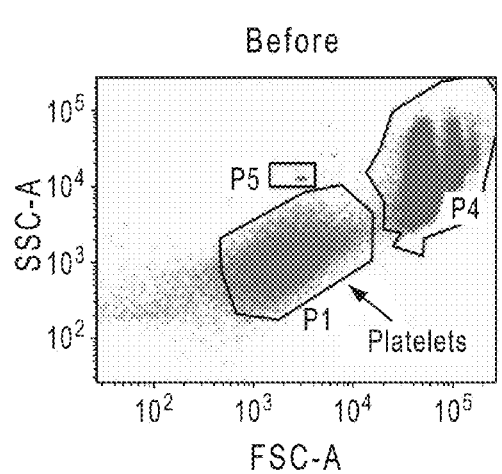
FIG. 9C shows flow cytometric analysis of whole blood from CD32A mice prior to injection of effector-deficient chimeric AT-10 human IgG1 mAbs.
Figure 9D:
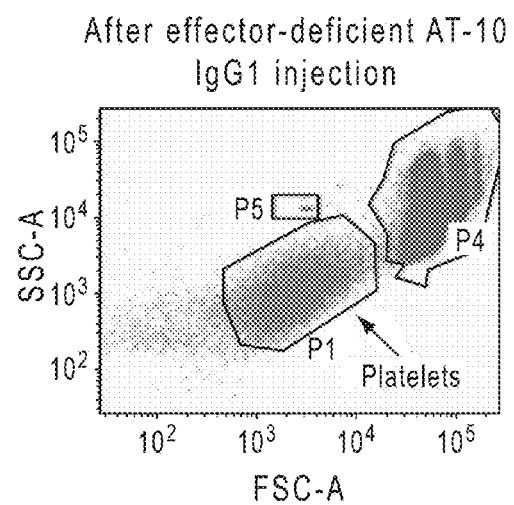
FIG. 9D shows flow cytometric analysis of whole blood from CD32A mice after the injection of effector-deficient chimeric AT-10 human IgG1 mAbs.

Effector-Deficient AT-10 mAbs do not Cause Infusion Reactions that are Seen with Effector Competent AT-10 Antibodies When injected intravenously into CD32A transgenic mice, native chimeric AT-10 mAbs cause infusion reactions characterized by thrombocytopenia (FIG. 8, bar 1). Notably, these mice did not have hypothermia (data not shown). Thrombocytopenia was ablated when effector-deficient chimeric AT-10 human IgG1 E269R mAbs were administered in lieu of native chimeric AT-10 human IgG1 (FIG. 8, column 2) (antibodies comprising the amino acids of SEQ ID NO: 22 together with SEQ ID NO: 16).

Flow cytometric analysis of whole blood from CD32A mice before (FIG. 9A) and after (FIG. 9B) intravenous injection of native chimeric AT-10 human IgG1 showed severe platelet depletion (FIG. 9B) despite having no hypothermia. Importantly, when native chimeric AT-10 human IgG1 mAbs were made effector-deficient, they no longer reduced circulating platelets (compare FIG. 9C [before injection] and FIG. 9D [after injection of effector-deficient chimeric AT-10 human IgG1 mAbs]). Thus, effector-deficient AT-10 mAbs did not deplete platelets. This data demonstrates that the IgG effector domain is responsible for AT-10 IgG-induced thrombocytopenia.

These experiments demonstrate that thrombocytopenia a drop in platelet count is independent of, and, in this case, a more sensitive indicator of infusion reaction than temperature drop, since native AT-10 mAbs in IgG1 format failed to cause hypothermia (data not shown) but caused severe platelet depletion. Importantly, effector-deficient AT-10 mAbs did not deplete platelets (i.e., cause thrombocytopenia) like their effector competent counterparts.

The results shown in FIGS. 8 and 9 demonstrate that the effector region of native AT-10 IgG mAbs mediate infusion reactions in CD32A mice, and that such infusion reactions are eliminated by altering the IgG-Fc region. Thus, ablating an anti-CD32a antibody's capacity to efficiently bind IgG Fc-receptors is beneficial in eliminating infusion reactions.

Effector-Deficient AT-10 mAbs Protect CD32A Transgenic Mice from Immune Complex-Induced Thrombocytopenia Next it was demonstrated that effector-deficient AT-10 mAbs were capable of protecting CD32A transgenic mice from immune complex-induced thrombocytopenia (FIG. 10). Three hours prior to immune complex challenge, mice were treated with PBS vehicle or an effector-deficient AT-10 mAb (IgG1 E269R,) (antibodies comprising the amino acid of SEQ ID NO: 22 together with SEQ ID NO: 16). Immune complexes (M90+CD40L (as in Example 1); 200 micro-grams) were injected intravenously and whole blood was collected 30 minutes after IC challenge. Platelets were counted from this collected blood.

FIG. 10 shows a bar graph depicting the % drop in circulating platelets following IC injection into CD32A mice pre-treated with either vehicle or effector-deficient chimeric AT-10 human IgG1 E269R antibodies. CD32A mice pre-treated with vehicle (PBS) became severely thrombocytopenic (FIG. 10 column 1), whereas mice pre-treated with effector-deficient chimeric AT-10 human IgG1 E269R (FIG.

10 columns 2 and 3) were largely protected from loss of circulating platelets. Effector-deficient chimeric AT-10 human IgG1 E269R protected mice from immune complex-induced thrombocytopenia (FIG. 10, columns 2 and 3 compared to control, column 1.

FIG. 11 shows a flow cytometric analysis of circulating platelets following IC injection into CD32A mice pre-treated with either vehicle or effector-deficient AT-10 antibodies as described above. FIG. 11A shows platelets depletion from a mouse that received vehicle. FIG. 11B shows that animals pre-treated with effector-deficient chimeric AT-10 human IgG1 E269R did not experience thrombocytopenia in response to IC injection. Furthermore, effector-deficient chimeric AT-10 human IgG1 E269R pre-treatment completely protected CD32A mice from observable signs of IC-mediated infusion reaction (chimeric AT-10 human IgG1 E269R-treated animals appeared unaffected by IC injection, whereas vehicle treated controls showed signs of impaired mobility, hunched posture, and shallow and rapid breathing, consistent with shock.

Effector-Deficient AT-10 Antibodies Protect CD32A Transgenic Mice from Pulmonary Thrombosis Caused by Immune Complexes (ICs)

Mice were pre-treated with vehicle (PBS) or with effector-deficient AT-10 mAbs (antibodies comprising the amino acids of SEQ ID NO: 22 together with SEQ ID NO: 16). Three hours later, mice were challenged with M90+CD40L IC (as in Example 1; 200 micro-grams). After thirty minutes, mice were sacrificed and their lungs removed for analysis. FIG. 12A shows a representative H&E stained lung section from a mouse pre-treated with vehicle 3 hours prior to IC challenge. Pervasive occlusive pulmonary thrombi (*) were detected in vehicle-treated mice. Surprisingly, mice pre-treated with effector-deficient AT-10 IgG1 E269R exhibited normal lung anatomy without evidence of thrombosis (FIG. 12B), despite the fact that these mice are immunologically intact (i.e., have the full repertoire of normal mouse IgG receptors, in addition to human CD32A). Effector-deficient AT-10 IgG1 E269R pre-treated mice also showed normal blood vessels having abundant red blood cells amidst healthy alveolar tissue (FIG. 12B), as compared to control (vehicle-treated) mice (FIG. 12A). These results demonstrate that effector-deficient chimeric AT-10 human IgG1 E269R mAbs are capable of protecting against IC-induced thrombosis.

Figure 12C:
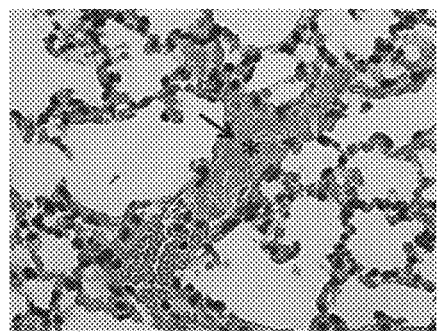
FIG. 12C shows the number of pulmonary thrombi in CD32A mice either treated with vehicle (#1) or with effector-deficient chimeric AT-10 human IgG1 E269R anti-CD32a mAb (#'s 2-3).
Figure 12C:
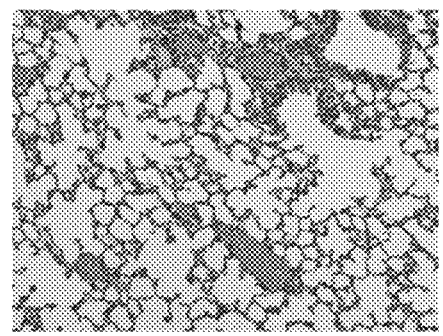
Figure 12C:
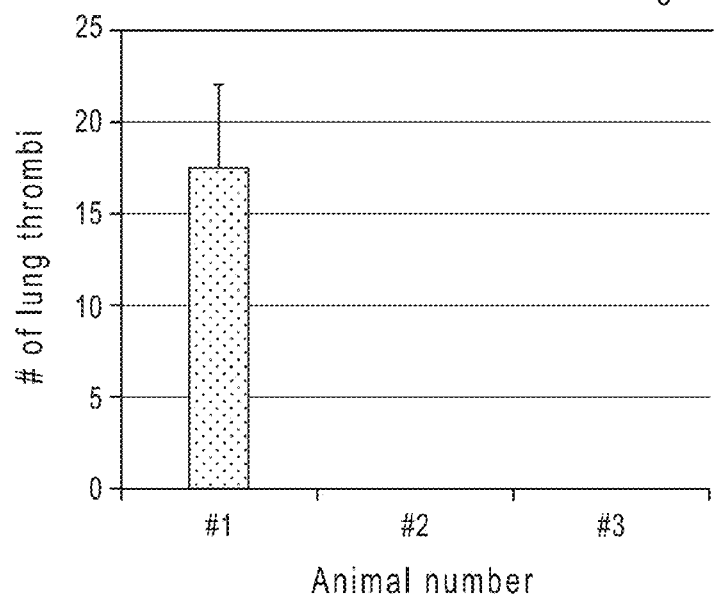

FIG. 12C shows H&E microscopy of mouse lungs following IC injection into CD32A mice pre-treated with either vehicle (control) or effector-deficient chimeric AT-10 antibodies as described above (See FIGS. 12A and 12B) Animal #1 (FIG. 12C, bar 1; control) showed pervasive pulmonary thrombosis (mean of 17.6 clots per field), whereas animals #2 and #3 (FIG. 12C, bars 2 and 3), which were pre-treated with effector-deficient chimeric AT-10 human IgG1 E269R, exhibited normal lung anatomy without evidence of thrombosis.

Humanized Effector-Deficient AT-10 mAbs

An effector-deficient humanized AT-10 IgG1 E269R mAb ("hAT-10") was made and tested (antibodies comprising the amino acids of SEQ ID NO: 24 together with SEQ ID NO: 20). In FIG. 13A, hAT-10 E269R mAb (116 µg) was administered to CD32A mice and core body temperature of the mice was assessed over time. hAT-10 E269R mAbs did not cause hypothermia (an indicator of infusion reaction). In addition to not exhibiting hypothermia, these animals exhibited no other signs of having infusion reactions. FIG. 13B shows the results of a study where platelets from CD32A mice were assessed before and after hAT-10 E269R injection (116 micro-grams). hAT-10 had no effect on circulating platelet counts (see the right side panel of FIG. 13B).

Furthermore, hAT-10 E269R completely protects mice against M90+CD40L IC-induced thrombocytopenia. Control animals that received vehicle (PBS control) pre-treatment became unconscious within 10 minutes of receiving IC challenge and subsequently showed signs consistent with severe shock. In contrast, mice pre-treated with hAT-10 E269R appeared unaffected by IC challenge (data not shown). hAT-10 E269R pre-treatment also protected CD32A mice from thrombocytopenia (compare FIG. 13C left panel (showing platelet loss in vehicle-treated group) and FIG. 13C right panel (showing no platelet loss in hAT-10 E269R-treated animals)).

Figures 13D, 13E:
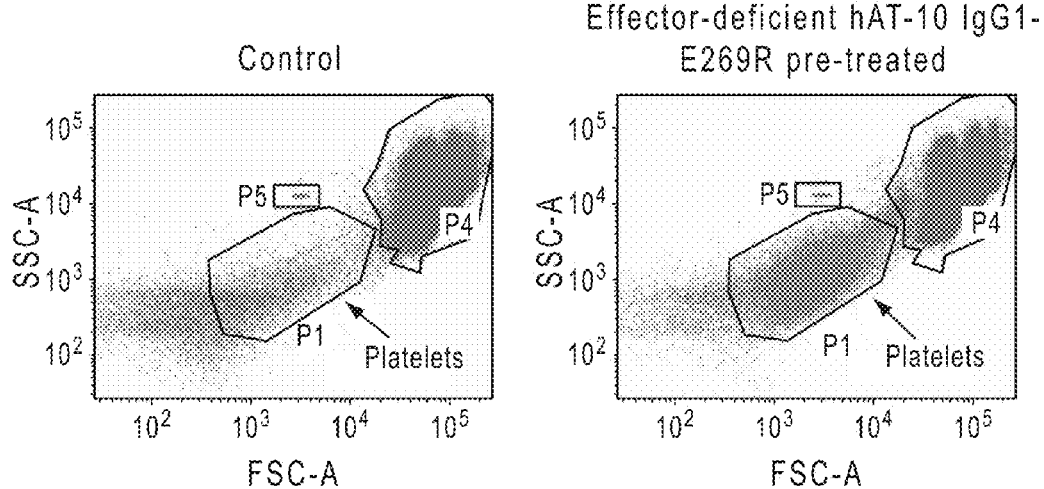
FIG. 13D shows flow cytometric analysis of whole blood from vehicle pre-treated CD32A mice after intravenous injection of IgG immune complexes.
FIG. 13E shows flow cytometric analysis of whole blood from effector-deficient humanized AT-10 IgG1 E269R anti-CD32a mAb pre-treated CD32A mice after intravenous injection of IgG immune complexes.
Figure 13F:
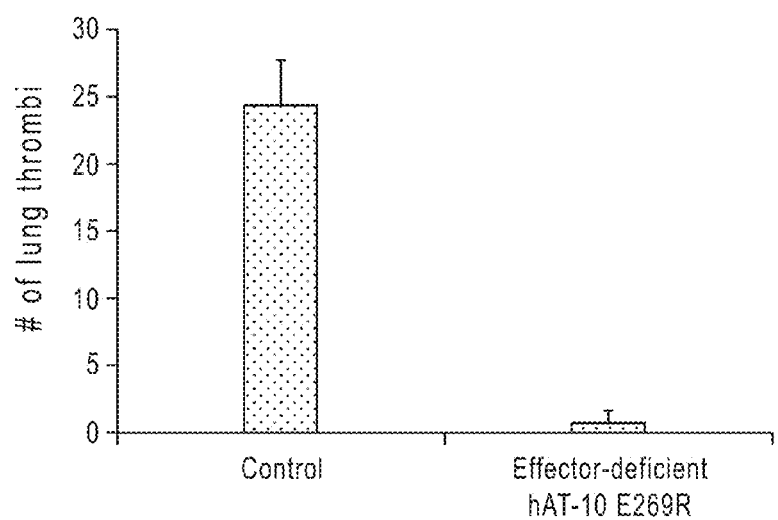
FIG. 13F shows the number of pulmonary thrombi in CD32A mice either treated with vehicle or with effector-deficient humanized AT-10 IgG1 E269R anti-CD32a mAb.

Finally, humanized effector-deficient AT-10 IgG1 E269R (hAT-10 E269R) antibody protected mice from immune complex-induced pulmonary thrombosis. As observed with AT-10 chimeric antibody (FIG. 12), pre-treatment with hAT-10 E269R completely prevented pulmonary thrombosis in CD32A mice after IC challenge (M90+CD40L; as in Example 1; 200 micro-grams). FIG. 13D shows significant thrombi in lungs of control treated mice and nearly complete lack of thrombi in hAT-10 E269R treated mice. See, also, FIG. 13E showing pervasive pulmonary thrombosis (mean of 24.4 clots per field) in control treated mice as compared to a lack of thrombi in mice pre-treated with hAT-10 E269R (FIG. 13F).

Taken together, the data presented in Example 2 demonstrate: (1) that native (effector competent) anti-CD32a IgG mAb AT-10 causes infusions reactions characterized by thrombocytopenia; (2) that altering AT-10 mAb to be effector-deficient renders AT-10 infusion-safe and hemostatically safe (in that it does not induce thrombocytopenia); (3) that native (effector competent) AT-10 antibody mediated infusion reactions and thrombocytopenia are dependent on the function of the IgG-Fc (effector) domain; (4) that effector-deficient AT-10 IgG mAb protects CD32A transgenic mice from immune complex-mediated infusion reactions, thrombocytopenia, and thrombosis; and (5) that the CD32a IgG receptor largely controls infusion reactions, thrombocytopenia, thrombosis, and shock, as mediated by ICs in these immunologically intact CD32A mice.

Example 3

Effector-Deficient Chimeric Monoclonal Antibody IV.3

The inventors have further demonstrated that native chimeric IV.3 mAbs cause infusion reactions in mice transgenic for its antigen (i.e., CD32A mice). Observable signs of IgG-mediated infusion reactions in CD32A mice include hypothermia, rapid or shallow breathing, hunched posture, and locomotor dysfunction; observable signs of severe infusion reactions also include impaired mobility, convulsion, apparent loss of consciousness, and (infrequently) fatality.

We show herein that altering the effector domain (i.e., Fc domain) of chimeric IV.3 to an effector-deficient IgG format eliminated infusion reactions following administration to CD32A mice.

Moreover, when effector-deficient IV.3 was provided to subjects prior to challenge with immune complexes, the effector-deficient IV.3 mAbs prevented immune complex-induced infusion reactions, as well as thrombocytopenia and thrombotic shock.

Thus, effector-deficient monoclonal IV.3 antibodies should be used in place of native IV.3 antibodies to treat any CD32a mediated disease or disorder. The reasons include that the effector-deficient IV.3 antibodies will not elicit infusion reactions as observed with native IV.3 mAbs. Moreover, effector-deficient IV.3 may be used to treat and/or prevent any disease or disorder caused by immune complexes when given prophylactically or therapeutically.

Materials and Methods

In this set of experiments, effector-competent and effector-deficient variants of chimeric IV.3 mAbs (human IgG2 and human IgG2 N297A, respectively) were injected intravenously (tail vein) into human CD32A transgenic mice (as in Example 1). After injection (100 micro-grams), animals were monitored for 30 minutes for assessment of infusion reactions. Blood was collected (retro-orbitally) before and 30 minutes after IV.3 mAb injection. Platelets were then counted by flow cytometry from this collected blood. After 3 hours, some animals were injected with immune complexes (ICs, as in Example 1, 200 micro-grams), after which (30 minutes) platelets were again counted. Lungs were then harvested, processed for H&E staining, and examined microscopically for the presence of thrombi.

Results

Figure 14A:
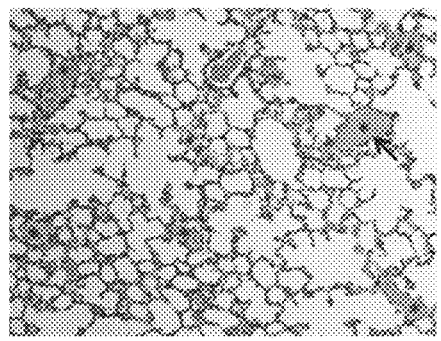
FIG. 14A shows dose-dependent severe thrombocytopenia following intravenous injection of native IV.3 human IgG2 mAbs into CD32A mice but not following intravenous injection of effector-deficient chimeric IV.3 human IgG2 N297A mAbs.
Figure 14A:
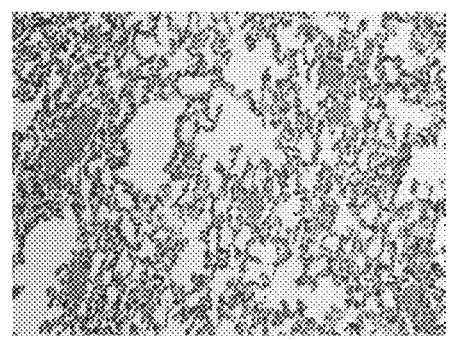
Figure 14A:
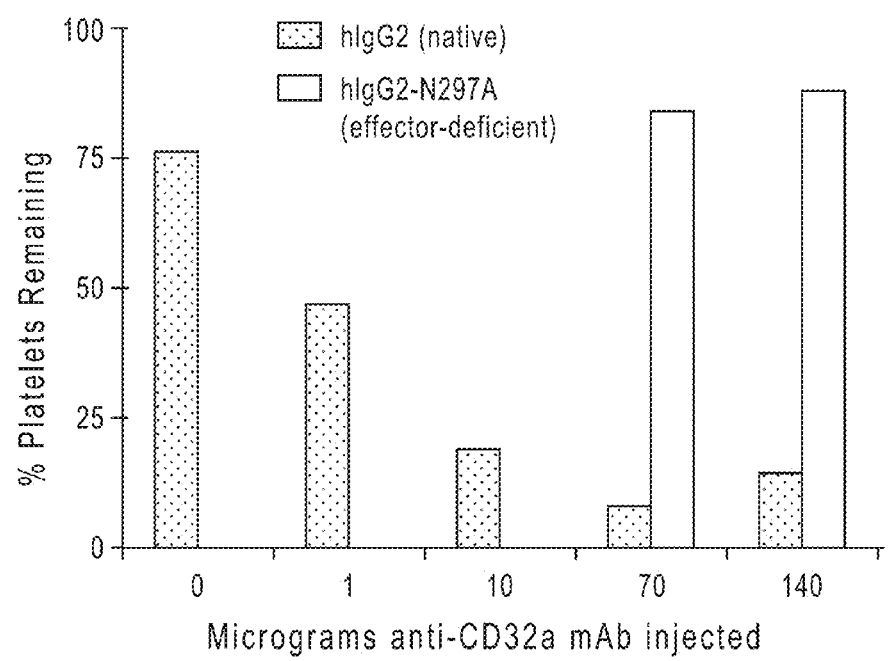
Figure 14B:
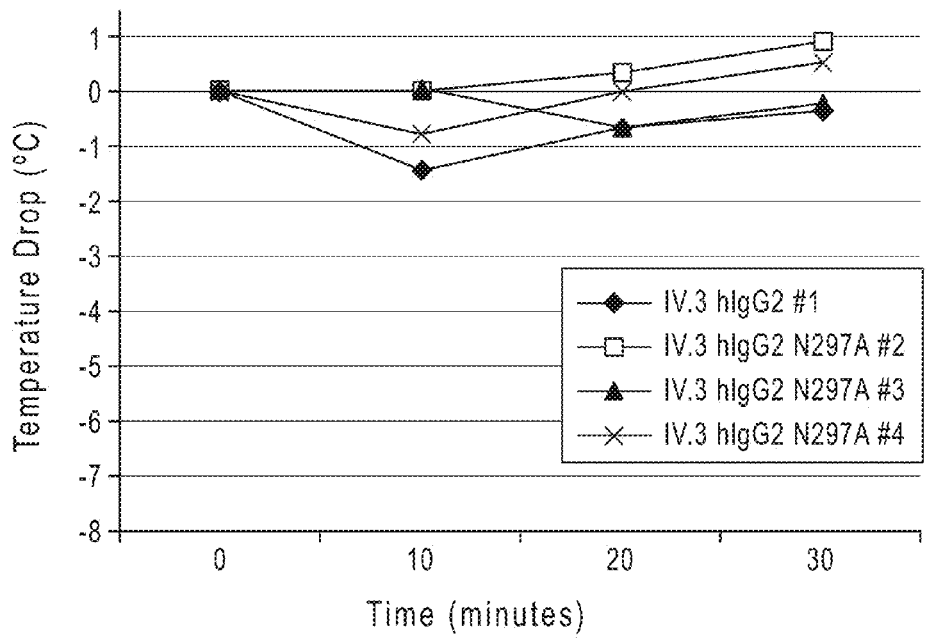
FIG. 14B shows no drop in body temperature of CD32A mice injected with native chimeric IV.3 human IgG2 or with effector-deficient chimeric IV.3 human IgG2 N297A.

Effector-Deficient IV.3 mAbs do not Cause Infusion Reactions that are Seen with Effector Competent IV.3 Antibodies We discovered that, when injected intravenously into CD32A transgenic mice, effector competent chimeric IV.3 human IgG2 mAb causes infusion reactions in a dose-dependent manner, as characterized by thrombocytopenia without hypothermia. FIG. 14 shows that, following intravenous injection of chimeric IV.3 in native human IgG2 format, CD32A transgenic mice became severely thrombocytopenic (FIG. 14A, solid bars). This thrombocytopenia was largely ablated when effector-deficient chimeric IV.3 human IgG2 N297A mAb (antibodies comprising the amino acids of SEQ ID NO: 51 together with SEQ ID NO: 45) was administered in lieu of native chimeric IV.3 (FIG. 14A, open bars). FIG. 14B shows that neither native chimeric IV.3 human IgG2 nor its effector-deficient (IV.3 IgG2 N297A) format caused hypothermia in CD32A transgenic mice.

These results again suggest that a drop in platelet count is independent of and, in this case, more sensitive than core body temperature drop as indicator for infusion reaction to antibodies that interact with platelets in vivo.

Figures 15A, 15B:
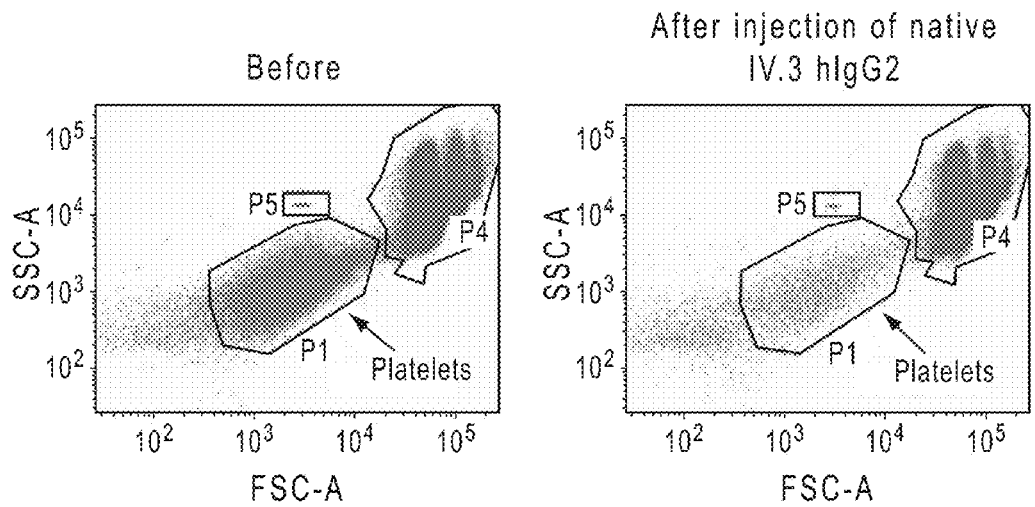
FIG. 15A shows flow cytometric analysis of whole blood from CD32A mice prior to injection of native chimeric IV.3 human IgG2 mAbs.
FIG. 15B shows flow cytometric analysis of whole blood from CD32A mice after intravenous injection of native chimeric IV.3 human IgG2 mAbs.
Figure 15C:
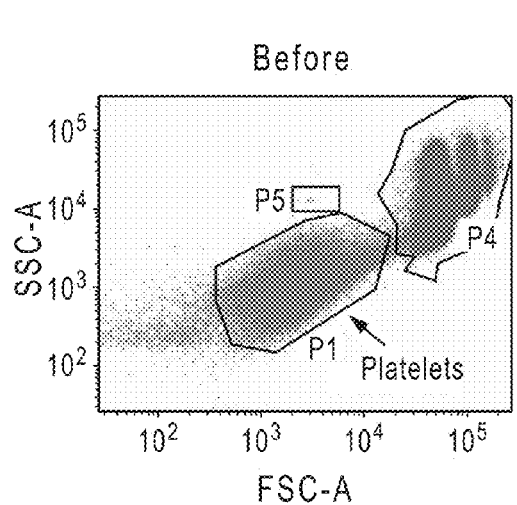
FIG. 15C shows flow cytometric analysis of whole blood from CD32A mice prior to injection of effector-deficient chimeric IV.3 human IgG2 N297A mAbs.
Figure 15D:
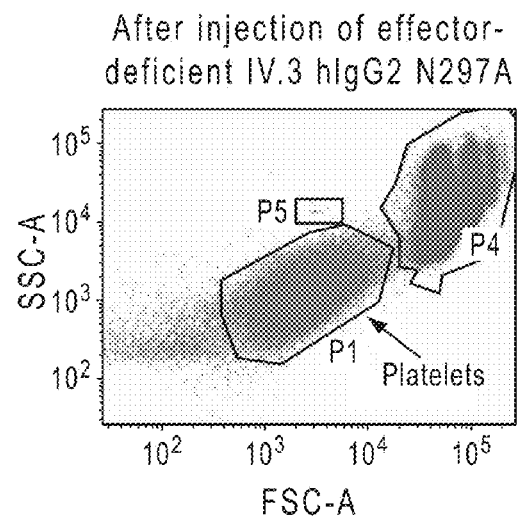
FIG. 15D shows flow cytometric analysis of whole blood from CD32A mice after intravenous injection of effector-deficient chimeric IV.3 human IgG2 N297A mAbs.

Flow cytometric analysis of whole blood from CD32A transgenic mice before (FIG. 15A) and after (FIG. 15B) intravenous injection of native chimeric IV.3 in human IgG2 showed severe platelet depletion (FIG. 15B). Importantly, when native chimeric IV.3 IgG2 mAb was made effector-deficient, it no longer reduced circulating platelets (compare FIG. 15C [before injection] and FIG. 15D [after injection of effector-deficient chimeric IV.3 mAbs]). Thus, effector-deficient IV.3 mAbs did not deplete platelets (FIG. 15D). This data demonstrate that the IgG effector domain is responsible for the IV.3 IgG-induced thrombocytopenia.

The results shown in FIGS. 14 and 15 demonstrate that the effector domain of native IV.3 IgG mAbs cause infusion reactions in CD32A mice, and such infusion reactions are eliminated by altering the IgG-Fc domain. Thus, ablating an anti-CD32a antibody's capacity to efficiently bind IgG Fc-receptors is beneficial in eliminating infusion reactions. Rendering IV.3 mAbs effector-deficient also abrogates the antibodies' capacity to clear platelets from circulating blood, indicating such clearance is also mediated by the IgG-Fc domain, which, in the case of IV.3, is immobilized on the surface of CD32A transgenic mouse platelets.

Figure 16A:
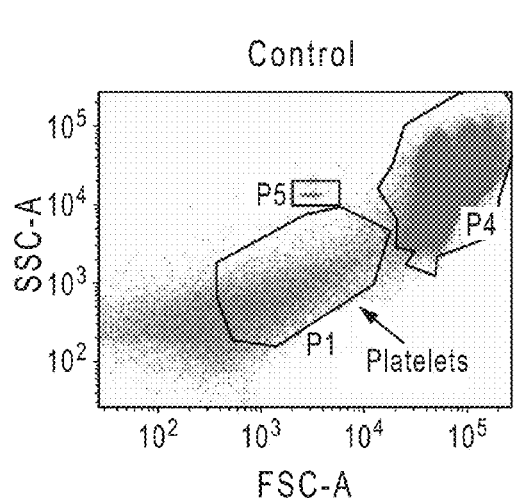
FIG. 16A shows flow cytometric analysis of whole blood from CD32A mice after intravenous injection of IgG immune complexes.
Figure 16B:
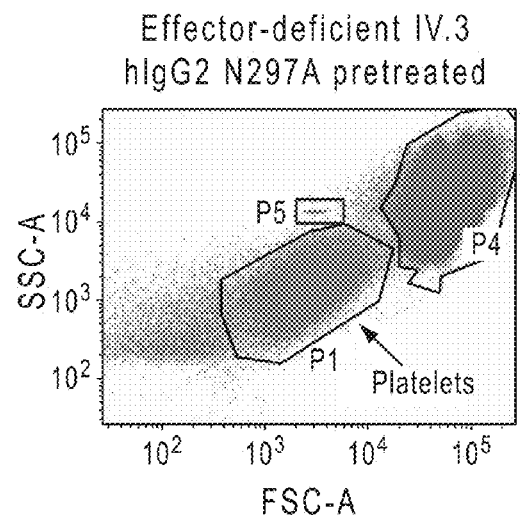
FIG. 16B shows flow cytometric analysis of whole blood from effector-deficient chimeric IV.3 human IgG2 N297A anti-CD32a mAb pre-treated CD32A mice after intravenous injection of IgG immune complexes.

Effector-Deficient IV.3 mAbs Protect CD32A Transgenic Mice from Immune Complex-Induced Thrombocytopenia It was next determined that effector-deficient chimeric IV.3 mAbs protect CD32A transgenic mice from immune complex-induced thrombocytopenia. Three hours prior to immune complex challenge, CD32A transgenic mice were pre-treated with PBS vehicle or 100 micro-grams of a representative effector-deficient chimeric IV.3 IgG2 N297A (antibodies comprising the amino acids of SEQ ID NO: 51 together with SEQ ID NO: 45). Whole blood was collected 30 minutes after mice were challenged with immune complexes (M90+CD40L, as in Example 1, 200 micro-grams). FIG. 16A shows platelet depleion in a whole blood sample from a mouse that received vehicle. FIG. 16B shows that animals pre-treated with chimeric IV.3 IgG2 N297A did not experience thrombocytopenia in response to IC.

Figure 17:
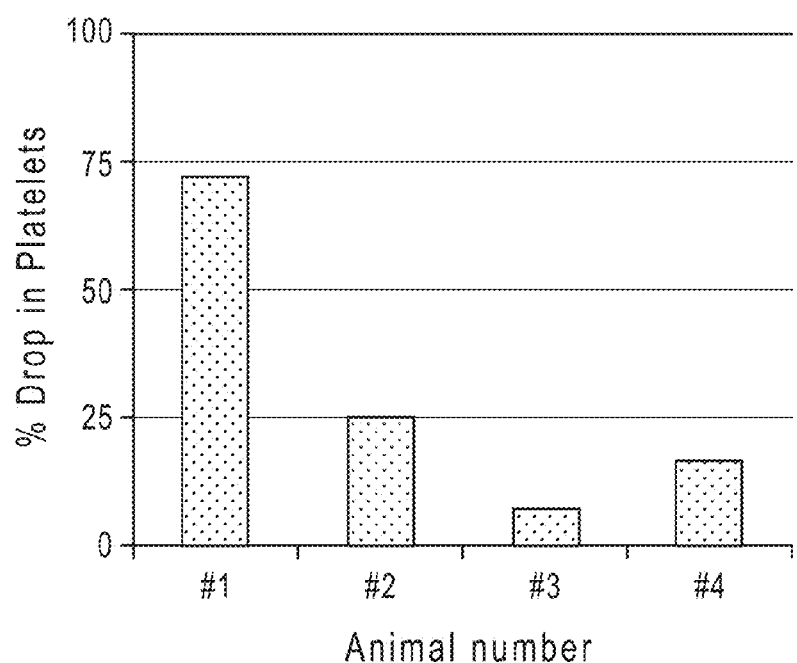
FIG. 17 shows severe thrombocytopenia following intravenous injection of IgG immune complexes into CD32A mice (#1) but not following immune complex injection into CD32A mice pretreated with effector-deficient chimeric IV.3 human IgG2 N297A mAbs (#2-#4).

FIG. 17 shows a bar graph depicting the % drop in circulating platelets following IC injection (M90+CD40L, as in Example 1, 200 micro-grams) into CD32A mice pre-treated with either vehicle or effector-deficient chimeric IV.3 antibodies as described above. CD32A mice pre-treated with vehicle (PBS) became severely thrombocytopenic (FIG. 17, bar 1), whereas mice pre-treated with effector-deficient chimeric IV.3 IgG2 N297A (FIG. 17, bars 2, 3 and 4) were largely protected from loss of circulating platelets. Thus, effector-deficient chimeric IV.3 human IgG2 N297A protected mice from immune complex-induced thrombocytopenia (FIG. 17).

Effector-Deficient Chimeric IV.3 Antibodies Protect CD32A Transgenic Mice from Pulmonary Thrombosis Caused by Immune Complexes (ICs).

In this experiment, CD32A mice were pre-treated with vehicle or with 100 micro-grams of effector-deficient chimeric IV.3 human IgG2 N297A mAb (SEQ ID NO: 51 together with SEQ ID NO: 45). Three hours later, pre-treated mice were challenged with M90+CD40L IC (as in Example 1, 200 micro-grams). Thirty minutes later, mice were sacrificed and their lungs removed for analysis. FIG. 18A shows an H&E stained lung section from a mouse pre-treated with vehicle 3 hours prior to IC challenge. Pervasive occlusive pulmonary thrombi (*) were detected in vehicle-treated mice. Surprisingly, mice pre-treated with effector-deficient chimeric IV.3 human IgG2 N297A exhibited normal lung anatomy without evidence of thrombosis (FIG. 18B). Chimeric IV.3 IgG2 human N297A-pre-treated mice also showed normal blood vessels having abundant red blood cells amidst healthy alveolar tissue (FIG. 18B), as compared to vehicle treated mice (FIG. 18A), which exhibited abnormal and occluded blood vessels. Notably, these mice were immunologically intact (having the full array of naturally occurring mouse IgG-Fc receptors), demonstrating the dominance of CD32a in IC-induced thrombocytopenia, thrombosis, and shock.

Figure 18C:
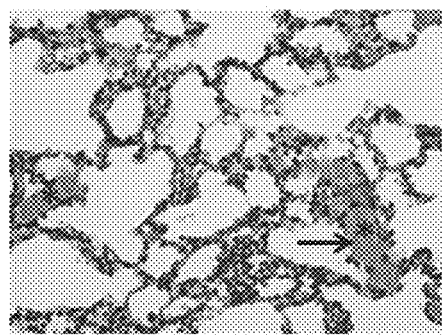
FIG. 18C shows the number of pulmonary thrombi in CD32A mice either treated with vehicle (#1) or with effector-deficient chimeric IV.3 IgG2 N297A anti-CD32a mAbs (#2-#4).
Figure 18C:
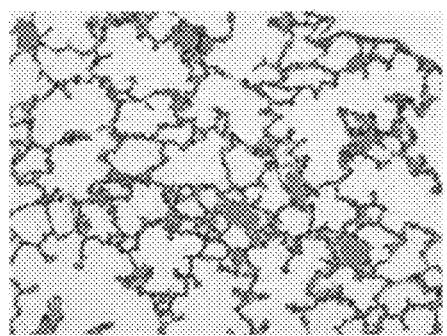
Figure 18C:
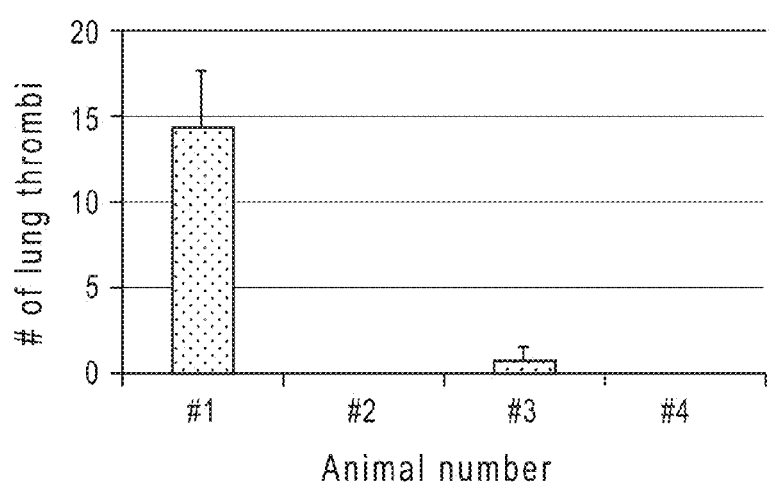

In FIG. 18C, the average number of pulmonary thrombi per 10 fields was determined by H&E microscopy of mouse lungs following IC challenge. Four mice were injected with M90+CD40L IC as described above. Animal #1 (PBS pre-treated control) showed pervasive pulmonary thrombosis (mean of 17.6 clots per field), whereas animals #2, #3, and #4 which were pre-treated with effector-deficient chimeric IV.3 human IgG2 N297A, exhibited normal lung anatomy without evidence of thrombosis.

Taken together, the data presented in Example 3 demonstrate: (1) that native chimeric IV.3 anti-CD32a IgG2 mAb causes infusions reactions and induces thrombocytopenia; (2) that altering chimeric IV.3 mAb to an effector-deficient format renders chimeric IV.3 infusion-safe and hemostatically safe (in that it does not induce thrombocytopenia); (3) that IV.3 mediated infusion reactions and thrombocytopenia are dependent on the function of the IgG-Fc (effector) domain; (4) that effector-deficient chimeric IV.3 IgG mAbs protects CD32A transgenic mice from immune complex-mediated infusion reactions, thrombocytopenia, thrombosis, and shock.

Example 4

Anti-CD32a mAbs Potently Inhibit CD32a-Mediated Immune Complex-Induced Human Platelet Aggregation and Degranulation In this example we analyzed immune complex-induced human platelet aggregation and degranulation in vitro to assess the potency and efficacy of anti-CD32a mAbs.

Methods

Platelet-activating immune complexes (IC) were prepared by combining CD40 ligand (CD40L, also called CD154), human platelet factor 4 (hPF4), human beta 2-Glycoprotein I (beta 2-GPI), or TNFalpha antibodies with their respective ligands typically at balanced stoichiometry (100-1000 nM). The following types of immune complexes were tested: (1) M90 anti-CD40L mAb+CD40L; (2) M91 anti-CD40L mAb+CD40L; (3) M90 anti-CD40L mAb+M91 anti-CD40L mAb+CD40L (a polyclonal immune complex); (4) anti-hPF4 mAb+hPF4+0.1 U/ml heparin (an HIT-like IC); (5) polyclonal anti-beta 2-GPI+beta 2-GPI (an APS-like IC); (6) infliximab+TNFalpha (a therapeutic mAb-like IC); (7) adalimumab+TNFalpha (a therapeutic mAb-like IC); and (8) goat F(ab')2-anti-human-IgG-F(ab')2+infliximab (to mimic anti-therapeutic antibody IC activity).

Isolated platelets were assessed via light-transmission aggregometry as follows. Platelets were acquired from healthy human donors (n=10) following informed consent, washed and suspended in assay buffer. Platelets were placed in cuvettes in the aggregometer and allowed to incubate at 37° C. until a stable baseline was achieved.

Anti-CD32a antibodies or saline were added to the cuvette 5-10 minutes before the addition of platelet-activating immune complexes. Following the addition of immune complexes, aggregation traces were monitored for at least 5 minutes. In cases where CD32a mAbs prevented immune complex-induced aggregation, the capacity of the platelets to aggregate was confirmed by the addition of the standard agonist collagen (7 micro-grams/milliliter final concentration).

Results

Figure 19:
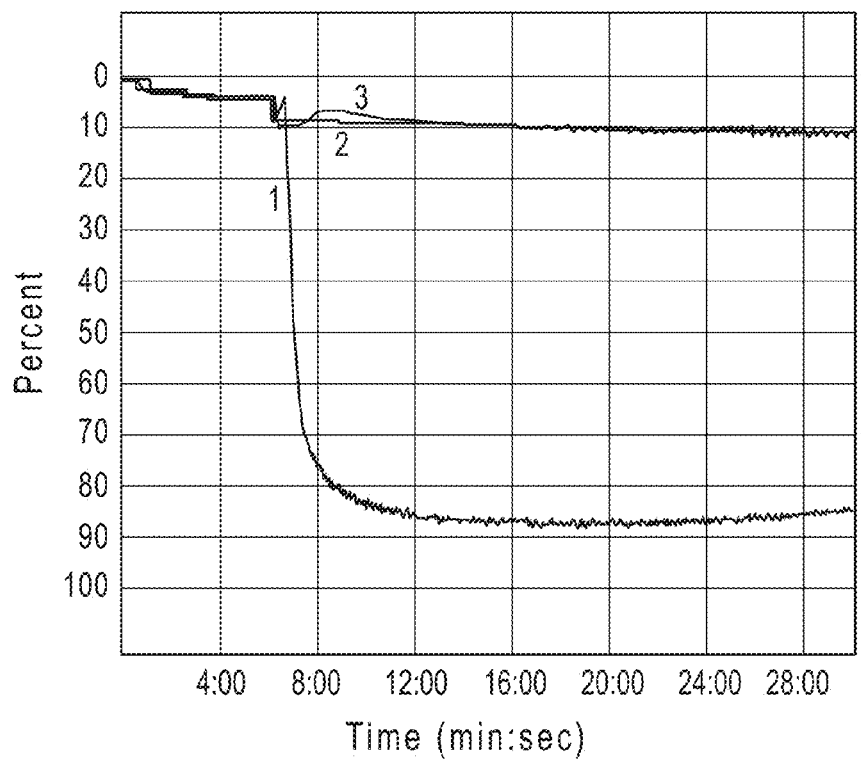
FIG. 19 shows platelet aggregation response to IgG immune complexes in the presence of vehicle (#1) or native mouse IV.3 IgG2b (#2) or native chimeric IV.3 human IgG1 (#3) mAbs.

In FIG. 19, 500 nM M90+CD40L IC activated CD32a on washed human platelets, leading to aggregation, which was not blocked by a control mAb (recombinant rabbit IgG) FIG. 19 (line 1). Platelet aggregation was completely blocked by mouse IV.3 mIgG2b (FIG. 19, line 2) and by native chimeric IV.3 hIgG1 (FIG. 19, line 3), which display similar potency (<5 nM required). This data demonstrates that cloned native chimeric IV.3 hIgG1 has CD32a blocking activity comparable to that of the parent mouse monoclonal antibody.

Figure 20:
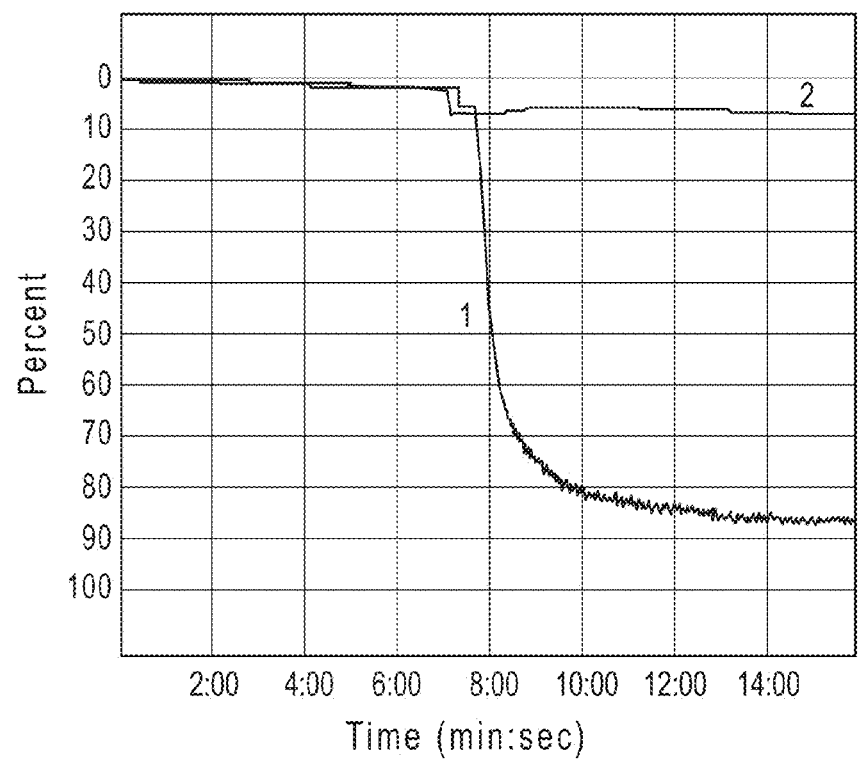
FIG. 20 shows platelet aggregation response to IgG immune complexes in the presence of vehicle (#1) or deglycosylated native mouse IV.3 IgG2b mAbs (#2).

In FIG. 20, 250 nM M90+CD40L IC potently induced CD32a-dependent aggregation (FIG. 20, line 1), which was blocked by 7 nM aglycosylated mouse IV.3 mIgG2b (FIG. 20, line 2). These results suggest that deglycosylation of the "Fc" effector domain of mouse IV.3 mIgG2b mAb, which renders the antibody effector-deficient, does not significantly alter its potency in blocking platelet CD32a (i.e., its Fab-dependent activity).

Figure 21:
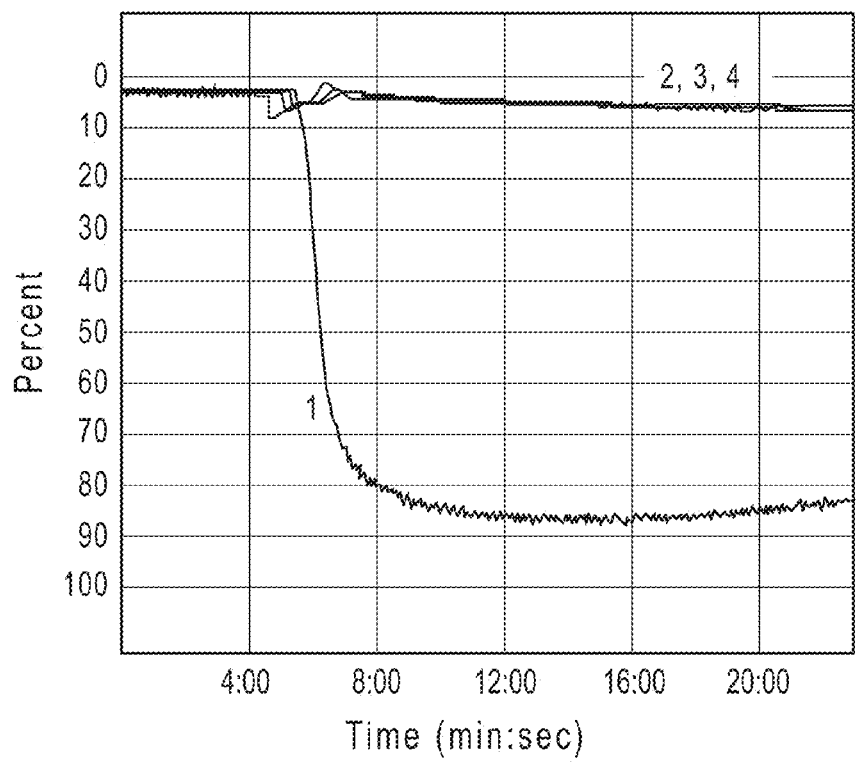
FIG. 21 shows platelet aggregation response to IgG immune complexes in the presence of vehicle (#1) or native chimeric IV.3 human IgG2 mAbs (#'s 2-4).

In FIG. 21, 500 nM M90+CD40L IC induced aggregation (FIG. 21, line 1), which was blocked by native chimeric IV.3 hIgG2 (FIG. 21, lines 2, 3, 4). Aggregation of platelets from a second donor tested with 500 nM M91+CD40L IC was also completely inhibited by native chimeric IV.3 hIgG2 (data not shown).

Figure 22:
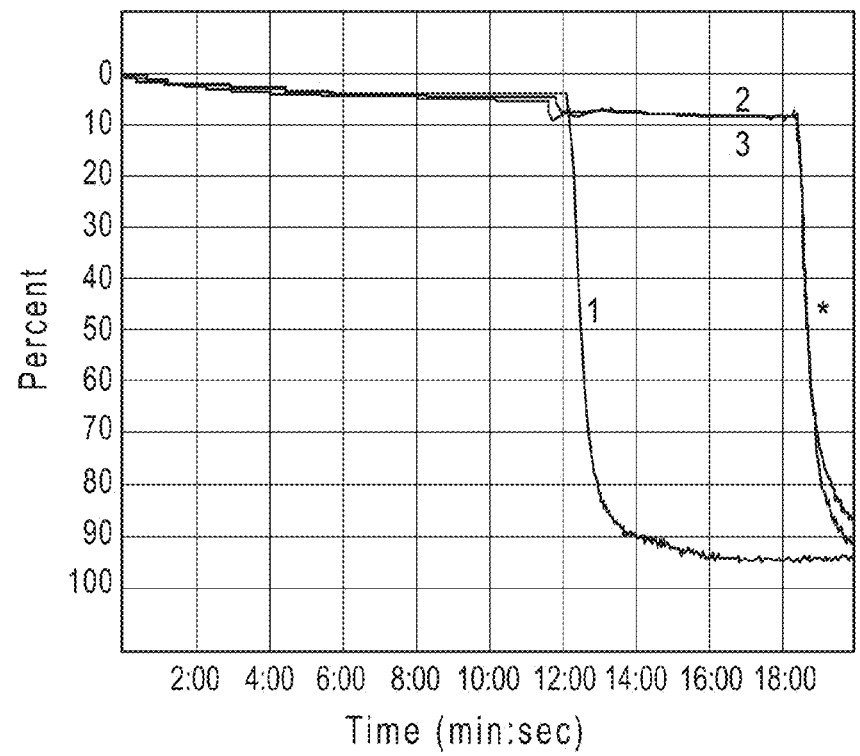
FIG. 22 shows platelet aggregation response to IgG immune complexes in the presence of vehicle (#1) or effector-deficient chimeric IV.3 human IgG2 N297A anti-CD32a mAbs (#'s 2-3).

In FIG. 22, 500 nM M90+CD40L IC-induced aggregation (FIG. 22, line 1) is blocked by 3.3 nM (FIG. 22, line 2) and by 1.7 nM (FIG. 22, line 3) effector-deficient chimeric IV.3 hIgG2 N297A mAb (SEQ ID NO: 51 together with SEQ ID NO: 45). Collagen (designated by * here and below), added at 19 min, demonstrated the anti-CD32a mAb-treated platelets remained aggregation competent.

Figure 23:
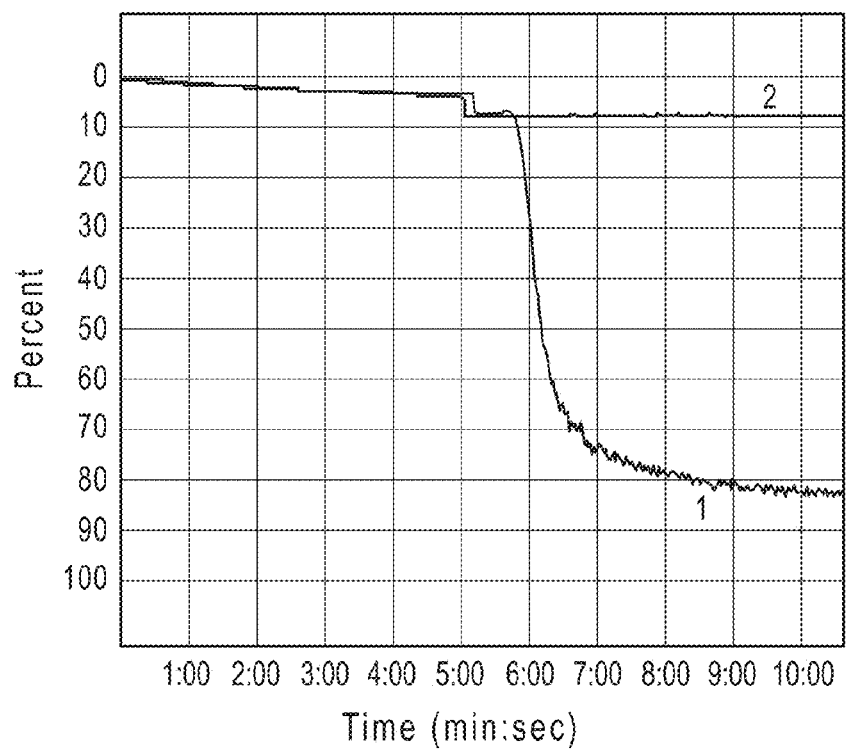
FIG. 23 shows platelet aggregation response to IgG immune complexes in the presence of vehicle (#1) or effector-deficient chimeric AT-10 human IgG1 E269R anti-CD32a mAbs (#2).

In FIG. 23, 500 nM M90+CD40L IC induced aggregation (FIG. 23, line 1) is blocked by 13 nM effector-deficient chimeric AT-10 hIgG1 E269R (FIG. 23, line 2) mAb (SEQ ID NO: 22 together with SEQ ID NO; 16). Also, native chimeric AT-10 hIgG1, hIgG2, and effector-deficient chimeric hIgG2 N297A formats (SEQ ID NO: 22 together with SEQ ID NO: 18) gave similar results with platelets from other donors (data not shown).

Figure 24:
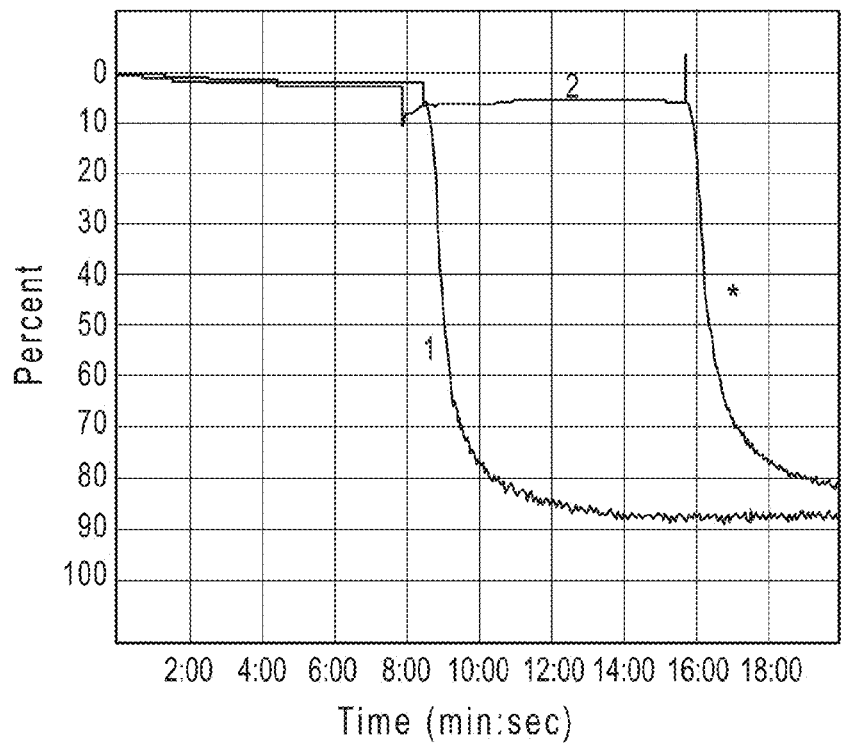
FIG. 24 shows platelet aggregation response to IgG immune complexes in the presence of vehicle (#1) or effector-deficient human MDE-8 IgG1 E269R anti-CD32a mAbs (#2). The standard platelet agonist collagen (*) was added to #2 as a positive control in order demonstrate aggregation competence of the platelets.

In FIG. 24, an IC composed of a 700 nM mix of M90+M91 plus CD40L caused platelet aggregation (FIG. 24, line 1). The activity of this IC was completely blocked by less than 3 nM of effector-deficient human MDE-8 IgG1 E269R (SEQ ID NO: 69 together with SEQ ID NO: 65) (FIG. 24, line 2). Collagen, added at 15 min, demonstrated aggregation competence (FIG. 24, line 2*). Native human MDE-8 IgG1, IgG2, and effector-deficient IgG2 N297A (SEQ ID NO: 69 together with SEQ ID NO: 67) similarly blocked IC-induced aggregation (data not shown).

Figure 25:
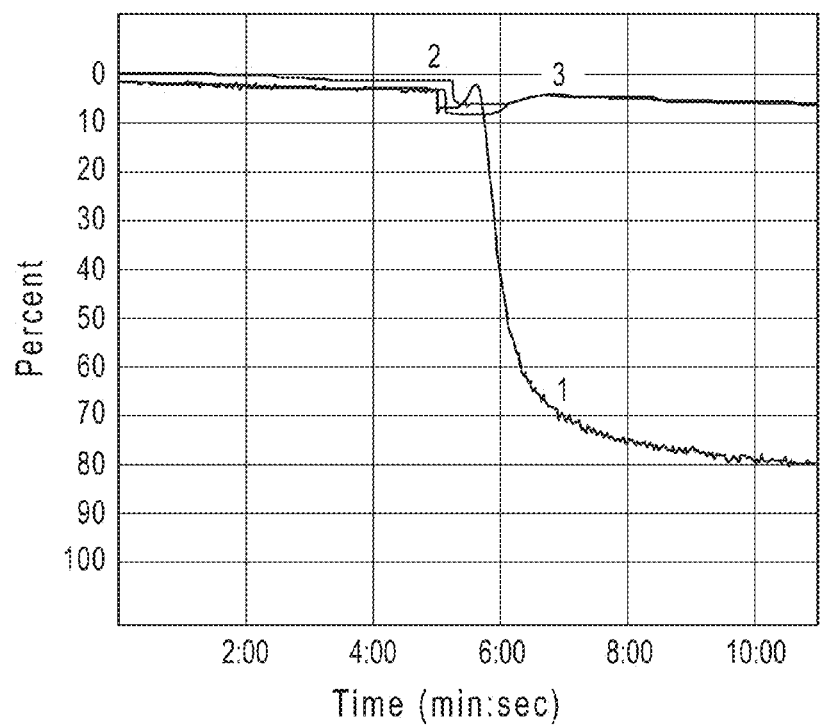
FIG. 25 shows platelet aggregation response to IgG immune complexes in the presence of vehicle (#1) or effector-deficient humanized IV.3.1 IgG1 E269R (here and below, this is "hIV.3.1") (#2) or native mouse IV.3 IgG2b anti-CD32a mAbs (3 nM) (#3).

In FIG. 25, 500 nM M90+CD40L IC-induced aggregation (FIG. 25, line 1) was inhibited similarly by 3 nM effector-deficient humanized IV.3.1 IgG1 E269R (SEQ ID NO: 53 together with SEQ ID NO: 47, FIG. 25, line 2) and by 3 nM mouse IV.3 mIgG2b (FIG. 25, line 3) mAbs. Identical concentration (3 nl\4) of effector-deficient humanized IV.3.2 IgG1 E269R mAbs (SEQ ID NO: 53 together with SEQ ID NO: 49) also inhibited the activity of this IC (data not shown). This data demonstrates similar potency between humanized and mouse IV.3 mAbs.

Figure 26:
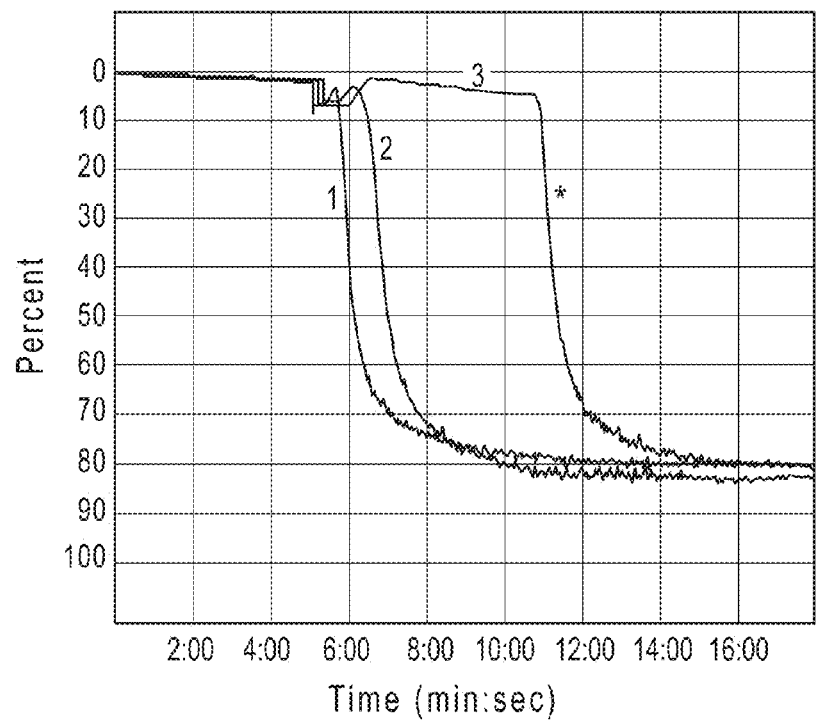
FIG. 26 shows platelet aggregation response to IgG immune complexes in the presence of vehicle (#1) or effector-deficient humanized IV.3.1 IgG1 E269R (#2) or native mouse IV.3 IgG2b anti-CD32a mAbs (2 nM) (#3). The standard platelet agonist collagen (*) was added to #3 as a positive control in order demonstrate aggregation competence of the platelets.

In FIG. 26, 500 nM M90+CD40L IC-induced aggregation (FIG. 26, line 1) was not inhibited by 2 nM effector-deficient humanized IV.3.1 IgG1 E269R mAb (SEQ ID NO: 53 together with SEQ ID NO: 47, FIG. 26, line 2) but was inhibited by 2 nM mouse IV.3 mIgG2b mAb (FIG. 26, line 3). Collagen, added at 10.5 min, demonstrated platelet aggregation competence.

Figure 27:
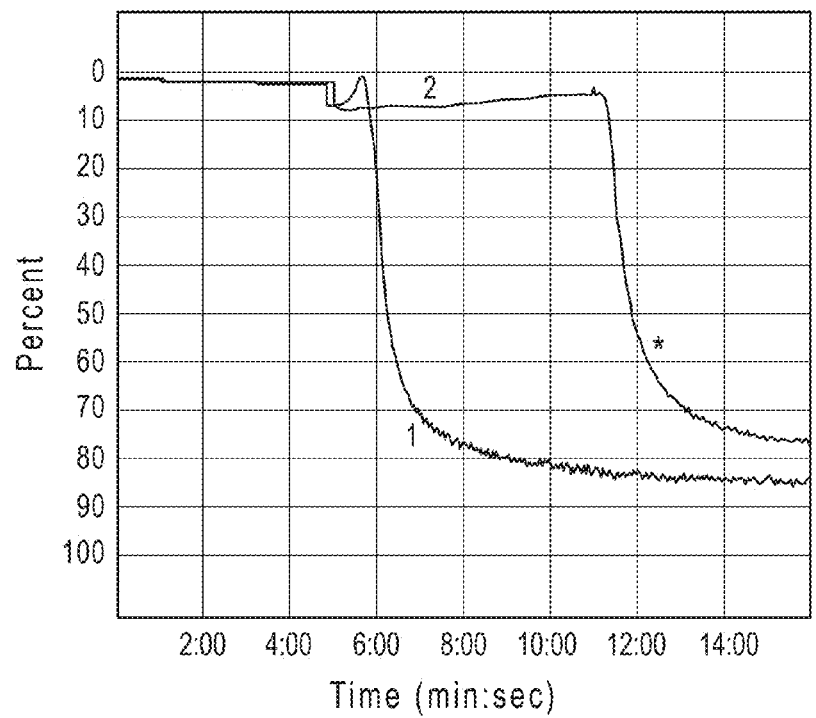
FIG. 27 shows platelet aggregation response to IgG immune complexes in the presence of vehicle (#1) or effector-deficient humanized IV.3.1 IgG1 E269R (6 nM) (#2). The standard platelet agonist collagen (*) was added to #2 as a positive control in order demonstrate aggregation competence of the platelets.

In FIG. 27, M90+CD40L (500 nM) IC-induced aggregation (FIG. 27, line 1) was blocked by 6 nM effector-deficient humanized IV.3.1 IgG1 E269R mAb (SEQ ID NO: 53 together with SEQ ID NO: 47, FIG. 27, line 2) Collagen (*) was added (FIG. 27, line 2) at 11 min and demonstrated platelet aggregation competence.

Figure 28:
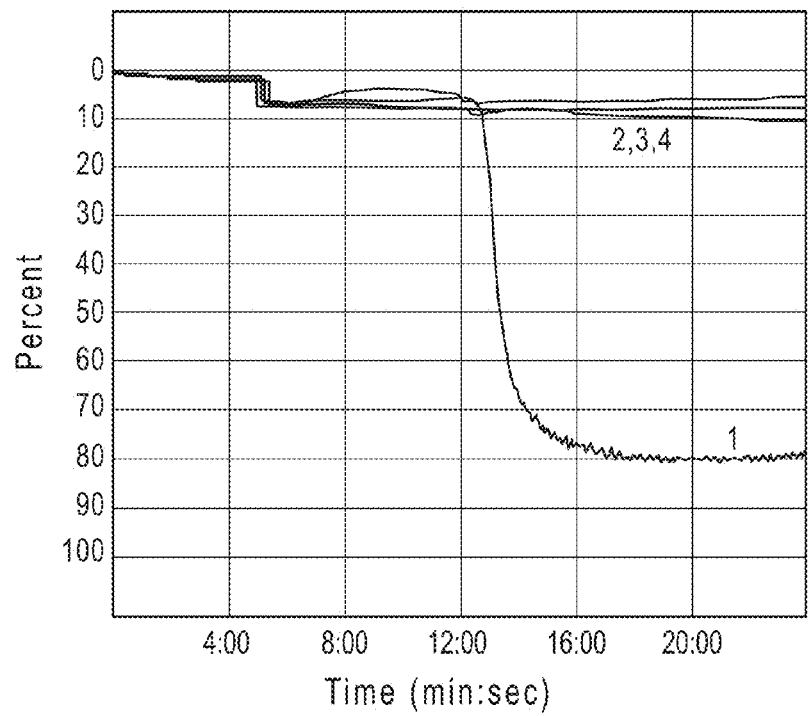
FIG. 28 shows platelet aggregation response to IgG immune complexes in the presence of vehicle (#1) or effector-deficient humanized IV.3.1 IgG1 E269R (#2) or native mouse IV.3 IgG2b anti-CD32a mAbs (25 nM) (#3). Buffer (PBS) alone was added as a negative control (#4).

In FIG. 28, an IC composed of a 1000 nM mix of M90+M91 plus CD40L caused platelet aggregation (FIG.

28, line 1). The activity of this IC was blocked by 25 nM effector-deficient humanized IV.3.1 IgG1 E269R mAb (SEQ ID NO: 53 together with SEQ ID NO: 47, FIG. 28, line 2) and by 25 nM mouse IV.3 mIgG2b (FIG. 28, line 3). Negative control (no IC added; FIG. 28, line 4) did not aggregate.

Figure 29:
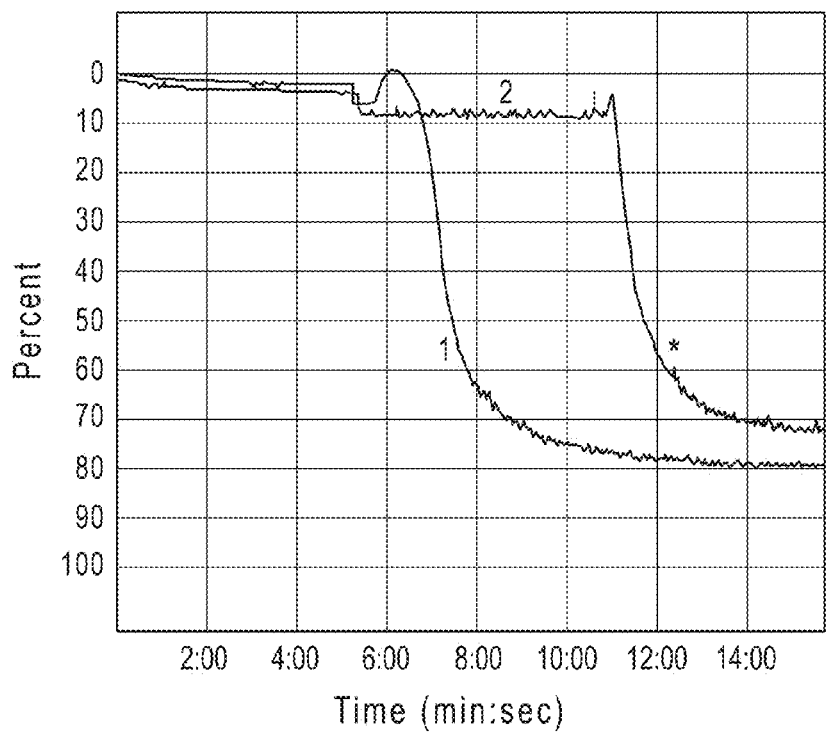
FIG. 29 shows platelet aggregation response to IgG immune complexes in the presence of vehicle (#1) or effector-deficient humanized IV.3.1 IgG1 E269R (40 nM) (#2). The standard platelet agonist collagen (*) was added to #2 as a positive control in order demonstrate aggregation competence of the platelets.

In FIG. 29, 250 nM hPF4+anti-hPF4+heparin (0.1 Units/ milliliter), an HIT-like IC (FIG. 29, line 1), was completely blocked by 40 nM of effector-deficient humanized IV.3.1 IgG1 E269R (SEQ ID NO: 53 together with SEQ ID NO: 47, FIG. 29, line 2). Collagen was added (FIG. 29, line 2) at 10.5 min Effector-deficient humanized IV.3.2 IgG1 E269R mAbs (SEQ ID NO: 53 together with SEQ ID NO: 49) also inhibited the activity of this IC (data not shown).

Figure 30:
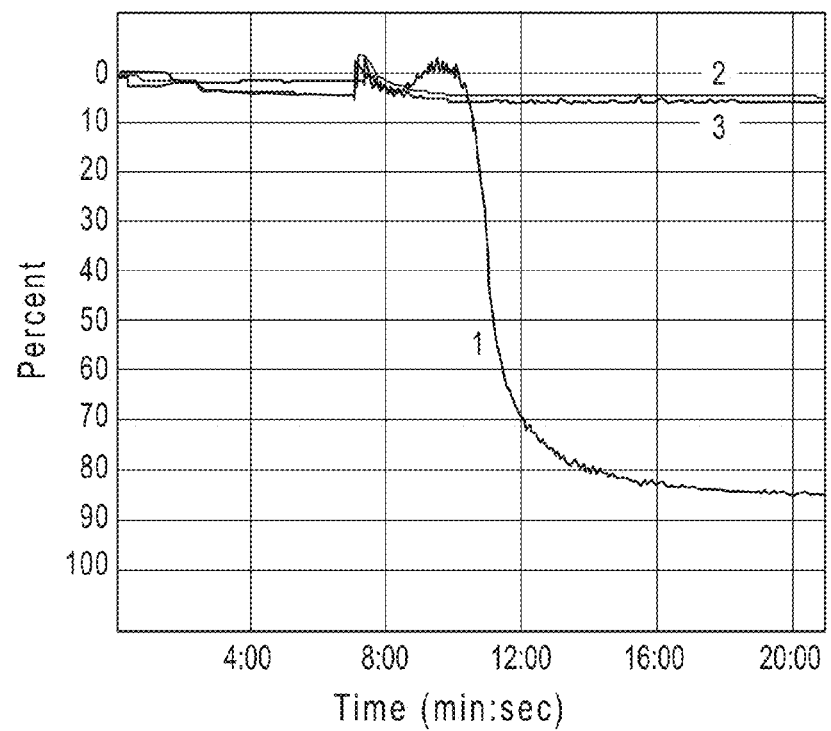
FIG. 30 shows platelet aggregation response to IgG immune complexes in the presence of vehicle (#1) or effector-deficient humanized IV.3.1 IgG1 E269R (33 nM) (#2) or effector-deficient human MDE-8 IgG1 E269R (50 nM) (#3).

In FIG. 30, 500 nM anti-human beta2GPI polyclonal antibody+125 nM human Beta2GPI IC (an APS-like IC) induced robust platelet aggregation (FIG. 30, line 1) which was blocked both by 33 nM of effector-deficient humanized IV.3.1 IgG1 E269R mAb (SEQ ID NO: 53 together with SEQ ID NO: 47, FIG. 30, line 2) and by 50 nM of effector-deficient human MDE-8 IgG1 E269R (SEQ ID NO: 69 together with SEQ ID NO: 65, FIG. 30, line 3).

Figure 31:
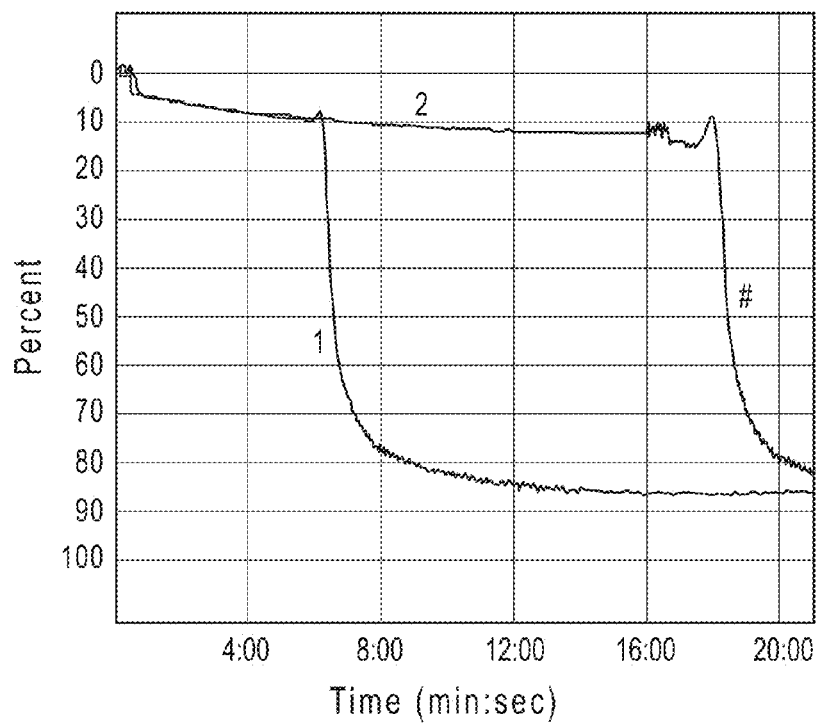
FIG. 31 shows platelet aggregation response to IgG immune complexes in the presence of vehicle (#1) or effector-deficient humanized AT-10 IgG1 E269R ("hAT-10"; 15 nM) (#2). F(ab')2 fragments of goat anti-human-F(ab')2 (#), which lack an Fc-domain, was added to #2 to demonstrate aggregation competence.

In FIG. 31, M90+CD40L (500 nM) IC-induced aggregation (FIG. 31, line 1) was inhibited by 15 nM effector-deficient humanized AT-10 IgG1 E269R mAb (SEQ ID NO: 24 together with SEQ ID NO: 20, FIG. 31, line 2). Addition of 375 nM of the F(ab')2 fragment of goat anti-human-F (ab')2 (designated as #; added at 16 min), which lacks an Fc-domain, cause platelet aggregation thus demonstrating platelet surface localization of effector-deficient humanized AT-10 IgG1 E269R as well as aggregation competence.

Taken together, the results depicted by FIG. 19-31 demonstrate that several different types of immune complexes (ICs) are capable of inducing platelet aggregation in a CD32a-dependent manner. These ICs are potently blocked by chimeric or humanized IV.3, by chimeric or humanized AT-10, and by MDE-8, including IgG1 and IgG2 isotype subclasses, in both effector-competent and effector-deficient formats. Because humanized AT-10 and humanized IV.3 mAbs exhibited CD32a blocking activity comparable to that of their parent murine mAbs, these previously undescribed and novel mAbs may be useful for treatment of human disorders in which immune complexes play a pathologic role via CD32a.

When considered together, the in vivo (mouse) and in vitro (aggregation, degranulation) data also demonstrate that effector-deficient formats of IV.3, AT-10, and MDE-8, whether in IgG1 or IgG2 format, and whether chimeric, humanized, or fully human, can be expected to have safe in vivo administration profiles while providing potent blockade of CD32a, thus preventing CD32a activation induced by ICs or by immobilized IgG.

Combined AT-10, IV.3 and MDE-8 mAbs do not Activate CD32a

We next considered whether the effector-deficient chimeric, humanized, and human anti-CD32a mAbs described herein were capable, when combined, of activating CD32a (i.e., by directly multimerizing or clustering the receptor). To this end, we combined 2 nM humanized AT-10 (SEQ ID NO: 24 together with SEQ ID NO: 20), 150 nM humanized IV.3.1 (SEQ ID NO: 53 together with SEQ ID NO: 47), and 150 nM human MDE-8 (SEQ ID NO: 69 together with SEQ ID NO: 65), all in effector-deficient IgG1 E269R format, and exposed the combination of these anti-CD32a mAbs to washed human platelets. FIG. 32 shows that 500 nM M90+ CD40L IC induced robust platelet aggregation (FIG. 32, line 1), while combined anti-CD32a mAbs did not caused aggregation (FIG. 32, line 2). Collagen (*), added at 18 min, demonstrated aggregation competence. FIG. 33 shows that the combination of 300 nM effector-deficient chimeric AT-10 hIgG1 E269R (SEQ ID NO: 22 together with SEQ ID NO: 16), 300 nM effector-deficient chimeric IV.3 hIgG2 N297A (SEQ ID NO: 51 together with SEQ ID NO: 45), and 300 nM effector-deficient human MDE-8 IgG1 E269R (SEQ ID NO: 69 together with SEQ ID NO: 65) also failed to induce platelet aggregation, whereas collagen (*) succeeded.

We next examined the capacity of combined CD32a mAbs to induce platelet degranulation, as occurs when CD32a is clustered by ICs. We also evaluated the capacity of these anti-CD32a mAbs to prevent platelet degranulation caused by therapeutic TNFalpha antibodies complexed with TNFalpha (100 nM). To that end, we tested murine IV.3 mIgG2b, effector-deficient humanized IV.3.1 hIgG1 E269R (SEQ ID NO: 53 together with SEQ ID NO: 47), effector-deficient chimeric AT-10 hIgG1 E269R (SEQ ID NO: 22 together with SEQ ID NO: 16, and effector-deficient human MDE-8 IgG1 E269R (SEQ ID NO: 69 together with SEQ ID NO: 65), as well as the combination of these four mAbs (all at 100 nM), for their capacity to activate washed human platelets, as measured by degranulation in the serotonin release assay (FIG. 34). The results showed that all tested anti-CD32a mAbs prevented TNFalpha-immune-complex induced platelet degranulation, and that the combination of all mAbs failed to degranulate platelets. FIG. 34.

Further, a combination of 25 nM humanized IV.3.1 (SEQ ID NO: 53 together with SEQ ID NO: 47), 90 nM humanized AT-10 (SEQ ID NO: 24 together with SEQ ID NO: 20), and 75 nM human MDE-8 (SEQ ID NO: 69 together with SEQ ID NO: 65), all in effector-deficient IgG1 E269R format, was also similarly tested with the same result (i.e., no activation of CD32a; data not shown).

Each of the tested mAbs blocked infliximab and adalimumab anti-TNFalpha IC-induced platelet activation. The combination of four anti-CD32a mAbs (mouse IV.3, humanized IV.3, chimeric AT-10, and human NDE-8) failed to cause any platelet activation (FIG. 34).

Taken together, the results shown in FIGS. 32-34 indicate that the tested mAbs are compatible in that they do not synergistically cluster CD32a to the point of activation, suggesting that these mAbs could potentially be delivered to patients without synergistic activation. Furthermore, the compatability of these mAbs provides a progressive treatment course for anti-CD32a therapy, wherein patients developing immune reactivity to a first therapeutic anti-CD32a mAb are provided with follow-up therapeutics compatible for long term treatment of chronic immune complex-mediated disorders.

Although humanized and human antibodies used for therapy in patients with immune complex-mediated disorders are expected to be less immunogenic, the evidence suggests that many such patients nevertheless develop immune reactions to the therapeutic antibody (e.g., anti-therapeutic-antibody-antibodies, or ATA). These host response antibodies can form immune complexes that activate CD32a; however, the effector-deficient CD32a mAbs described herein are candidates for use in protecting patients from these ATA immune complexes.

Following this rationale, we examined the capacity of anti-CD32a mAbs to prevent platelet degranulation induced by ICs formed from infliximab and F(ab')2 fragments of goat anti-human IgG-F(ab')2 antibodies, wherein the only functional Fc-domain of such ICs is that of the therapeutic mAb, infliximab FIG. 35 shows that infliximab+goat anti-human IgG F(ab')2 ICs induced platelet degranulation (FIG. 35, first column) The activity of this IC was blocked by mouse IV.3 mIgG2b mAb (FIG. 35, second column), by effector-deficient human MDE-8 IgG1 E269R (SEQ ID NO: 69 together with SEQ ID NO: 65, FIG. 35, third column), by effector-deficient chimeric AT-10 hIgG1 E269R (SEQ ID NO: 22 together with SEQ ID NO: 16, FIG. 35, fourth column), and by effector-deficient humanized IV.3.1 hIgG1 E269R (SEQ ID NO: 53 together with SEQ ID NO: 47, FIG. 35, fifth column) These results demonstrate that CD32a blockade can prevent activation of platelets by ICs formed from antibodies that cluster the therapeutic mAb, infliximab, and that the effector-deficient CD32a antibodies of the present invention are useful in methods to prevent activation of platelets by ICs, and in particular, by ICs formed from clusters of therapeutic non-CD32a monoclonal antibodies.

Furthermore, patients who are immunologically reactive to such therapeutic non-CD32a mAbs are typically transitioned, or "switched" to alternative therapeutic mAbs having the same antigen target, as is the case in anti-TNF alpha therapy, where a reactive patient might be switched, for example, from infliximab to adalimumab. This concern may require lengthy treatment gaps to ensure that residual previous therapeutic antibody is no longer present. However, our data shows that an immune reactive recipient (i.e., a patient having an immune reaction to administered non-anti-CD32a antibodies) could safely be switched to an effector-deficient CD32a antibody described herein with no treatment gap, and also that a patient could be treated with multiple effector-deficient CD32a antibodies as described herein without concern for synergistic platelet activation.

Following this rationale, we injected the combination of three anti-CD32a mAbs into CD32A transgenic mice and examined core body temperature and platelet counts as measures of possible synergistic infusion reactions. Effector-deficient chimeric AT-10 hIgG1 E269R (SEQ ID NO: 22 together with SEQ ID NO: 16), effector-deficient chimeric IV.3 hIgG2 N297A (SEQ ID NO: 51 together with SEQ ID NO: 45), and effector-deficient human MDE-8 IgG1 E269R (SEQ ID NO: 69 together with SEQ ID NO: 65) were premixed and injected intravenously as a single bolus into two CD32A transgenic mice. The first animal received 50 micro-grams of each mAb (total of 150 micro-grams of anti-CD32a IgG injected). The second animal received 100 micro-grams of each mAb (300 micro-grams total IgG injected). Platelet counts (in whole blood) of each animal were measured before (FIGS. 36A and 36C) and 30 minutes after mAb injection (FIG. 36B=50 micro-grams×3, and FIG. 36D=100 micro-grams 3). Gate P1 identifies platelets (gate P4 is other blood cells). FIG. 36E shows core body temperature in CD32A transgenic mice as monitored for 30 minutes following injection of effector-deficient mAbs. These results show that these effector-deficient anti-CD32a clones (i.e., IV.3, AT-10, MDE-8), when combined, do not confer the capacity either to cluster CD32a or to induce thrombocytopenia in CD32A mice.

Taken together, the results depicted by FIGS. 32-36 demonstrate a surprising functional compatability of IV.3, AT-10, and MDE-8, such that, when combined, these antibodies retain their non-activating profile, both in vitro and in vivo, thus providing a therapeutic strategy for continued anti-CD32a immunotherapy, for example, in the presence of anti-drug antibodies (ATA).

EQUIVALENTS

The foregoing written specification is considered to be sufficient to enable one skilled in the art to practice the embodiments. The foregoing description and Examples detail certain embodiments and describes the best mode contemplated by the inventors. It will be appreciated, however, that no matter how detailed the foregoing may appear in text, the embodiment may be practiced in many ways and should be construed in accordance with the appended claims and any equivalents thereof.

As used herein, the term about refers to a numeric value, including, for example, whole numbers, fractions, and percentages, whether or not explicitly indicated. The term about generally refers to a range of numerical values (e.g., +/−5-10% of the recited range) that one of ordinary skill in the art would consider equivalent to the recited value (e.g., having the same function or result). In some instances, the term about may include numerical values that are rounded to the nearest significant figure.

What is claimed is:

1. A method for inhibiting IgG-Fc ligand binding to CD32a in a human subject comprising: administering a therapeutically effective amount of an effector-deficient anti-CD32a monoclonal antibody to a human subject, wherein the antibody comprises two CD32a binding domains and at least a portion of $C_H2$ and $C_H3$ domains, and the CD32a binding domains comprise:

(i)
  a. a heavy chain variable region CDR1 sequence comprising a sequence that is identical to the sequence YYWMN (SEQ ID NO: 1) or GFTFSYYW (SEQ ID NO: 73 and SEQ ID NO: 88);
  b. a heavy chain variable region CDR2 sequence comprising a sequence that is identical to the sequence EIRLKSNNYATHYAESVKG (SEQ ID NO: 2) or IRLKSNNYAT (SEQ ID NO: 74 and SEQ ID NO: 89);
  c. a heavy chain variable region CDR3 sequence comprising a sequence that is identical to the sequence RDEYYAMDY (SEQ ID NO: 3) or NRRDEYYAMDY (SEQ ID NO: 75 and SEQ ID NO: 90);
  d. a light chain variable region CDR1 sequence comprising a sequence that is identical to the sequence RASESVDNFGISFMN (SEQ ID NO: 4) or ESVDNFGISF (SEQ ID NO: 76 and SEQ ID NO: 91);
  e. a light chain variable region CDR2 sequence comprising a sequence that is identical to the sequence GASNQGS (SEQ ID NO: 5) or GAS (SEQ ID NO: 77 and SEQ ID NO: 92); and
  f. a light chain variable region CDR3 sequence comprising a sequence that is identical to the sequence QQSKEVPWT (SEQ ID NO: 6) or QQSKEVPWT (SEQ ID NO:78 and SEQ ID NO: 93);

(ii)
  a. a heavy chain variable region CDR1 sequence comprising a sequence that is identical to the sequence NYGMN (SEQ ID NO: 25) or GYTFTNYG (SEQ ID NO: 79);
  b. a heavy chain variable region CDR2 sequence comprising a sequence that identical to the sequence WLNTYTGESIYPDDFKG (SEQ ID NO: 26) or LNTYTGES (SEQ ID NO: 80);
  c. a heavy chain variable region CDR3 sequence comprising a sequence that is identical to the sequence GDYGYDDPLDY (SEQ ID NO: 27) or ARGDYGYDDPLDY (SEQ ID NO: 81);
  d. a light chain variable region CDR1 sequence comprising a sequence that is identical to the sequence RSSKSLLHTNGNTYLH (SEQ ID NO: 28) or KSLLHTNGNTY (SEQ ID NO: 82 and SEQ ID NO: 100);
  e. a light chain variable region CDR2 sequence comprising a sequence identical to the sequence RMSVLAS (SEQ ID NO: 29) or RMS (SEQ ID NO: 83 and SEQ ID NO: 101); and
  f. a light chain variable region CDR3 sequence comprising a sequence that is identical to the sequence MQHLEYPLT (SEQ ID NO: 30 and SEQ ID NO: 84 and SEQ ID NO: 102); or (iii)
  a. a heavy chain variable region CDR1 sequence comprising a sequence that is identical to the sequence SYGMH (SEQ ID NO: 54) or GFTFSSYG (SEQ ID NO: 94;
  b. a heavy chain variable region CDR2 sequence comprising a sequence that is identical to the sequence VIWYDGSNYYYTDSVKG (SEQ ID NO: 55) or IWYDGSNY (SEQ ID NO: 95);
  c. a heavy chain variable region CDR3 sequence comprising a sequence that is identical to the sequence DLGAAASDY (SEQ ID NO: 56) or ARDLGAAASDY (SEQ ID NO: 96);
  d. a light chain variable region CDR1 sequence comprising a sequence that is identical to the sequence RASQGINSALA (SEQ ID NO: 57) or QGINSA (SEQ ID NO: 97);
  e. a light chain variable region CDR2 sequence comprising a sequence that is identical to the sequence DASSLES (SEQ ID NO: 58) or DAS (SEQ ID NO: 98); and
  f. a light chain variable region CDR3 sequence comprising a sequence that is identical to the sequence QQFNSYPHT (SEQ ID NO: 59) or QQFNSYPHT (SEQ ID NO: 99);

thereby inhibiting IgG-Fc ligand binding to CD32a.

2. The method of claim 1, wherein the effector-deficient antibody satisfies both the IgG Immune Complex Test and the Immobilized IgG Test, and wherein the FC region of the effector-deficient antibody has been altered so as to reduce or eliminate Fc-binding to CD16, CD32, and/or CD64 type IgG receptors.

3. The method of claim 1, wherein the subject has an IgG-mediated hemostatic disorder.

4. The method of claim 3, wherein the hemostatic disorder is thrombosis with or without thrombocytopenia.

5. The method of claim 3, wherein the hemostatic disorder is selected from the group consisting of IgG-mediated-thrombocytopenia, immune-mediated-thrombocytopenia (ITP), antiphospholipid syndrome (APS), anti-platelet-antibody disorders, heparin-induced thrombocytopenia heparin-induced thrombocytopenia with thrombosis (HITT), cancer-induced platelet activation, cancer-induced hypercoagulability, platelet-mediated tumor cell metastasis, and platelet-mediated cancer metastasis.

6. The method of claim 1, wherein the subject is characterized by IgG-Fc-mediated activation of CD32a on platelets, monocytes, neutrophils, basophils, eosinophils, macrophages, dendritic cells, synovial cells, mast cells, or dermal microvascular endothelial cells.

7. The method of claim 1, wherein the subject has an IgG-mediated immune, autoimmune, or inflammatory disease or disorder.

8. The method of claim 7, wherein the IgG-mediated immune, autoimmune or inflammatory disorder is selected from the group consisting of rheumatoid arthritis (RA), psoriasis, psoriatic arthritis, ankylosing spondylitis, inflammatory bowel disease, ulcerative colitis, Crohn's disease, antiphospholipid syndrome (APS), osteoarthritis, systemic lupus erythematous (SLE), lupus nephritis, IgG antibody-induced anemia, and IgG-mediated cytopenia.

9. The method of claim 1, wherein the subject has an IgG immune complex-mediated disease or disorder.

10. The method of claim 9, wherein the IgG immune complex-mediated disease or disorder is an anti-therapeutic-antibody (ATA) response caused by administration of a non-anti-CD32a monoclonal antibody or fragment thereof.

11. The method of claim 10, wherein the non-anti-CD32a antibody is infliximab, adalimumab, certolizumab pegol (antibody-like), golimumab, etanercept (antibody-like), ustekinumab, omalizumab, or bevacizumab.

12. The method of claim 10, wherein the effector deficient anti-CD32a antibody is administered prior to, concurrently with, or following the non-anti-CD32a monoclonal antibody.

13. The method of claim 10, wherein the IgG immune complex-mediated disease or disorder occurs in a patient being treated with a non-anti-CD32a monoclonal antibody for the treatment of rheumatoid arthritis, systemic lupus erythematosus (SLE), lupus nephritis, or inflammatory bowel disease (IBD), including ulcerative colitis and Crohn's disease.

14. The method of claim 1, wherein the subject has a disease or disorder characterized by IgG localized on the surface of cells circulating in the blood of the human subject.

15. The method of claim 14, wherein the circulating cell type is comprised of one or more of the following: platelets, erythrocytes, monocytes, neutrophils, basophils, eosinophils, B-lymphocytes, macrophages, mast cells, leukemia cells, or microbes.

16. The method of claim 14, wherein the disease or disorder is selected from one or more of the following: thrombocytopenia, leukopenia, neutropenia, lymphopenia, monocytopenia, anemia, hemolytic anemia, or sepsis.

17. A method for treating antibody-mediated allergic or hypersensitivity reactions of type I, type II, or type III in a human subject comprising: administering a therapeutically effective amount of an effector-deficient anti-CD32a monoclonal antibody to a human subject, wherein the antibody comprises two CD32a binding domains and at least a portion of $C_H2$ and $C_H3$ domains, and the CD32a binding domains comprise:

(i)
   a. a heavy chain variable region CDR1 sequence comprising a sequence that is identical to the sequence YYWMN (SEQ ID NO: 1) or GFTFSYYW (SEQ ID NO: 73 and SEQ ID NO: 88);
   b. a heavy chain variable region CDR2 sequence comprising a sequence that is identical to the sequence EIRLKSNNYATHYAESVKG (SEQ ID NO: 2) or IRLKSNNYAT (SEQ ID NO: 74 and SEQ ID NO: 89);
   c. a heavy chain variable region CDR3 sequence comprising a sequence that is identical to the sequence RDEYYAMDY (SEQ ID NO: 3) or NRRDEYYAMDY (SEQ ID NO: 75 and SEQ ID NO: 90);
   d. a light chain variable region CDR1 sequence comprising a sequence that is identical to the sequence RASESVDNFGISFMN (SEQ ID NO: 4) or ESVDNFGISF (SEQ ID NO: 76 and SEQ ID NO: 91);
   e. a light chain variable region CDR2 sequence comprising a sequence that is identical to the sequence GASNQGS (SEQ ID NO: 5) or GAS (SEQ ID NO: 77 and SEQ ID NO: 92); and
   f. a light chain variable region CDR3 sequence comprising a sequence that is identical to the sequence QQSKEVPWT (SEQ ID NO: 6) or QQSKEVPWT (SEQ ID NO:78 and SEQ ID NO: 93);

(ii)
   a. a heavy chain variable region CDR1 sequence comprising a sequence that is identical to the sequence NYGMN (SEQ ID NO: 25) or GYTFTNYG (SEQ ID NO: 79);
   b. a heavy chain variable region CDR2 sequence comprising a sequence that identical to the sequence WLNTYTGESIYPDDFKG (SEQ ID NO: 26) or LNTYTGES (SEQ ID NO: 80);
   c. a heavy chain variable region CDR3 sequence comprising a sequence that is identical to the sequence GDYGYDDPLDY (SEQ ID NO: 27) or ARGDYGYDDPLDY (SEQ ID NO: 81);
   d. a light chain variable region CDR1 sequence comprising a sequence that is identical to the sequence RSSKSLLHTNGNTYLH (SEQ ID NO: 28) or KSLLHTNGNTY (SEQ ID NO: 82 and SEQ ID NO: 100);
   e. a light chain variable region CDR2 sequence comprising a sequence identical to the sequence RMSVLAS (SEQ ID NO: 29) or RMS (SEQ ID NO: 83 and SEQ ID NO: 101); and
   f. a light chain variable region CDR3 sequence comprising a sequence that is identical to the sequence MQHLEYPLT (SEQ ID NO: 30 and SEQ ID NO: 84 and SEQ ID NO: 102); or (iii)
   a. a heavy chain variable region CDR1 sequence comprising a sequence that is identical to the sequence SYGMH (SEQ ID NO: 54) or GFTFSSYG (SEQ ID NO: 94);
   b. a heavy chain variable region CDR2 sequence comprising a sequence that is identical to the sequence VIWYDGSNYYYTDSVKG (SEQ ID NO: 55) or IWYDGSNY (SEQ ID NO: 95);
   c. a heavy chain variable region CDR3 sequence comprising a sequence that is identical to the sequence DLGAAASDY (SEQ ID NO: 56) or ARDLGAA-ASDY (SEQ ID NO: 96);
d. a light chain variable region CDR1 sequence comprising a sequence that is identical to the sequence RASQGINSALA (SEQ ID NO: 57) or QGINSA (SEQ ID NO: 97);
e. a light chain variable region CDR2 sequence comprising a sequence that is identical to the sequence DASSLES (SEQ ID NO: 58) or DAS (SEQ ID NO: 98); and
f. a light chain variable region CDR3 sequence comprising a sequence that is identical to the sequence QQFNSYPHT (SEQ ID NO: 59) or QQFNSYPHT (SEQ ID NO: 99);

thereby treating the antibody-mediated allergic or hypersensitivity reactions of type I, type II, or type III.

18. The method of claim 17, wherein the allergic disorder is selected from the group consisting of atopy, contact dermatitis, allergic rhinitis, systemic anaphylaxis, localized anaphylaxis as exhibited in hay fever, asthma, hives, food allergies, and eczema, allergic reactions to vaccines, allergic reactions to foods, allergic reactions to, allergic reactions to insect products, allergic reactions to drugs, allergic reactions to mold spores, allergic reactions to animal hair and dander, allergic reactions to latex, blood transfusion reactions, platelet transfusion reactions, erythrocyte transfusion reactions, erythroblastosis fetalis, hemolytic anemia, serum sickness, infusion reactions, necrotizing vasculitis, glomerulonephritis, rheumatoid arthritis, systemic lupus erythematosus, and allergic reactions to microorganisms.

19. The method of claim 1, wherein the effector-deficient anti-CD32a antibody is an effector-deficient MDE-8, IV.3, or AT-10 monoclonal antibody.

20. The method of claim 1, wherein the monoclonal antibody is humanized.

21. The method of claim 1, wherein the antibody comprises:
a. a heavy chain variable region CDR1 sequence comprising a sequence that is identical to the sequence YYWMN (SEQ ID NO: 1) or GFTFSYYW (SEQ ID NO: 73 and SEQ ID NO: 88);
b. a heavy chain variable region CDR2 sequence comprising a sequence that is identical to the sequence EIRLKSNNYATHYAESVKG (SEQ ID NO: 2) or IRLKSNNYAT (SEQ ID NO: 74 and SEQ ID NO: 89);
c. a heavy chain variable region CDR3 sequence comprising a sequence that is identical to the sequence RDEYYAMDY (SEQ ID NO: 3) or NRRDEYYAMDY (SEQ ID NO: 75 and SEQ ID NO: 90);
d. a light chain variable region CDR1 sequence comprising a sequence that is identical to the sequence RASESVDNFGISFMN (SEQ ID NO: 4) or ESVDNFGISF (SEQ ID NO: 76 and SEQ ID NO: 91);
e. a light chain variable region CDR2 sequence comprising a sequence that is identical to the sequence GASNQGS (SEQ ID NO: 5) or GAS (SEQ ID NO: 77 and SEQ ID NO: 92); and
f. a light chain variable region CDR3 sequence comprising a sequence that is identical to the sequence QQSKEVPWT (SEQ ID NO: 6) or QQSKEVPWT (SEQ ID NO:78 and SEQ ID NO: 93).

22. The method of claim 21, wherein the antibody comprises a variable heavy chain sequence comprising a sequence that is at least 75%, 80%, 85%, 90%, 95%, 96%, 97%, 98%, or 99% identical to the sequence shown in SEQ ID NO: 8 or SEQ ID NO: 12, and a variable light chain sequence comprising a sequence that is at least 75%, 80%, 85%, 90%, 95%, 96%, 97%, 98%, or 99% identical to the sequence shown in SEQ ID NO: 10 or SEQ ID NO: 14.

23. The method of claim 21, wherein the antibody comprises:
a. a heavy chain sequence that is at least 75%, 80%, 85%, 90%, 95%, 96%, 97%, 98%, or 99% identical to the sequence shown in SEQ ID NO: 16, SEQ ID NO: 18, or SEQ ID NO: 20; and
b. a light chain sequence that is at least 75%, 80%, 85%, 90%, 95%, 96%, 97%, 98%, or 99% identical to the sequence shown in SEQ ID NO: 22, or SEQ ID NO: 24.

24. The method of claim 1, wherein the antibody comprises:
a. a heavy chain variable region CDR1 sequence comprising a sequence that is identical to the sequence NYGMN (SEQ ID NO: 25) or GYTFTNYG (SEQ ID NO: 79);
b. a heavy chain variable region CDR2 sequence comprising a sequence that identical to the sequence WLNTYTGESIYPDDFKG (SEQ ID NO: 26) or LNTYTGES (SEQ ID NO: 80);
c. a heavy chain variable region CDR3 sequence comprising a sequence that is identical to the sequence GDYGYDDPLDY (SEQ ID NO: 27) or ARGDYGYDDPLDY (SEQ ID NO: 81);
d. a light chain variable region CDR1 sequence comprising a sequence that is identical to the sequence RSSKSLLHTNGNTYLH (SEQ ID NO: 28) or KSLLHTNGNTY (SEQ ID NO: 82 and SEQ ID NO: 100);
e. a light chain variable region CDR2 sequence comprising a sequence identical to the sequence RMSVLAS (SEQ ID NO: 29) or RMS (SEQ ID NO: 83 and SEQ ID NO: 101); and
a light chain variable region CDR3 sequence comprising a sequence that is identical to the sequence MQHLEYPLT (SEQ ID NO: 30 and SEQ ID NO: 84 and SEQ ID NO: 102).

25. The method of claim 24, wherein the antibody comprises:
a. a variable heavy chain sequence comprising a sequence that is at least 75%, 80%, 85%, 90%, 95%, 96%, 97%, 98%, or 99% identical to the sequence shown in SEQ ID NO: 32, SEQ ID NO: 36, or SEQ ID NO: 38; and
b. a variable light chain sequence comprising a sequence that is at least 75%, 80%, 85%, 90%, 95%, 96%, 97%, 98%, or 99% identical to the sequence shown in SEQ ID NO: 34, SEQ ID NO: 41 or SEQ ID 85.

26. The method of claim 24, wherein the antibody comprises:
a. a heavy chain sequence that is at least 75%, 80%, 85%, 90%, 95%, 96%, 97%, 98%, or 99% identical to the sequence shown in SEQ ID NO: 43, SEQ ID NO: 45, SEQ ID NO: 47, or SEQ ID NO: 49; and
b. a light chain sequence that is at least 75%, 80%, 85%, 90%, 95%, 96%, 97%, 98%, or 99% identical to the sequence shown in SEQ ID NO: 51, SEQ ID NO: 53 or SEQ ID NO: 87.

27. The method of claim 1, wherein the antibody comprises:
a. a heavy chain variable region CDR1 sequence comprising a sequence that is identical to the sequence SYGMH (SEQ ID NO: 54) or GFTFSSYG (SEQ ID NO: 94);
b. a heavy chain variable region CDR2 sequence comprising a sequence that is identical to the sequence VIWYDGSNYYYTDSVKG (SEQ ID NO: 55) or IWYDGSNY (SEQ ID NO: 95);

c. a heavy chain variable region CDR3 sequence comprising a sequence that is identical to the sequence DLGAAASDY (SEQ ID NO: 56) or ARDLGAAASDY (SEQ ID NO: 96);

d. a light chain variable region CDR1 sequence comprising a sequence that is identical to the sequence RASQGINSALA (SEQ ID NO: 57) or QGINSA (SEQ ID NO: 97);

e. a light chain variable region CDR2 sequence comprising a sequence that is identical to the sequence DASSLES (SEQ ID NO: 58) or DAS (SEQ ID NO: 98); and f. a light chain variable region CDR3 sequence comprising a sequence that is identical to the sequence QQFNSYPHT (SEQ ID NO: 59) or QQFNSYPHT (SEQ ID NO: 99).

28. The method of claim 27, wherein the antibody comprises:

a. a variable heavy chain sequence comprising a sequence that is at least 75%, 80%, 85%, 90%, 95%, 96%, 97%, 98%, or 99% identical to the sequence shown in SEQ ID NO: 61; and b. a variable light chain sequence comprising a sequence that is at least 75%, 80%, 85%, 90%, 95%, 96%, 97%, 98%, or 99% identical to the sequence shown in SEQ ID NO: 63.

29. The method of claim 27, wherein the antibody comprises:

a. a heavy chain sequence that is at least 75%, 80%, 85%, 90%, 95%, 96%, 97%, 98%, or 99% identical to the sequence shown in SEQ ID NO: 65 or SEQ ID NO: 67; and b. a light chain sequence that is at least 75%, 80%, 85%, 90%, 95%, 96%, 97%, 98%, or 99% identical to the sequence shown in SEQ ID NO: 69.

* * * * *

UNITED STATES PATENT AND TRADEMARK OFFICE
CERTIFICATE OF CORRECTION

PATENT NO. : 10,184,001 B2
APPLICATION NO. : 15/171734
DATED : January 22, 2019
INVENTOR(S) : John Francis et al.

Page 1 of 1

It is certified that error appears in the above-identified patent and that said Letters Patent is hereby corrected as shown below:

In the Claims

Column 165
Line 61, delete "identical" and insert --is identical--

Column 168
Line 37, delete "identical" and insert --is identical--

Column 169
Line 22, delete "allergic reactions to,"

Column 170
Line 20, delete "identical" and insert --is identical--

Signed and Sealed this
Twenty-first Day of May, 2019

Andrei Iancu
*Director of the United States Patent and Trademark Office*